US008206932B2

(12) United States Patent
Gudas et al.

(10) Patent No.: US 8,206,932 B2
(45) Date of Patent: *Jun. 26, 2012

(54) ANTIBODIES AND RELATED MOLECULES THAT BIND TO PSCA PROTEINS

(75) Inventors: Jean Gudas, Los Angeles, CA (US);
Aya Jakobovits, Beverly Hills, CA (US);
Xiao-chi Jia, Los Angeles, CA (US);
Robert Kendall Morrison, Santa Monica, CA (US); Pia M. Challita-Eid, Encino, CA (US); Arthur B. Raitano, Los Angeles, CA (US)

(73) Assignee: Agensys, Inc., Santa Monica, CA (US)

( * ) Notice: Subject to any disclaimer, the term of this patent is extended or adjusted under 35 U.S.C. 154(b) by 314 days.

This patent is subject to a terminal disclaimer.

(21) Appl. No.: 12/413,435

(22) Filed: Mar. 27, 2009

(65) Prior Publication Data

US 2009/0202548 A1 Aug. 13, 2009

Related U.S. Application Data

(60) Division of application No. 11/355,464, filed on Feb. 15, 2006, now Pat. No. 7,541,442, which is a continuation-in-part of application No. 11/131,648, filed on May 17, 2005, now Pat. No. 7,595,379, which is a continuation-in-part of application No. 10/857,484, filed on May 28, 2004.

(60) Provisional application No. 60/616,381, filed on Oct. 5, 2004, provisional application No. 60/617,881, filed on Oct. 12, 2004, provisional application No. 60/621,310, filed on Oct. 21, 2004, provisional application No. 60/633,077, filed on Dec. 2, 2004, provisional application No. 60/672,000, filed on Apr. 14, 2005, provisional application No. 60/475,064, filed on May 30, 2003.

(51) Int. Cl.
*G01N 33/53* (2006.01)
*G01N 33/567* (2006.01)
*G01N 33/574* (2006.01)
*C12P 21/08* (2006.01)

(52) U.S. Cl. ..... 435/7.1; 435/7.21; 435/7.23; 530/388.1; 530/388.15; 530/388.8; 530/388.85

(58) Field of Classification Search .......... None
See application file for complete search history.

(56) References Cited

U.S. PATENT DOCUMENTS

| 6,258,939 | B1 | 7/2001 | Reiter et al. |
| 6,635,468 | B2 | 10/2003 | Ashkenazi et al. |
| 6,824,780 | B1 | 11/2004 | Devaux et al. |
| 6,979,730 | B2 | 12/2005 | Reiter et al. |
| 7,541,442 | B2 * | 6/2009 | Gudas et al. ............ 530/388.1 |
| 7,595,379 | B2 | 9/2009 | Gudas et al. |
| 7,622,564 | B2 | 11/2009 | Ge et al. |
| 2003/0023054 | A1 | 1/2003 | Ashkenazi et al. |
| 2004/0018571 | A1 | 1/2004 | Reiter et al. |
| 2005/0221400 | A1 * | 10/2005 | Gudas et al. ............ 435/7.23 |
| 2009/0181034 | A1 | 7/2009 | Gudas et al. |
| 2010/0055120 | A1 | 3/2010 | Ge et al. |

FOREIGN PATENT DOCUMENTS

| EP | 1 514 876 | 3/2005 |
| JP | 2001-516580 | 10/2001 |
| JP | 2002-511740 | 4/2002 |
| JP | 2003-515330 | 5/2003 |
| WO | WO-98/00540 | 1/1998 |
| WO | WO-98/40403 | 9/1998 |
| WO | WO-98/51805 | 11/1998 |
| WO | WO-98/51824 | 11/1998 |
| WO | WO-99/14328 | 3/1999 |
| WO | WO-00/015796 | 3/2000 |
| WO | WO-01/40309 | 6/2001 |
| WO | WO-03/074654 | 9/2003 |

OTHER PUBLICATIONS

Abaza et al., Journal of Protein Chemistry (1992) 11(5):433-444.
Algate et al., Blood (1994) 83(9):2459-2468.
Arlen et al., Critical Review in Immunology (1998) 18:133-138.
Arnon et al., "Monoclonal Antibodies for Immunotargeting of Drugs in Cancer Therapy," in Monoclonal Antibodies and Cancer Therapy, Reisfeld and Sell (eds.), (1985) pp. 243-256.
Arthur et al., Cancer Gene Therapy (1997) 4:17-25.
Ashley et al., Journal of Experimental Medicine (1997) 186:1177-1182.
Bacchetti and Graham, Proc. Nat'l. Acad. Sci. USA (1977) 74(4):1590-1594.
Bahrenberg et al., Biochem Biophys Res Commun (2000) 275(3):783-788.
Bamezai and Rock, Nat'l. Acad. Sci USA (1995) 92:4294-4298.
Berent et al., BioTechniques (1985) 3:208-219.
Berkner, BioTechniques (1988) 6(7):616-626.
Bonkhoff and Remberger, The Prostate (1996) 28(2):98-106.
Bonkhoff et al., The Prostate (1994) 24:114-118.
Boshart et al., Cell (1985) 41(2):521-530.
Boulianne et al., Nature (1984) 312:643-646.
Brakenhoff et al., Journal of Cell Biology (1995) 129:1677-1689.
Braun et al., Molecular and Cell Biology (1995) 15:4623-4630.
Breviario et al., The Journal of Biological Chemistry (1992) 267(31):22190-22197.
Brinster et al., Cell (1984) 37:367-379.
Brinster et al., Proc. Nat'l. Acad. Sci. USA (1988) 85:836-840.
Burgess et al., Journal of Cell Biology (1990) 111:2129-2138.
Bzdega et al., Journal of Neurochemistry (1997) 69(6):2270-2277.

(Continued)

*Primary Examiner* — Peter J Reddig
(74) *Attorney, Agent, or Firm* — Morrison & Foerster LLP

(57) ABSTRACT

Antibodies and molecules derived therefrom that bind to novel PSCA protein, and variants thereof, are described wherein PSCA exhibits tissue specific expression in normal adult tissue, and is aberrantly expressed in the cancers listed in Table I. Consequently, PSCA provides a diagnostic, prognostic, prophylactic and/or therapeutic target for cancer. The PSCA gene or fragment thereof, or its encoded protein, or variants thereof, or a fragment thereof, can be used to elicit a humoral or cellular immune response; antibodies or T cells reactive with PSCA can be used in active or passive immunization.

7 Claims, 31 Drawing Sheets

OTHER PUBLICATIONS

Cama et al., The Journal of Urology (1995) 153:1373-1378.
Caron et al., Journal of Experimental Medicine (1992) 176(4):1191-1195.
Carter et al., Proc. Nat'l. Acad. Sci. USA (1992) 89:4285-4289.
Carter et al., Proc. Nat'l. Acad. Sci. USA (1996) 93:749-753.
Cher et al., Genes Chromosomes and Cancer (1994) 11:153-162.
Cluitmans et al., Annals of Hematology (1994) 68:293-298.
Cohen et al., Proc. Nat'l. Acad. Sci. USA (1972) 69:2110-2114.
Coleman et al., Research in Immunology (1994) 145:33-36.
Coloma et al., Journal of Immunological Methods (1992) 152:89-104.
Cupp and Oesterling, Mayo Clinic Proceedings, (1993) 68:297-306.
Dannull et al., Cancer Research (2000) 60(19):5522-5528.
Deleersnijder et al., Journal of Biological Chemistry (1996) 271:19475-19482.
Depamphilis et al., BioTechniques (1988) 6(7):662-680.
De Wit et al., British Journal of Hematology (1994) 86:259-264.
Espinoza-Delgado et al., The Journal of Immunology (1992) 149(9):2961-2968.
Felgner et al., Proc. Nat'l. Acad. Sci. USA (1987) 84:7413-7417.
Felgner et al., Proceedings of the Western Pharmacology Society (1989) 32:115-121.
Fell et al., Proc. Nat'l. Acad. Sci. USA (1989) 86:8507-8511.
Fields and Song, Nature (1989) 340:245-246.
Fong et al., Journal of Immunology (1997) 159:3113-3117.
Foon et al., Journal of Clinical Investigation (1995) 96:334-342.
Freireich et al., Cancer Chemotherapy Reports (1966) 50(4):219-244.
Fritz and Lowe, American Journal of Physiology (1996) 270:G176-G183.
Funakoshi et al., Journal of Immunotherapy (1996) 19(2):93-101.
Gao et al., The Prostate (1997) 31:264-281.
Garabedian et al., Proc. Nat'l. Acad. Sci. USA (1998) 95:15382-15387.
Geller et al., Proc. Nat'l. Acad. Sci. USA (1990) 87:8950-8954.
Ghosh-Choudhury et al., Gene (1986) 50:161-171.
Graham and Van Der Eb, Virology (1973) 52:456-467.
Greenberg et al., Proc. Nat'l. Acad. Sci. USA (1995) 92:3439-3443.
Gu et al., Oncogene (2000) 19:1288-1296.
Hellstrom et al., Proc. Nat'l. Acad. Sci. USA (1985) 82:1499-1502.
Hellstrom et al., "Antibodies for Drug Delivery," in Controlled Drug Delivery, 2nd ed., Robinson et al. (eds.), (1987) pp. 623-653.
Henderson et al., Cancer Research (1996) 56:3763-3770.
Herlyn et al., Cancer Immunology Immunotherapy (1996) 43:65-76.
Hock and Miller, Nature (1986) 320:275-277.
Hodge et al., International Journal of Cancer (1995) 63:231-237.
Hooijberg et al., Cancer Research (1995) 55:2627-2634.
Horisberger et al., Journal of Virology (1990) 64(3):1171-1181.
Horoszewicz et al., Anticancer Research (1987) 7:927-936.
Huang et al., Cancer Research (1995) 55:610-616.
Israeli et al., Cancer Research (1993) 53:227-230.
Israeli et al., Cancer Research (1994) 54(7):1807-1811.
Israeli et al., Cancer Research (1994) 54:6306-6310.
Jenkins et al., Cancer Research (1997) 57:524-531.
Jones et al., Nature (1986) 321:522-525.
Kasprzyk et al., Cancer Research (1992) 52:2771-2776.
Katz et al., International Journal of Cancer (1994) 59:684-691.
Kaufman, Proc. Nat'l. Acad. Sci. USA (1985) 82:689-693.
Kaufman, Methods in Enzymology (1990) 185:487-511.
Kay et al., Journal of Experimental Medicine (1991) 173:775-778.
Kieffer et al., Biochemistry (1994) 33:4471-4482.
Kiessling et al., International Journal of Cancer (2002) 102(4):390-397.
Klein et al., Nature Medicine (1997) 3:402-408.
Lagoo et al., The Journal of Immunology (1994) 152(4):1641-1652.
Lalani et al., Cancer and Metastasis Reviews (1997) 16:29-66.
Lam et al., Clin. Cancer Res. (2005) 11(7):2591-2596.
Larson et al., International Journal of Cancer (1988) 42(6):877-882.
Lee and Oesterling, "Cancer of the Prostate: Diagnosis and Staging," in Urologic Oncology, Oesterling and Richie (eds.), (1997) pp. 357-377.
Li and Stashenko, The Journal of Immunology (1992) 148(3):788-794.
Liu et al., Cancer Research (1998) 58:4055-4060.
Magi-Galluzzi et al., Laboratory Investigation (1997) 76:37-51.
Mao et al., Proc. Nat'l. Acad. Sci. USA (1996) 93:5910-5914.
Maroulakou et al., Proc. Nat'l. Acad. Sci. USA (1994) 91:11236-11240.
Martinez et al., Transplantation (1993) 55(5):1159-1166.
Matsueda et al., The Prostate (2004) 60:205-213.
Mauviel et al., The Journal of Immunology (1992) 149(9):2969-2976.
Maxam and Gilbert, Methods in Enzymology (1980) 65:499-560.
Morton and Myszka, Methods in Enzymology (1998) 295:268-294.
Mount et al., Cancer Research (1994) 54:6160-6166.
Muller et al., Molec. Cell. Biol. (1991) 11:1785-1792.
Murphy et al., The Prostate (1996) 29:371-380.
Neuberger et al., Nature (1984) 312:604-608.
Noda et al., Journal of Experimental Medicine (1996) 183:2355-2360.
Ozaki et al., Blood (1997) 90:3179-3186.
Pang et al., Clinical and Experimental Immunology (1994) 96:437-443.
Panicali and Paoletti, Proc. Nat'l. Acad. Sci. USA (1982) 79:4927-4931.
Pizarro et al., Transplantation (1993) 56(2):399-404.
Qian et al., Cancer Research (1995) 55:5408-5414.
Reiter et al., PNAS USA (1998) 95:1735-1740.
Restifo, Current Opinion in Immunology (1996) 8:658-663.
Ribas et al., Cancer Research (1997) 57:2865-2869.
Riechmann et al., Nature (1988) 332:323-327.
Rosenfeld et al., Science (1991) 252:431-434.
Ross et al., Cancer Research (2002) 62(9):2546-2553.
Rowley et al., Proc. Nat'l. Acad. Sci. USA (1990) 87:9358-9362.
Rudikoff et al., PNAS USA (1982) 79:1979-1983.
Saffran et al., PNAS (2001) 98(5):2658-2663.
Sahagan et al., The Journal of Immunology (1986) 137:1066-1074.
Sarver et al., Molecular and Cellular Biology (1981) 1(6):486-496.
Schaefer-Ridder et al., Science (1982) 215:166-168.
Sharon et al., Nature (1984) 309:364-367.
Shepard et al., Journal of Clinical Immunology (1991) 2:117-127.
Shimane et al., Biochemical and Biophysical Research Communications (1994) 199:26-32.
Shizuya et al., Proc. Nat'l. Acad. Sci. USA (1992) 89:8794-8797.
Shopes, The Journal of Immunology (1992) 148:2918-2922.
Sims et al., The Journal of Immunology (1993) 151(4):2296-2308.
Slovin et al., Program/Proceedings American Society of Clinical Oncology (1997) 16:311a.
Smith et al., Cancer Research (1995) 55:2640-2644.
Smith et al., Nature (1993) 302:490-495.
Sodee et al., Clinical Nuclear Medicine (1996) 21:759-767.
Southern and Berg, Journal of Molecular and Applied Genetics (1982) 1:327-341.
Southern, Journal of Molecular Biology (1975) 98:503-517.
Sprecher and Becker, Archives of Virology (1992) 126:253-269.
Stavridis et al., Experimental Cell Research (1986) 164:568-572.
Strausberg, Database Accession No. B1763933, GI: 1575511 [Sep. 25, 2001].
Su et al., Proc. Nat'l. Acad. Sci. USA (1996) 93:7252-7257.
Tan et al., The Journal of Immunology (1985) 135:3564-3567.
Thomas and Samelson, The Journal of Biological Chemistry (1992) 267:12317-12322.
Thorpe and Ross, Immunological Review (1982) 62:119-158.
Tjoa et al., The Prostate (1996) 28:65-69.
Towbin et al., Proc. Nat'l. Acad. Sci. USA (1979) 76:4350-4354.
Tsunenari et al., Blood (1997) 90:2437-2444.
Udenfriend and Kodukula, Annual Review of Biochemistry (1995) 64:563-591.
Ulich et al., The Journal of Immunology (1991) 146(7):2316-2323.
Vaughan et al., Nature Biotechnology (1998) 16:535-539.
Veis et al., Cell (1993) 75:229-240.
Velders et al., Cancer Research (1995) 55:4398-4403.
Verhoeyen et al., Science (1988) 239:1534-1536.

Vitetta et al., "Immunotoxin Therapy," in Cancer: Principles and Practice of Oncology, 4th edition, DeVita Jr., et al ., (eds,), (1993) pp. 2624-2636.
Wagner et al., Hybridoma (1997) 16:33-40.
Wigler et al., Proc. Nat'l. Acad. Sci. USA (1979) 76:1373-1376.
Wolff et al., Cancer Research (1993) 53(11):2560-2565.
Wong et al., Science (1985) 228:810-815.
Wu, Journal of Clinical Laboratory Analysis (1994) 8:51-62.
Yang et al., American Journal of Pathology (1997) 150:693-704.
Yang et al., Cancer Research (1999) 59(6):1236-1243.
Zhigang et al., World Journal of Surgical Oncology (2004) 2:13.
Zhong et al., Leukemia Research (1996) 20:581-589.
Non-Final Office Action for U.S. Appl. No. 10/857,484, mailed on Sep. 18, 2008, 15 pages.
International Search Report for PCT/US04/17231, mailed on Jan. 19, 2007, 4 pages.
Written Opinion for PCT/US04/17231, mailed on Jan. 19, 2007, 3 pages.
International Search Report for PCT/US05/17412, mailed on Dec. 16, 2005, 4 pages.
Nucleic acid sequence database from issued US patents, Jul. 10, 2001, 98.9% identical to SEQ ID No. 1.
International Preliminary Report on Patentability for PCT/US2006/005693, mailed Oct. 25, 2007, 9 pages.
Supplementary Partial European Search Report for EP 04785910.3, mailed Feb. 29, 2008, 5 pages.
Office Action for European Patent Application No. 04 785 910.3, mailed on Jan. 29, 2009, 5 pages.
Office Action for Russian Patent Application No. 2006146666, mailed on Dec. 11, 2008, 7 pages [English translation included].
Supplementary European Search Report for EP 05752076.9, mailed Apr. 23, 2009, 3 pages.
Notice of the Grounds for Rejection (translation) for JP 2006-515056, mailed Jun. 29, 2010, 9 pages.
Sigma Biosciences Immunochemicals 1996 Catalog (1996) pp. 342-345.
Stratagene Catalog (1988) p. 39.
U.S. Appl. No. 13/094,730, filed Apr. 26, 2011.
Roitt et al., Immunology, 3$^{rd}$ ed., Mosby, St. Louis (1993) pp. 6.4-6.5.

* cited by examiner

Figure 1:

Figure 1A. The cDNA (SEQ ID. NO. : 1) and amino acid sequence (SEQ ID. NO. : 2) of PSCA v.1.

```
  1                   M  K  A  V  L  L  A  L  L  M  A  G  L  A  L
  1 agggagaggcagtgaccATGAAGGCTGTGCTGCTTGCCCTGTTGATGGCAGGCTTGGCCC
 16   Q  P  G  T  A  L  L  C  Y  S  C  K  A  Q  V  S  N  E  D  C
 61 TGCAGCCAGGCACTGCCCTGCTGTGCTACTCCTGCAAAGCCCAGGTGAGCAACGAGGACT
 36   L  Q  V  E  N  C  T  Q  L  G  E  Q  C  W  T  A  R  I  R  A
121 GCCTGCAGGTGGAGAACTGCACCCAGCTGGGGGAGCAGTGCTGGACCGCGCGCATCCGCG
 56   V  G  L  L  T  V  I  S  K  G  C  S  L  N  C  V  D  D  S  Q
181 CAGTTGGCCTCCTGACCGTCATCAGCAAAGGCTGCAGCTTGAACTGCGTGGATGACTCAC
 76   D  Y  Y  V  G  K  K  N  I  T  C  C  D  T  D  L  C  N  A  S
241 AGGACTACTACGTGGGCAAGAAGAACATCACGTGCTGTGACACCGACTTGTGCAACGCCA
 96   G  A  H  A  L  Q  P  A  A  A  I  L  A  L  L  P  A  L  G  L
301 GCGGGGCCCATGCCCTGCAGCCGGCTGCCGCCATCCTTGCGCTGCTCCCTGCACTCGGCC
116   L  L  W  G  P  G  Q  L  *
361 TGCTGCTCTGGGGACCCGGCCAGCTATAGgctctgggggggccccgctgcagcccacactg
421 ggtgtggtgccccaggccttt gtgccactcctcacagaacctggcccagtgggagcctgt
481 cctggttcctgaggcacatcctaacgcaagtttgaccatgtatgtttgcacccctttcc
541 ccnaaccctgaccttcccatgggccttttccaggattcccacccggcagatcagttttag
601 tgacacagatccgcctgcagatggcccctccaaccctttctgttgctgtttccatggccc
661 agcattttccacccttaaccctgtgttcaggcacttcttccccaggaagccttccctgc
721 ccaccccatttatgaattgagccaggtttggtccgtggtgtccccgcacccagcagggg
781 acaggcaatcaggagggcccagtaaaggctgagatgaagtggactgagtagaactggagg
841 acaagagttgacgtgagttcctgggagtttccagagatggggcctggaggcctggaggaa
901 ggggccaggcctcacatttgtggggctcccgaatggcagcctgagcacagcgtaggccct
961 taataaacacctgttggataagccaaaaaa
```

Figure 1B. The cDNA (SEQ ID. NO. : 3) and amino acid sequence (SEQ ID. NO. : 4) of PSCA v.2.

```
  1                                                          M  K
  1 tttgaggccatatataaagtcacctgaggccctctccaccacagcccaccagtgaccATGAA
  3 A  V  L  L  A  L  L  M  A  G  L  A  L  Q  P  G  T  A  L  L
 61 GGCTGTGCTGCTTGCCCTGTTGATGGCAGGCTTGGCCCTGCAGCCAGGCACTGCCCTGCT
 23 C  Y  S  C  K  A  Q  V  S  N  E  D  C  L  Q  V  E  N  C  T
121 GTGCTACTCCTGCAAAGCCCAGGTGAGCAACGAGGACTGCCTGCAGGTGGAGAACTGCAC
 43 Q  L  G  E  Q  C  W  T  A  R  I  R  A  V  G  L  L  T  V  I
181 CCAGCTGGGGGAGCAGTGCTGGACCGCGCGCATCCGCGCAGTTGGCCTCCTGACCGTCAT
 63 S  K  G  C  S  L  N  C  V  D  D  S  Q  D  Y  Y  V  G  K  K
241 CAGCAAAGGCTGCAGCTTGAACTGCGTGGATGACTCACAGGACTACTACGTGGGCAAGAA
 83 N  I  T  C  C  D  T  D  L  C  N  A  S  G  A  H  A  L  Q  P
301 GAACATCACGTGCTGTGACACCGACTTGTGCAACGCCAGCGGGGCCCATGCCCTGCAGCC
103 A  A  A  I  L  A  L  L  P  A  L  G  L  L  W  G  P  G  Q
361 GGCTGCCGCCATCCTTGCGCTGCTCCCTGCACTCGGCCTGCTGCTCTGGGGACCCGGCCA
123 L  *
421 GCTATAGgctctggggggccccgctgcagcccacactgggtgtggtgccccaggcctctg
481 tgccactcctcacacacccggcccagtgggagcctgtcctggttcctgaggcacatccta
541 acgcaagtctgaccatgtatgtctgcgcccctgtccccaccctgaccctcccatggccc
601 tctccaggactcccaccggcagatcggctctattgacacagatccgcctgcagatggcc
661 cctccaaccctctctgctgctgtttccatggcccagcattctccacccttaaccctgtgc
721 tcaggcacctcttcccccaggaagccttccctgcccaccccatctatgacttgagccagg
781 tctggtccgtggtgtccccgcacccagcaggggacaggcactcaggagggcccggtaaa
841 ggctgagatgaagtggactgagtagaactggaggacaggagtcgacgtgagttcctggga
901 gtctccagagatggggcctggaggcctggaggaaggggccaggcctcacattcgtgggc
961 tccctgaatggcagcctcagcacagcgtaggcccttaataaacacctgttggataagcca
```

Figure 1C. The cDNA (SEQ ID. NO.: 5) and amino acid sequence (SEQ ID. NO.: 6) of PSCA v.3.

```
  1 tttgaggccatataaagtcacctgaggccctctccaccacagcccaccagtgaccatgaa
 61 ggctgtgctgcttgccctgttgatggcaggcttggccctgcagccaggcactgccctgct
121 gtgctactcctgcaaagcccaggcgcagttggcctcctgaccgtcatcagcaaaggctgc
181 agcttgaactgcgtggatgactcacaggactactacgtgggcaagaagaacatcacgtgc
241 tgtgacaccgacttgtgcactcggcctgctgctctggggacccggccagctataggctct
301 ggggggccccgctgcagcccacactgggtgtggtgccccaggcctctgtgccactcctca
361 cacacccggcccagtgggagcctgtcctggttcctgaggcacatcctaacgcaagtctga
  1        M   Y   V   C   A   P   V   P   H   P   D   P   P   M   A   L   S   R   T   P
421 ccATGTATGTCTGCGCCCCTGTCCCCCACCCTGACCCTCCCATGGCCCTCTCCAGGACTC
 21    T   R   Q   I   G   S   I   D   T   D   P   P   A   D   G   P   S   N   P   L
481 CCACCCGGCAGATCGGCTCTATTGACACAGATCCGCCTGCAGATGGCCCCTCCAACCCTC
 41    C   C   C   F   H   G   P   A   F   S   T   L   N   P   V   L   R   H   L   F
541 TCTGCTGCTGTTTCCATGGCCCAGCATTCTCCACCCTTAACCCTGTGCTCAGGCACCTCT
 61    P   Q   E   A   F   P   A   H   P   I   Y   D   L   S   Q   V   W   S   V   V
601 TCCCCCAGGAAGCCTTCCCTGCCCACCCCATCTATGACTTGAGCCAGGTCTGGTCCGTGG
 81    S   P   A   P   S   R   G   Q   A   L   R   R   A   R   *
661 TGTCCCCGCACCCAGCAGGGGACAGGCACTCAGGAGGGCCCGGTAAaggctgagatgaa
721 gtggactgagtagaactggaggacaggagtcgacgtgagttcctgggagtctccagagat
781 ggggcctggaggcctggaggaaggggccaggcctcacattcgtggggctccctgaatggc
841 agcctcagcacagcgtaggcccttaataaacacctgttggataagcca
```

Figure 1D. The cDNA (SEQ ID. NO. : 7) and amino acid sequence (SEQ ID. NO. : 8) of PSCA v.4.

```
   1 gacagtgaaccctgcgctgaaggcgttggggctcctgcagttctggggcagccacaggcg
  61 cccagggtttcgtgccgatcagcccaggacggtcttcccggtgcagtttctgatgcgggg
 121 agggcagtgctgccttccggtcaccaggaccagtgctcagcccgcctgcttgaccccctt
 181 acttagctggggtccaatccatacccaatttagatgattcagacgatgggatttgaaact
 241 tttgaactgggtgcgacttaagcactgccctgctgtgctactcctgcaaagcccaggtga
 301 gcaacgaggactgcctgcaggtggagaactgcacccagctgggggagcagtgctggaccg
 361 cgcgcatccgcgcagttggcctcctgaccgtcatcagcaaaggctgcagcttgaactgcg
    1     M  T  H  R  T  T  T  W  A  R  R  T  S  R  A  V  T  P  T
 421 tggATGACTCACAGGACTACTACGTGGGCAAGAAGAACATCACGTGCTGTGACACCGACT
   20 C  A  T  P  A  G  P  M  P  C  S  R  L  P  P  S  L  R  C  S
 481 TGTGCAACGCCAGCGGGGCCCATGCCCTGCAGCCGGCTGCCGCCATCCTTGCGCTGCTCC
   40 L  H  S  A  C  C  S  G  D  P  A  S  Y  R  L  W  G  A  P  L
 541 CTGCACTCGGCCTGCTGCTCTGGGGACCCGGCCAGCTATAGGCTCTGGGGGGCCCCGCTG
   60 Q  P  T  L  G  V  V  P  Q  A  S  V  P  L  L  T  H  P  A  Q
 601 CAGCCCACACTGGGTGTGGTGCCCCAGGCCTCTGTGCCACTCCTCACACACCCGGCCCAG
   80 W  E  P  V  L  V  P  E  A  H  P  N  A  S  L  T  M  Y  V  C
 661 TGGGAGCCTGTCCTGGTTCCTGAGGCACATCCTAACGCAAGTCTGACCATGTATGTCTGC
  100 A  P  V  P  H  P  D  P  P  M  A  L  S  R  T  P  T  R  Q  I
 721 GCCCCTGTCCCCCACCCTGACCCTCCCATGGCCCTCTCCAGGACTCCCACCCGGCAGATC
  120 G  S  I  D  T  D  P  P  A  D  G  P  S  N  P  L  C  C  C  F
 781 GGCTCTATTGACACAGATCCGCCTGCAGATGGCCCCTCCAACCCTCTCTGCTGCTGTTTC
  140 H  G  P  A  F  S  T  L  N  P  V  L  R  H  L  F  P  Q  E  A
 841 CATGGCCCAGCATTCTCCACCCTTAACCCTGTGCTCAGGCACCTCTTCCCCCAGGAAGCC
  160 F  P  A  H  P  I  Y  D  L  S  Q  V  W  S  V  V  S  P  A  P
 901 TTCCCTGCCCACCCCATCTATGACTTGAGCCAGGTCTGGTCCGTGGTGTCCCCCGCACCC
  180 S  R  G  Q  A  L  R  R  A  R  *
 961 AGCAGGGACAGGCACTCAGGAGGGCCCGGTAAaggctgagatgaagtggactgagtaga
1021 actggaggacaggagtcgacgtgagttcctgggagtctccagagatggggcctggaggcc
1081 tggaggaagggccaggcctcacattcgtggggctccctgaatggcagcctcagcacagc
1141 gtaggcccttaataaacacctgttggataagcca
```

Figure 1E. The cDNA (SEQ ID. NO.: 9) and amino acid sequence (SEQ ID. NO.: 10) of PSCA v.5.

```
   1 gacagtgaaccctgcgctgaaggcgttggggctcctgcagttctggggcagccacaggcg
  61 cccagggtttcgtgccgatcagcccaggacggtcttcccggtgcagtttctgatgcgggg
 121 agggcagtgctgccttccggtcaccaggaccagtgctcagcccgcctgcttgaccccctt
 181 acttagctggggtccaatccatacccaatttagatgattcagacgatgggatttgaaact
 241 tttgaactgggtgcgacttaagcactgccctgctgtgctactcctgcaaagcccaggtga
 301 gcaacgaggactgcctgcaggtggagaactgcacccagctgggggagcagtgctggaccg
 361 cgcgcatccgtgagtgggggacgacagccgccaggcctaggtctctgccactgaactat
 421 taatctttctggccatctgtccgcatctgtgtgctgttttccttccacctgtccccgacc
 481 cgtcccgcacctgcacccccaacaatcacccagcatctgtccctccagccatcctcctcc
 541 atctgccactcctccactcatctgtccctccccatcctccatcttccactcctccaccca
 601 tctgtccctccccatccctgagctcacttactcactcaccccatttctgacgctcagcgg
 661 gtggtccatctgcctcggacatctggatagggctgagaccagggccgagaccaggccctc
 721 gcactgcttgcaatcctgaggccagcccaggggactctagagcattaggcagggtggga
 781 caggaggaggcctggggcaggtcaggcaggtgagcacacagggcagccccatccccggat
 841 cccgctgctcccaggcgcagttggcctcctgaccgtcatcagcaaaggctgcagcttga
```

```
                M  T  H  R  T  T  T  W  A  R  R  T  S  R  A  V  T
 901 actgcgtggATGACTCACAGGACTACTACGTGGGCAAGAAGAACATCACGTGCTGTGACA
  18 P  T  C  A  T  P  A  G  P  M  P  C  S  R  L  P  P  S  L  R
 961 CCGACTTGTGCAACGCCAGCGGGGCCCATGCCCTGCAGCCGGCTGCCGCCATCCTTGCGC
  38 C  S  L  H  S  A  C  C  S  G  D  P  A  S  Y  R  L  W  G  A
1021 TGCTCCCTGCACTCGGCCTGCTGCTCTGGGGACCCGGCCAGCTATAGGCTCTGGGGGGCC
  58 P  L  Q  P  T  L  G  V  V  P  Q  A  S  V  P  L  L  T  H  P
1081 CCGCTGCAGCCCACACTGGGTGTGGTGCCCCAGGCCTCTGTGCCACTCCTCACACACCCG
  78 A  Q  W  E  P  V  L  V  P  E  A  H  P  N  A  S  L  T  M  Y
1141 GCCCAGTGGGAGCCTGTCCTGGTTCCTGAGGCACATCCTAACGCAAGTCTGACCATGTAT
  98 V  C  A  P  V  P  H  P  D  P  P  M  A  L  S  R  T  P  T  R
1201 GTCTGCGCCCCTGTCCCCCACCCTGACCCTCCCATGGCCCTCTCCAGGACTCCCACCCGG
 118 Q  I  G  S  I  D  T  D  P  P  A  D  G  P  S  N  P  L  C  C
1261 CAGATCGGCTCTATTGACACAGATCCGCCTGCAGATGGCCCCTCCAACCCTCTCTGCTGC
 138 C  F  H  G  P  A  F  S  T  L  N  P  V  L  R  H  L  F  P  Q
1321 TGTTTCCATGGCCCAGCATTCTCCACCCTTAACCCTGTGCTCAGGCACCTCTTCCCCCAG
 158 E  A  F  P  A  H  P  I  Y  D  L  S  Q  V  W  S  V  V  S  P
1381 GAAGCCTTCCCTGCCCACCCCATCTATGACTTGAGCCAGGTCTGGTCCGTGGTGTCCCCC
 178 A  P  S  R  G  Q  A  L  R  R  A  R  *
1441 GCACCCAGCAGGGGACAGGCACTCAGGAGGGCCCGGTAAaggctgagatgaagtggactg
1501 agtagaactggaggacaggagtcgacgtgagttcctgggagtctccagagatggggcctg
1561 gaggcctggaggaaggggccaggcctcacattcgtggggctccctgaatggcagcctcag
1621 cacagcgtaggcccttaataaacacctgttggataagcca
```

Figure 1F. The cDNA (SEQ ID. NO.: 11) and amino acid sequence (SEQ ID. NO.: 12) of PSCA v.6.

```
  1 tttgaggccatataaagtcacctgaggccctctccaccacagcccaccagtgaccatgaa
  1                                     M  A  G  L  A  L  Q  P  G  T  A  L  L
 61 ggctgtgctgcttgccctgttgATGGCAGGCTTGGCCCTGCAGCCAGGCACTGCCCTGCT
 14  C  Y  S  C  K  A  Q  V  S  N  E  D  C  L  Q  V  E  N  C  T
121 GTGCTACTCCTGCAAAGCCCAGGTGAGCAACGAGGACTGCCTGCAGGTGGAGAACTGCAC
 34  Q  L  G  E  Q  C  W  T  A  R  I  R  A  V  G  L  L  T  V  I
181 CCAGCTGGGGGAGCAGTGCTGGACCGCGCGCATCCGCGCAGTTGGCCTCCTGACCGTCAT
 54  S  K  G  C  S  L  N  C  V  D  D  S  Q  D  Y  Y  V  G  K  K
241 CAGCAAAGGCTGCAGCTTGAACTGCGTGGATGACTCACAGGACTACTACGTGGGCAAGAA
 74  N  I  T  C  C  D  T  D  L  C  N  A  S  G  A  H  A  L  Q  P
301 GAACATCACGTGCTGTGACACCGACTTGTGCAACGCCAGCGGGGCCCATGCCCTGCAGCC
 94  A  A  A  I  L  A  L  L  P  A  L  G  L  L  L  W  G  P  G  Q
361 GGCTGCCGCCATCCTTGCGCTGCTCCCTGCACTCGGCCTGCTGCTCTGGGGACCCGGCCA
114  L  *
421 GCTATAGgctctggggggccccgctgcagcccacactgggtgtggtgccccaggcctctg
481 tgccactcctcacacacccggcccagtgggagcctgtcctggttcctgaggcacatccta
541 acgcaagtctgaccatgtatgtctgcgccctgtcccccaccctgaccctcccatggccc
601 tctccaggactccacccggcagatcggctctattgacacagatccgcctgcagatggcc
661 cctccaaccctctctgctgctgtttccatggcccagcattctccaccttaaccctgtgc
721 tcaggcacctcttcccccaggaagccttccctgcccaccccatctatgacttgagccagg
781 tctggtccgtggtgtccccgcacccagcaggggacaggcactcaggagggcccggtaaa
841 ggctgagatgaagtggactgagtagaactggaggacaggagtcgacgtgagttcctggga
901 gtctccagagatggggcctggaggcctggaggaagggccaggcctcacattcgtggggc
961 tccctgaatggcagcctcagcacagcgtaggcccttaataaacacctgttggataagcca
```

Figure 1G. SNP variants of PSCA v.2, PSCA v.7 through v.18.

| Variant | Nucleic acid position | Nucleic Acid Variation | Amino Acid Variation |
|---|---|---|---|
| PSCA v.7 | 367 | C/T | Silent Variant |
| PSCA v.8 | 424 | A/C | Silent Variant |
| PSCA v.9 | 495 | C/G | Silent Variant |
| PSCA v.10 | 499 | C/T | Silent Variant |
| PSCA v.11 | 563 | C/T | Silent Variant |
| PSCA v.12 | 567 | G/A | Silent Variant |
| PSCA v.13 | 627 | G/A | Silent Variant |
| PSCA v.14 | 634 | T/G | Silent Variant |
| PSCA v.15 | 835 | G/A | Silent Variant |
| PSCA v.16 | 847 | G/A | Silent Variant |
| PSCA v.17 | 878 | G/A | Silent Variant |
| PSCA v.18 | 978 | C/G | Silent Variant |

Figure 1H. SNP variants of PSCA v.4, PSCA v.19 through v.30.

| Variant | Nucleic acid position | Nucleic Acid Variation | Amino Acid Position | Amino Acid Variation |
|---|---|---|---|---|
| PSCA v.19 | 521 | C/T | 33 | P/L |
| PSCA v.20 | 578 | A/C | 52 | Y/S |
| PSCA v.21 | 649 | C/G | 76 | H/D |
| PSCA v.22 | 653 | C/T | 77 | P/L |
| PSCA v.23 | 717 | C/T | 98 | Silent variant |
| PSCA v.24 | 721 | G/A | 100 | A/T |
| PSCA v.25 | 781 | G/A | 120 | G/S |
| PSCA v.26 | 788 | T/G | 122 | I/S |
| PSCA v.27 | 989 | G/A | 189 | R/Q |
| PSCA v.28 | 1001 | G/A | | Silent Variant |
| PSCA v.29 | 1032 | G/A | | Silent Variant |
| PSCA v.30 | 1132 | C/G | | Silent Variant |

Expression of PSCA variants.

Expression of PSCA variants.

M = Marker
- Bladder
- Brain
- Heart
- Kidney
- Liver
- Lung
- Prostate
- Spleen
- Skeletal Muscle
- Testis
- Pancreas
- Colon
- Stomach

- Prostate cancer
- Bladder cancer
- Kidney cancer
- Colon cancer
- Lung cancer
- Ovary cancer
- Breast cancer
- Cancer metastasis
- Pancreas cancer Expression of PSCA v.4 and PSCA v.5

Expression of PSCA v.4 and PSCA v.5.

M = Marker
- Bladder
- Brain
- Heart
- Kidney
- Liver
- Lung
- Prostate
- Spleen
- Skeletal Muscle
- Testis
- Pancreas
- Colon
- Stomach

- Prostate cancer
- Bladder cancer
- Multi-xenograft pool

Figure 2:

Figure 2A. The amino acid sequence (SEQ ID NO: 13) of H1-1.10 VH.

```
  1 QLQESGPGLV KPSQTLSLTC TVSGGSISSG GYYWSWIRQH PGKGLEWIGY IYYSGSTYYN
 61 PSLKSRVTIS VDTSKNQFSL KLSSGTAADT AVYYCARDHI TMVRGVPKGM DVWGQGTTVT
121 VSSASTKGPS VFPLAPSSKS TSGGTAALG
```

Figure 2B. The amino acid sequence (SEQ ID NO: 14) of H1-1.10 VL.

```
  1 QLTQSPSSLS ASVGDRVTIT CRASQSISRH LNWYQQKPGK APKFLIYVAS SLQSGVPSRF
 61 SGSGSGTDFT LTISSLQPED FATYFCQQSY SIPRTFGQGT KVEIKRTVAA PSVFIFPPSD
121 EQLKSGTASV VCLLNNFYPR EAKVQWK
```

Figure 3:

Figure 3A. The cDNA (SEQ ID NO.: 15) and amino acid sequence (SEQ ID NO: 16) of H1-1.10 VH.

```
  1 Q   L   Q   E   S   G   P   G   L   V   K   P   S   Q   T   L   S   L   T   C
  1 cagctgcaggagtcgggcccaggactggtgaagccttcacagaccctgtccctcacctgc
 21 T   V   S   G   G   S   I   S   S   G   G   Y   Y   W   S   W   I   R   Q   H
 61 actgtctctggtggctccatcagcagtggtggttactactggagctggatccgccagcac
 41 P   G   K   G   L   E   W   I   G   Y   I   Y   Y   S   G   S   T   Y   Y   N
121 ccagggaagggcctggagtggattgggtacatctattacagtgggagcacctactacaac
 61 P   S   L   K   S   R   V   T   I   S   V   D   T   S   K   N   Q   F   S   L
181 ccgtccctcaagagtcgagttaccatatcagtagacacgtctaagaaccagttctccctg
 81 K   L   S   S   G   T   A   A   D   T   A   V   Y   Y   C   A   R   D   H   I
241 aagctgagctctgggactgccgcggacacggccgtgtattactgtgcgagagaccacatt
101 T   M   V   R   G   V   P   K   G   M   D   V   W   G   Q   G   T   T   V   T
301 actatggttcggggagtccccaagggcatggacgtctggggccaagggaccacggtcacc
121 V   S   S   A   S   T   K   G   P   S   V   F   P   L   A   P   S   S   K   S
361 gtctcctcagcctccaccaagggcccatcggtcttccccctggcaccctcctccaagagc
141 T   S   G   G   T   A   A   L   G
421 acctctggggggcacagcggccctgggc
```

Figure 3B. The cDNA (SEQ ID NO: 17) and amino acid sequence (SEQ ID NO: 18) of H1-1.10 VL.

```
  1 Q   L   T   Q   S   P   S   S   L   S   A   S   V   G   D   R   V   T   I   T
  1 cagctgactcagtctccatcctcCctgtctgcatctgtaggagacagagtcaccatcact
 21 C   R   A   S   Q   S   I   S   R   H   L   N   W   Y   Q   Q   K   P   G   K
 61 tgccgggcaagtcagagcattagcaggcatttaaattggtatcagcagaaaccagggaaa
 41 A   P   K   F   L   I   Y   V   A   S   S   L   Q   S   G   V   P   S   R   F
121 gcccctaagttcctgatctatgttgcatccagtttgcaaagtggggtcccatcaagattc
 61 S   G   S   G   S   G   T   D   F   T   L   T   I   S   S   L   Q   P   E   D
181 agtggcagtggatctgggacagatttcactctcaccatcagcagtctgcaacctgaagat
 81 F   A   T   Y   F   C   Q   Q   S   Y   S   I   P   R   T   F   G   Q   G   T
241 tttgcaacttacttctgtcaacagagttacagtatcccccggacgttcggccaagggacc
101 K   V   E   I   K   R   T   V   A   A   P   S   V   F   I   F   P   P   S   D
301 aaggtggaaatcaaacgaactgtggctgcaccatctgtcttcatcttcccgccatctgat
121 E   Q   L   K   S   G   T   A   S   V   V   C   L   L   N   N   F   Y   P   R
361 gagcagttgaaatctggaactgcctctgttgtgtgcctgctgaataacttctatcccaga
141 E   A   K   V   Q   W   K
421 gaggccaaagtacagtggaag
```

Figure 4

Figure 4A Alignment of H1-1.10 VH to human VH4-31

```
                 <-------FWR1--------->  <--CDR1-->  <-----FWR2----->  <-------CDR2-------->  <---
H1-1.10 VH    1  --QLQESGPGLVKPSQTLSLTCTVSGGSIS  SGGYYWS  WIRQHPGKGLEWI-G  YIY--YSG-S-T-Y--YNPSLKS  RVTI  69
(VH4-31/D3-10/JH6)
VH4-31        1  QV............................  .......  ...............  .......-.-.-.-..-.......  ....  71

--------FWR3-------->            <----CDR3---->             <constant region>
H1-1.10 VH   70  SVDTSKNQFSLKLSSGTAADTAVYYCAR     DHITMVRGVPKGMDV  WGQGTTVTVSS  ASTKGPSVKGPSVF
(VH4-31/D3-10/JH6)
VH4-31       72  ...........V................     ---------------  -----------  --------------
```

Figure 4B Alignment of H1-1.10 VL to human O2

```
                 <--------FWR1--------->   <---CDR1---->  <-----FWR2----->  <--CDR2-->        <-------FWR3------>
H1-1.10 VL    1  --QLTQSPSSLSASVGDRVTITC    RASQSISR-HLN   WYQQKPGKAPKFLIY   VASSLQS   GVPSRFSGSGSGTDFTLTISSLQ  77
(O2/JK1)
O2            1  DI.M..................    ........S-Y..  ...............L  A......   .......................  79

--------->   <--CDR3-->                       <constant region>
H1-1.10 VL   78  PEDFATYFC    QQ---SYSIP   RTFGQGTKVEIK       RTVAAPSVFIFPPSDEQ
(O2/JK1)
O2           80  .......Y.    ..---..T..   ------------       -----------------
```

Expression of PSCA in Recombinant Murine, Rat and Human Cell Lines

Purification of PSCA from *E. coli*

Purification of Recombinant Glycoslated PSCA
Expressed from 293T cells

Purification GST-PSCA from *E. coli*

FACS Analysis of PSCA Antibodies
(LAPC9AI)

FACS Analysis of PSCA Antibodies
(LAPC9AI)

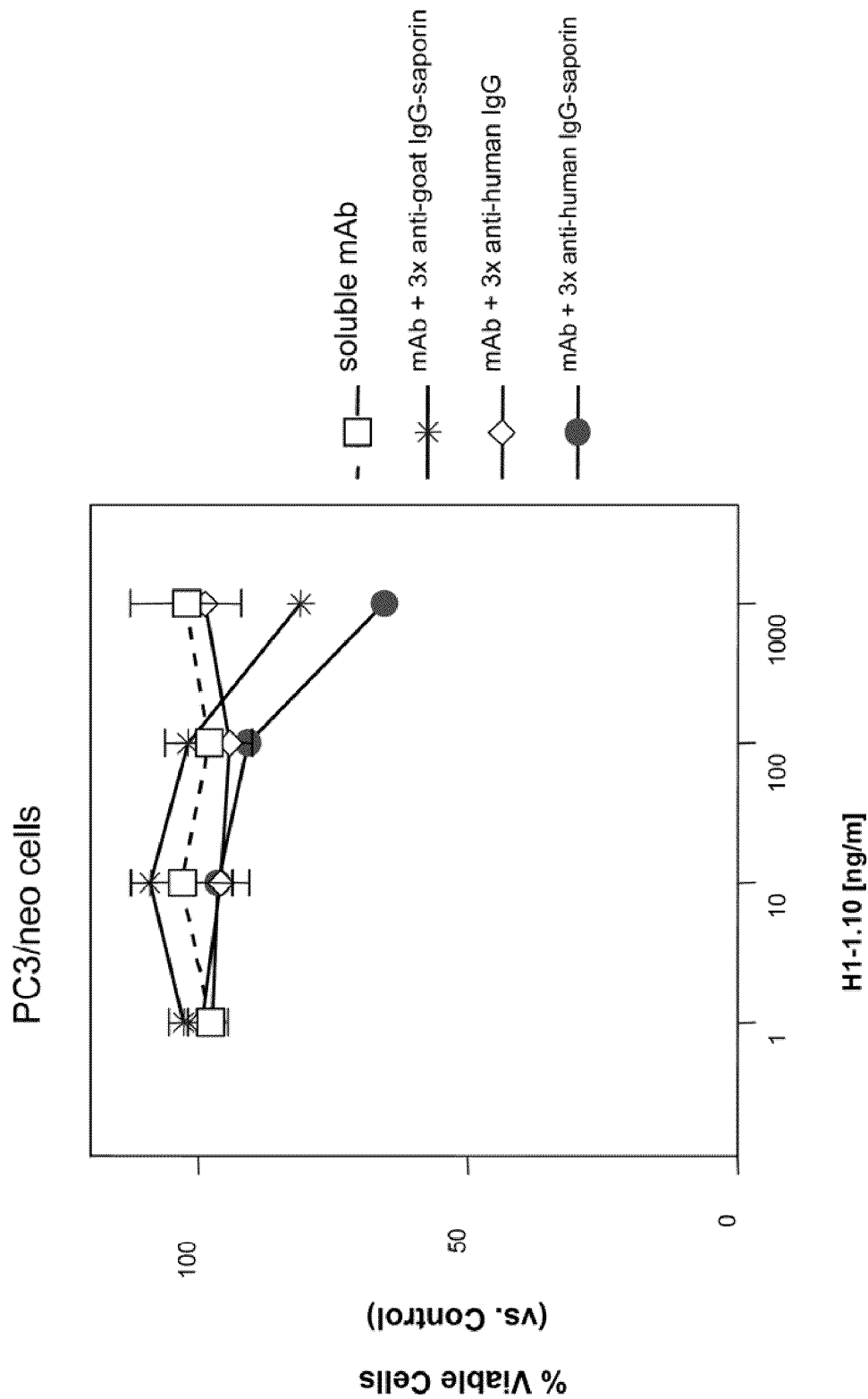

SEQUENCE LISTING

```
<160> NUMBER OF SEQ ID NOS: 161

<210> SEQ ID NO 1
<211> LENGTH: 990
<212> TYPE: DNA
<213> ORGANISM: Homo sapiens
<220> FEATURE:
<221> NAME/KEY: CDS
<222> LOCATION: (18)...(389)
<220> FEATURE:
<221> NAME/KEY: misc_feature
<222> LOCATION: 543
<223> OTHER INFORMATION: n = a, t, c, or g

<400> SEQUENCE: 1
agggagaggc agtgacc atg aag gct gtg ctg ctt gcc ctg ttg atg gca      50
                   Met Lys Ala Val Leu Leu Ala Leu Leu Met Ala
                    1               5                      10 ggc ttg gcc ctg cag cca ggc act gcc ctg ctg tgc tac tcc tgc aaa     98
Gly Leu Ala Leu Gln Pro Gly Thr Ala Leu Leu Cys Tyr Ser Cys Lys
             15                  20                  25 gcc cag gtg agc aac gag gac tgc ctg cag gtg gag aac tgc acc cag    146
Ala Gln Val Ser Asn Glu Asp Cys Leu Gln Val Glu Asn Cys Thr Gln
         30                  35                  40 ctg ggg gag cag tgc tgg acc gcg cgc atc cgc gca gtt ggc ctc ctg    194
```

```
acc gtc atc agc aaa ggc tgc agc ttg aac tgc gtg gat gac tca cag     242
Thr Val Ile Ser Lys Gly Cys Ser Leu Asn Cys Val Asp Asp Ser Gln
 60          65                  70                  75 gac tac tac gtg ggc aag aag aac atc acg tgc tgt gac acc gac ttg     290
Asp Tyr Tyr Val Gly Lys Lys Asn Ile Thr Cys Cys Asp Thr Asp Leu
                 80                  85                  90 tgc aac gcc agc ggg gcc cat gcc ctg cag ccg gct gcc gcc atc ctt     338
Cys Asn Ala Ser Gly Ala His Ala Leu Gln Pro Ala Ala Ala Ile Leu
                 95                 100                 105 gcg ctg ctc cct gca ctc ggc ctg ctc tgg gga ccc ggc cag cta         386
Ala Leu Leu Pro Ala Leu Gly Leu Leu Trp Gly Pro Gly Gln Leu
         110                 115                 120 tag gctctggggg gccccgctgc agcccacact gggtgtggtg ccccaggcct          439
ttgtgccact cctcacagaa cctggcccag tgggagcctg tcctggttcc tgaggcacat   499
cctaacgcaa gtttgaccat gtatgtttgc acccctttc cccnaaccct gaccttccca    559
tgggcctttt ccaggattcc cacccggcag atcagtttta gtgacacaga tccgcctgca   619 gatggccccct ccaaccctttt ctgttgctgt tccatggcc cagcattttc cacccttaac  679
cctgtgttca ggcacttctt cccccaggaa gccttccctg cccacccat ttatgaattg    739 agccaggttt ggtccgtggt gtccccgca cccagcaggg acaggcaat caggagggcc    799 cagtaaaggc tgagatgaag tggactgagt agaactggag acaagagtt gacgtgagtt    859 cctgggagtt tccagagatg gggcctggag gcctggagga aggggccagg cctcacattt   919
gtggggctcc cgaatggcag cctgagcaca gcgtaggccc ttaataaaca cctgttggat   979
aagccaaaaa a                                                         990

<210> SEQ ID NO 2
<211> LENGTH: 123
<212> TYPE: PRT
<213> ORGANISM: Homo sapiens

<400> SEQUENCE: 2

Met Lys Ala Val Leu Ala Leu Leu Met Ala Gly Leu Ala Leu Gln
 1               5                  10                  15

Pro Gly Thr Ala Leu Leu Cys Tyr Ser Cys Lys Ala Gln Val Ser Asn
             20                  25                  30

Glu Asp Cys Leu Gln Val Glu Asn Cys Thr Gln Leu Gly Glu Gln Cys
         35                  40                  45

Trp Thr Ala Arg Ile Arg Ala Val Gly Leu Leu Thr Val Ile Ser Lys
 50                  55                  60

Gly Cys Ser Leu Asn Cys Val Asp Asp Ser Gln Asp Tyr Tyr Val Gly
 65                  70                  75                  80

Lys Lys Asn Ile Thr Cys Cys Asp Thr Asp Leu Cys Asn Ala Ser Gly
                 85                  90                  95

Ala His Ala Leu Gln Pro Ala Ala Ala Ile Leu Ala Leu Leu Pro Ala
            100                 105                 110

Leu Gly Leu Leu Trp Gly Pro Gly Gln Leu
            115                 120

<210> SEQ ID NO 3
<211> LENGTH: 1020
<212> TYPE: DNA
<213> ORGANISM: Homo sapiens
<220> FEATURE:
<221> NAME/KEY: CDS
```

Leu Gly Glu Gln Cys Trp Thr Ala Arg Ile Arg Ala Val Gly Leu Leu
            45                  50                  55

<222> LOCATION: (56)...(427)

<400> SEQUENCE: 3

```
tttgaggcca tataaagtca cctgaggccc tctccaccac agcccaccag tgacc atg       58
                                                              Met
                                                              1 aag gct gtg ctg ctt gcc ctg ttg atg gca ggc ttg gcc ctg cag cca      106
Lys Ala Val Leu Leu Ala Leu Leu Met Ala Gly Leu Ala Leu Gln Pro
      5                  10                  15 ggc act gcc ctg ctg tgc tac tcc tgc aaa gcc cag gtg agc aac gag      154
Gly Thr Ala Leu Leu Cys Tyr Ser Cys Lys Ala Gln Val Ser Asn Glu
 20                  25                  30 gac tgc ctg cag gtg gag aac tgc acc cag ctg ggg gag cag tgc tgg      202
Asp Cys Leu Gln Val Glu Asn Cys Thr Gln Leu Gly Glu Gln Cys Trp
 35                  40                  45 acc gcg cgc atc cgc gca gtt ggc ctc ctg acc gtc atc agc aaa ggc      250
Thr Ala Arg Ile Arg Ala Val Gly Leu Leu Thr Val Ile Ser Lys Gly
 50                  55                  60                  65 tgc agc ttg aac tgc gtg gat gac tca cag gac tac tac gtg ggc aag      298
Cys Ser Leu Asn Cys Val Asp Asp Ser Gln Asp Tyr Tyr Val Gly Lys
                 70                  75                  80 aag aac atc acg tgc tgt gac acc gac ttg tgc aac gcc agc ggg gcc      346
Lys Asn Ile Thr Cys Cys Asp Thr Asp Leu Cys Asn Ala Ser Gly Ala
             85                  90                  95 cat gcc ctg cag ccg gct gcc gcc atc ctt gcg ctg ctc cct gca ctc      394
His Ala Leu Gln Pro Ala Ala Ala Ile Leu Ala Leu Leu Pro Ala Leu
        100                 105                 110 ggc ctg ctg ctc tgg gga ccc ggc cag cta tag gctctggggg gccccgctgc    447
Gly Leu Leu Leu Trp Gly Pro Gly Gln Leu *
    115                 120 agcccacact gggtgtggtg ccccaggcct ctgtgccact cctcacacac ccggcccagt    507
gggagcctgt cctggttcct gaggcacatc ctaacgcaag tctgaccatg tatgtctgcg    567
cccctgtccc ccaccctgac cctcccatgg ccctctccag gactcccacc cggcagatcg    627
gctctattga cacagatccg cctgcagatg gcccctccaa ccctctctgc tgctgtttcc    687
atggcccagc attctccacc cttaaccctg tgctcaggca cctcttcccc caggaagcct    747
tccctgccca ccccatctat gacttgagcc aggtctggtc cgtggtgtcc cccgcaccca    807
gcaggggaca ggcactcagg agggcccggt aaaggctgag atgaagtgga ctgagtagaa    867
ctggaggaca ggagtcgacg tgagttcctg ggagtctcca gagatggggc ctggaggcct    927
ggaggaaggg gccaggcctc acattcgtgg ggctccctga atggcagcct cagcacagcg    987
taggccctta ataaacacct gttggataag cca                                1020
```

<210> SEQ ID NO 4
<211> LENGTH: 123
<212> TYPE: PRT
<213> ORGANISM: Homo sapiens

<400> SEQUENCE: 4

```
Met Lys Ala Val Leu Leu Ala Leu Leu Met Ala Gly Leu Ala Leu Gln
  1               5                  10                  15

Pro Gly Thr Ala Leu Leu Cys Tyr Ser Cys Lys Ala Gln Val Ser Asn
             20                  25                  30

Glu Asp Cys Leu Gln Val Glu Asn Cys Thr Gln Leu Gly Glu Gln Cys
         35                  40                  45

Trp Thr Ala Arg Ile Arg Ala Val Gly Leu Leu Thr Val Ile Ser Lys
     50                  55                  60
```

```
Gly Cys Ser Leu Asn Cys Val Asp Asp Ser Gln Asp Tyr Tyr Val Gly
 65                  70                  75                  80

Lys Lys Asn Ile Thr Cys Cys Asp Thr Asp Leu Cys Asn Ala Ser Gly
                 85                  90                  95

Ala His Ala Leu Gln Pro Ala Ala Ile Leu Ala Leu Leu Pro Ala
            100                 105                 110

Leu Gly Leu Leu Leu Trp Gly Pro Gly Gln Leu
        115                 120
```

<210> SEQ ID NO 5
<211> LENGTH: 888
<212> TYPE: DNA
<213> ORGANISM: Homo sapiens
<220> FEATURE:
<221> NAME/KEY: CDS
<222> LOCATION: (423)...(707)

<400> SEQUENCE: 5

```
tttgaggcca tataaagtca cctgaggccc tctccaccac agcccaccag tgaccatgaa      60
ggctgtgctg cttgccctgt tgatggcagg cttggccctg cagccaggca ctgccctgct     120
gtgctactcc tgcaaagccc aggcgcagtt ggcctcctga ccgtcatcag caaaggctgc     180
agcttgaact gcgtggatga ctcacaggac tactacgtgg caagaagaa catcacgtgc      240 tgtgacaccg acttgtgcac tcggcctgct gctctgggga cccggccagc tataggctct     300
gggggggccc gctgcagccc acactgggtg tggtgcccca ggcctctgtg ccactcctca     360
cacacccggc ccagtgggag cctgtcctgg ttcctgaggc atcctaac gcaagtctga      420 cc atg tat gtc tgc gcc cct gtc ccc cac cct gac cct ccc atg gcc        467
   Met Tyr Val Cys Ala Pro Val Pro His Pro Asp Pro Pro Met Ala
     1               5                  10                  15 ctc tcc agg act ccc acc cgg cag atc ggc tct att gac aca gat ccg       515
Leu Ser Arg Thr Pro Thr Arg Gln Ile Gly Ser Ile Asp Thr Asp Pro
             20                  25                  30 cct gca gat ggc ccc tcc aac cct ctc tgc tgc tgt ttc cat ggc cca       563
Pro Ala Asp Gly Pro Ser Asn Pro Leu Cys Cys Cys Phe His Gly Pro
         35                  40                  45 gca ttc tcc acc ctt aac cct gtg ctc agg cac ctc ttc ccc cag gaa       611
Ala Phe Ser Thr Leu Asn Pro Val Leu Arg His Leu Phe Pro Gln Glu
     50                  55                  60 gcc ttc cct gcc cac ccc atc tat gac ttg agc cag gtc tgg tcc gtg       659
Ala Phe Pro Ala His Pro Ile Tyr Asp Leu Ser Gln Val Trp Ser Val
 65                  70                  75 gtg tcc ccc gca ccc agc agg gga cag gca ctc agg agg gcc cgg taa       707
Val Ser Pro Ala Pro Ser Arg Gly Gln Ala Leu Arg Arg Ala Arg  *
 80                  85                  90 aggctgagat gaagtggact gagtagaact ggaggacagg agtcgacgtg agttcctggg     767
agtctccaga gatggggcct ggaggcctgg aggaagggc caggcctcac attcgtgggg     827
ctccctgaat ggcagcctca gcacagcgta ggcccttaat aaacacctgt tggataagcc    887
a                                                                    888
```

<210> SEQ ID NO 6
<211> LENGTH: 94
<212> TYPE: PRT
<213> ORGANISM: Homo sapiens

<400> SEQUENCE: 6

```
Met Tyr Val Cys Ala Pro Val Pro His Pro Asp Pro Pro Met Ala Leu
  1               5                  10                  15
```

-continued

```
Ser Arg Thr Pro Thr Arg Gln Ile Gly Ser Ile Asp Thr Asp Pro Pro
         20                  25                  30

Ala Asp Gly Pro Ser Asn Pro Leu Cys Cys Cys Phe His Gly Pro Ala
     35                  40                  45

Phe Ser Thr Leu Asn Pro Val Leu Arg His Leu Phe Pro Gln Glu Ala
 50                  55                  60

Phe Pro Ala His Pro Ile Tyr Asp Leu Ser Gln Val Trp Ser Val Val
 65                  70                  75                  80

Ser Pro Ala Pro Ser Arg Gly Gln Ala Leu Arg Arg Ala Arg
                 85                  90
```

<210> SEQ ID NO 7
<211> LENGTH: 1174
<212> TYPE: DNA
<213> ORGANISM: Homo sapiens
<220> FEATURE:
<221> NAME/KEY: CDS
<222> LOCATION: (424)...(993)

<400> SEQUENCE: 7

```
gacagtgaac cctgcgctga aggcgttggg gctcctgcag ttctggggca gccacaggcg      60
cccagggttt cgtgccgatc agcccaggac ggtcttcccg gtgcagtttc tgatgcgggg     120
agggcagtgc tgccttccgg tcaccaggac cagtgctcag cccgcctgct tgaccccctt     180
acttagctgg ggtccaatcc atacccaatt tagatgattc agacgatggg atttgaaact     240
tttgaactgg gtgcgactta agcactgccc tgctgtgcta ctcctgcaaa gcccaggtga     300
gcaacgagga ctgcctgcag gtggagaact gcacccagct gggggagcag tgctggaccg     360
cgcgcatccg cgcagttggc ctcctgaccg tcatcagcaa aggctgcagc ttgaactgcg     420 tgg atg act cac agg act act acg tgg gca aga aga aca tca cgt gct      468
    Met Thr His Arg Thr Thr Thr Trp Ala Arg Arg Thr Ser Arg Ala
     1               5                  10                  15 gtg aca ccg act tgt gca acg cca gcg ggg ccc atg ccc tgc agc cgg      516
Val Thr Pro Thr Cys Ala Thr Pro Ala Gly Pro Met Pro Cys Ser Arg
             20                  25                  30 ctg ccg cca tcc ttg cgc tgc tcc ctg cac tcg gcc tgc tgc tct ggg      564
Leu Pro Pro Ser Leu Arg Cys Ser Leu His Ser Ala Cys Cys Ser Gly
         35                  40                  45 gac ccg gcc agc tat agg ctc tgg ggg gcc ccg ctg cag ccc aca ctg      612
Asp Pro Ala Ser Tyr Arg Leu Trp Gly Ala Pro Leu Gln Pro Thr Leu
     50                  55                  60 ggt gtg gtg ccc cag gcc tct gtg cca ctc ctc aca cac ccg gcc cag      660
Gly Val Val Pro Gln Ala Ser Val Pro Leu Leu Thr His Pro Ala Gln
 65                  70                  75 tgg gag cct gtc ctg gtt cct gag gca cat cct aac gca agt ctg acc      708
Trp Glu Pro Val Leu Val Pro Glu Ala His Pro Asn Ala Ser Leu Thr
 80                  85                  90                  95 atg tat gtc tgc gcc cct gtc ccc cac cct gac cct ccc atg gcc ctc      756
Met Tyr Val Cys Ala Pro Val Pro His Pro Asp Pro Pro Met Ala Leu
                 100                 105                 110 tcc agg act ccc acc cgg cag atc ggc tct att gac aca gat ccg cct      804
Ser Arg Thr Pro Thr Arg Gln Ile Gly Ser Ile Asp Thr Asp Pro Pro
             115                 120                 125 gca gat ggc ccc tcc aac cct ctc tgc tgc tgt ttc cat ggc cca gca      852
Ala Asp Gly Pro Ser Asn Pro Leu Cys Cys Cys Phe His Gly Pro Ala
         130                 135                 140 ttc tcc acc ctt aac cct gtg ctc agg cac ctc ttc ccc cag gaa gcc      900
Phe Ser Thr Leu Asn Pro Val Leu Arg His Leu Phe Pro Gln Glu Ala
145                 150                 155
```

```
ttc cct gcc cac ccc atc tat gac ttg agc cag gtc tgg tcc gtg gtg      948
Phe Pro Ala His Pro Ile Tyr Asp Leu Ser Gln Val Trp Ser Val Val
160                 165                 170                 175 tcc ccc gca ccc agc agg gga cag gca ctc agg agg gcc cgg taa          993
Ser Pro Ala Pro Ser Arg Gly Gln Ala Leu Arg Arg Ala Arg *
                180                 185 aggctgagat gaagtggact gagtagaact ggaggacagg agtcgacgtg agttcctggg   1053
agtctccaga gatggggcct ggaggcctgg aggaagggc caggcctcac attcgtgggg   1113
ctccctgaat ggcagcctca gcacagcgta ggcccttaat aaacacctgt tggataagcc   1173
a                                                                    1174

<210> SEQ ID NO 8
<211> LENGTH: 189
<212> TYPE: PRT
<213> ORGANISM: Homo sapiens

<400> SEQUENCE: 8

Met Thr His Arg Thr Thr Thr Trp Ala Arg Arg Thr Ser Arg Ala Val
1               5                   10                  15

Thr Pro Thr Cys Ala Thr Pro Ala Gly Pro Met Pro Cys Ser Arg Leu
            20                  25                  30

Pro Pro Ser Leu Arg Cys Ser Leu His Ser Ala Cys Cys Ser Gly Asp
        35                  40                  45

Pro Ala Ser Tyr Arg Leu Trp Gly Ala Pro Leu Gln Pro Thr Leu Gly
    50                  55                  60

Val Val Pro Gln Ala Ser Val Pro Leu Leu Thr His Pro Ala Gln Trp
65                  70                  75                  80

Glu Pro Val Leu Val Pro Glu Ala His Pro Asn Ala Ser Leu Thr Met
            85                  90                  95

Tyr Val Cys Ala Pro Val Pro His Pro Asp Pro Met Ala Leu Ser
            100                 105                 110

Arg Thr Pro Thr Arg Gln Ile Gly Ser Ile Asp Thr Asp Pro Pro Ala
        115                 120                 125

Asp Gly Pro Ser Asn Pro Leu Cys Cys Cys Phe His Gly Pro Ala Phe
    130                 135                 140

Ser Thr Leu Asn Pro Val Leu Arg His Leu Phe Pro Gln Glu Ala Phe
145                 150                 155                 160

Pro Ala His Pro Ile Tyr Asp Leu Ser Gln Val Trp Ser Val Val Ser
                165                 170                 175

Pro Ala Pro Ser Arg Gly Gln Ala Leu Arg Arg Ala Arg
            180                 185

<210> SEQ ID NO 9
<211> LENGTH: 1660
<212> TYPE: DNA
<213> ORGANISM: Homo sapiens
<220> FEATURE:
<221> NAME/KEY: CDS
<222> LOCATION: (910)...(1479)

<400> SEQUENCE: 9
gacagtgaac cctgcgctga aggcgttggg gctcctgcag ttctggggca gccacaggcg    60
cccagggttt cgtgccgatc agcccaggac ggtcttcccg gtgcagtttc tgatgcgggg   120
agggcagtgc tgccttccgg tcaccaggac cagtgctcag cccgcctgct tgaccccctt   180
acttagctgg ggtccaatcc atacccaatt tagatgattc agacgatggg atttgaaact   240
tttgaactgg gtgcgactta agcactgccc tgctgtgcta ctcctgcaaa gcccaggtga   300
```

```
gcaacgagga ctgcctgcag gtggagaact gcacccagct gggggagcag tgctggaccg    360
cgcgcatccg tgagtggggg gacgacagcc gccaggccta ggtctctgcc actgaactat    420
taatctttct ggccatctgt ccgcatctgt gtgctgtttt ccttccacct gtccccgacc    480
cgtcccgcac ctgcaccccc aacaatcacc cagcatctgt ccctccagcc atcctcctcc    540
atctgccact cctccactca tctgtccctc cccatcctcc atcttccact cctcccccca    600
tctgtccctc cccatccctg agctcactta ctcactcacc ccatttctga cgctcagcgg    660
gtggtccatc tgcctcggac atctggatag ggctgagacc agggccgaga ccaggccctc    720
gcactgcttg caatcctgag gccagcccag ggggactcta gagcattagg cagggtggga    780
caggaggagg cctggggcag gtcaggcagg tgagcacaca gggcagcccc atccccggat    840
cccgctgctc cccaggcgca gttggcctcc tgaccgtcat cagcaaaggc tgcagcttga    900 actgcgtgg atg act cac agg act act acg tgg gca aga aga aca tca cgt    951
          Met Thr His Arg Thr Thr Thr Trp Ala Arg Arg Thr Ser Arg
            1               5                  10 gct gtg aca ccg act tgt gca acg cca gcg ggg ccc atg ccc tgc agc     999
Ala Val Thr Pro Thr Cys Ala Thr Pro Ala Gly Pro Met Pro Cys Ser
 15                  20                  25                  30 cgg ctg ccg cca tcc ttg cgc tgc tcc ctg cac tcg gcc tgc tgc tct    1047
Arg Leu Pro Pro Ser Leu Arg Cys Ser Leu His Ser Ala Cys Cys Ser
                 35                  40                  45 ggg gac ccg gcc agc tat agg ctc tgg ggg gcc ccg ctg cag ccc aca    1095
Gly Asp Pro Ala Ser Tyr Arg Leu Trp Gly Ala Pro Leu Gln Pro Thr
         50                  55                  60 ctg ggt gtg gtg ccc cag gcc tct gtg cca ctc ctc aca cac ccg gcc    1143
Leu Gly Val Val Pro Gln Ala Ser Val Pro Leu Leu Thr His Pro Ala
 65                  70                  75 cag tgg gag cct gtc ctg gtt cct gag gca cat cct aac gca agt ctg    1191
Gln Trp Glu Pro Val Leu Val Pro Glu Ala His Pro Asn Ala Ser Leu
         80                  85                  90 acc atg tat gtc tgc gcc cct gtc ccc cac cct gac cct ccc atg gcc    1239
Thr Met Tyr Val Cys Ala Pro Val Pro His Pro Asp Pro Pro Met Ala
 95                 100                 105                 110 ctc tcc agg act ccc acc cgg cag atc ggc tct att gac aca gat ccg    1287
Leu Ser Arg Thr Pro Thr Arg Gln Ile Gly Ser Ile Asp Thr Asp Pro
                115                 120                 125 cct gca gat ggc ccc tcc aac cct ctc tgc tgc tgt ttc cat ggc cca    1335
Pro Ala Asp Gly Pro Ser Asn Pro Leu Cys Cys Cys Phe His Gly Pro
        130                 135                 140 gca ttc tcc acc ctt aac cct gtg ctc agg cac ctc ttc ccc cag gaa    1383
Ala Phe Ser Thr Leu Asn Pro Val Leu Arg His Leu Phe Pro Gln Glu
145                 150                 155 gcc ttc cct gcc cac ccc atc tat gac ttg agc cag gtc tgg tcc gtg    1431
Ala Phe Pro Ala His Pro Ile Tyr Asp Leu Ser Gln Val Trp Ser Val
        160                 165                 170 gtg tcc ccc gca ccc agc agg gga cag gca ctc agg agg gcc cgg taa    1479
Val Ser Pro Ala Pro Ser Arg Gly Gln Ala Leu Arg Arg Ala Arg *
175                 180                 185 aggctgagat gaagtggact gagtagaact ggaggacagg agtcgacgtg agttcctggg   1539
agtctccaga gatggggcct ggaggcctgg aggaaggggc caggcctcac attcgtgggg   1599
ctccctgaat ggcagcctca gcacagcgta ggcccttaat aaacacctgt tggataagcc   1659
a                                                                  1660

<210> SEQ ID NO 10
<211> LENGTH: 189
```

-continued

```
<212> TYPE: PRT
<213> ORGANISM: Homo sapiens

<400> SEQUENCE: 10

Met Thr His Arg Thr Thr Thr Trp Ala Arg Arg Thr Ser Arg Ala Val
  1               5                  10                  15

Thr Pro Thr Cys Ala Thr Pro Ala Gly Pro Met Pro Cys Ser Arg Leu
             20                  25                  30

Pro Pro Ser Leu Arg Cys Ser Leu His Ser Ala Cys Cys Ser Gly Asp
         35                  40                  45

Pro Ala Ser Tyr Arg Leu Trp Gly Ala Pro Leu Gln Pro Thr Leu Gly
     50                  55                  60

Val Val Pro Gln Ala Ser Val Pro Leu Leu Thr His Pro Ala Gln Trp
 65                  70                  75                  80

Glu Pro Val Leu Val Pro Glu Ala His Pro Asn Ala Ser Leu Thr Met
                 85                  90                  95

Tyr Val Cys Ala Pro Val Pro His Pro Asp Pro Pro Met Ala Leu Ser
            100                 105                 110

Arg Thr Pro Thr Arg Gln Ile Gly Ser Ile Asp Thr Asp Pro Pro Ala
        115                 120                 125

Asp Gly Pro Ser Asn Pro Leu Cys Cys Cys Phe His Gly Pro Ala Phe
    130                 135                 140

Ser Thr Leu Asn Pro Val Leu Arg His Leu Phe Pro Gln Glu Ala Phe
145                 150                 155                 160

Pro Ala His Pro Ile Tyr Asp Leu Ser Gln Val Trp Ser Val Val Ser
                165                 170                 175

Pro Ala Pro Ser Arg Gly Gln Ala Leu Arg Arg Ala Arg
            180                 185

<210> SEQ ID NO 11
<211> LENGTH: 1020
<212> TYPE: DNA
<213> ORGANISM: Homo sapiens
<220> FEATURE:
<221> NAME/KEY: CDS
<222> LOCATION: (83)...(427)

<400> SEQUENCE: 11
tttgaggcca tataaagtca cctgaggccc tctccaccac agcccaccag tgaccatgaa      60
ggctgtgctg cttgccctgt tg atg gca ggc ttg gcc ctg cag cca ggc act     112
                         Met Ala Gly Leu Ala Leu Gln Pro Gly Thr
                           1               5                  10 gcc ctg ctg tgc tac tcc tgc aaa gcc cag gtg agc aac gag gac tgc       160
Ala Leu Leu Cys Tyr Ser Cys Lys Ala Gln Val Ser Asn Glu Asp Cys
             15                  20                  25 ctg cag gtg gag aac tgc acc cag ctg ggg gag cag tgc tgg acc gcg       208
Leu Gln Val Glu Asn Cys Thr Gln Leu Gly Glu Gln Cys Trp Thr Ala
         30                  35                  40 cgc atc cgc gca gtt ggc ctc ctg acc gtc atc agc aaa ggc tgc agc       256
Arg Ile Arg Ala Val Gly Leu Leu Thr Val Ile Ser Lys Gly Cys Ser
     45                  50                  55 ttg aac tgc gtg gat gac tca cag gac tac tac gtg ggc aag aag aac       304
Leu Asn Cys Val Asp Asp Ser Gln Asp Tyr Tyr Val Gly Lys Lys Asn
 60                  65                  70 atc acg tgc tgt gac acc gac ttg tgc aac gcc agc ggg gcc cat gcc       352
Ile Thr Cys Cys Asp Thr Asp Leu Cys Asn Ala Ser Gly Ala His Ala
 75                  80                  85                  90 ctg cag ccg gct gcc gcc atc ctt gcg ctg ctc cct gca ctc ggc ctg       400
Leu Gln Pro Ala Ala Ala Ile Leu Ala Leu Leu Pro Ala Leu Gly Leu
```

-continued

```
                  95                  100                 105
ctg ctc tgg gga ccc ggc cag cta tag gctctggggg gccccgctgc         447
Leu Leu Trp Gly Pro Gly Gln Leu  *
            110 agcccacact gggtgtggtg ccccaggcct ctgtgccact cctcacacac ccggcccagt  507 gggagcctgt cctggttcct gaggcacatc ctaacgcaag tctgaccatg tatgtctgcg  567 cccctgtccc ccaccctgac cctcccatgg ccctctccag gactcccacc cggcagatcg  627 gctctattga cacagatccg cctgcagatg gcccctccaa ccctctctgc tgctgtttcc  687 atggcccagc attctccacc cttaaccctg tgctcaggca cctcttcccc caggaagcct  747 tccctgccca ccccatctat gacttgagcc aggtctggtc cgtggtgtcc cccgcaccca  807 gcagggaca ggcactcagg agggcccggt aaaggctgag atgaagtgga ctgagtagaa   867 ctggaggaca ggagtcgacg tgagttcctg ggagtctcca gagatggggc ctggaggcct  927 ggaggaaggg gccaggcctc acattcgtgg ggctccctga atggcagcct cagcacagcg  987 taggcccttc ataaacacct gttggataag cca                              1020
```

<210> SEQ ID NO 12
<211> LENGTH: 114
<212> TYPE: PRT
<213> ORGANISM: Homo sapiens

<400> SEQUENCE: 12

```
Met Ala Gly Leu Ala Leu Gln Pro Gly Thr Ala Leu Leu Cys Tyr Ser
 1               5                  10                  15

Cys Lys Ala Gln Val Ser Asn Glu Asp Cys Leu Gln Val Glu Asn Cys
            20                  25                  30

Thr Gln Leu Gly Glu Gln Cys Trp Thr Ala Arg Ile Arg Ala Val Gly
        35                  40                  45

Leu Leu Thr Val Ile Ser Lys Gly Cys Ser Leu Asn Cys Val Asp Asp
    50                  55                  60

Ser Gln Asp Tyr Tyr Val Gly Lys Lys Asn Ile Thr Cys Cys Asp Thr
65                  70                  75                  80

Asp Leu Cys Asn Ala Ser Gly Ala His Ala Leu Gln Pro Ala Ala Ala
                85                  90                  95

Ile Leu Ala Leu Leu Pro Ala Leu Gly Leu Leu Leu Trp Gly Pro Gly
            100                 105                 110

Gln Leu
```

<210> SEQ ID NO 13
<211> LENGTH: 149
<212> TYPE: PRT
<213> ORGANISM: Homo sapiens

<400> SEQUENCE: 13

```
Gln Leu Gln Glu Ser Gly Pro Gly Leu Val Lys Pro Ser Gln Thr Leu
 1               5                  10                  15

Ser Leu Thr Cys Thr Val Ser Gly Gly Ser Ile Ser Ser Gly Gly Tyr
            20                  25                  30

Tyr Trp Ser Trp Ile Arg Gln His Pro Gly Lys Gly Leu Glu Trp Ile
        35                  40                  45

Gly Tyr Ile Tyr Tyr Ser Gly Ser Thr Tyr Tyr Asn Pro Ser Leu Lys
    50                  55                  60

Ser Arg Val Thr Ile Ser Val Asp Thr Ser Lys Asn Gln Phe Ser Leu
65                  70                  75                  80
```

```
Lys Leu Ser Ser Gly Thr Ala Ala Asp Thr Ala Val Tyr Tyr Cys Ala
                85                  90                  95

Arg Asp His Ile Thr Met Val Arg Gly Val Pro Lys Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly
145

<210> SEQ ID NO 14
<211> LENGTH: 147
<212> TYPE: PRT
<213> ORGANISM: Homo sapiens

<400> SEQUENCE: 14

Gln Leu Thr Gln Ser Pro Ser Ser Leu Ser Ala Ser Val Gly Asp Arg
1               5                   10                  15

Val Thr Ile Thr Cys Arg Ala Ser Gln Ser Ile Ser Arg His Leu Asn
            20                  25                  30

Trp Tyr Gln Gln Lys Pro Gly Lys Ala Pro Lys Phe Leu Ile Tyr Val
        35                  40                  45

Ala Ser Ser Leu Gln Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Phe Cys Gln Gln Ser Tyr Ser Ile Pro Arg Thr Phe
                85                  90                  95

Gly Gln Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys
145

<210> SEQ ID NO 15
<211> LENGTH: 447
<212> TYPE: DNA
<213> ORGANISM: Homo sapiens

<400> SEQUENCE: 15
cagctgcagg agtcgggccc aggactggtg aagccttcac agaccctgtc cctcacctgc     60
actgtctctg gtggctccat cagcagtggt ggttactact ggagctggat ccgccagcac    120
ccagggaagg gcctggagtg gattgggtac atctattaca gtgggagcac ctactacaac    180
ccgtccctca agagtcgagt taccatatca gtagacacgt ctaagaacca gttctccctg    240
aagctgagct ctgggactgc cgcggacacg gccgtgtatt actgtgcgag agaccacatt    300
actatggttc ggggagtccc caagggcatg gacgtctggg gccaagggac cacggtcacc    360
gtctcctcag cctccaccaa gggcccatcg gtcttccccc tggcaccctc ctccaagagc    420
acctctgggg gcacagcggc cctgggc                                        447

<210> SEQ ID NO 16
<211> LENGTH: 149
```

```
<212> TYPE: PRT
<213> ORGANISM: Homo sapiens

<400> SEQUENCE: 16

Gln Leu Gln Glu Ser Gly Pro Gly Leu Val Lys Pro Ser Gln Thr Leu
1               5                   10                  15

Ser Leu Thr Cys Thr Val Ser Gly Gly Ser Ile Ser Ser Gly Gly Tyr
            20                  25                  30

Tyr Trp Ser Trp Ile Arg Gln His Pro Gly Lys Gly Leu Glu Trp Ile
        35                  40                  45

Gly Tyr Ile Tyr Tyr Ser Gly Ser Thr Tyr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Gly Thr Ala Ala Asp Thr Ala Val Tyr Tyr Cys Ala
                85                  90                  95

Arg Asp His Ile Thr Met Val Arg Gly Val Pro Lys Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly
145

<210> SEQ ID NO 17
<211> LENGTH: 441
<212> TYPE: DNA
<213> ORGANISM: Homo sapiens

<400> SEQUENCE: 17
cagctgactc agtctccatc ctccctgtct gcatctgtag gagacagagt caccatcact      60
tgccgggcaa gtcagagcat tagcaggcat ttaaattggt atcagcagaa accagggaaa     120
gcccctaagt tcctgatcta tgttgcatcc agtttgcaaa gtggggtccc atcaagattc     180
agtggcagtg gatctgggac agatttcact ctcaccatca gcagtctgca acctgaagat     240
tttgcaactt acttctgtca acagagttac agtatccccc ggacgttcgg ccaagggacc     300
aaggtggaaa tcaaacgaac tgtggctgca ccatctgtct tcatcttccc gccatctgat     360
gagcagttga aatctggaac tgcctctgtt gtgtgcctgc tgaataactt ctatcccaga     420
gaggccaaag tacagtggaa g                                               441

<210> SEQ ID NO 18
<211> LENGTH: 147
<212> TYPE: PRT
<213> ORGANISM: Homo sapiens

<400> SEQUENCE: 18

Gln Leu Thr Gln Ser Pro Ser Ser Leu Ser Ala Ser Val Gly Asp Arg
1               5                   10                  15

Val Thr Ile Thr Cys Arg Ala Ser Gln Ser Ile Ser Arg His Leu Asn
            20                  25                  30

Trp Tyr Gln Gln Lys Pro Gly Lys Ala Pro Lys Phe Leu Ile Tyr Val
        35                  40                  45

Ala Ser Ser Leu Gln Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
```

```
                65                  70                  75                  80
Phe Ala Thr Tyr Phe Cys Gln Gln Ser Tyr Ser Ile Pro Arg Thr Phe
                    85                  90                  95
Gly Gln Gly Thr Lys Val Glu Ile Lys Arg Thr Val Ala Ala Pro Ser
            100                 105                 110
Val Phe Ile Phe Pro Pro Ser Asp Glu Gln Leu Lys Ser Gly Thr Ala
        115                 120                 125
Ser Val Val Cys Leu Leu Asn Asn Phe Tyr Pro Arg Glu Ala Lys Val
    130                 135                 140
Gln Trp Lys
145

<210> SEQ ID NO 19
<211> LENGTH: 24
<212> TYPE: DNA
<213> ORGANISM: Homo sapiens

<400> SEQUENCE: 19
gattacaagg atgacgacga taag                                              24

<210> SEQ ID NO 20
<211> LENGTH: 24
<212> TYPE: DNA
<213> ORGANISM: Homo sapiens

<400> SEQUENCE: 20
aagggacgaa gacgaacacu uctt                                              24

<210> SEQ ID NO 21
<211> LENGTH: 23
<212> TYPE: DNA
<213> ORGANISM: Homo sapiens

<400> SEQUENCE: 21
aactgaagac ctgaagacaa taa                                               23

<210> SEQ ID NO 22
<211> LENGTH: 6
<212> TYPE: PRT
<213> ORGANISM: Homo sapiens

<400> SEQUENCE: 22

Thr Ile Leu Val Met Ser
1               5

<210> SEQ ID NO 23
<211> LENGTH: 7
<212> TYPE: PRT
<213> ORGANISM: Homo sapiens

<400> SEQUENCE: 23

Leu Ile Val Met Ala Thr Gln
1               5

<210> SEQ ID NO 24
<211> LENGTH: 7
<212> TYPE: PRT
<213> ORGANISM: Homo sapiens

<400> SEQUENCE: 24

Val Ser Met Ala Thr Leu Ile
1               5
```

```
<210> SEQ ID NO 25
<211> LENGTH: 8
<212> TYPE: PRT
<213> ORGANISM: Homo sapiens

<400> SEQUENCE: 25

Tyr Phe Trp Ile Val Leu Met Thr
1               5

<210> SEQ ID NO 26
<211> LENGTH: 6
<212> TYPE: PRT
<213> ORGANISM: Homo sapiens

<400> SEQUENCE: 26

Gln Leu Ile Val Met Pro
1               5

<210> SEQ ID NO 27
<211> LENGTH: 7
<212> TYPE: PRT
<213> ORGANISM: Homo sapiens

<400> SEQUENCE: 27

Leu Met Val Gln Ile Ala Thr
1               5

<210> SEQ ID NO 28
<211> LENGTH: 11
<212> TYPE: PRT
<213> ORGANISM: Homo sapiens

<400> SEQUENCE: 28

Leu Met Val Ile Ser Ala Thr Phe Cys Gly Asp
1               5                   10

<210> SEQ ID NO 29
<211> LENGTH: 12
<212> TYPE: PRT
<213> ORGANISM: Homo sapiens

<400> SEQUENCE: 29

Val Thr Met Leu Ile Ser Ala Gly Asn Cys Asp Phe
1               5                   10

<210> SEQ ID NO 30
<211> LENGTH: 4
<212> TYPE: PRT
<213> ORGANISM: Homo sapiens

<400> SEQUENCE: 30

Tyr Phe Trp Met
1

<210> SEQ ID NO 31
<211> LENGTH: 7
<212> TYPE: PRT
<213> ORGANISM: Homo sapiens

<400> SEQUENCE: 31

Met Val Thr Ala Leu Ile Ser
1               5

<210> SEQ ID NO 32
<211> LENGTH: 8
```

```
<212> TYPE: PRT
<213> ORGANISM: Homo sapiens

<400> SEQUENCE: 32

Met Val Ala Leu Phe Ile Ser Thr
1               5

<210> SEQ ID NO 33
<211> LENGTH: 7
<212> TYPE: PRT
<213> ORGANISM: Homo sapiens

<400> SEQUENCE: 33

Ala Val Thr Met Ser Leu Ile
1               5

<210> SEQ ID NO 34
<211> LENGTH: 4
<212> TYPE: PRT
<213> ORGANISM: Homo sapiens

<400> SEQUENCE: 34

Asp Glu Ala Ser
1

<210> SEQ ID NO 35
<211> LENGTH: 6
<212> TYPE: PRT
<213> ORGANISM: Homo sapiens

<400> SEQUENCE: 35

Ile Val Met Ala Thr Leu
1               5

<210> SEQ ID NO 36
<211> LENGTH: 6
<212> TYPE: PRT
<213> ORGANISM: Homo sapiens

<400> SEQUENCE: 36

Phe Ile Tyr Trp Leu Met
1               5

<210> SEQ ID NO 37
<211> LENGTH: 8
<212> TYPE: PRT
<213> ORGANISM: Homo sapiens

<400> SEQUENCE: 37

Val Ile Leu Phe Met Trp Tyr Ala
1               5

<210> SEQ ID NO 38
<211> LENGTH: 8
<212> TYPE: PRT
<213> ORGANISM: Homo sapiens

<400> SEQUENCE: 38

Phe Tyr Leu Trp Met Ile Val Ala
1               5

<210> SEQ ID NO 39
<211> LENGTH: 8
<212> TYPE: PRT
<213> ORGANISM: Homo sapiens
```

```
<400> SEQUENCE: 39

Phe Trp Tyr Leu Ile Met Val Ala
 1               5

<210> SEQ ID NO 40
<211> LENGTH: 8
<212> TYPE: PRT
<213> ORGANISM: Homo sapiens

<400> SEQUENCE: 40

Phe Trp Tyr Leu Ile Val Met Ala
 1               5

<210> SEQ ID NO 41
<211> LENGTH: 8
<212> TYPE: PRT
<213> ORGANISM: Homo sapiens

<400> SEQUENCE: 41

Phe Trp Tyr Met Ile Val Leu Ala
 1               5

<210> SEQ ID NO 42
<211> LENGTH: 6
<212> TYPE: PRT
<213> ORGANISM: Homo sapiens

<400> SEQUENCE: 42

Val Leu Ile Met Ala Thr
 1               5

<210> SEQ ID NO 43
<211> LENGTH: 6
<212> TYPE: PRT
<213> ORGANISM: Homo sapiens

<400> SEQUENCE: 43

Lys Tyr Arg His Phe Ala
 1               5

<210> SEQ ID NO 44
<211> LENGTH: 4
<212> TYPE: PRT
<213> ORGANISM: Homo sapiens

<400> SEQUENCE: 44

Lys Arg Tyr His
 1

<210> SEQ ID NO 45
<211> LENGTH: 4
<212> TYPE: PRT
<213> ORGANISM: Homo sapiens

<400> SEQUENCE: 45

Phe Leu Ile Trp
 1

<210> SEQ ID NO 46
<211> LENGTH: 8
<212> TYPE: PRT
<213> ORGANISM: Homo sapiens

<400> SEQUENCE: 46

Leu Met Phe Trp Tyr Ala Ile Val
```

```
<210> SEQ ID NO 47
<211> LENGTH: 8
<212> TYPE: PRT
<213> ORGANISM: Homo sapiens

<400> SEQUENCE: 47

Leu Met Phe Trp Tyr Ile Val Ala
 1               5

<210> SEQ ID NO 48
<211> LENGTH: 8
<212> TYPE: PRT
<213> ORGANISM: Homo sapiens

<400> SEQUENCE: 48

Leu Ile Val Phe Trp Tyr Ala Met
 1               5

<210> SEQ ID NO 49
<211> LENGTH: 8
<212> TYPE: PRT
<213> ORGANISM: Homo sapiens

<400> SEQUENCE: 49

Ile Met Phe Trp Tyr Ala Leu Val
 1               5

<210> SEQ ID NO 50
<211> LENGTH: 9
<212> TYPE: PRT
<213> ORGANISM: Homo sapiens

<400> SEQUENCE: 50

Ala Thr Ile Val Leu Met Phe Trp Tyr
 1               5

<210> SEQ ID NO 51
<211> LENGTH: 7
<212> TYPE: PRT
<213> ORGANISM: Homo sapiens

<400> SEQUENCE: 51

Phe Met Tyr Leu Ile Val Trp
 1               5

<210> SEQ ID NO 52
<211> LENGTH: 9
<212> TYPE: PRT
<213> ORGANISM: Homo sapiens

<400> SEQUENCE: 52

Val Ser Thr Cys Pro Ala Leu Ile Met
 1               5

<210> SEQ ID NO 53
<211> LENGTH: 7
<212> TYPE: PRT
<213> ORGANISM: Homo sapiens

<400> SEQUENCE: 53

Met Phe Leu Ile Val Trp Tyr
 1               5
```

```
<210> SEQ ID NO 54
<211> LENGTH: 4
<212> TYPE: PRT
<213> ORGANISM: Homo sapiens

<400> SEQUENCE: 54

Pro Ala Met Gln
 1

<210> SEQ ID NO 55
<211> LENGTH: 9
<212> TYPE: PRT
<213> ORGANISM: Homo sapiens

<400> SEQUENCE: 55

Val Met Ala Thr Ser Pro Leu Ile Cys
 1               5

<210> SEQ ID NO 56
<211> LENGTH: 7
<212> TYPE: PRT
<213> ORGANISM: Homo sapiens

<400> SEQUENCE: 56

Met Phe Leu Ile Val Trp Tyr
 1               5

<210> SEQ ID NO 57
<211> LENGTH: 9
<212> TYPE: PRT
<213> ORGANISM: Homo sapiens

<400> SEQUENCE: 57

Ile Val Met Ser Ala Cys Thr Pro Leu
 1               5

<210> SEQ ID NO 58
<211> LENGTH: 6
<212> TYPE: PRT
<213> ORGANISM: Homo sapiens

<400> SEQUENCE: 58

Leu Ile Val Met Phe Tyr
 1               5

<210> SEQ ID NO 59
<211> LENGTH: 7
<212> TYPE: PRT
<213> ORGANISM: Homo sapiens

<400> SEQUENCE: 59

Leu Ile Val Met Phe Ala Tyr
 1               5

<210> SEQ ID NO 60
<211> LENGTH: 6
<212> TYPE: PRT
<213> ORGANISM: Homo sapiens

<400> SEQUENCE: 60

Asp Asn Gln Glu Ser Thr
 1               5

<210> SEQ ID NO 61
<211> LENGTH: 7
<212> TYPE: PRT
```

<213> ORGANISM: Homo sapiens

<400> SEQUENCE: 61

Met Phe Leu Ile Val Trp Tyr
1               5

<210> SEQ ID NO 62
<211> LENGTH: 9
<212> TYPE: PRT
<213> ORGANISM: Homo sapiens

<400> SEQUENCE: 62

Val Met Ser Thr Ala Cys Pro Leu Ile
1               5

<210> SEQ ID NO 63
<211> LENGTH: 6
<212> TYPE: PRT
<213> ORGANISM: Homo sapiens

<400> SEQUENCE: 63

Thr Ile Leu Val Met Ser
1               5

<210> SEQ ID NO 64
<211> LENGTH: 7
<212> TYPE: PRT
<213> ORGANISM: Homo sapiens

<400> SEQUENCE: 64

Leu Ile Val Met Ala Thr Gln
1               5

<210> SEQ ID NO 65
<211> LENGTH: 6
<212> TYPE: PRT
<213> ORGANISM: Homo sapiens

<400> SEQUENCE: 65

Leu Ile Val Met Ala Thr
1               5

<210> SEQ ID NO 66
<211> LENGTH: 7
<212> TYPE: PRT
<213> ORGANISM: Homo sapiens

<400> SEQUENCE: 66

Val Ser Met Ala Thr Leu Ile
1               5

<210> SEQ ID NO 67
<211> LENGTH: 8
<212> TYPE: PRT
<213> ORGANISM: Homo sapiens

<400> SEQUENCE: 67

Tyr Phe Trp Ile Val Leu Met Thr
1               5

<210> SEQ ID NO 68
<211> LENGTH: 6
<212> TYPE: PRT
<213> ORGANISM: Homo sapiens

<400> SEQUENCE: 68

Phe Ile Tyr Trp Leu Met
1               5

<210> SEQ ID NO 69
<211> LENGTH: 8
<212> TYPE: PRT
<213> ORGANISM: Homo sapiens

<400> SEQUENCE: 69

Val Ile Leu Phe Met Trp Tyr Ala
1               5

<210> SEQ ID NO 70
<211> LENGTH: 8
<212> TYPE: PRT
<213> ORGANISM: Homo sapiens

<400> SEQUENCE: 70

Phe Tyr Leu Trp Met Ile Val Ala
1               5

<210> SEQ ID NO 71
<211> LENGTH: 8
<212> TYPE: PRT
<213> ORGANISM: Homo sapiens

<400> SEQUENCE: 71

Phe Trp Tyr Leu Ile Met Val Ala
1               5

<210> SEQ ID NO 72
<211> LENGTH: 8
<212> TYPE: PRT
<213> ORGANISM: Homo sapiens

<400> SEQUENCE: 72

Phe Trp Tyr Leu Ile Val Met Ala
1               5

<210> SEQ ID NO 73
<211> LENGTH: 6
<212> TYPE: PRT
<213> ORGANISM: Homo sapiens

<400> SEQUENCE: 73

Gln Leu Ile Val Met Pro
1               5

<210> SEQ ID NO 74
<211> LENGTH: 8
<212> TYPE: PRT
<213> ORGANISM: Homo sapiens

<400> SEQUENCE: 74

Phe Trp Tyr Met Ile Val Leu Ala
1               5

<210> SEQ ID NO 75
<211> LENGTH: 4
<212> TYPE: PRT
<213> ORGANISM: Homo sapiens

<400> SEQUENCE: 75

Gly Phe Tyr Trp
1

```
<210> SEQ ID NO 76
<211> LENGTH: 8
<212> TYPE: PRT
<213> ORGANISM: Homo sapiens

<400> SEQUENCE: 76

Arg His Lys Leu Ile Val Met Pro
 1               5

<210> SEQ ID NO 77
<211> LENGTH: 4
<212> TYPE: PRT
<213> ORGANISM: Homo sapiens

<400> SEQUENCE: 77

Gly Arg His Lys
 1

<210> SEQ ID NO 78
<211> LENGTH: 8
<212> TYPE: PRT
<213> ORGANISM: Homo sapiens

<400> SEQUENCE: 78

Ala Ser Thr Cys Leu Ile Val Met
 1               5

<210> SEQ ID NO 79
<211> LENGTH: 4
<212> TYPE: PRT
<213> ORGANISM: Homo sapiens

<400> SEQUENCE: 79

Gly Ser Thr Cys
 1

<210> SEQ ID NO 80
<211> LENGTH: 4
<212> TYPE: PRT
<213> ORGANISM: Homo sapiens

<400> SEQUENCE: 80

Ala Ser Thr Cys
 1

<210> SEQ ID NO 81
<211> LENGTH: 4
<212> TYPE: PRT
<213> ORGANISM: Homo sapiens

<400> SEQUENCE: 81

Leu Ile Val Met
 1

<210> SEQ ID NO 82
<211> LENGTH: 9
<212> TYPE: PRT
<213> ORGANISM: Homo sapiens

<400> SEQUENCE: 82

Arg His Lys Asp Glu Pro Tyr Phe Trp
 1               5

<210> SEQ ID NO 83
```

```
<211> LENGTH: 5
<212> TYPE: PRT
<213> ORGANISM: Homo sapiens

<400> SEQUENCE: 83

Asp Glu Ala Gln Asn
1               5

<210> SEQ ID NO 84
<211> LENGTH: 5
<212> TYPE: PRT
<213> ORGANISM: Homo sapiens

<400> SEQUENCE: 84

Tyr Phe Trp Gln Asn
1               5

<210> SEQ ID NO 85
<211> LENGTH: 5
<212> TYPE: PRT
<213> ORGANISM: Homo sapiens

<400> SEQUENCE: 85

Pro Ala Ser Thr Cys
1               5

<210> SEQ ID NO 86
<211> LENGTH: 8
<212> TYPE: PRT
<213> ORGANISM: Homo sapiens

<400> SEQUENCE: 86

Arg His Lys Gly Leu Ile Val Met
1               5

<210> SEQ ID NO 87
<211> LENGTH: 6
<212> TYPE: PRT
<213> ORGANISM: Homo sapiens

<400> SEQUENCE: 87

Arg His Lys Tyr Phe Trp
1               5

<210> SEQ ID NO 88
<211> LENGTH: 7
<212> TYPE: PRT
<213> ORGANISM: Homo sapiens

<400> SEQUENCE: 88

Ser Thr Cys Leu Ile Val Met
1               5

<210> SEQ ID NO 89
<211> LENGTH: 4
<212> TYPE: PRT
<213> ORGANISM: Homo sapiens

<400> SEQUENCE: 89

Asp Glu Ala Ser
1

<210> SEQ ID NO 90
<211> LENGTH: 9
<212> TYPE: PRT
<213> ORGANISM: Homo sapiens
```

```
<400> SEQUENCE: 90

Arg His Lys Asp Glu Pro Tyr Phe Trp
 1               5

<210> SEQ ID NO 91
<211> LENGTH: 4
<212> TYPE: PRT
<213> ORGANISM: Homo sapiens

<400> SEQUENCE: 91

Pro Arg His Lys
 1

<210> SEQ ID NO 92
<211> LENGTH: 7
<212> TYPE: PRT
<213> ORGANISM: Homo sapiens

<400> SEQUENCE: 92

Leu Met Ile Val Gln Ala Thr
 1               5

<210> SEQ ID NO 93
<211> LENGTH: 6
<212> TYPE: PRT
<213> ORGANISM: Homo sapiens

<400> SEQUENCE: 93

Val Leu Ile Met Ala Thr
 1               5

<210> SEQ ID NO 94
<211> LENGTH: 5
<212> TYPE: PRT
<213> ORGANISM: Homo sapiens

<400> SEQUENCE: 94

Asp Glu Arg Lys His
 1               5

<210> SEQ ID NO 95
<211> LENGTH: 4
<212> TYPE: PRT
<213> ORGANISM: Homo sapiens

<400> SEQUENCE: 95

Ala Tyr Phe Trp
 1

<210> SEQ ID NO 96
<211> LENGTH: 7
<212> TYPE: PRT
<213> ORGANISM: Homo sapiens

<400> SEQUENCE: 96

Leu Met Ile Val Gln Ala Thr
 1               5

<210> SEQ ID NO 97
<211> LENGTH: 4
<212> TYPE: PRT
<213> ORGANISM: Homo sapiens

<400> SEQUENCE: 97
```

Leu Val Ile Met
1

<210> SEQ ID NO 98
<211> LENGTH: 7
<212> TYPE: PRT
<213> ORGANISM: Homo sapiens

<400> SEQUENCE: 98

Phe Tyr Trp Leu Val Ile Met
1               5

<210> SEQ ID NO 99
<211> LENGTH: 4
<212> TYPE: PRT
<213> ORGANISM: Homo sapiens

<400> SEQUENCE: 99

Arg Lys His Ala
1

<210> SEQ ID NO 100
<211> LENGTH: 8
<212> TYPE: PRT
<213> ORGANISM: Homo sapiens

<400> SEQUENCE: 100

Asp Glu Arg Lys His Arg Lys His
1               5

<210> SEQ ID NO 101
<211> LENGTH: 4
<212> TYPE: PRT
<213> ORGANISM: Homo sapiens

<400> SEQUENCE: 101

Asp Glu Gln Asn
1

<210> SEQ ID NO 102
<211> LENGTH: 11
<212> TYPE: PRT
<213> ORGANISM: Homo sapiens

<400> SEQUENCE: 102

Leu Met Val Ile Ser Ala Thr Phe Cys Gly Asp
1               5                   10

<210> SEQ ID NO 103
<211> LENGTH: 7
<212> TYPE: PRT
<213> ORGANISM: Homo sapiens

<400> SEQUENCE: 103

Pro Arg His Lys Tyr Phe Trp
1               5

<210> SEQ ID NO 104
<211> LENGTH: 6
<212> TYPE: PRT
<213> ORGANISM: Homo sapiens

<400> SEQUENCE: 104

Lys Tyr Arg His Phe Ala
1               5

<210> SEQ ID NO 105
<211> LENGTH: 12
<212> TYPE: PRT
<213> ORGANISM: Homo sapiens

<400> SEQUENCE: 105

Val Thr Leu Met Ile Ser Ala Gly Asn Cys Asp Phe
1               5                   10

<210> SEQ ID NO 106
<211> LENGTH: 4
<212> TYPE: PRT
<213> ORGANISM: Homo sapiens

<400> SEQUENCE: 106

Lys Arg Tyr His
1

<210> SEQ ID NO 107
<211> LENGTH: 6
<212> TYPE: PRT
<213> ORGANISM: Homo sapiens

<400> SEQUENCE: 107

Tyr Phe Trp Arg His Lys
1               5

<210> SEQ ID NO 108
<211> LENGTH: 4
<212> TYPE: PRT
<213> ORGANISM: Homo sapiens

<400> SEQUENCE: 108

Tyr Phe Trp Met
1

<210> SEQ ID NO 109
<211> LENGTH: 4
<212> TYPE: PRT
<213> ORGANISM: Homo sapiens

<400> SEQUENCE: 109

Phe Leu Ile Trp
1

<210> SEQ ID NO 110
<211> LENGTH: 6
<212> TYPE: PRT
<213> ORGANISM: Homo sapiens

<400> SEQUENCE: 110

Asp Glu Arg His Lys Gly
1               5

<210> SEQ ID NO 111
<211> LENGTH: 4
<212> TYPE: PRT
<213> ORGANISM: Homo sapiens

<400> SEQUENCE: 111

Tyr Phe Trp Met
1

<210> SEQ ID NO 112
<211> LENGTH: 4

```
<212> TYPE: PRT
<213> ORGANISM: Homo sapiens

<400> SEQUENCE: 112

Tyr Phe Trp Pro
 1

<210> SEQ ID NO 113
<211> LENGTH: 4
<212> TYPE: PRT
<213> ORGANISM: Homo sapiens

<400> SEQUENCE: 113

Phe Leu Ile Trp
 1

<210> SEQ ID NO 114
<211> LENGTH: 7
<212> TYPE: PRT
<213> ORGANISM: Homo sapiens

<400> SEQUENCE: 114

Met Val Thr Ala Leu Ile Ser
 1               5

<210> SEQ ID NO 115
<211> LENGTH: 8
<212> TYPE: PRT
<213> ORGANISM: Homo sapiens

<400> SEQUENCE: 115

Met Val Ala Leu Phe Ile Ser Thr
 1               5

<210> SEQ ID NO 116
<211> LENGTH: 4
<212> TYPE: PRT
<213> ORGANISM: Homo sapiens

<400> SEQUENCE: 116

Ala Tyr Phe Trp
 1

<210> SEQ ID NO 117
<211> LENGTH: 6
<212> TYPE: PRT
<213> ORGANISM: Homo sapiens

<400> SEQUENCE: 117

Tyr Phe Trp Ser Thr Cys
 1               5

<210> SEQ ID NO 118
<211> LENGTH: 7
<212> TYPE: PRT
<213> ORGANISM: Homo sapiens

<400> SEQUENCE: 118

Ala Val Thr Met Ser Leu Ile
 1               5

<210> SEQ ID NO 119
<211> LENGTH: 7
<212> TYPE: PRT
<213> ORGANISM: Homo sapiens
```

```
<400> SEQUENCE: 119

Tyr Phe Trp Leu Ile Val Met
1               5

<210> SEQ ID NO 120
<211> LENGTH: 6
<212> TYPE: PRT
<213> ORGANISM: Homo sapiens

<400> SEQUENCE: 120

Arg His Lys Phe Trp Tyr
1               5

<210> SEQ ID NO 121
<211> LENGTH: 8
<212> TYPE: PRT
<213> ORGANISM: Homo sapiens

<400> SEQUENCE: 121

Leu Met Phe Trp Tyr Ala Ile Val
1               5

<210> SEQ ID NO 122
<211> LENGTH: 5
<212> TYPE: PRT
<213> ORGANISM: Homo sapiens

<400> SEQUENCE: 122

Asp Glu Gln Asn Pro
1               5

<210> SEQ ID NO 123
<211> LENGTH: 7
<212> TYPE: PRT
<213> ORGANISM: Homo sapiens

<400> SEQUENCE: 123

Phe Trp Tyr Leu Ile Val Met
1               5

<210> SEQ ID NO 124
<211> LENGTH: 8
<212> TYPE: PRT
<213> ORGANISM: Homo sapiens

<400> SEQUENCE: 124

Leu Met Phe Trp Tyr Ile Val Ala
1               5

<210> SEQ ID NO 125
<211> LENGTH: 8
<212> TYPE: PRT
<213> ORGANISM: Homo sapiens

<400> SEQUENCE: 125

Arg His Lys Leu Ile Val Met Pro
1               5

<210> SEQ ID NO 126
<211> LENGTH: 4
<212> TYPE: PRT
<213> ORGANISM: Homo sapiens

<400> SEQUENCE: 126

Asp Glu Gln Asn
```

<210> SEQ ID NO 127
<211> LENGTH: 8
<212> TYPE: PRT
<213> ORGANISM: Homo sapiens

<400> SEQUENCE: 127

Ala Ser Thr Cys Leu Ile Val Met
1               5

<210> SEQ ID NO 128
<211> LENGTH: 4
<212> TYPE: PRT
<213> ORGANISM: Homo sapiens

<400> SEQUENCE: 128

Asp Glu Ala Ser
1

<210> SEQ ID NO 129
<211> LENGTH: 4
<212> TYPE: PRT
<213> ORGANISM: Homo sapiens

<400> SEQUENCE: 129

Ala Ser Thr Cys
1

<210> SEQ ID NO 130
<211> LENGTH: 9
<212> TYPE: PRT
<213> ORGANISM: Homo sapiens

<400> SEQUENCE: 130

Arg His Lys Asp Glu Pro Tyr Phe Trp
1               5

<210> SEQ ID NO 131
<211> LENGTH: 8
<212> TYPE: PRT
<213> ORGANISM: Homo sapiens

<400> SEQUENCE: 131

Leu Ile Val Phe Trp Tyr Ala Met
1               5

<210> SEQ ID NO 132
<211> LENGTH: 7
<212> TYPE: PRT
<213> ORGANISM: Homo sapiens

<400> SEQUENCE: 132

Leu Ile Val Met Phe Trp Tyr
1               5

<210> SEQ ID NO 133
<211> LENGTH: 11
<212> TYPE: PRT
<213> ORGANISM: Homo sapiens

<400> SEQUENCE: 133

Ala Gly Pro Asp Glu Arg His Lys Ser Thr Cys
1               5                   10

```
<210> SEQ ID NO 134
<211> LENGTH: 7
<212> TYPE: PRT
<213> ORGANISM: Homo sapiens

<400> SEQUENCE: 134

Leu Ile Val Met Phe Trp Tyr
 1               5

<210> SEQ ID NO 135
<211> LENGTH: 8
<212> TYPE: PRT
<213> ORGANISM: Homo sapiens

<400> SEQUENCE: 135

Ile Met Phe Trp Tyr Ala Leu Val
 1               5

<210> SEQ ID NO 136
<211> LENGTH: 5
<212> TYPE: PRT
<213> ORGANISM: Homo sapiens

<400> SEQUENCE: 136

Ala Gly Pro Gln Asn
 1               5

<210> SEQ ID NO 137
<211> LENGTH: 5
<212> TYPE: PRT
<213> ORGANISM: Homo sapiens

<400> SEQUENCE: 137

Arg His Lys Gln Asn
 1               5

<210> SEQ ID NO 138
<211> LENGTH: 7
<212> TYPE: PRT
<213> ORGANISM: Homo sapiens

<400> SEQUENCE: 138

Phe Trp Tyr Leu Ile Val Met
 1               5

<210> SEQ ID NO 139
<211> LENGTH: 4
<212> TYPE: PRT
<213> ORGANISM: Homo sapiens

<400> SEQUENCE: 139

Leu Ile Val Met
 1

<210> SEQ ID NO 140
<211> LENGTH: 5
<212> TYPE: PRT
<213> ORGANISM: Homo sapiens

<400> SEQUENCE: 140

Ala Leu Ile Val Met
 1               5

<210> SEQ ID NO 141
<211> LENGTH: 5
<212> TYPE: PRT
```

<213> ORGANISM: Homo sapiens

<400> SEQUENCE: 141

Phe Trp Tyr Ala Pro
 1               5

<210> SEQ ID NO 142
<211> LENGTH: 9
<212> TYPE: PRT
<213> ORGANISM: Homo sapiens

<400> SEQUENCE: 142

Ala Thr Ile Val Leu Met Phe Trp Tyr
 1               5

<210> SEQ ID NO 143
<211> LENGTH: 6
<212> TYPE: PRT
<213> ORGANISM: Homo sapiens

<400> SEQUENCE: 143

Gly Pro Gln Asn Asp Glu
 1               5

<210> SEQ ID NO 144
<211> LENGTH: 6
<212> TYPE: PRT
<213> ORGANISM: Homo sapiens

<400> SEQUENCE: 144

Gly Asp Glu Ser Thr Cys
 1               5

<210> SEQ ID NO 145
<211> LENGTH: 5
<212> TYPE: PRT
<213> ORGANISM: Homo sapiens

<400> SEQUENCE: 145

Arg His Lys Asp Glu
 1               5

<210> SEQ ID NO 146
<211> LENGTH: 5
<212> TYPE: PRT
<213> ORGANISM: Homo sapiens

<400> SEQUENCE: 146

Gln Asn Asp Gly Glu
 1               5

<210> SEQ ID NO 147
<211> LENGTH: 8
<212> TYPE: PRT
<213> ORGANISM: Homo sapiens

<400> SEQUENCE: 147

Ala Ile Leu Met Val Phe Trp Tyr
 1               5

<210> SEQ ID NO 148
<211> LENGTH: 7
<212> TYPE: PRT
<213> ORGANISM: Homo sapiens

<400> SEQUENCE: 148

```
Ala Ile Leu Met Val Ser Thr
1               5
```

<210> SEQ ID NO 149
<211> LENGTH: 6
<212> TYPE: PRT
<213> ORGANISM: Homo sapiens

<400> SEQUENCE: 149

```
Ala Ile Leu Met Val Thr
1               5
```

<210> SEQ ID NO 150
<211> LENGTH: 6
<212> TYPE: PRT
<213> ORGANISM: Homo sapiens

<400> SEQUENCE: 150

```
Ala Ile Leu Met Val Thr
1               5
```

<210> SEQ ID NO 151
<211> LENGTH: 8
<212> TYPE: PRT
<213> ORGANISM: Homo sapiens

<400> SEQUENCE: 151

```
Tyr Phe Trp Ile Val Leu Met Thr
1               5
```

<210> SEQ ID NO 152
<211> LENGTH: 6
<212> TYPE: PRT
<213> ORGANISM: Homo sapiens

<400> SEQUENCE: 152

```
Phe Ile Tyr Trp Leu Met
1               5
```

<210> SEQ ID NO 153
<211> LENGTH: 8
<212> TYPE: PRT
<213> ORGANISM: Homo sapiens

<400> SEQUENCE: 153

```
Phe Trp Tyr Leu Ile Met Val Ala
1               5
```

<210> SEQ ID NO 154
<211> LENGTH: 6
<212> TYPE: PRT
<213> ORGANISM: Homo sapiens

<400> SEQUENCE: 154

```
Thr Ile Leu Val Met Ser
1               5
```

<210> SEQ ID NO 155
<211> LENGTH: 6
<212> TYPE: PRT
<213> ORGANISM: Homo sapiens

<400> SEQUENCE: 155

```
Phe Tyr Leu Trp Met Ile
1               5
```

-continued

```
<210> SEQ ID NO 156
<211> LENGTH: 6
<212> TYPE: PRT
<213> ORGANISM: Homo sapiens

<400> SEQUENCE: 156

Gln Leu Ile Val Met Pro
1               5

<210> SEQ ID NO 157
<211> LENGTH: 6
<212> TYPE: PRT
<213> ORGANISM: Homo sapiens

<400> SEQUENCE: 157

Phe Trp Tyr Met Ile Val
1               5

<210> SEQ ID NO 158
<211> LENGTH: 6
<212> TYPE: PRT
<213> ORGANISM: Homo sapiens

<400> SEQUENCE: 158

Phe Trp Tyr Leu Ile Val
1               5

<210> SEQ ID NO 159
<211> LENGTH: 137
<212> TYPE: PRT
<213> ORGANISM: Artificial Sequence
<220> FEATURE:
<223> OTHER INFORMATION: H1-1.10 VH

<400> SEQUENCE: 159

Gln Leu Gln Glu Ser Gly Pro Gly Leu Val Lys Pro Ser Gln Thr Leu
1               5                   10                  15

Ser Leu Thr Cys Thr Val Ser Gly Gly Ser Ile Ser Ser Gly Gly Tyr
            20                  25                  30

Tyr Trp Ser Trp Ile Arg Gln His Pro Gly Lys Gly Leu Glu Trp Ile
        35                  40                  45

Gly Tyr Ile Tyr Tyr Ser Gly Ser Thr Tyr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Gly Thr Ala Ala Asp Thr Ala Val Tyr Tyr Cys Ala
                85                  90                  95

Arg Asp His Ile Thr Met Val Arg Gly Val Pro Lys Gly Met Asp Val
            100                 105                 110

Trp Gly Gln Gly Thr Thr Val Thr Val Ser Ser Ala Ser Thr Lys Gly
        115                 120                 125

Pro Ser Val Lys Gly Pro Ser Val Phe
    130                 135

<210> SEQ ID NO 160
<211> LENGTH: 122
<212> TYPE: PRT
<213> ORGANISM: Artificial Sequence
<220> FEATURE:
<223> OTHER INFORMATION: H1-1.10 VL

<400> SEQUENCE: 160
```

```
Gln Leu Thr Gln Ser Pro Ser Ser Leu Ser Ala Ser Val Gly Asp Arg
  1               5                  10                  15

Val Thr Ile Thr Cys Arg Ala Ser Gln Ser Ile Ser Arg His Leu Asn
             20                  25                  30

Trp Tyr Gln Gln Lys Pro Gly Lys Ala Pro Lys Phe Leu Ile Tyr Val
         35                  40                  45

Ala Ser Ser Leu Gln Ser Gly Val Pro Ser Arg Phe Ser Gly Ser Gly
     50                  55                  60

Ser Gly Thr Asp Phe Thr Leu Thr Ile Ser Ser Leu Gln Pro Glu Asp
 65              70                  75                  80

Phe Ala Thr Tyr Phe Cys Gln Gln Ser Tyr Ser Ile Pro Arg Thr Phe
                 85                  90                  95

Gly Gln Gly Thr Lys Val Glu Ile Lys Arg Thr Val Ala Ala Pro Ser
            100                 105                 110

Val Phe Ile Phe Pro Pro Ser Asp Glu Gln
            115             120

<210> SEQ ID NO 161
<211> LENGTH: 9
<212> TYPE: PRT
<213> ORGANISM: Artificial Sequence
<220> FEATURE:
<223> OTHER INFORMATION: Human O2

<400> SEQUENCE: 161

Asp Ile Met Ser Tyr Leu Ala Tyr Thr
  1               5
```

ANTIBODIES AND RELATED MOLECULES THAT BIND TO PSCA PROTEINS

CROSS-REFERENCE TO RELATED APPLICATIONS

This patent application is a divisional of U.S. patent application Ser. No. 11/355,464, filed 15 Feb. 2006, now U.S. Pat. No. 7,541,442, which is a continuation-in-part of U.S. patent application Ser. No. 11/131,648, filed 17 May 2005, now U.S. Pat. No. 7,595,379, which claims the benefit of priority of United States Provisional Patent Application No. 60/616,381, filed 5 Oct. 2004, United States Provisional Patent Application No.: 60/617,881, filed 12 Oct. 2004, and United States Provisional Patent Application No.: 60/621,310, filed 21 Oct. 2004, United States Provisional Patent Application No.: 60/633,077, filed 2 Dec. 2004, and United States Provisional Patent Application No.: 60/672,000, filed 14 Apr. 2005, which is a continuation-in-part of pending U.S. patent application Ser. No. 10/857,484, filed 28 May 2004, which claims priority to U.S. Provisional Patent Application No. 60/475,064, filed 30 May 2003. The contents of each application listed in this paragraph are fully incorporated by reference herein.

REFERENCE TO SEQUENCE LISTING SUBMITTED VIA EFS-WEB

The entire content of the following electronic submission of the sequence listing via the USPTO EFS-WEB server, as authorized and set forth in MPEP § 1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 511582008812.Seqlist.txt | Mar. 20, 2009 | 50,741 bytes |

FIELD OF THE INVENTION

The invention described herein relates to antibodies, as well as binding fragments thereof and molecules engineered therefrom, that bind proteins, termed PSCA. The invention further relates to diagnostic, prognostic, prophylactic and therapeutic methods and compositions useful in the treatment of cancers that express PSCA.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, ovary, and bladder represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, *Nat. Med.* 3:402). More recently identified prostate cancer markers include PCTA-1 (Su et al., 1996, *Proc. Natl. Acad. Sci.* USA 93: 7252), prostate-specific membrane (PSM) antigen (Pinto et al., *Clin Cancer Res* 1996 September 2 (9): 1445-51), STEAP (Hubert, et al., *Proc Natl Acad Sci USA.* 1999 Dec. 7; 96(25): 14523-8) and prostate stem cell antigen (PSCA) (Reiter et al., 1998, *Proc. Natl. Acad. Sci. USA* 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and eight per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992-1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is, however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy.

There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for cancers. These include the use of antibodies, vaccines, and small molecules as treatment modalities. Additionally, there is also a need to use these modalities as research tools to diagnose, detect, monitor, and further the state of the art in all areas of cancer treatment and studies.

The therapeutic utility of monoclonal antibodies (mAbs) (G. Kohler and C. Milstein, Nature 256:495-497 (1975)) is being realized. Monoclonal antibodies have now been approved as therapies in transplantation, cancer, infectious disease, cardiovascular disease and inflammation. Different isotypes have different effector functions. Such differences in function are reflected in distinct 3-dimensional structures for the various immunoglobulin isotypes (P. M. Alzari et al., Annual Rev. Immunol., 6:555-580 (1988)).

Because mice are convenient for immunization and recognize most human antigens as foreign, mAbs against human targets with therapeutic potential have typically been of murine origin. However, murine mAbs have inherent disadvantages as human therapeutics. They require more frequent dosing as mAbs have a shorter circulating half-life in humans than human antibodies. More critically, the repeated administration of murine antibodies to the human immune system causes the human immune system to respond by recognizing the mouse protein as a foreign and generating a human anti-mouse antibody (HAMA) response. Such a HAMA response may result in allergic reaction and the rapid clearing of the murine antibody from the system thereby rendering the treatment by murine antibody useless. To avoid such affects, attempts to create human immune systems within mice have been attempted.

Initial attempts hoped to create transgenic mice capable of responding to antigens with antibodies having human sequences (See Bruggemann et al., Proc. Nat'l. Acad. Sci. USA 86:6709-6713 (1989)), but were limited by the amount of DNA that could be stably maintained by available cloning vehicles. The use of yeast artificial chromosome (YAC) cloning vectors led the way to introducing large germline fragments of human Ig locus into transgenic mammals. Essentially a majority of the human V, D, and J region genes arranged with the same spacing found in the human genome and the human constant regions were introduced into mice using YACs. One such transgenic mouse strain is known as XenoMouse® mice and is commercially available from Abgenix, Inc. (Fremont Calif.).

SUMMARY OF THE INVENTION

The invention provides antibodies as well as binding fragments thereof and molecules engineered therefrom, that bind to PSCA proteins and polypeptide fragments of PSCA proteins. The invention comprises polyclonal and monoclonal antibodies, murine and other mammalian antibodies, chimeric antibodies, humanized and fully human antibodies, and antibodies labeled with a detectable marker or therapeutic agent. In certain embodiments, there is a proviso that the entire nucleic acid sequence of FIG. 3 is not encoded and/or the entire amino acid sequence of FIG. 2 is not prepared. In certain embodiments, the entire nucleic acid sequence of FIG. 3 is encoded and/or the entire amino acid sequence of FIG. 2 is prepared, either of which are in respective human unit dose forms.

The invention further provides methods for detecting the presence and status of PSCA polynucleotides and proteins in various biological samples, as well as methods for identifying cells that express PSCA. An embodiment of this invention provides methods for monitoring PSCA gene products in a tissue or hematology sample having or suspected of having some form of growth dysregulation such as cancer.

The invention further provides various immunogenic or therapeutic compositions and strategies for treating cancers that express PSCA such as cancers of tissues listed in Table I, including therapies aimed at inhibiting the transcription, translation, processing or function of PSCA as well as cancer vaccines. In one aspect, the invention provides compositions, and methods comprising them, for treating a cancer that expresses PSCA in a human subject wherein the composition comprises a carrier suitable for human use and a human unit dose of one or more than one agent that inhibits the production or function of PSCA. Preferably, the carrier is a uniquely human carrier. In another aspect of the invention, the agent is a moiety that is immunoreactive with PSCA protein. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety. In another aspect, the agent is a small molecule as defined herein.

Figure 1I:
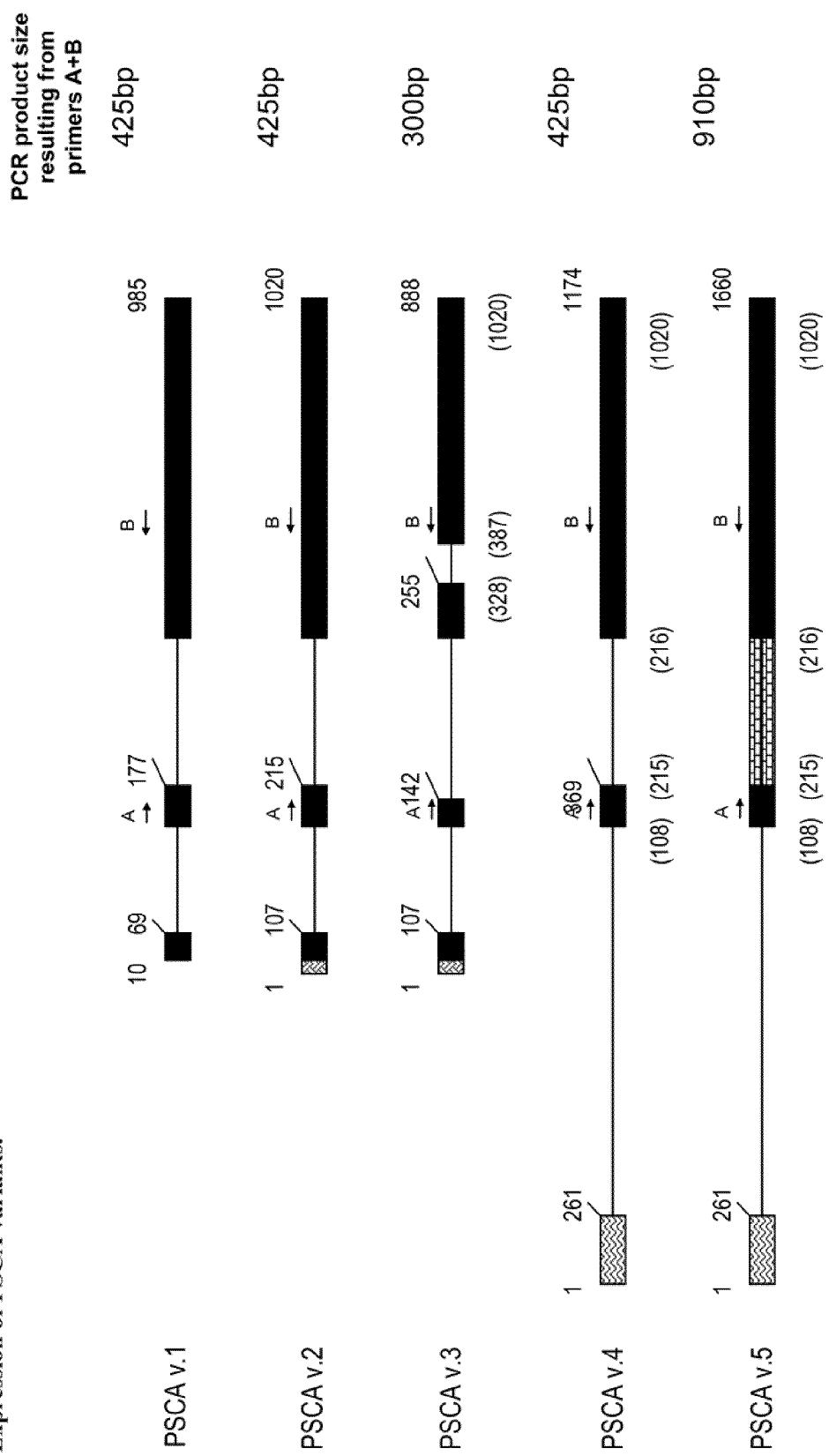
FIG. 1. The cDNA and amino acid sequence of PSCA (also called "PSCA v.1" or "PSCA variant 1") is shown in FIG. 1A. The start methionine is underlined. The open reading frame extends from nucleic acid 18-389 including the stop codon.
Figure 1I:
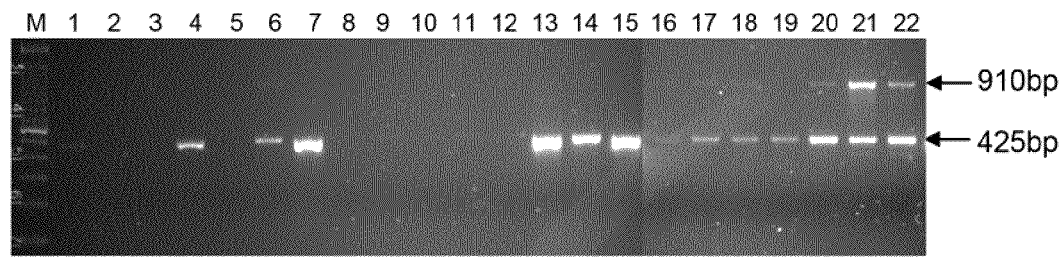

The cDNA and amino acid sequence of PSCA variant 2 (also called "PSCA v.2") is shown in FIG. 1B. The codon for the start methionine is underlined. The open reading frame extends from nucleic acid 56-427 including the stop codon.

The cDNA and amino acid sequence of PSCA variant 3 (also called "PSCA v.3") is shown in FIG. 1C. The codon for the start methionine is underlined. The open reading frame extends from nucleic acid 423-707 including the stop codon.

The cDNA and amino acid sequence of PSCA variant 4 (also called "PSCA v.4") is shown in FIG. 1D. The codon for the start methionine is underlined. The open reading frame extends from nucleic acid 424-993 including the stop codon.

The cDNA and amino acid sequence of PSCA variant 5 (also called "PSCA v.5") is shown in FIG. 1E. The codon for the start methionine is underlined. The open reading frame extends from nucleic acid 910-1479 including the stop codon.

The cDNA and amino acid sequence of PSCA variant 6 (also called "PSCA v.6") is shown in FIG. 1F. The codon for the start methionine is underlined. The open reading frame extends from nucleic acid 83-427 including the stop codon.

FIG. 1G. SNP variants of PSCA v.2, PSCA v.7 through v.18. The PSCA v.7 through v.18 proteins have 123 amino acids. Variants PSCA v.7 through v.18 are variants with single nucleotide difference from PSCA v.2, and code for the same protein as v.2. Though these SNP variants are shown separately, they can also occur in any combinations and in any of the transcript variants listed above in FIGS. 1A through 1F.

FIG. 1H. SNP variants of PSCA v.4, PSCA v.19 through v.30. The PSCA v.19 through v.30 proteins have 189 amino acids. Variants PSCA v.19 through v.30 are variants with single nucleotide difference from PSCA v.4. PSCA v.9, v.10, v.11, v.24 and v.25 proteins differ from PSCA v.1 by one amino acid. PSCA v.23, v.28, v.29 and v.30 code for the same protein as v.4. Though these SNP variants are shown separately, they can also occur in any combinations and in any of the transcript variants v.3 and v.4.

FIG. 1I. Expression of PSCA variants. (1I(a)) Primers were designed to differentiate between the variants PSCA v.1/v.2/v.4, PSCA v.3 and PSCA v.5. Primers A and B, indicated by small arrows above exons in the figure result in a PCR product of 425 bp for PSCA v.1/v.2/v4, a PCR product of 300 bp for PSCA v3 and a PCR product of 910 bp for PSCA v.5. (1I(b)) First strand cDNA was prepared from normal bladder, brain, heart, kidney, liver, lung, prostate, spleen, skeletal muscle, testis, pancreas, colon, stomach, pools of prostate cancer, bladder cancer, kidney cancer, colon cancer, lung cancer, ovary cancer, breast cancer, cancer metastasis, and pancreas cancer. Normalization was performed by PCR using primers to actin. Semi-quantitative PCR, using the variant specific primers was performed at 30 cycles of amplification. Results show expression of PSCA v.5 mainly in breast cancer, cancer metastasis, and pancreas cancer, and at lower level in colon cancer and lung cancer. PSCA v.1/v.2/v.4 PCR product was detected in prostate cancer, bladder cancer, kidney cancer, colon cancer, lung cancer, ovary cancer, breast cancer, cancer metastasis, and pancreas cancer. Amongst normal tissues, PSCA v.1/v.2/v.4 PCR product was detected only in prostate, stomach and at lower level in kidney and lung, whereas PSCA v.5 was not detected in any normal tissue. PSCA v.3 PCR detected product was not detected in any of the samples tested.

Figure 1J:
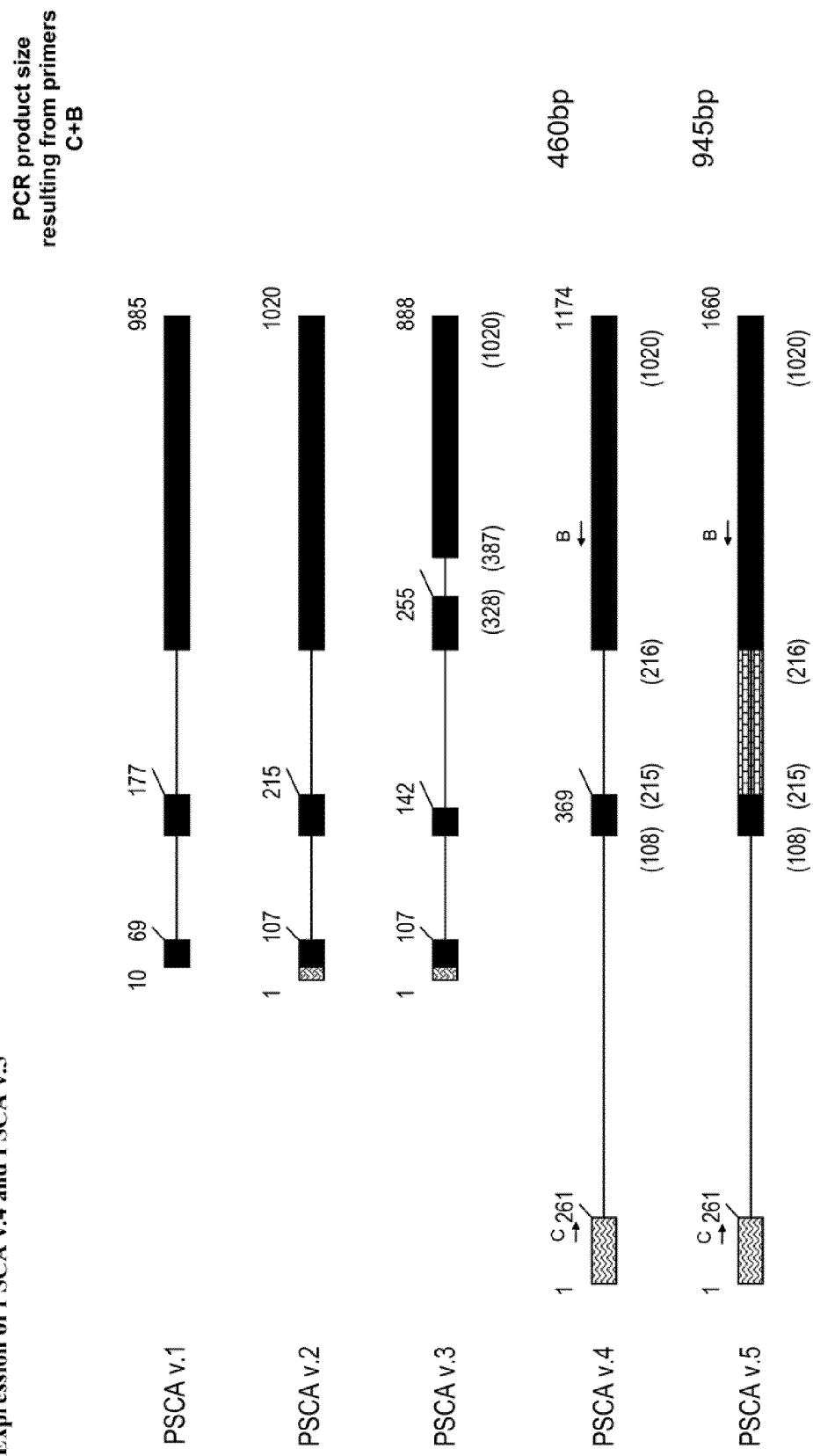
Figure 1J:
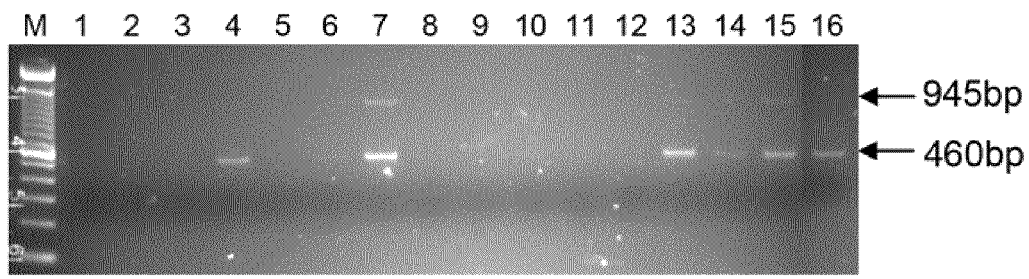

FIG. 1J. Expression of PSCA v.4 and PSCA v.5. 1J(a) Primers were designed to differentiate between PSCA v.4 and PSCA v.5 as indicated by the arrows labeled B and C in the figure. Primers specific for PSCA v.4 lead to a PCR product of 460 bp, whereas primers specific for PSCA v.5 leads to a PCR product of 945 bp in size. 1J(b) First strand cDNA was prepared from normal bladder, brain, heart, kidney, liver, lung, prostate, spleen, skel. muscle, testis, pancreas, colon, stomach, pools of prostate cancer, bladder cancer, and multi-xenograft pool (prostate cancer, kidney cancer and bladder cancer xenografts). Normalization was performed by PCR using primers to actin. Semi-quantitative PCR, using the variant specific primers was performed at 30 cycles of amplification. Results show expression of PSCA v.4 in prostate cancer, bladder cancer, and multi-xenograft pool, normal kidney and prostate. PSCA v.5 was detected only in normal prostate and bladder cancer.

FIG. 2. Amino Acid Sequences of PSCA antibodies. FIG. 2A. The amino acid sequence of H1-1.10 VH. Underlined is the heavy chain constant region. FIG. 2B. The amino acid sequence of H1-1.10 VL. Underlined is the light chain constant region.

FIG. 3. Nucleotide and Amino Acid sequences of PSCA antibodies. FIG. 3A. The cDNA and amino acid sequence of H1-1.10 VH. Underlined is portion of the heavy chain constant region. FIG. 3B. The cDNA and amino acid sequence of H1-1.10 VL. Underlined is portion of the light chain constant region.

FIG. 4. Alignment of PSCA antibodies to germline V-D-J Sequences. FIG. 4A. Alignment of H1-1.10 VH (SEQ ID NO:159) to human VH4-31. FIG. 4B. Alignment of H1-1.10 VL (SEQ ID NO:160) to human O2 (SEQ ID NO:161).

Figure 5:
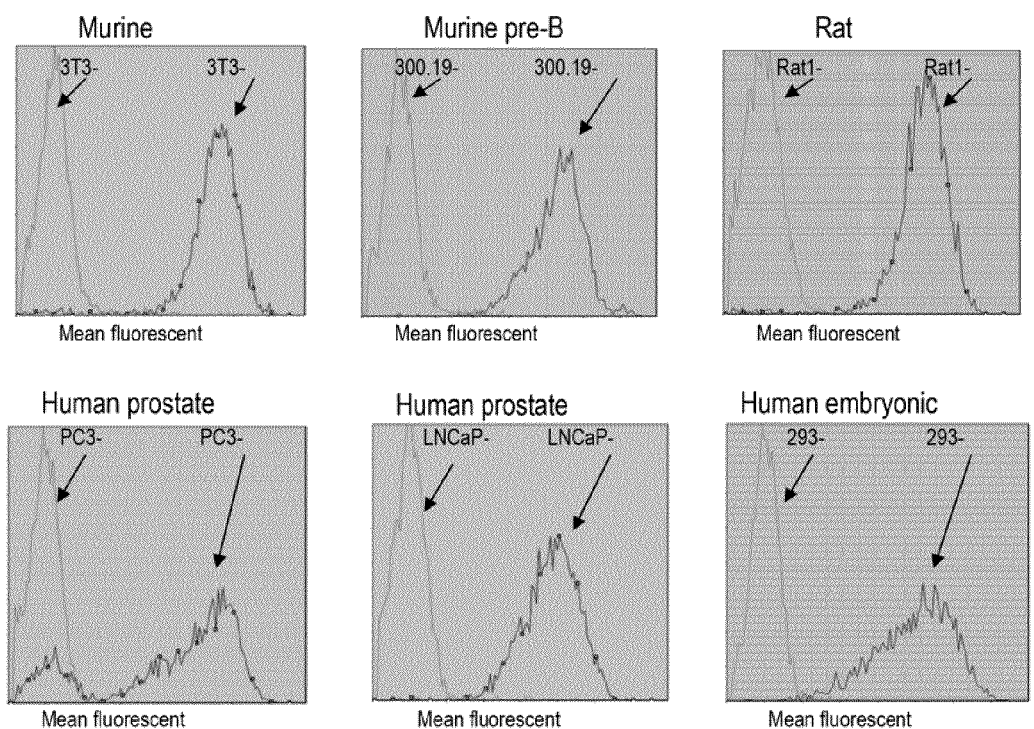

FIG. 5. Expression of PSCA protein in recombinant murine, rat and human cell lines. The indicated murine, rat, and human cell lines were infected with retroviruses carrying the human PSCA cDNA and a neomycin resistance gene or control virus with only the neomycin resistance gene. Stable recombinant cell lines were selected in the presence of G418. PSCA expression was determined by FACS staining with the 1G8 anti-PSCA MAb (5 ug/ml). Shown is the FACS profile of each cell line demonstrating a fluorescent shift only in the PSCA infected line indicative of cell surface PSCA expression. These lines are useful in MAb development as immunogens, MAb screening reagents, and in functional assays.

Figure 6:
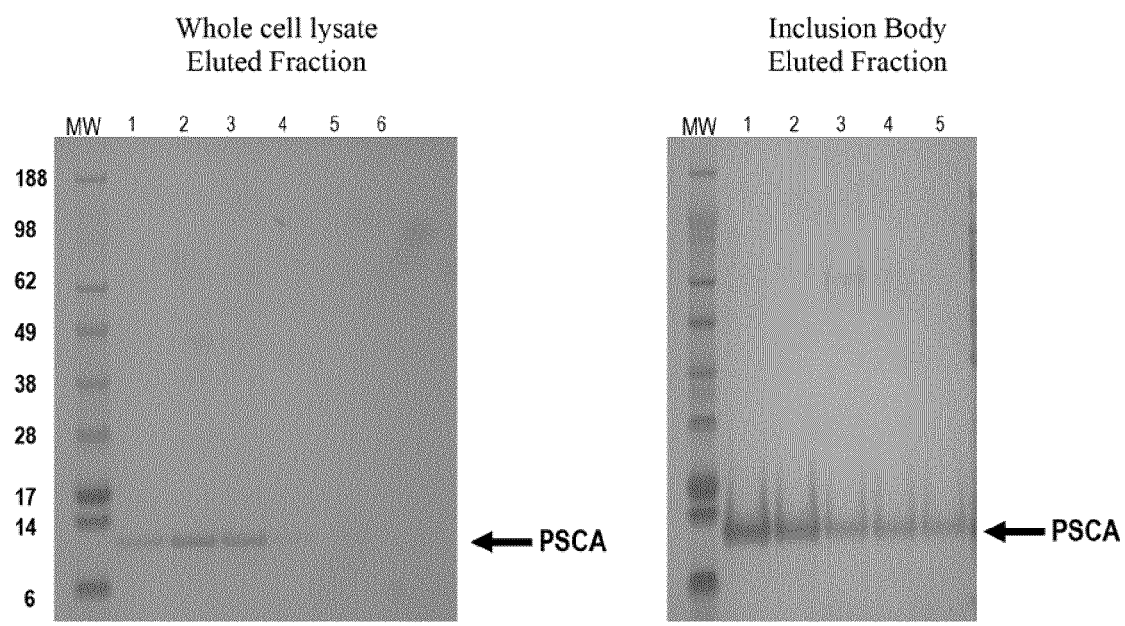

FIG. 6. Purification of PSCA protein from *E. coli*. *E. coli*. Strain BL21 pLysS was transformed with pET-21b vector encoding amino acids 21-94 of the PSCA cDNA. PSCA protein was expressed by induction of log phase cultures with IPTG and purified by affinity chromatography from either the soluble or insoluble fractions of the lysed bacteria. Shown are SDS-PAGE Coomassie blue stained gels of the eluted fractions. This protein is useful as a MAb and pAb immunogen and as an antibody screening reagent.

Figure 7:
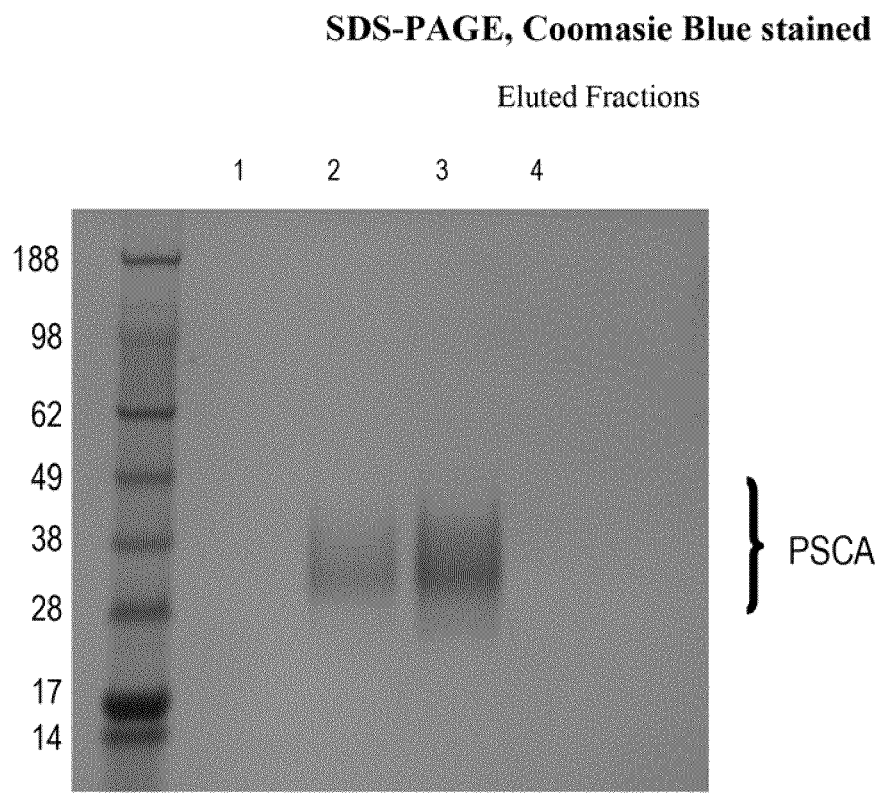

FIG. 7. Purification of recombinant glycosylated PSCA protein expressed from 293T cells. 293T cells were transfected with the psecTag2 vector carrying a PSCA cDNA encoding amino acids 28-100. A stable recombinant PSCA-secreting cell line was created by drug selection with hygromycin B. PSCA protein present in conditioned culture medium was purified by affinity chromatography using the 1G8 MAb. Shown is a Coomassie blue stained SDS-PAGE gel of the low pH eluted fractions. The broad molecular weight smear of the protein demonstrates glycosylation of recombinant PSCA protein as is seen in endogenously expressed PSCA.

Figure 8:
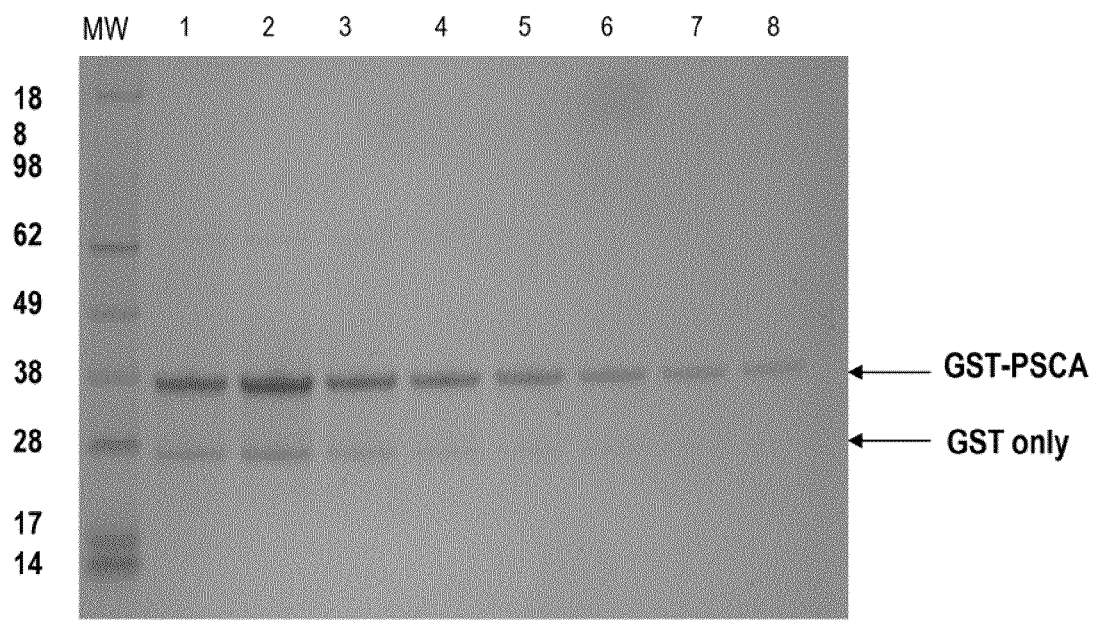

FIG. 8. Purification GST-PSCA protein from *E. coli*. *E. coli* strain BL21 DE3 was transformed with pGEX-2T encoding amino acids 18-98 of PSCA fused to glutathione-S-transferase (GST). GST-PSCA protein was induced with isopropyl-beta-D-thiogalactopyranoside (IPTG) from log phase cultures and purified from lysed bacteria by affinity chromatography with glutathione agarose matrix. Shown is an SDS-PAGE Coomassie blue stained gel of the glutathione eluted fractions containing GST-PSCA. Indicated are the intact GST-PSCA fusion protein and a minor degradation product containing GST. This protein is useful as a MAb and pAb immunogen and as an Ab screening reagent.

Figure 9A:
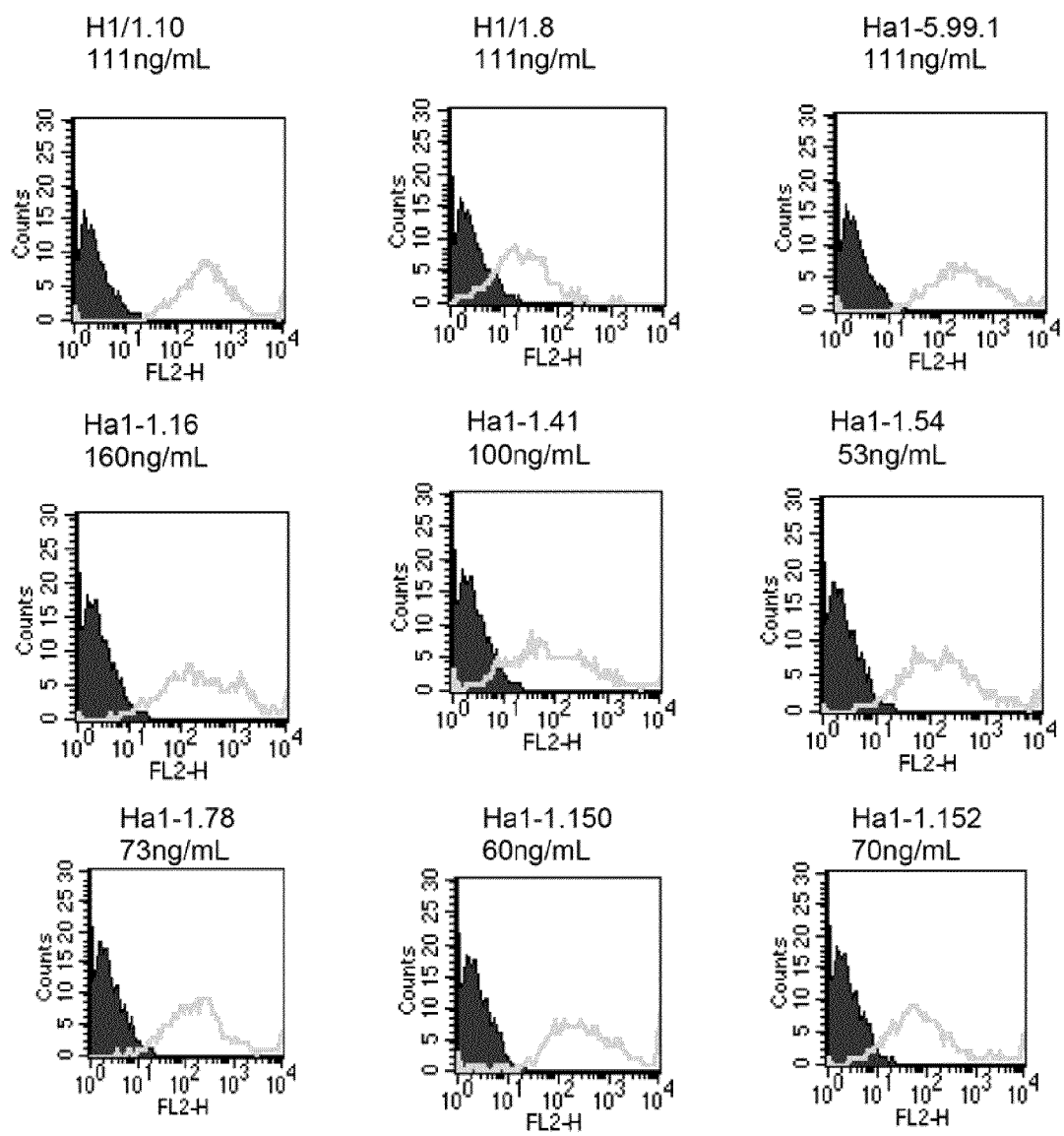
Figure 9B:
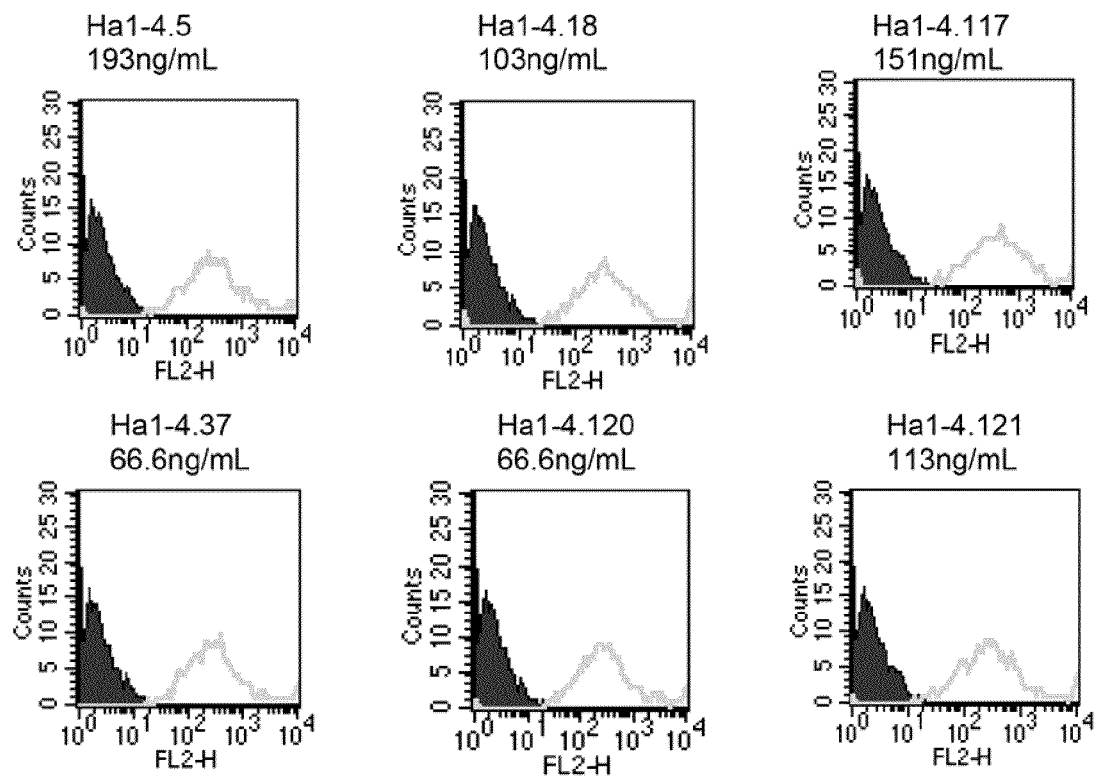

FIG. 9. Screening for human PSCA antibodies by FACS. FIG. 9A shows the FACS analysis of PSCA antibodies Ha1-1.16, Ha1-1.41, Ha1-1.54, Ha1-1.78, Ha1-1.150, and Ha1-1.152. FIG. 9B shows the FACS analysis of PSCA antibodies Ha1-4.5, Ha1-4.18, Ha1-4.117, Ha1-4.37, Ha1-4.120, and Ha1-4.121. Antibody concentration from supernatants was determined by ELISA. 50 ul/well of (neat) was added to 96-well FACS plates and serially diluted. PSCA-expressing cells were added (endogenous or recombinant, 50,000 cells/well) and the mixture incubated at 4° C. for two hours. Following incubation, the cells were washed with FACS Buffer and further incubated with 100 ul of detection antibody (anti-hIgG-PE) for 45 minutes at 4° C. At the end of incubation, the cells were washed with FACS Buffer, fixed with formaldehyde and analyzed using FACScan. Data were analyzed using CellQuest Pro software. Solid histograms represent data from negative control antibody and open histograms indicate data from PSCA-positive cells.

Figure 10:
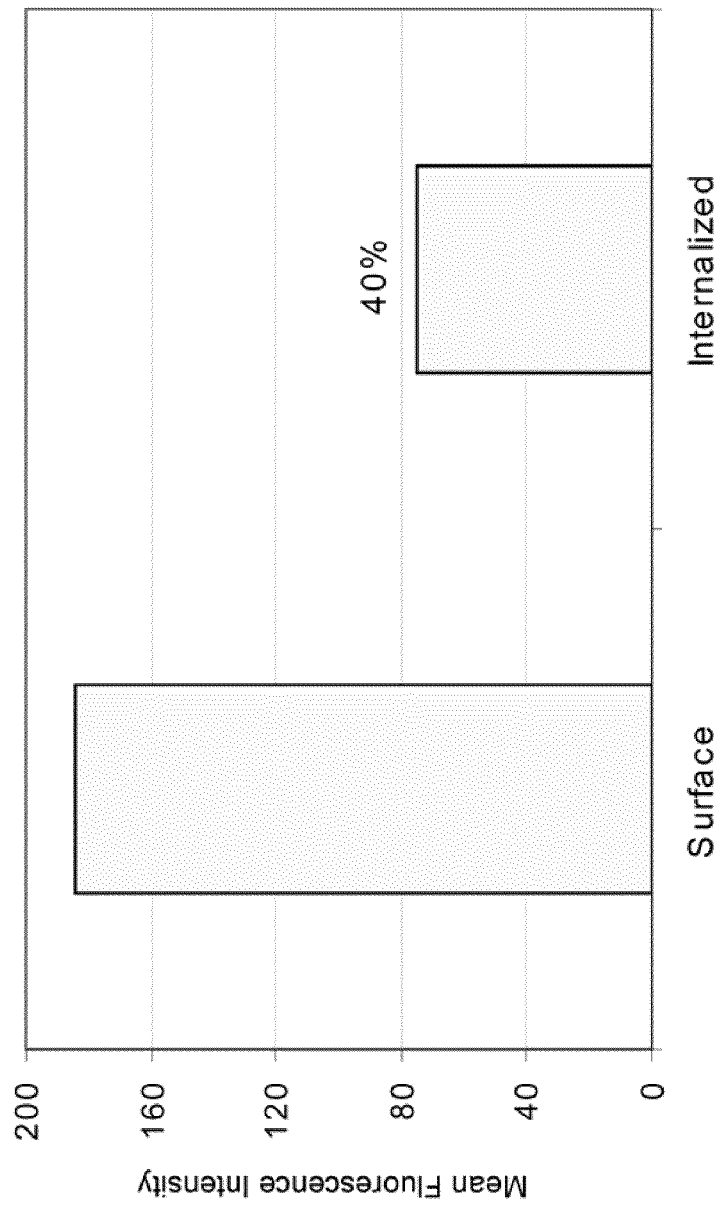

FIG. 10. Internalization of H1-1.10 on PC3-PSCA cells detected by FACS analysis. Internalization of H1-1.10 was studied using PC3-PSCA cells. The cells were first incubated at 4° C. for 90 minutes to have the antibodies bound to the cell surface. Then the cells were split into two groups and either incubated at 37° C. to allow antibody internalization or at 4° C. as control (no internalization). An acid-wash after 37° C./4° C. incubation was used to strip off H1-1.10 bound on cell surface. A permeabilization stop was included to allow detection antibodies to bind internalized H1-1.10. After incubation with detection antibodies, cells were analyzed using FACS and mean fluorescence intensity was calculated. The results show 40% of H1-1.10 internalized after incubation at 37° C. for two hours.

Figure 11B:
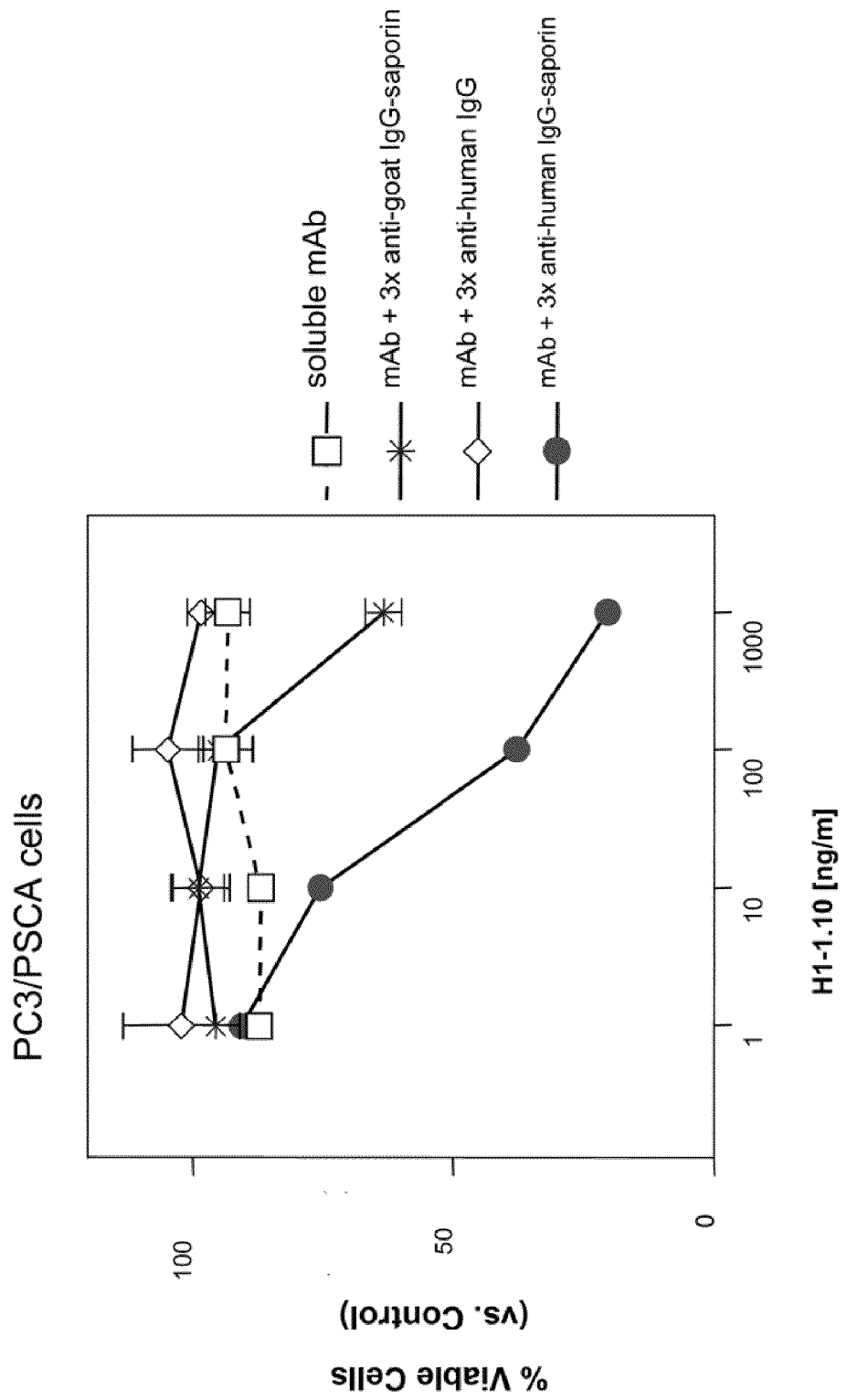

FIG. 11. PC-3 cells engineered to express either the neomycin resistance gene (neo) or PSCA were plated in triplicate into 96 well tissue culture dishes. After allowing the cells to attach overnight, medium was removed and replaced with fresh medium containing the indicated concentrations of anti-PSCA MAb H1-1.10 or H1-1.10 together with a 3 fold excess of the indicated saporin conjugated secondary antibody (Advanced Targeting systems, San Diego, Calif.). The cells were allowed to incubate for 4 days and the percent viability determined using an MTT assay (Promega Corp). The PSCA antibody H1-1.10 was specific as it did not mediate killing of cells that did not express PSCA (Panel A). H1-1.10 mediated cell killing when incubated together with a secondary antibody that recognized the human Fc region but not with a secondary antibody that recognized the Fc region of a goat antibody (Panel B).

Figure 12:
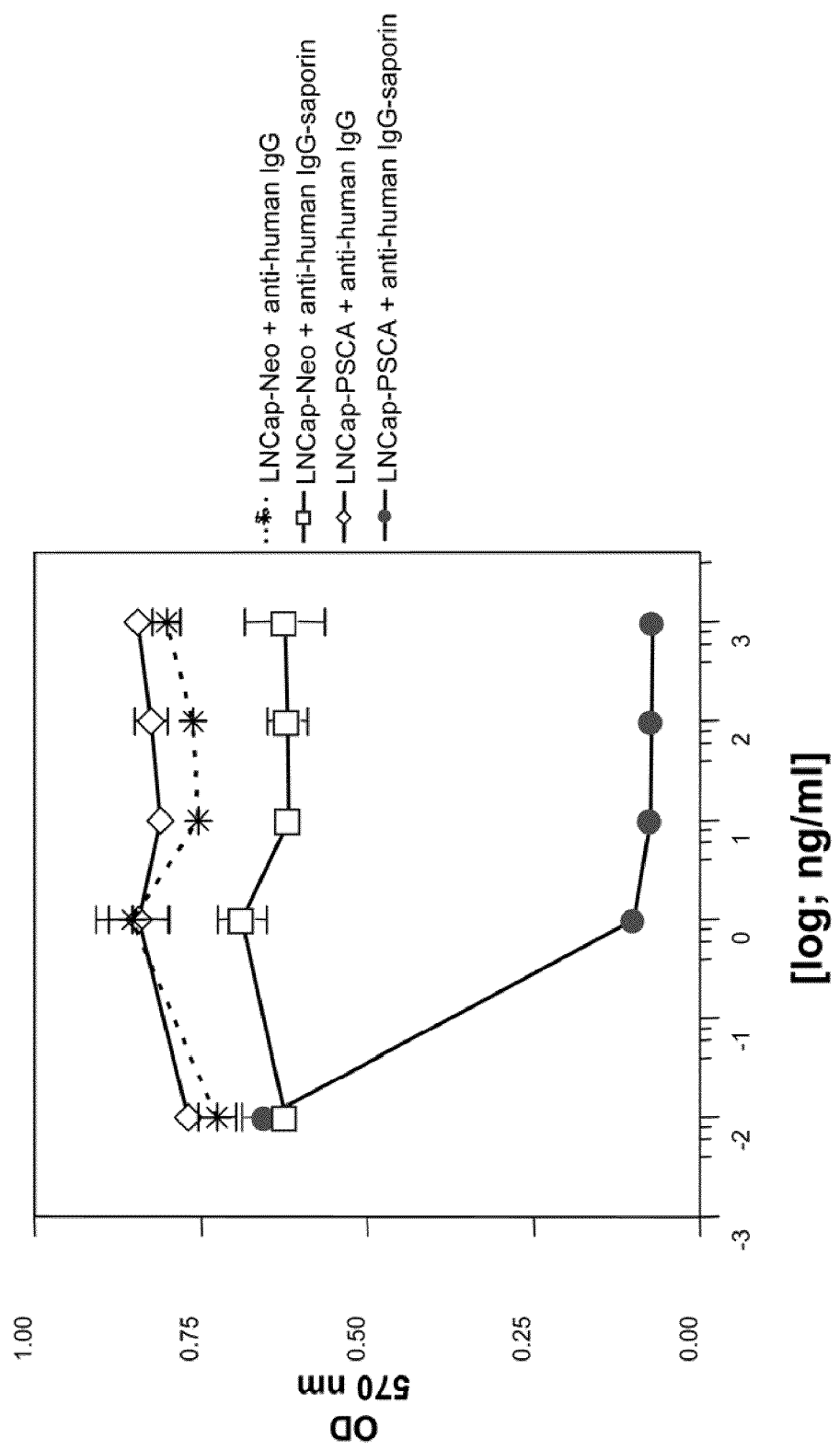

FIG. 12. LNCap cells engineered to express either the neomycin resistance gene (neo) or PSCA were plated in triplicate into 96 well tissue culture dishes. After allowing the cells to attach overnight, medium was removed and replaced with fresh medium containing the indicated concentrations of anti-PSCA MAb H1-1.10 or H1-1.10 together with a 3 fold excess of anti-human or anti-human saporin conjugated secondary antibody (Advanced Targeting systems, San Diego, Calif.). The cells were allowed to incubate for 4 days and the percent viability determined using an MTT assay (Promega Corp). The PSCA antibody H1-1.10 was specific as it did not mediate killing of LNCap cells that did not express PSCA.

Figure 13:
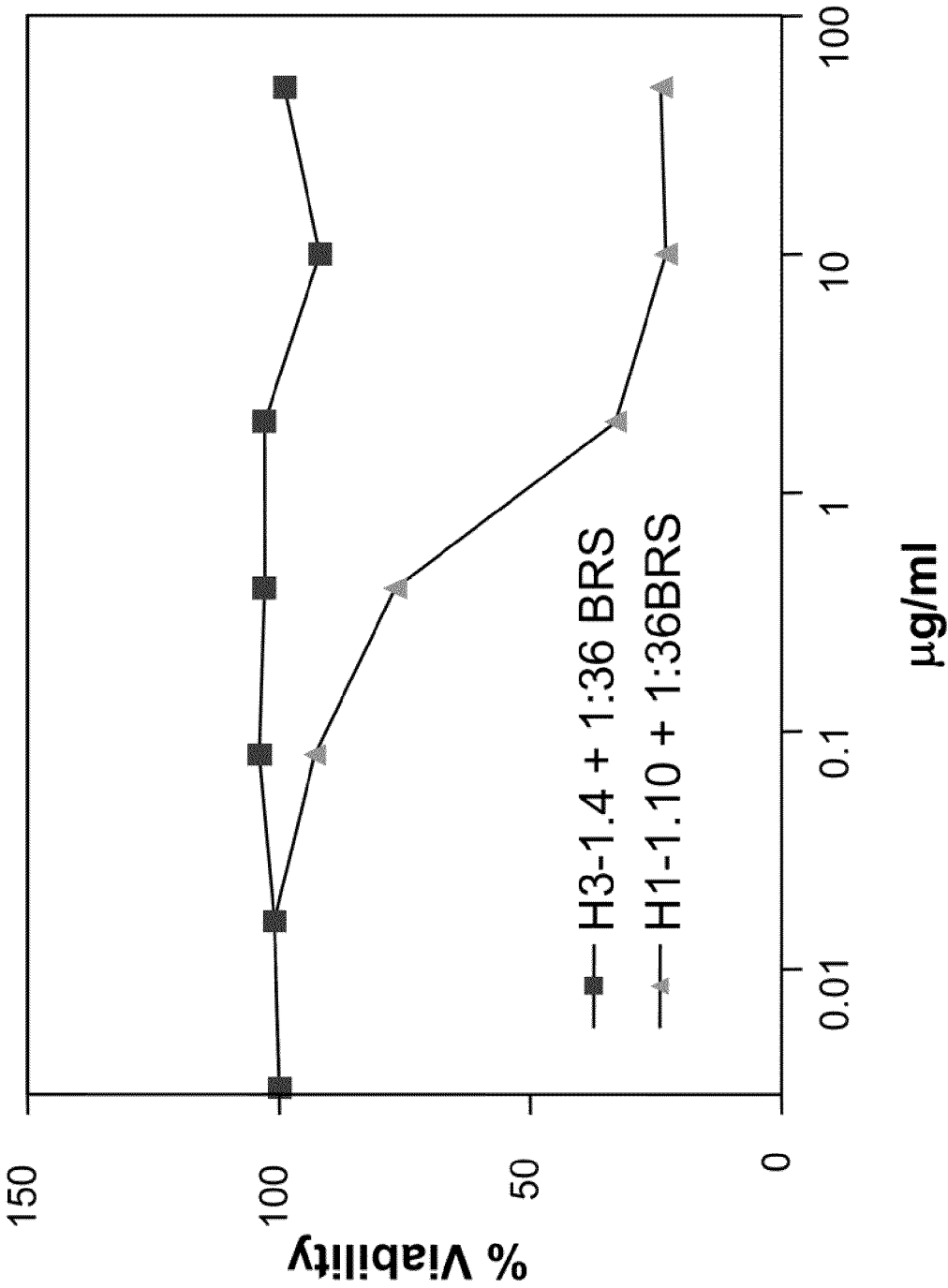

FIG. 13. Complement mediated cytotoxicity of anti-H1-1.10 antibody. H1-1.10 (0-50 μg/ml) was diluted with RHB buffer (RPMI 1640, Gibco Life Technologies, 20 mM HEPES). B300.19-PSCA expressing cells were washed in RHB buffer and resuspended at a density of $10^6$ cells/ml. In a typical assay, 50 μl of PSCA antibody, 50 μl of diluted rabbit complement serum (Cedarlane, Ontario, Can), and 50 μl of a cell suspension were added together into a flat-bottom tissue culture 96-well plate. The mixture was incubated for 2 hr. at 37° C. in a 5% CO2 incubator to facilitate complement-mediated cell lysis. 50 μl of Alamar Blue (Biosource Intl. Camarillo, Calif.) was added to each well and incubation continued for an additional 4-5 hr at 37° C. The fluorescence in each well was read using a 96-well fluorometer with excitation at 530 nm and emission at 590 nm. The results show that H1-1.10, a human Ig1, was able to mediate complement dependent lysis of target cells while a control human IgG1 (H3-1.4) was not.

Figure 14:
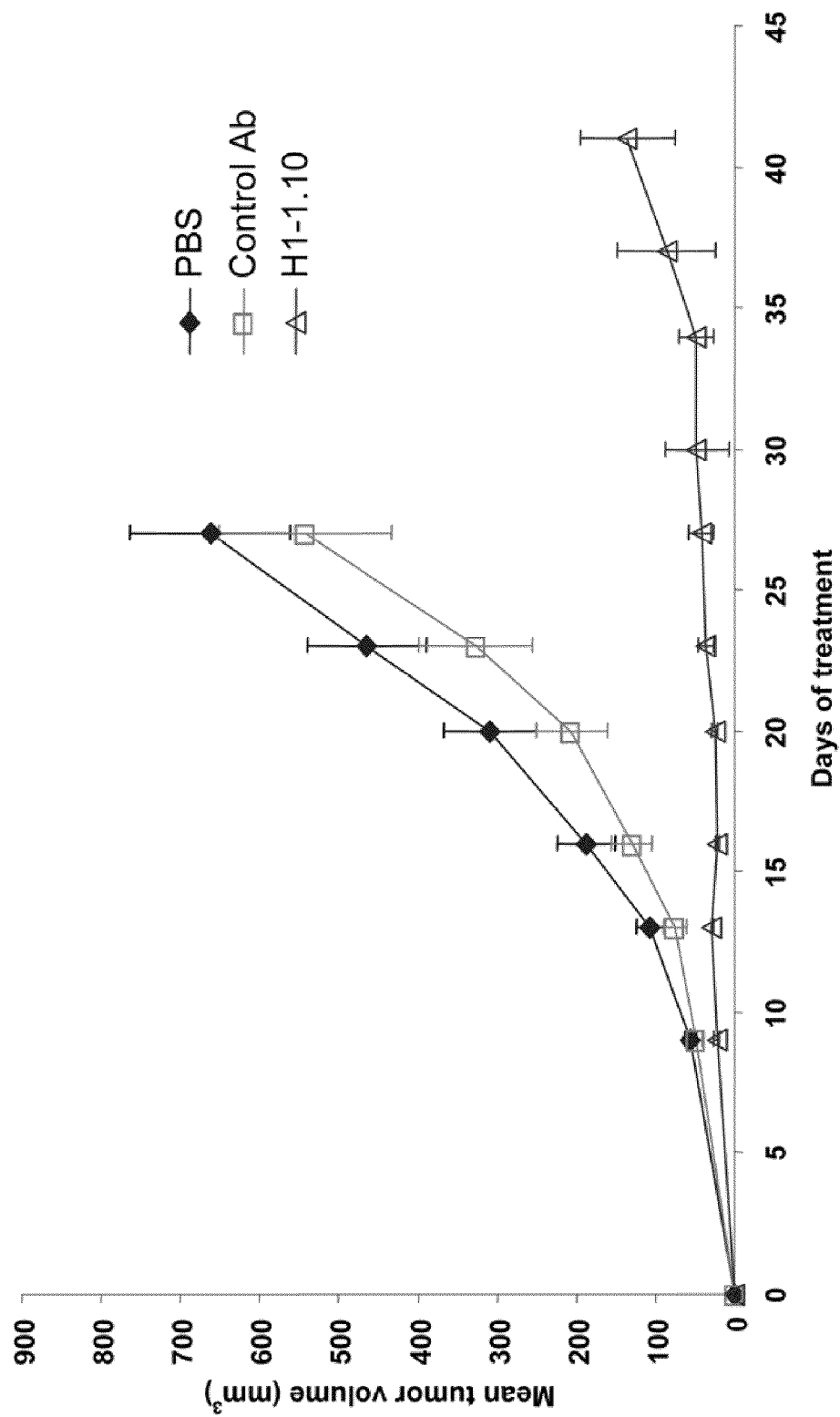

FIG. 14. PSCA MAb H1-1.10 inhibits the subcutaneous growth of human androgen-independent prostate cancer xenografts implanted in SCID mice. UGB-1, human androgen-independent prostate tumor cells (2.0×106 cells/mouse) were injected subcutaneously into male SCID mice. The mice were randomized into groups (n=10 mice in each group) and treatment initiated intraperitoneally (i.p.) on Day 0 with H1-1.10, PBS or control human IgG1 MAb as indicated. Animals were treated twice weekly for a total of 5 doses until study day 16. Tumor growth was monitored using caliper measurements every 3 to 4 days as indicated. Tumor volume was calculated as Width2×Length/2, where width is the smallest dimension and length is the largest. The results show human anti-PSCA monoclonal antibody H1-1.10 significantly inhibited the growth of human prostate cancer xenografts implanted subcutaneously in SCID mice (p<0.01, by Kiruskal-Wallis test).

Figure 15:
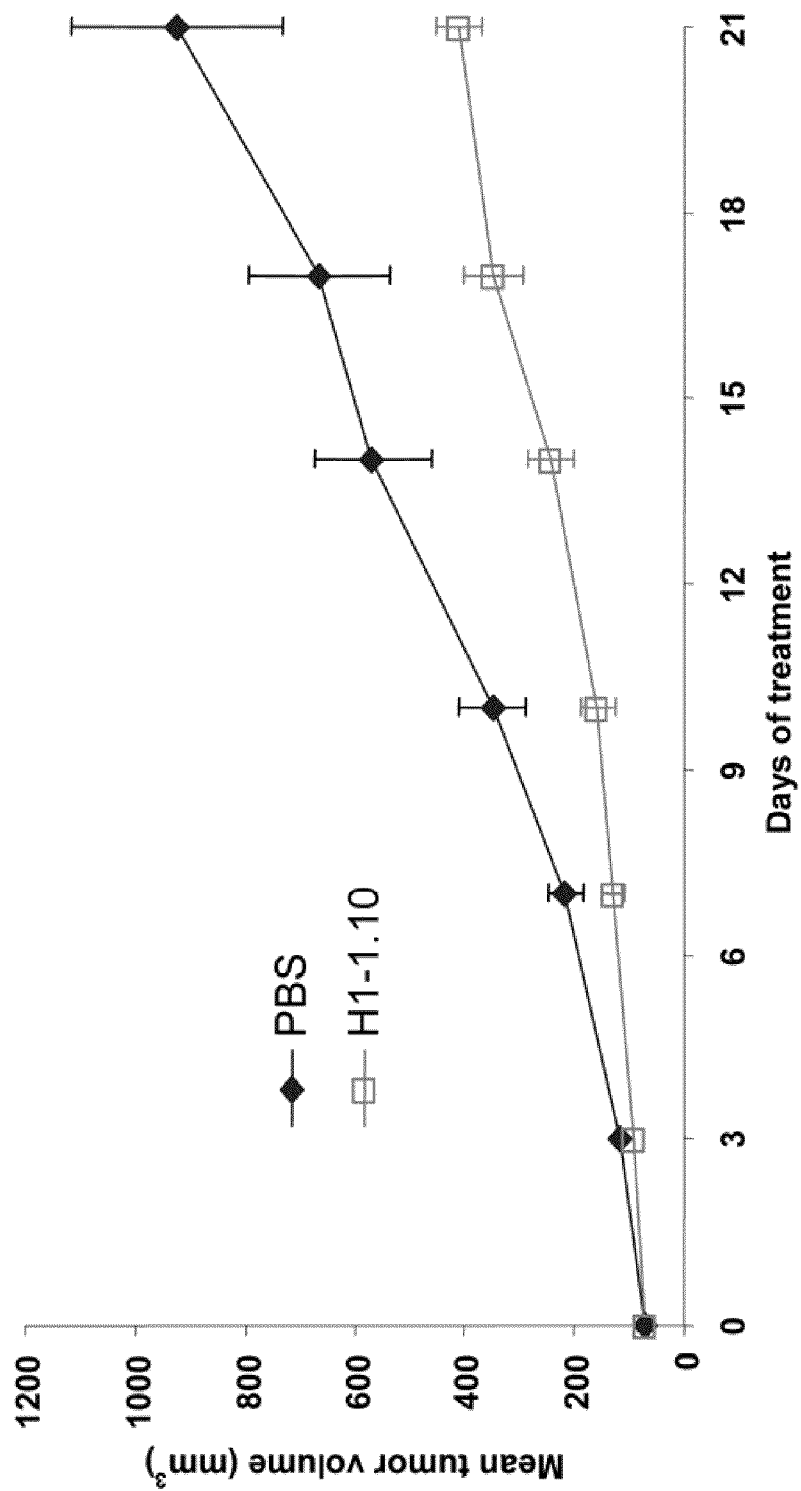

FIG. 15. PSCA MAb H1-1.10 inhibits the subcutaneous growth of established human androgen-independent prostate cancer xenografts in SCID mice. UGB-1, human androgen independent human prostate tumor cells (1.5×$10^6$ cells/mouse) were injected subcutaneously into male SCID mice. When tumors reached about 70 mm3, mice were randomized into groups (n=10 mice in each group) and treatment initiated intraperitoneally (i.p.) on Day 0 with H1-1.0 or with vehicle control as indicated. Animals were treated twice weekly for a total of 7 doses until study day 21. Tumor growth was monitored using caliper measurements every 3 to 4 days as indicated. Tumor volume was calculated as Width2×Length/2, where width is the smallest dimension and length is the largest. The results show human anti-PSCA monoclonal antibody H1-1.10 significantly inhibited the growth of established human prostate cancer xenografts implanted subcutaneously in SCID mice (p<0.05, by the Student's t-test).

Figure 16:
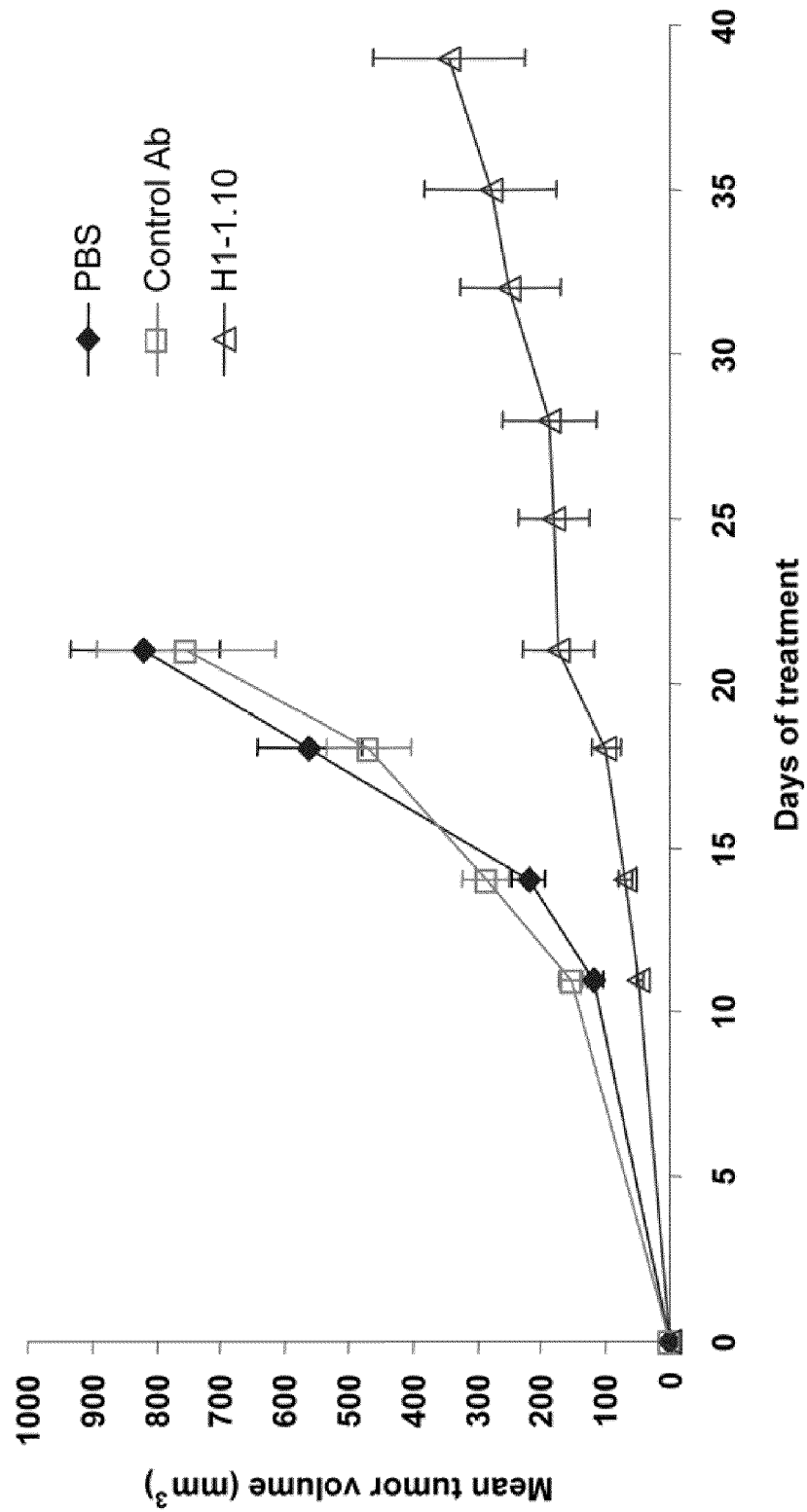

FIG. 16. PSCA MAb H1-1.10 inhibits the subcutaneous growth of human androgen dependent prostate cancer xenografts implanted in SCID mice. LAPC9-AD, human androgen-dependent tumor cells (2.0×$10^6$ cells/mouse) were injected subcutaneously into male SCID mice. The mice were randomized into groups (n=10 mice in each group) and treatment initiated intraperitoneally (i.p.) on Day 0 with H1-1.0 or controls as indicated. Animals were treated twice weekly for a total of 6 doses until study day 18. Tumor growth was monitored using caliper measurements every 3 to 4 days as indicated. Tumor volume was calculated as Width2×Length/2, where width is the smallest dimension and length is the largest. The results show human anti-PSCA monoclonal antibody H1-1.0 significantly inhibited the growth of human prostate cancer xenografts implanted subcutaneously in SCID mice (p<0.01, by Kruskal-Wallis test).

Figure 17:
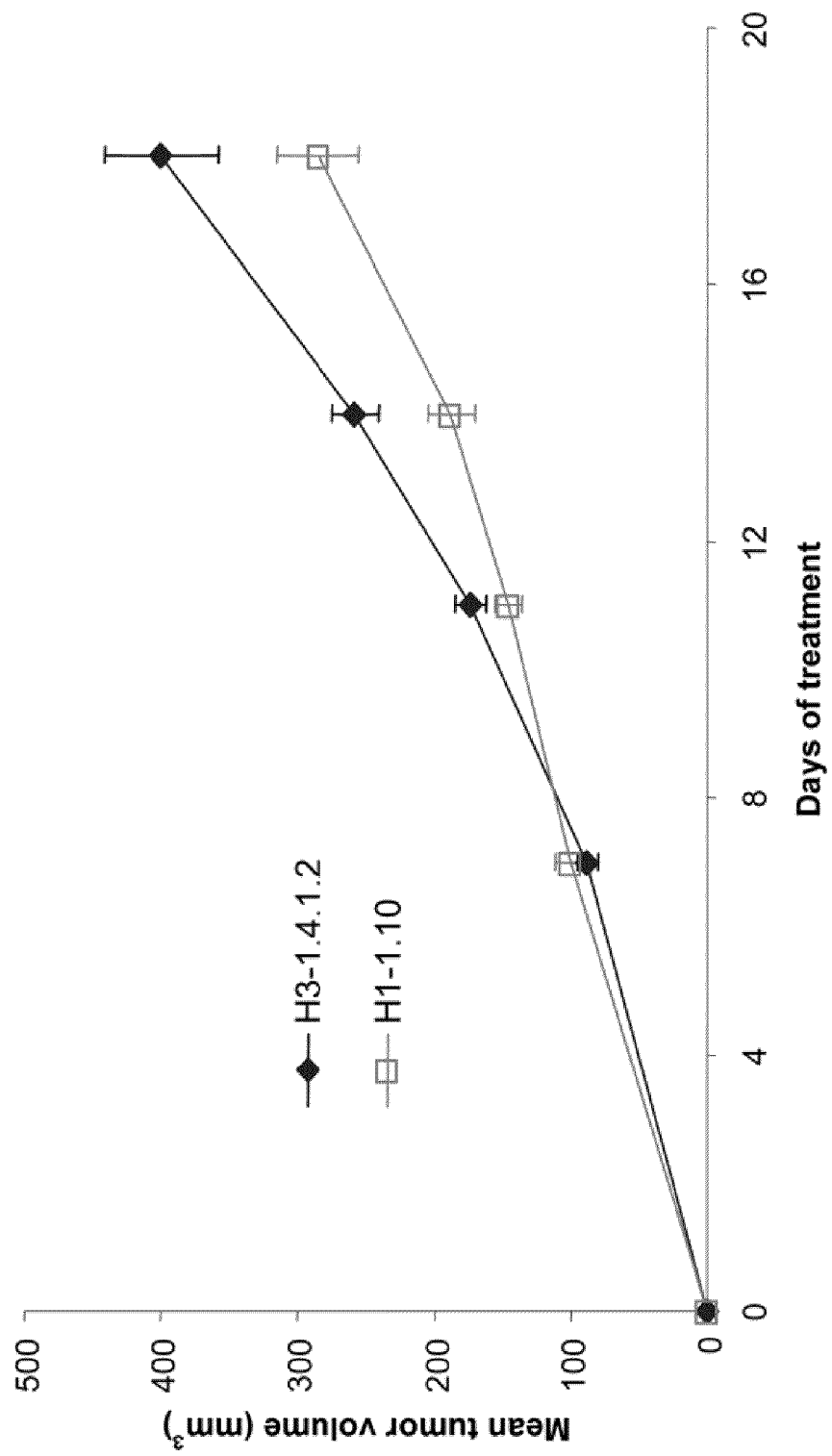

FIG. 17. PSCA MAb H1-1.10 inhibits the subcutaneous growth of human pancreatic cancer xenografts implanted in SCID mice. HPAC, human pancreatic tumor cells (3.0×106 cells/mouse) were injected subcutaneously into male SCID mice. The mice were randomized into groups (n=10 mice in each group) and treatment initiated intraperitoneally (i.p.) on Day 0 with H1-1.10 or control human IgG1 as indicated. Animals were treated twice weekly for a total of 5 doses until study day 18. Tumor growth was monitored using caliper measurements every 3 to 4 days as indicated. Tumor volume was calculated as Width2×Length/2, where width is the smallest dimension and length is the largest. The results show human anti-PSCA monoclonal antibody H1-1.10 inhibited the growth of human pancreatic cancer xenografts implanted subcutaneously in SCID mice (p<0.05, by the Student's t-test).

Figure 18:
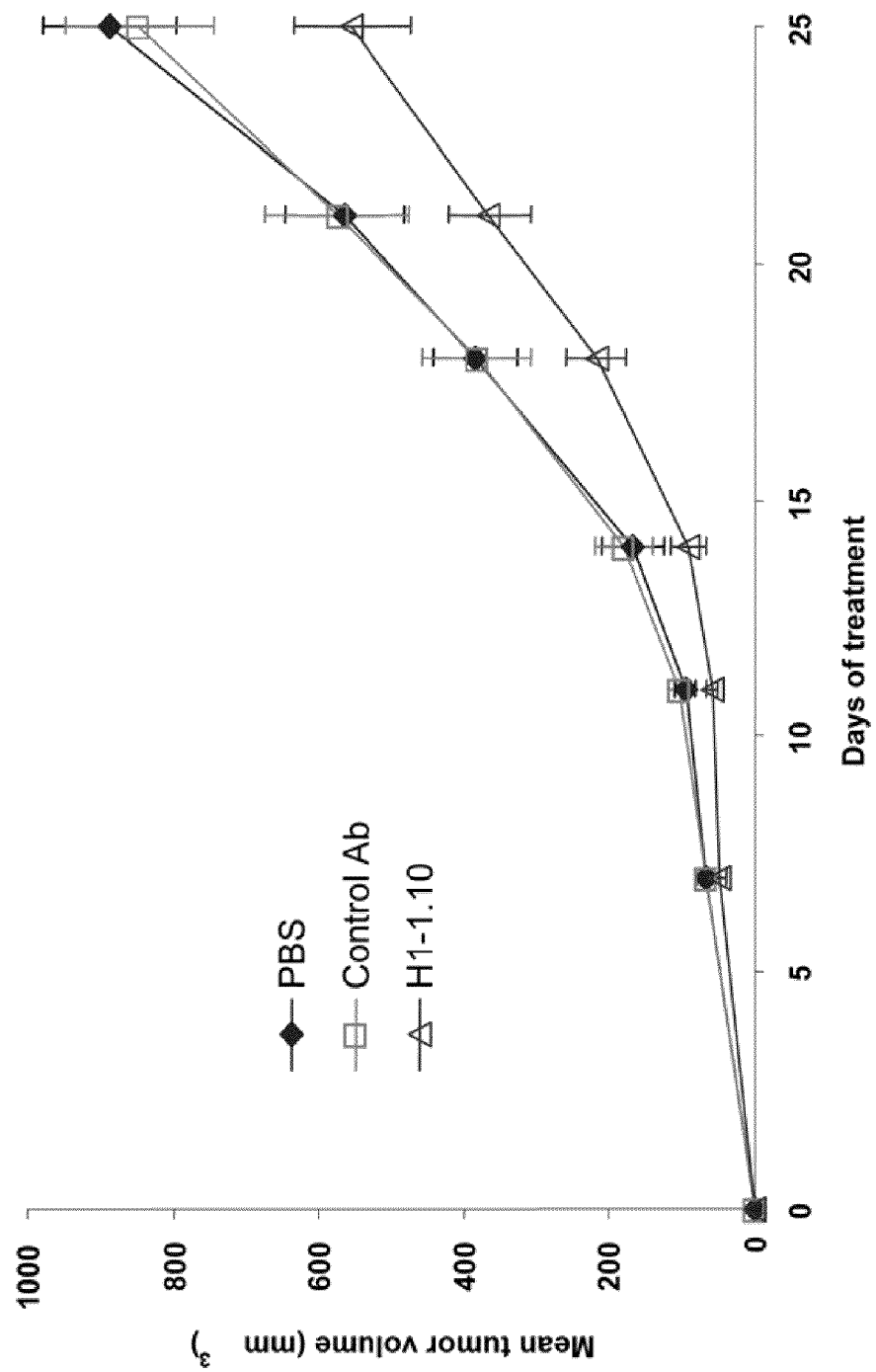

FIG. 18. PSCA MAb H1-1.10 inhibits the subcutaneous growth of human bladder cancer xenografts implanted in SCID mice. Human bladder cancer SW780 cells (2.0×106 cells/mouse) were injected subcutaneously into male SCID mice. The mice were randomized into groups (n=10 mice in each group) and treatment initiated intraperitoneally (i.p.) on Day 0 with H1-1.0, PBS or control human IgG1 MAb as indicated. Animals were treated twice weekly for a total of 6 doses until study day 18. Tumor growth was monitored using caliper measurements every 3 to 4 days as indicated. Tumor volume was calculated as Width2×Length/2, where width is the smallest dimension and length is the largest. The results show human anti-PSCA monoclonal antibody H1-1.0 inhibited the growth of SW780 human bladder cancer xenografts implanted subcutaneously in SCID mice (p<0.05, by Dunnett test).

DETAILED DESCRIPTION OF THE INVENTION

Outline of Sections
I.) Definitions
II.) PSCA Polynucleotides
    II.A.) Uses of PSCA Polynucleotides
        II.A.1.) Monitoring of Genetic Abnormalities
        II.A.2.) Antisense Embodiments
        II.A.3.) Primers and Primer Pairs
        II.A.4.) Isolation of PSCA-Encoding Nucleic Acid Molecules
        II.A.5.) Recombinant Nucleic Acid Molecules and Host-Vector Systems
III.) PSCA-related Proteins
    III.A.) Motif-bearing Protein Embodiments
    III.B.) Expression of PSCA-related Proteins
    III.C.) Modifications of PSCA-related Proteins
    III.D.) Uses of PSCA-related Proteins
IV.) PSCA Antibodies
V.) PSCA Cellular Immune Responses
VI.) PSCA Transgenic Animals
VII.) Methods for the Detection of PSCA
VIII.) Methods for Monitoring the Status of PSCA-related Genes and Their Products
IX.) Identification of Molecules That Interact With PSCA
X.) Therapeutic Methods and Compositions
    X.A.) Anti-Cancer Vaccines
    X.B.) PSCA as a Target for Antibody-Based Therapy
    X.C.) PSCA as a Target for Cellular Immune Responses
        X.C.1. Minigene Vaccines
        X.C.2. Combinations of CTL Peptides with Helper Peptides
        X.C.3. Combinations of CTL Peptides with T Cell Priming Agents
        X.C.4. Vaccine Compositions Comprising DC Pulsed with CTL and/or HTL Peptides
    X.D.) Adoptive Immunotherapy
    X.E.) Administration of Vaccines for Therapeutic or Prophylactic Purposes
XI.) Diagnostic and Prognostic Embodiments of PSCA.
XII.) Inhibition of PSCA Protein Function
    XII.A.) Inhibition of PSCA With Intracellular Antibodies
    XII.B.) Inhibition of PSCA with Recombinant Proteins
    XII.C.) Inhibition of PSCA Transcription or Translation
    XII.D.) General Considerations for Therapeutic Strategies
XIII.) Identification, Characterization and Use of Modulators of PSCA
XIV.) RNAi and Therapeutic use of small interfering RNA (siRNAs)
XV.) KITS/Articles of Manufacture
I.) Definitions Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al, *Molecular Cloning: A Laboratory Manual* 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence PSCA (either by removing the underlying glycosylation site or by deleting the glycosylation by chemical and/or enzymatic means), and/or adding one or more glycosylation sites that are not present in the native sequence PSCA. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a PSCA-related protein). For example, an analog of a PSCA protein can be specifically bound by an antibody or T cell that specifically binds to PSCA.

The term "antibody" is used in the broadest sense unless clearly indicated otherwise. Therefore, an "antibody" can be naturally occurring or man-made such as monoclonal antibodies produced by conventional hybridoma technology. Anti-PSCA antibodies comprise monoclonal and polyclonal antibodies as well as fragments containing the antigen-binding domain and/or one or more complementarity determining regions of these antibodies. As used herein, the term "antibody" refers to any form of antibody or fragment thereof that specifically binds PSCA and/or exhibits the desired biological activity and specifically covers monoclonal antibodies (including full length monoclonal antibodies), polyclonal antibodies, multispecific antibodies (e.g., bispecific antibodies), and antibody fragments so long as they specifically bind PSCA and/or exhibit the desired biological activity. Any specific antibody can be used in the methods and compositions provided herein. Thus, in one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody.

For example, the antibody is a IgG1, IgG2, IgG3, or IgG4 antibody. The antibodies useful in the present methods and compositions can be generated in cell culture, in phage, or in various animals, including but not limited to cows, rabbits, goats, mice, rats, hamsters, guinea pigs, sheep, dogs, cats, monkeys, chimpanzees, apes. Therefore, in one embodiment, an antibody of the present invention is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, *Antibody Production: Essential Techniques* (Wiley, 1997); Shephard, et al., *Monoclonal Antibodies* (Oxford University Press, 2000); Goding, *Monoclonal Antibodies: Principles And Practice* (Academic Press, 1993); *Current Protocols In Immunology* (John Wiley & Sons, most recent edition). An antibody of the present invention can be modified by recombinant means to increase greater efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. Nos 5,624,821, 6,194,551, Application No. WO 9958572; and Angal, et al., *Mol. Immunol.* 30: 105-08 (1993). The modification in amino acids includes deletions, additions, substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to normal or defective PSCA. See e.g., *Antibody Engineering: A Practical Approach* (Oxford University Press, 1996). Suitable antibodies with the desired biologic activities can be identified the following in vitro assays including but not limited to: proliferation, migration, adhesion, soft agar growth, angiogenesis, cell-cell communication, apoptosis, transport, signal transduction, and the following in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays. They can also be used to quantify the PSCA or its receptor.

An "antibody fragment" is defined as at least a portion of the variable region of the immunoglobulin molecule that binds to its target, i.e., the antigen-binding region. In one embodiment it specifically covers single anti-PSCA antibodies and clones thereof (including agonist, antagonist and neutralizing antibodies) and anti-PSCA antibody compositions with polyepitopic specificity. The antibody of the present methods and compositions can be monoclonal or polyclonal. An antibody can be in the form of an antigen binding antibody fragment including a Fab fragment, F(ab')$_2$ fragment, a single chain variable region, and the like. Fragments of intact molecules can be generated using methods well known in the art and include enzymatic digestion and recombinant means.

As used herein, any form of the "antigen" can be used to generate an antibody that is specific for PSCA. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids. In one embodiment, the antibody of the methods and compositions herein specifically bind at least a portion of the extracellular domain of the PSCA of interest.

The antibodies or antigen binding fragments thereof provided herein may be conjugated to a "bioactive agent." As used herein, the term "bioactive agent" refers to any synthetic or naturally occurring compound that binds the antigen and/or enhances or mediates a desired biological effect to enhance cell-killing toxins.

In one embodiment, the binding fragments useful in the present invention are biologically active fragments. As used herein, the term "biologically active" refers to an antibody or antibody fragment that is capable of binding the desired the antigenic epitope and directly or indirectly exerting a biologic effect. Direct effects include, but are not limited to the modulation, stimulation, and/or inhibition of a growth signal, the modulation, stimulation, and/or inhibition of an anti-apoptotic signal, the modulation, stimulation, and/or inhibition of an apoptotic or necrotic signal, modulation, stimulation, and/or inhibition the ADCC cascade, and modulation, stimulation, and/or inhibition the CDC cascade.

"Bispecific" antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al., *Nature* 305:537-39 (1983). Alternatively, bispecific antibodies can be prepared using chemical linkage. See, e.g., Brennan, et al., *Science* 229:81 (1985). Bispecific antibodies include bispecific antibody fragments. See, e.g., Hollinger, et al., *Proc. Natl. Acad. Sci. U.S.A.* 90:6444-48 (1993), Gruber, et al., *J. Immunol.* 152:5368 (1994).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison et al., *Proc. Natl. Acad. Sci. USA* 81: 6851-6855 (1984)).

The term "Chemotherapeutic Agent" refers to all chemical compounds that are effective in inhibiting tumor growth. Non-limiting examples of chemotherapeutic agents include alkylating agents; for example, nitrogen mustards, ethyleneimine compounds and alkyl sulphonates; antimetabolites; for example, folic acid, purine or pyrimidine antagonists; mitotic inhibitors; for example, vinca alkaloids and derivatives of podophyllotoxin, cytotoxic antibiotics, compounds that damage or interfere with DNA expression, and growth factor receptor antagonists. In addition, chemotherapeutic agents include cytotoxic agents (as defined herein), antibodies, biological molecules and small molecules.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

A "combinatorial library" is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Numerous chemical compounds are synthesized through such combinatorial mixing of chemical building blocks (Gallop et al., *J. Med. Chem.* 37(9): 1233-1251 (1994)).

Preparation and screening of combinatorial libraries is well known to those of skill in the art. Such combinatorial chemical libraries include, but are not limited to, peptide libraries (see, e.g., U.S. Pat. No. 5,010,175, Furka, *Pept. Prot. Res.* 37:487-493 (1991), Houghton et al., *Nature,* 354:84-88 (1991)), peptoids (PCT Publication No. WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with a Beta-D-Glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbarnates (Cho, et al., *Science* 261: 1303 (1993)), and/or peptidyl phosphonates (Campbell et al., *J. Org. Chem.* 59:658 (1994)). See, generally, Gordon et al., *J. Med. Chem.* 37:1385 (1994), nucleic acid libraries (see, e.g., Stratagene, Corp.), peptide nucleic acid libraries (see, e.g., U.S. Pat. No. 5,539,083), antibody libraries (see, e.g., Vaughn et al., *Nature Biotechnology* 14(3): 309-314 (1996), and PCT/US96/10287), carbohydrate libraries (see, e.g., Liang et al., *Science* 274:1520-1522 (1996), and U.S. Pat. No. 5,593,853), and small organic molecule libraries (see, e.g., benzodiazepines, Baum, *C&EN, Jan* 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514; and the like).

Devices for the preparation of combinatorial libraries are commercially available (see, e.g., 357 NIPS, 390 NIPS, Advanced Chem Tech, Louisville Ky.; Symphony, Rainin, Woburn, Mass.; 433A, Applied Biosystems, Foster City, Calif.; 9050, Plus, Millipore, Bedford, NIA). A number of well-known robotic systems have also been developed for solution phase chemistries. These systems include automated workstations such as the automated synthesis apparatus developed by Takeda Chemical Industries, LTD. (Osaka, Japan) and many robotic systems utilizing robotic arms (Zymate H, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J.; Asinex, Moscow, RU; Tripos, Inc., St. Louis, Mo.; ChemStar, Ltd, Moscow, RU; 3D Pharmaceuticals, Exton, Pa.; Martek Biosciences, Columbia, Md.; etc.).

As used herein, the term "conservative substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., *Molecular Biology Of The Gene*, The Benjamin/Cummings Pub. Co., p. 224 (4th Edition 1987)). Such exemplary substitutions are preferably made in accordance with those set forth in Table(s) III(a-b). For example, such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III(a) herein; pages 13-15 *Biochemistry* 2nd ED. Lubert Stryer ed (Stanford University); Henikoff et al., *PNAS* 1992 Vol 89 10915-10919; Lei et al., *J Biol Chem* 1995 May 19; 270(20):11882-6). Other substitutions are also permissible and may be determined empirically or in accord with known conservative substitutions.

The term "cytotoxic agent" refers to a substance that inhibits or prevents the expression activity of cells, function of cells and/or causes destruction of cells. The term is intended to include radioactive isotopes, chemotherapeutic agents, and toxins such as small molecule toxins or enzymatically active toxins of bacterial, fungal, plant or animal origin, including fragments and/or variants thereof. Examples of cytotoxic agents include, but are not limited to auristatins, auristatin e, auromycins, maytansinoids, yttrium, bismuth, ricin, ricin A-chain, combrestatin, duocarmycins, dolostatins, doxorubicin, daunorubicin, taxol, cisplatin, cc 1065, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, retstrictocin, phenomycin, enomycin, curicin, crotin, calicheamicin, Sapaonaria officinalis inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212}$ or $^{213}$, $P^{32}$ and radioactive isotopes of Lu including $Lu^{177}$. Antibodies may also be conjugated to an anticancer pro-drug activating enzyme capable of converting the pro-drug to its active form.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Hollinger et al., Proc. Natl. Acad. Sci. USA 90:6444-48 (1993).

The "gene product" is used herein to indicate a peptide/protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I", etc. In one embodiment, the cancer protein is encoded by a nucleic acid of FIG. 1. The cancer protein can be a fragment, or alternatively, be the full-length protein encoded by nucleic acids of FIG. 1. In one embodiment, a cancer amino acid sequence is used to determine sequence identity or similarity. In another embodiment, the sequences are naturally occurring allelic variants of a protein encoded by a nucleic acid of FIG. 1. In another embodiment, the sequences are sequence variants as further described herein.

"Heteroconjugate" antibodies are useful in the present methods and compositions. As used herein, the term "heteroconjugate antibody" refers to two covalently joined antibodies. Such antibodies can be prepared using known methods in synthetic protein chemistry, including using crosslinking agents. See, e.g., U.S. Pat. No. 4,676,980.

"High throughput screening" assays for the presence, absence, quantification, or other properties of particular nucleic acids or protein products are well known to those of skill in the art. Similarly, binding assays and reporter gene assays are similarly well known. Thus, e.g., U.S. Pat. No. 5,559,410 discloses high throughput screening methods for proteins; U.S. Pat. No. 5,585,639 discloses high throughput screening methods for nucleic acid binding (i.e., in arrays); while U.S. Pat. Nos. 5,576,220 and 5,541,061 disclose high throughput methods of screening for ligand/antibody binding.

In addition, high throughput screening systems are commercially available (see, e.g., Amersham Biosciences, Piscataway, N.J.; Zymark Corp., Hopkinton, Mass.; Air Technical Industries, Mentor, Ohio; Beckman Instruments, Inc. Fullerton, Calif.; Precision Systems, Inc., Natick, Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, e.g., Zymark Corp. provides technical bulletins describing screening systems for detecting the modulation of gene transcription, ligand binding, and the like.

The term "homolog" refers to a molecule which exhibits homology to another molecule, by for example, having sequences of chemical residues that are the same or similar at corresponding positions.

In one embodiment, the antibody provided herein is a "human antibody." As used herein, the term "human antibody" refers to an antibody in which essentially the entire sequences of the light chain and heavy chain sequences, including the complementary determining regions (CDRs), are from human genes. In one embodiment, human monoclonal antibodies are prepared by the trioma technique, the human B-cell technique (see, e.g., Kozbor, et al., Immunol. Today 4: 72 (1983), EBV transformation technique (see, e.g., Cole et al. Monoclonal Antibodies And Cancer Therapy 77-96 (1985)), or using phage display (see, e.g., Marks et al., J. Mol. Biol. 222:581 (1991)). In a specific embodiment, the human antibody is generated in a transgenic mouse. Techniques for making such partially to fully human antibodies are known in the art and any such techniques can be used. According to one particularly preferred embodiment, fully human antibody sequences are made in a transgenic mouse engineered to express human heavy and light chain antibody genes. An exemplary description of preparing transgenic mice that produce human antibodies found in Application No. WO 02/43478 and U.S. Pat. No. 6,657,103 (Abgenix) and its progeny. B cells from transgenic mice that produce the desired antibody can then be fused to make hybridoma cell lines for continuous production of the antibody. See, e.g., U.S. Pat. Nos. 5,569,825; 5,625,126; 5,633,425; 5,661,016; and 5,545,806; and Jakobovits, Adv. Drug Del. Rev. 31:33-42 (1998); Green, et al., J. Exp. Med. 188:483-95 (1998).

"Human Leukocyte Antigen" or "HLA" is a human class I or class II Major Histocompatibility Complex (MHC) protein (see, e.g., Stites, et al., Immunology, 8th ED., Lange Publishing, Los Altos, Calif. (1994).

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. See e.g., Cabilly U.S. Pat. No. 4,816,567; Queen et al. (1989) Proc. Nat'l Acad. Sci. USA 86:10029-10033; and Antibody Engineering: A Practical Approach (Oxford University Press 1996).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/100 μg/ml ssDNA, in which temperatures for hybridization are above 37° C. and temperatures for washing in 0.1×SSC/0.1% SDS are above 55° C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the PSCA genes or that encode polypeptides other than PSCA gene product or fragments thereof. A skilled artisan can readily employ nucleic acid isolation procedures to obtain an isolated PSCA polynucleotide. A protein is said to be "isolated," for example, when physical, mechanical or chemical methods are employed to remove the PSCA proteins from cellular constituents that are normally associated with the protein. A skilled artisan can readily employ standard purification methods to obtain an isolated PSCA protein. Alternatively, an isolated protein can be prepared by chemical means.

Suitable "labels" include radionuclides, enzymes, substrates, cofactors, inhibitors, fluorescent moieties, chemiluminescent moieties, magnetic particles, and the like. Patents teaching the use of such labels include U.S. Pat. Nos. 3,817, 837; 3,850,752; 3,939,350; 3,996,345; 4,277,437; 4,275,149; and 4,366,241. In addition, the antibodies provided herein can be useful as the antigen-binding component of fluorobodies. See e.g., Zeytun et al., *Nat. Biotechnol.* 21:1473-79 (2003).

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage TxNxM+under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "modulator" or "test compound" or "drug candidate" or grammatical equivalents as used herein describe any molecule, e.g., protein, oligopeptide, small organic molecule, polysaccharide, polynucleotide, etc., to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways. In one embodiment, the modulator suppresses a cancer phenotype, e.g. to a normal tissue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or, has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, can be linked to each other or to other amino acids to create a longer peptide/protein. The modulatory peptides can be digests of naturally occurring proteins as is outlined above, random peptides, or "biased" random peptides. In a preferred embodiment, peptide/protein-based modulators are antibodies, and fragments thereof, as defined herein.

Modulators of cancer can also be nucleic acids. Nucleic acid modulating agents can be naturally occurring nucleic acids, random nucleic acids, or "biased" random nucleic acids. For example, digests of prokaryotic or eukaryotic genomes can be used in an approach analogous to that outlined above for proteins.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. In one embodiment, the polyclonal antibody contains a plurality of monoclonal antibodies with different epitope specificities, affinities, or avidities within a single antigen that contains multiple antigenic epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256: 495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352: 624-628 (1991) and Marks et al., *J. Mol. Biol.* 222: 581-597 (1991), for example. These monoclonal antibodies will usually bind with at least a Kd of about 1 µM, more usually at least about 300 nM, typically at least about 30 nM, preferably at least about 10 nM, more preferably at least about 3 nM or better, usually determined by ELISA.

A "motif", as in biological motif of a PSCA-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues. Frequently occurring motifs are set forth in Table V.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxyribonucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 1, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. Alternatively, in another embodiment, the primary anchor residues of a peptide binds an HLA class II molecule are spaced relative to each other, rather than to the termini of a peptide, where the peptide is generally of at least 9 amino acids in length. The primary anchor positions for each motif and supermotif are set forth in Table IV(a). For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

"Radioisotopes" include, but are not limited to the following (non-limiting exemplary uses are also set forth in Table IV(I)).

By "randomized" or grammatical equivalents as herein applied to nucleic acids and proteins is meant that each nucleic acid and peptide consists of essentially random nucleotides and amino acids, respectively. These random peptides (or nucleic acids, discussed herein) can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, a library is "fully randomized," with no sequence preferences or constants at any position. In another embodiment, the library is a "biased random" library. That is, some positions within the sequence either are held constant, or are selected from a limited number of possibilities. For example, the nucleotides or amino acid residues are randomized within a defined class, e.g., of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

A "recombinant" DNA or RNA molecule is a DNA or RNA molecule that has been subjected to molecular manipulation in vitro.

As used herein, the term "single-chain Fv" or "scFv" or "single chain" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun, *The Pharmacology Of Monoclonal Antibodies*, vol. 113, Rosenburg and Moore eds. Springer-Verlag, New York, pp. 269-315 (1994).

Non-limiting examples of "small molecules" include compounds that bind or interact with PSCA, ligands including hormones, neuropeptides, chemokines, odorants, phospholipids, and functional equivalents thereof that bind and preferably inhibit PSCA protein function. Such non-limiting small molecules preferably have a molecular weight of less than about 10 kDa, more preferably below about 9, about 8, about 7, about 6, about 5 or about 4 kDa. In certain embodiments, small molecules physically associate with, or bind, PSCA protein; are not found in naturally occurring metabolic pathways; and/or are more soluble in aqueous than non-aqueous solutions.

As used herein, the term "specific" refers to the selective binding of the antibody to the target antigen epitope. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific. In one embodiment, a specific antibody is one that only binds the PSCA antigen, but does not bind to the irrelevant antigen. In another embodiment, a specific antibody is one that binds human PSCA antigen but does not bind a non-human PSCA antigen with 70%, 75%, 80%, 85%, 90%, 91%, 92%, 93%, 94%, 95%, 96%, 97%, 98%, 99% or greater amino acid homology with the PSCA antigen. In another embodiment, a specific antibody is one that binds human PSCA antigen and binds murine PSCA antigen, but with a higher degree of binding the human antigen. In another embodiment, a specific antibody is one that binds human PSCA antigen and binds primate PSCA antigen, but with a higher degree of binding the human antigen. In another embodiment, the specific antibody binds to human PSCA antigen and any non-human PSCA antigen, but with a higher degree of binding the human antigen or any combination thereof.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C. "Moderately stringent conditions" are described by, but not limited to, those in Sambrook et al, *Molecular Cloning: A Laboratory Manual*, New York: Cold Spring Harbor Press, 1989, and include the use of washing solution and hybridization conditions (e.g., temperature, ionic strength and % SDS) less stringent than those described above. An example of moderately stringent conditions is overnight incubation at 65° C. in a solution comprising: 1% bovine serum albumin, 0.5M sodium phosphate pH 7.5, 1.25 mM EDTA, and 7% SDS 5×SSC (150 mM NaCl, 15 mM trisodium citrate), followed by washing the filters in 2×SSC/1% SDS at 50° C. and 0.2×SSC/0.1% SDS at 50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles. Overall phenotypic frequencies of HLA-supertypes in different ethnic populations are set forth in Table IV (f). The non-limiting constituents of various supertypes are as follows:

A2: A*0201, A*0202, A*0203, A*0204, A*0205, A*0206, A*6802, A*6901, A*0207

A3: A3, A11, A31, A*3301, A*6801, A*0301, A*1101, A*3101

B7: B7, B*3501-03, B*51, B*5301, B*5401, B*5501, B*5502, B*5601, B*6701, B*7801, B*0702, B*5101, B*5602

B44: B*3701, B*4402, B*4403, B*60 (B*4001), B61 (B*4006)

A1: A*0102, A*2604, A*3601, A*4301, A*8001

A24: A*24, A*30, A*2403, A*2404, A*3002, A*3003

B27: B*1401-02, B*1503, B*1509, B*1510, B*1518, B*3801-02, B*3901, B*3902, B*3903-04, B*4801-02, B*7301, B*2701-08

B58: B*1516, B*1517, B*5701, B*5702, B58

B62: B*4601, B52, B*1501 (B62), B*1502 (B75), B*1513 (B77)

Calculated population coverage afforded by different HLA-supertype combinations are set forth in Table IV(g).

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred out albeit not a requirement for a treatment act.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1-150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the PSCA protein shown in FIG. 1. An analog is an example of a variant protein. Splice isoforms and single nucleotides polymorphisms (SNPs) are further examples of variants.

The "PSCA-related proteins" of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different PSCA proteins or fragments thereof, as well as fusion proteins of a PSCA protein and a heterologous polypeptide are also included. Such PSCA proteins are collectively referred to as the PSCA-related proteins, the proteins of the invention, or PSCA. The term "PSCA-related protein" refers to a polypeptide fragment or a PSCA protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 330, 335, 339 or more amino acids.

II.) PSCA Polynucleotides

One aspect of the invention provides polynucleotides corresponding or complementary to all or part of a PSCA gene, mRNA, and/or coding sequence, preferably in isolated form, including polynucleotides encoding a PSCA-related protein and fragments thereof, DNA, RNA, DNA/RNA hybrid, and related molecules, polynucleotides or oligonucleotides complementary to a PSCA gene or mRNA sequence or a part thereof, and polynucleotides or oligonucleotides that hybridize to a PSCA gene, mRNA, or to a PSCA encoding polynucleotide (collectively, "PSCA polynucleotides"). In all instances when referred to in this section, T can also be U in FIG. 1.

Embodiments of a PSCA polynucleotide include: a PSCA polynucleotide having the sequence shown in FIG. 1, the nucleotide sequence of PSCA as shown in FIG. 1 wherein T is U; at least 10 contiguous nucleotides of a polynucleotide having the sequence as shown in FIG. 1; or, at least 10 contiguous nucleotides of a polynucleotide having the sequence as shown in FIG. 1 where T is U.

Polynucleotides encoding relatively long portions of a PSCA protein are also within the scope of the invention. For example, polynucleotides encoding from about amino acid 1 (or 20 or 30 or 40 etc.) to about amino acid 20, (or 30, or 40 or 50 etc.) of the PSCA protein "or variant" shown in FIG. 1 or FIG. 3 can be generated by a variety of techniques well known in the art. These polynucleotide fragments can include any portion of the PSCA sequence as shown in FIG. 1.

II.A.) Uses of PSCA Polynucleotides

II.A.1. Monitoring of Genetic Abnormalities

The polynucleotides of the preceding paragraphs have a number of different specific uses. The human PSCA gene maps to the chromosomal location set forth in the Example entitled "Chromosomal Mapping of PSCA." For example, because the PSCA gene maps to this chromosome, polynucleotides that encode different regions of the PSCA proteins are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., *Mutat. Res.* 382(3-4): 81-83 (1998); Johansson et al, *Blood* 86(10): 3905-3914 (1995) and Finger et al., *P.N.A.S.* 85(23): 9158-9162 (1988)). Thus, polynucleotides encoding specific regions of the PSCA proteins provide new tools that can be used to delineate, with greater precision than previously possible, cytogenetic abnormalities in the chromosomal region that encodes PSCA that may contribute to the malignant phenotype. In this context, these polynucleotides satisfy a need in the art for expanding the sensitivity of chromosomal screening in order to identify more subtle and less common chromosomal abnormalities (see e.g. Evans et al., *Am. J. Obstet. Gynecol* 171(4): 1055-1057 (1994)).

Furthermore, as PSCA was shown to be highly expressed in prostate and other cancers, PSCA polynucleotides are used in methods assessing the status of PSCA gene products in normal versus cancerous tissues. Typically, polynucleotides that encode specific regions of the PSCA proteins are used to assess the presence of perturbations (such as deletions, insertions, point mutations, or alterations resulting in a loss of an antigen etc.) in specific regions of the PSCA gene, such as regions containing one or more motifs. Exemplary assays include both RT-PCR assays as well as single-strand conformation polymorphism (SSCP) analysis (see, e.g., Marrogi et al., *J. Cutan. Pathol.* 26(8): 369-378 (1999), both of which utilize polynucleotides encoding specific regions of a protein to examine these regions within the protein.

II.A.2. Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of PSCA. For example, antisense molecules can be RNAs or other molecules, including peptide nucleic acids (PNAs) or non-nucleic acid molecules such as phosphorothioate derivatives that specifically bind DNA or RNA in a base pair-dependent manner. A skilled artisan can readily obtain these classes of nucleic acid molecules using the PSCA polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., PSCA. See for example, Jack Cohen, *Oligodeoxynucleotides, Antisense Inhibitors of Gene Expression*, CRC Press, 1989; and Synthesis 1:1-5 (1988). The PSCA antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See, e.g., Iyer, R. P. et al, *J. Org. Chem.* 55:4693-4698 (1990); and Iyer, R. P. et al., *J. Am. Chem. Soc.* 112:1253-1254 (1990). Additional PSCA antisense oligonucleotides of the present invention include morpholino antisense oligonucleotides known in the art (see, e.g., Partridge et al., 1996, *Antisense & Nucleic Acid Drug Development* 6: 169-175).

The PSCA antisense oligonucleotides of the present invention typically can be RNA or DNA that is complementary to and stably hybridizes with the first 100 5' codons or last 100 3' codons of a PSCA genomic sequence or the corresponding mRNA. Absolute complementarity is not required, although high degrees of complementarity are preferred. Use of an oligonucleotide complementary to this region allows for the selective hybridization to PSCA mRNA and not to mRNA specifying other regulatory subunits of protein kinase. In one embodiment, PSCA antisense oligonucleotides of the present invention are 15 to 30-mer fragments of the antisense DNA molecule that have a sequence that hybridizes to PSCA mRNA. Optionally, PSCA antisense oligonucleotide is a 30-mer oligonucleotide that is complementary to a region in the first 10 5' codons or last 10 3' codons of PSCA. Alternatively, the antisense molecules are modified to employ ribozymes in the inhibition of PSCA expression, see, e.g., L. A. Couture & D. T. Stinchcomb; *Trends Genet* 12: 510-515 (1996).

II.A.3. Primers and Primer Pairs

Further specific embodiments of these nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a PSCA polynucleotide in a sample and as a means for detecting a cell expressing a PSCA protein.

Examples of such probes include polypeptides comprising all or part of the human PSCA cDNA sequence shown in FIG. 1. Examples of primer pairs capable of specifically amplifying PSCA mRNAs are also described in the Examples. As will be understood by the skilled artisan, a great many different primers and probes can be prepared based on the sequences provided herein and used effectively to amplify and/or detect a PSCA mRNA.

The PSCA polynucleotides of the invention are useful for a variety of purposes, including but not limited to their use as probes and primers for the amplification and/or detection of the PSCA gene(s), mRNA(s), or fragments thereof, as reagents for the diagnosis and/or prognosis of prostate cancer and other cancers; as coding sequences capable of directing the expression of PSCA polypeptides; as tools for modulating or inhibiting the expression of the PSCA gene(s) and/or translation of the PSCA transcript(s); and as therapeutic agents.

The present invention includes the use of any probe as described herein to identify and isolate a PSCA or PSCA related nucleic acid sequence from a naturally occurring source, such as humans or other mammals, as well as the isolated nucleic acid sequence per se, which would comprise all or most of the sequences found in the probe used.

II.A.4. Isolation of PSCA-Encoding Nucleic Acid Molecules

The PSCA cDNA sequences described herein enable the isolation of other polynucleotides encoding PSCA gene product(s), as well as the isolation of polynucleotides encoding PSCA gene product homologs, alternatively spliced isoforms, allelic variants, and mutant forms of a PSCA gene product as well as polynucleotides that encode analogs of PSCA-related proteins. Various molecular cloning methods that can be employed to isolate full length cDNAs encoding a PSCA gene are well known (see, for example, Sambrook, J. et al., *Molecular Cloning: A Laboratory Manual*, 2d edition, Cold Spring Harbor Press, New York, 1989; *Current Protocols in Molecular Biology*. Ausubel et al., Eds., Wiley and Sons, 1995). For example, lambda phage cloning methodologies can be conveniently employed, using commercially available cloning systems (e.g., Lambda ZAP Express, Stratagene). Phage clones containing PSCA gene cDNAs can be identified by probing with a labeled PSCA cDNA or a fragment thereof. For example, in one embodiment, a PSCA cDNA (e.g., FIG. 1) or a portion thereof can be synthesized and used as a probe to retrieve overlapping and full-length cDNAs corresponding to a PSCA gene. A PSCA gene itself can be isolated by screening genomic DNA libraries, bacterial artificial chromosome libraries (BACs), yeast artificial chromosome libraries (YACs), and the like, with PSCA DNA probes or primers.

II.A.5. Recombinant Nucleic Acid Molecules and Host-Vector Systems

The invention also provides recombinant DNA or RNA molecules containing a PSCA polynucleotide, a fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a PSCA polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of PSCA or a fragment, analog or homolog thereof can be used to generate PSCA proteins or fragments thereof using any number of host-vector systems routinely used and widely known in the art.

A wide range of host-vector systems suitable for the expression of PSCA proteins or fragments thereof are available, see for example, Sambrook et al., 1989, supra; *Current Protocols in Molecular Biology*, 1995, supra). Preferred vectors for mammalian expression include but are not limited to pcDNA 3.1 myc-His-tag (Invitrogen) and the retroviral vector pSRωtkneo (Muller et al., 1991, MCB 11:1785). Using these expression vectors, PSCA can be expressed in several prostate cancer and non-prostate cell lines, including for example 293, 293T, rat-1, NIH 3T3 and TsuPr1. The host-vector systems of the invention are useful for the production of a PSCA protein or fragment thereof. Such host-vector systems can be employed to study the functional properties of PSCA and PSCA mutations or analogs.

Recombinant human PSCA protein or an analog or homolog or fragment thereof can be produced by mammalian cells transfected with a construct encoding a PSCA-related nucleotide. For example, 293T cells can be transfected with an expression plasmid encoding PSCA or fragment, analog or homolog thereof, a PSCA-related protein is expressed in the 293T cells, and the recombinant PSCA protein is isolated using standard purification methods (e.g., affinity purification using anti-PSCA antibodies). In another embodiment, a PSCA coding sequence is subcloned into the retroviral vector pSRαMSVtkneo and used to infect various mammalian cell lines, such as NIH 3T3, TsuPr1, 293 and rat-1 in order to establish PSCA expressing cell lines. Various other expression systems well known in the art can also be employed. Expression constructs encoding a leader peptide joined in frame to a PSCA coding sequence can be used for the generation of a secreted form of recombinant PSCA protein.

As discussed herein, redundancy in the genetic code permits variation in PSCA gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET such as at URL dna.affrc.go.jp/~nakamura/codon.html.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell. Biol.*, 9:5073-5080 (1989). Skilled artisans understand that the general rule that eukaryotic ribosomes initiate translation exclusively at the 5' proximal AUG codon is abrogated only under rare conditions (see, e.g., Kozak *PNAS* 92(7): 2662-2666, (1995) and Kozak *NAR* 15(20): 8125-8148 (1987)).

III.) PSCA-related Proteins

Another aspect of the present invention provides PSCA-related proteins. Specific embodiments of PSCA proteins comprise a polypeptide having all or part of the amino acid sequence of human PSCA as shown in FIG. 1, preferably FIG. 1A. Alternatively, embodiments of PSCA proteins comprise variant, homolog or analog polypeptides that have alterations in the amino acid sequence of PSCA shown in FIG. 1.

Embodiments of a PSCA polypeptide include: a PSCA polypeptide having a sequence shown in FIG. 1, a peptide sequence of a PSCA as shown in FIG. 1 wherein T is U; at least 10 contiguous nucleotides of a polypeptide having the sequence as shown in FIG. 1; or, at least 10 contiguous peptides of a polypeptide having the sequence as shown in FIG. 1 where T is U.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions.

Embodiments of the invention disclosed herein include a wide variety of art-accepted variants or analogs of PSCA proteins such as polypeptides having amino acid insertions, deletions and substitutions. PSCA variants can be made using methods known in the art such as site-directed mutagenesis, alanine scanning, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., *Gene*, 34:315 (1985)), restriction selection mutagenesis (Wells et al., *Philos. Trans. R. Soc. London Ser.A*, 317:415 (1986)) or other known techniques can be performed on the cloned DNA to produce the PSCA variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, *J. Mol. Biol.*, 150:1 (1976)). If alanine substitution does not yield adequate amounts of variant, an isosteric amino acid can be used.

As defined herein, PSCA variants, analogs or homologs, have the distinguishing attribute of having at least one epitope that is "cross reactive" with a PSCA protein having an amino acid sequence of FIG. 1. As used in this sentence, "cross reactive" means that an antibody or T cell that specifically binds to a PSCA variant also specifically binds to a PSCA protein having an amino acid sequence set forth in FIG. 1. A polypeptide ceases to be a variant of a protein shown in FIG. 1, when it no longer contains any epitope capable of being recognized by an antibody or T cell that specifically binds to the starting PSCA protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., *J. Immunol* 2000 165(12): 6949-6955; Hebbes et al., *Mol Immunol* (1989) 26(9):865-73; Schwartz et al., *J Immunol* (1985) 135(4):2598-608.

Other classes of PSCA-related protein variants share 70%, 75%, 80%, 85% or 90% or more similarity with an amino acid sequence of FIG. 1, or a fragment thereof. Another specific class of PSCA protein variants or analogs comprises one or more of the PSCA biological motifs described herein or presently known in the art. Thus, encompassed by the present invention are analogs of PSCA fragments (nucleic or amino acid) that have altered functional (e.g. immunogenic) properties relative to the starting fragment. It is to be appreciated that motifs now or which become part of the art are to be applied to the nucleic or amino acid sequences of FIG. 1.

As discussed herein, embodiments of the claimed invention include polypeptides containing less than the full amino acid sequence of a PSCA protein shown in FIG. 1. For example, representative embodiments of the invention comprise peptides/proteins having any 4, 5, 6, 7, 8, 9, 10, 11, 12, 13, 14, 15 or more contiguous amino acids of a PSCA protein shown in FIG. 1.

PSCA-related proteins are generated using standard peptide synthesis technology or using chemical cleavage methods well known in the art. Alternatively, recombinant methods can be used to generate nucleic acid molecules that encode a PSCA-related protein. In one embodiment, nucleic acid molecules provide a means to generate defined fragments of a PSCA protein (or variants, homologs or analogs thereof).

III.A.) Motif-bearing Protein Embodiments

Additional illustrative embodiments of the invention disclosed herein include PSCA polypeptides comprising the amino acid residues of one or more of the biological motifs contained within a PSCA polypeptide sequence set forth in FIG. 1. Various motifs are known in the art, and a protein can be evaluated for the presence of such motifs by a number of publicly available Internet sites (see, e.g., URL addresses: pfam.wustl.edu/; searchlauncher.bcm.tmc.edu/seq-search/ struc-predict.html; psort.ims.u-tokyo.ac.jp/; cbs.dtu.dk/; ebi-.ac.uk/interpro/scan.html; expasy.ch/tools/scnpsit1.html; Epimatrix™ and Epimer™, Brown University, brown.edu/Research/TB-HIV_Lab/epimatrix/epimatrix.html; and BIMAS, bimas.dcrt.nih.gov/.).

Motif bearing subsequences of all PSCA variant proteins are set forth and identified in Tables V-XVIII and XXII-LI.

Table IV(h) sets forth several frequently occurring motifs based on pfam searches (see URL address pfam.wustl.edu/). The columns of Table IV(h) list (1) motif name abbreviation, (2) percent identity found amongst the different member of the motif family, (3) motif name or description and (4) most common function; location information is included if the motif is relevant for location.

Polypeptides comprising one or more of the PSCA motifs discussed above are useful in elucidating the specific characteristics of a malignant phenotype in view of the observation that the PSCA motifs discussed above are associated with growth dysregulation and because PSCA is overexpressed in certain cancers (See, e.g., Table I). Casein kinase II, cAMP and camp-dependent protein kinase, and Protein Kinase C, for example, are enzymes known to be associated with the development of the malignant phenotype (see e.g. Chen et al., *Lab Invest.*, 78(2): 165-174 (1998); Gaiddon et al., *Endocrinology* 136(10): 4331-4338 (1995); Hall et al., *Nucleic Acids Research* 24(6): 1119-1126 (1996); Peterziel et al., *Oncogene* 18(46): 6322-6329 (1999) and O'Brian, *Oncol. Rep.* 5(2): 305-309 (1998)). Moreover, both glycosylation and myristoylation are protein modifications also associated with cancer and cancer progression (see e.g. Dennis et al., *Biochem. Biophys. Acta* 1473(1):21-34 (1999); Raju et al., *Exp. Cell Res.* 235(1): 145-154 (1997)). Amidation is another protein modification also associated with cancer and cancer progression (see e.g. Treston et al., *J. Natl. Cancer Inst. Monogr.* (13): 169-175 (1992)).

In another embodiment, proteins of the invention comprise one or more of the immunoreactive epitopes identified in accordance with art-accepted methods, such as the peptides set forth in Tables V-XVIII and XXII-LI. CTL epitopes can be determined using specific algorithms to identify peptides within a PSCA protein that are capable of optimally binding to specified HLA alleles (e.g., Table IV; Epimatrix™ and Epimer™, Brown University, URL brown.edu/Research/TB-HIV_Lab/epimatrix/epimatrix.html; and BIMAS, URL bimas.dcrt.nih.gov/.) Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/supermotifs of Table IV). The epitope is analoged by substituting out an amino acid at one of the specified positions, and replacing it with another amino acid specified for that position. For example, on the basis of residues defined in Table IV, one can substitute out a deleterious residue in favor of any other residue, such as a preferred residue; substitute a less-preferred residue with a preferred residue; or substitute an originally-occurring preferred residue with another preferred residue. Substitutions can occur at primary anchor positions or at other positions in a peptide; see, e.g., Table IV.

A variety of references reflect the art regarding the identification and generation of epitopes in a protein of interest as well as analogs thereof. See, for example, WO 97/33602 to Chesnut et al.; Sette, *Immunogenetics* 1999 50(3-4): 201-212; Sette et al., *J. Immunol.* 2001 166(2): 1389-1397; Sidney et al., *Hum. Immunol.* 1997 58(1): 12-20; Kondo et al., *Immunogenetics* 1997 45(4): 249-258; Sidney et al., *J. Immunol.* 1996 157(8): 3480-90; and Falk et al., *Nature* 351: 290-6 (1991); Hunt et al., *Science* 255:1261-3 (1992); Parker et al., *J. Immunol.* 149:3580-7 (1992); Parker et al., *J. Immunol.* 152:163-75 (1994)); Kast et al., 1994 152(8): 3904-12; Borras-Cuesta et al., *Hum. Immunol.* 2000 61(3): 266-278; Alexander et al., *J. Immunol.* 2000 164(3); 164(3): 1625-1633; Alexander et al., *PMID:* 7895164, UI: 95202582; O'Sullivan et al., *J. Immunol.* 1991 147(8): 2663-2669; Alexander et al., *Immunity* 1994 1(9): 751-761 and Alexander et al., *Immunol. Res.* 1998 18(2): 79-92.

Related embodiments of the invention include polypeptides comprising combinations of the different motifs set forth in Table(s) IV(a), IV(b), IV(c), IV(d), and IV(h), and/or, one or more of the predicted CTL epitopes of Tables V-XVIII and XXII-LI, and/or, one or more of the predicted HTL epitopes of Tables XLVIII-LI, and/or, one or more of the T cell binding motifs known in the art. Preferred embodiments contain no insertions, deletions or substitutions either within the motifs or within the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically, the number of N-terminal and/or C-terminal amino acid residues on either side of a motif is between about 1 to about 100 amino acid residues, preferably 5 to about 50 amino acid residues.

PSCA-related proteins are embodied in many forms, preferably in isolated form. A purified PSCA protein molecule will be substantially free of other proteins or molecules that impair the binding of PSCA to antibody, T cell or other ligand. The nature and degree of isolation and purification will depend on the intended use. Embodiments of a PSCA-related proteins include purified PSCA-related proteins and functional, soluble PSCA-related proteins. In one embodiment, a functional, soluble PSCA protein or fragment thereof retains the ability to be bound by antibody, T cell or other ligand.

The invention also provides PSCA proteins comprising biologically active fragments of a PSCA amino acid sequence shown in FIG. 1. Such proteins exhibit properties of the starting PSCA protein, such as the ability to elicit the generation of antibodies that specifically bind an epitope associated with the starting PSCA protein; to be bound by such antibodies; to elicit the activation of HTL or CTL; and/or, to be recognized by HTL or CTL that also specifically bind to the starting protein.

PSCA-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or based on immunogenicity. Fragments that contain such structures are particularly useful in generating sub-unit-specific anti-PSCA antibodies or T cells or in identifying cellular factors that bind to PSCA. For example, hydrophilicity profiles can be generated, and immunogenic peptide fragments identified, using the method of Hopp, T. P. and Woods, K. R., 1981, *Proc. Natl. Acad. Sci. U.S.A.* 78:3824-3828. Hydropathicity profiles can be generated, and immunogenic peptide fragments identified, using the method of Kyte, J. and Doolittle, R. F., 1982, *J. Mol. Biol.* 157:105-132. Percent (%) Accessible Residues profiles can be generated, and immunogenic peptide fragments identified, using the method of Janin J., 1979, *Nature* 277:491-492. Average Flexibility profiles can be generated, and immunogenic peptide fragments identified, using the method of Bhaskaran R., Ponnuswamy P. K., 1988, *Int. J. Pept. Protein Res.* 32:242-255. Beta-turn profiles can be generated, and immunogenic peptide fragments identified, using the method of Deleage, G., Roux B., 1987, *Protein Engineering* 1:289-294.

CTL epitopes can be determined using specific algorithms to identify peptides within a PSCA protein that are capable of optimally binding to specified HLA alleles (e.g., by using the SYFPEITHI site at World Wide Web URL syfpeithi.bmi-heidelberg.com/; the listings in Table IV(A)-(E); Epimatrix™ and Epimer™, Brown University, URL (brown.edu/ Research/TB-HIV_Lab/epimatrix/epimatrix.html); and BIMAS, URL bimas.dcrt.nih.gov/). Illustrating this, peptide epitopes from PSCA that are presented in the context of human MHC Class I molecules, e.g., HLA-A1, A2, A3, A11, A24, B7 and B35 were predicted (see, e.g., Tables V-XVIII, XXII-LI). Specifically, the complete amino acid sequence of the PSCA protein and relevant portions of other variants, i.e., for HLA Class I predictions 9 flanking residues on either side of a point mutation or exon junction, and for HLA Class II predictions 14 flanking residues on either side of a point mutation or exon junction corresponding to that variant, were entered into the HLA Peptide Motif Search algorithm found in the Bioinformatics and Molecular Analysis Section (BIMAS) web site listed above; in addition to the site SYFPEITHI, at URL syfpeithi.bmi-heidelberg.com/.

The HLA peptide motif search algorithm was developed by Dr. Ken Parker based on binding of specific peptide sequences in the groove of HLA Class I molecules, in particular HLA-A2 (see, e.g., Falk et al., *Nature* 351: 290-6 (1991); Hunt et al., *Science* 255:1261-3 (1992); Parker et al., *J. Immunol.* 149:3580-7 (1992); Parker et al., *J. Immunol.* 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for Class I HLA-A2, the epitopes preferably contain a leucine (L) or methionine (M) at position 2 and a valine (V) or leucine (L) at the C-terminus (see, e.g., Parker et al., *J. Immunol.* 149: 3580-7 (1992)). Selected results of PSCA predicted binding peptides are shown in Tables V-XVIII and XXII-LI herein. In Tables V-XVIII and XXII-XLVIII, selected candidates, 9-mers and 10-mers, for each family member are shown along with their location, the amino acid sequence of each specific peptide, and an estimated binding score. In Tables XLVIII-LI, selected candidates, 15-mers, for each family member are shown along with their location, the amino acid sequence of each specific peptide, and an estimated binding score. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., *Prostate* 30:73-8 (1997) and Peshwa et al., *Prostate* 36:129-38 (1998)). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class II motifs available in the art or which become part of the art such as set forth in Table IV (or determined using World Wide Web site URL syfpeithi.bmi-heidelberg.com/, or BIMAS, bimas.dcrt.nih.gov/) are to be "applied" to a PSCA protein in accordance with the invention. As used in this context "applied" means that a PSCA protein is evaluated, e.g., visually or by computer-based patterns finding methods, as appreciated by those of skill in the relevant art. Every subsequence of a PSCA protein of 8, 9, 10, or 11 amino acid residues that bears an HLA Class I motif, or a subsequence of 9 or more amino acid residues that bear an HLA Class II motif are within the scope of the invention.

III.B.) Expression of PSCA-related Proteins

In an embodiment described in the examples that follow, PSCA can be conveniently expressed in cells (such as 293T cells) transfected with a commercially available expression vector such as a CMV-driven expression vector encoding PSCA with a C-terminal 6×His and MYC tag (pcDNA3.1/ mycHIS, Invitrogen or Tag5, GenHunter Corporation, Nashville Tenn.). The Tag5 vector provides an IgGK secretion signal that can be used to facilitate the production of a secreted PSCA protein in transfected cells. The secreted HIS-tagged PSCA in the culture media can be purified, e.g., using a nickel column using standard techniques.

III.C.) Modifications of PSCA-related Proteins

Modifications of PSCA-related proteins such as covalent modifications are included within the scope of this invention. One type of covalent modification includes reacting targeted amino acid residues of a PSCA polypeptide with an organic derivatizing agent that is capable of reacting with selected side chains or the N- or C-terminal residues of a PSCA protein. Another type of covalent modification of a PSCA polypeptide included within the scope of this invention comprises altering the native glycosylation pattern of a protein of the invention. Another type of covalent modification of PSCA comprises linking a PSCA polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PSCA-related proteins of the present invention can also be modified to form a chimeric molecule comprising PSCA fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of a PSCA sequence (amino or nucleic acid) such that a molecule is created that is not, through its length, directly homologous to the amino or nucleic acid sequences shown in FIG. 1. Such a chimeric molecule can comprise multiples of the same subsequence of PSCA. A chimeric molecule can comprise a fusion of a PSCA-related protein with a polyhistidine epitope tag, which provides an epitope to which immobilized nickel can selectively bind, with cytokines or with growth factors. The epitope tag is generally placed at the amino- or carboxyl-terminus of a PSCA protein. In an alternative embodiment, the chimeric molecule can comprise a fusion of a PSCA-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PSCA polypeptide in place of at least one variable region within an Ig molecule. In a preferred embodiment, the immunoglobulin fusion includes the hinge, CH2 and CH3, or the hinge, CHI, CH2 and CH3 regions of an IgGI molecule. For the production of immunoglobulin fusions see, e.g., U.S. Pat. No. 5,428,130 issued Jun. 27, 1995.

III.D.) Uses of PSCA-related Proteins

The proteins of the invention have a number of different specific uses. As PSCA is highly expressed in prostate and other cancers, PSCA-related proteins are used in methods that assess the status of PSCA gene products in normal versus cancerous tissues, thereby elucidating the malignant phenotype. Typically, polypeptides from specific regions of a PSCA protein are used to assess the presence of perturbations (such as deletions, insertions, point mutations etc.) in those regions (such as regions containing one or more motifs). Exemplary assays utilize antibodies or T cells targeting PSCA-related proteins comprising the amino acid residues of one or more of the biological motifs contained within a PSCA polypeptide sequence in order to evaluate the characteristics of this region in normal versus cancerous tissues or to elicit an immune response to the epitope. Alternatively, PSCA-related proteins that contain the amino acid residues of one or more of the biological motifs in a PSCA protein are used to screen for factors that interact with that region of PSCA.

PSCA protein fragments/subsequences are particularly useful in generating and characterizing domain-specific antibodies (e.g., antibodies recognizing an extracellular or intracellular epitope of a PSCA protein), for identifying agents or cellular factors that bind to PSCA or a particular structural domain thereof, and in various therapeutic and diagnostic contexts, including but not limited to diagnostic assays, cancer vaccines and methods of preparing such vaccines.

Proteins encoded by the PSCA genes, or by analogs, homologs or fragments thereof, have a variety of uses, including but not limited to generating antibodies and in methods for identifying ligands and other agents and cellular constituents that bind to a PSCA gene product. Antibodies raised against a PSCA protein or fragment thereof are useful in diagnostic and prognostic assays, and imaging methodologies in the management of human cancers characterized by expression of PSCA protein, such as those listed in Table I. Such antibodies can be expressed intracellularly and used in methods of treating patients with such cancers. PSCA-related nucleic acids or proteins are also used in generating HTL or CTL responses.

Various immunological assays useful for the detection of PSCA proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting PSCA-expressing cells (e.g., in radioscintigraphic imaging methods). PSCA proteins are also particularly useful in generating cancer vaccines, as further described herein.

IV.) PSCA Antibodies

Another aspect of the invention provides antibodies that bind to PSCA-related proteins. Preferred antibodies specifically bind to a PSCA-related protein and do not bind (or bind weakly) to peptides or proteins that are not PSCA-related proteins under physiological conditions. In this context, examples of physiological conditions include: 1) phosphate buffered saline; 2) Tris-buffered saline containing 25 mM Tris and 150 mM NaCl; or normal saline (0.9% NaCl); 4) animal serum such as human serum; or, 5) a combination of any of 1) through 4); these reactions preferably taking place at pH 7.5, alternatively in a range of pH 7.0 to 8.0, or alternatively in a range of pH 6.5 to 8.5; also, these reactions taking place at a temperature between 4° C. to 37° C. For example, antibodies that bind PSCA can bind PSCA-related proteins such as the homologs or analogs thereof.

PSCA antibodies of the invention are particularly useful in cancer (see, e.g., Table I) diagnostic and prognostic assays, and imaging methodologies. Similarly, such antibodies are useful in the treatment, diagnosis, and/or prognosis of prostate and other cancers, to the extent PSCA is also expressed or overexpressed in these other cancers. Moreover, intracellularly expressed antibodies (e.g., single chain antibodies) are therapeutically useful in treating cancers in which the expression of PSCA is involved, such as advanced or metastatic prostate cancers or other advanced or metastatic cancers.

The invention also provides various immunological assays useful for the detection and quantification of PSCA and mutant PSCA-related proteins. Such assays can comprise one or more PSCA antibodies capable of recognizing and binding a PSCA-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting prostate cancer and other cancers expressing PSCA are also provided by the invention, including but not limited to radioscintigraphic imaging methods using labeled PSCA antibodies. Such assays are clinically useful in the detection, monitoring, and prognosis of PSCA expressing cancers such as prostate cancer.

PSCA antibodies are also used in methods for purifying a PSCA-related protein and for isolating PSCA homologues and related molecules. For example, a method of purifying a PSCA-related protein comprises incubating a PSCA antibody, which has been coupled to a solid matrix, with a lysate or other solution containing a PSCA-related protein under conditions that permit the PSCA antibody to bind to the PSCA-related protein; washing the solid matrix to eliminate impurities; and eluting the PSCA-related protein from the coupled antibody. Other uses of PSCA antibodies in accordance with the invention include generating anti-idiotypic antibodies that mimic a PSCA protein.

Various methods for the preparation of antibodies are well known in the art. For example, antibodies can be prepared by immunizing a suitable mammalian host using a PSCA-related protein, peptide, or fragment, in isolated or immunoconjugated form (*Antibodies: A Laboratory Manual*, CSH Press, Eds., Harlow, and Lane (1988); Harlow, *Antibodies*, Cold Spring Harbor Press, NY (1989)). In addition, fusion proteins of PSCA can also be used, such as a PSCA GST-fusion protein. In a particular embodiment, a GST fusion protein comprising all or most of the amino acid sequence of FIG. 1 is produced, then used as an immunogen to generate appropriate antibodies. In another embodiment, a PSCA-related protein is synthesized and used as an immunogen.

In addition, naked DNA immunization techniques known in the art are used (with or without purified PSCA-related protein or PSCA expressing cells) to generate an immune response to the encoded immunogen (for review, see Donnelly et al., 1997, *Ann. Rev. Immunol.* 15: 617-648).

The amino acid sequence of a PSCA protein as shown in FIG. 1 can be analyzed to select specific regions of the PSCA protein for generating antibodies. For example, hydrophobicity and hydrophilicity analyses of a PSCA amino acid sequence are used to identify hydrophilic regions in the PSCA structure. Regions of a PSCA protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Hydrophilicity profiles can be generated using the method of Hopp, T. P. and Woods, K. R., 1981, *Proc. Natl. Acad. Sci. U.S.A.* 78:3824-3828. Hydropathicity profiles can be generated using the method of Kyte, J. and Doolittle, R. F., 1982, *J. Mol. Biol.* 157: 105-132. Percent (%) Accessible Residues profiles can be generated using the method of Janin J., 1979, *Nature* 277:491-492. Average Flexibility profiles can be generated using the method of Bhaskaran R., Ponnuswamy P. K., 1988, *Int. J. Pept. Protein Res.* 32:242-255. Beta-turn profiles can be generated using the method of Deleage, G., Roux B., 1987, *Protein Engineering* 1:289-294. Thus, each region identified by any of these programs or methods is within the scope of the present invention. Preferred methods for the generation of PSCA antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a PSCA immunogen is often conducted by injection over a suitable time period and with use of a suitable adjuvant, as is understood in the art. During the immunization schedule, titers of antibodies can be taken to determine adequacy of antibody formation.

PSCA monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a PSCA-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of a PSCA protein can also be produced in the context of chimeric or complementarity-determining region (CDR) grafted antibodies of multiple species origin. Humanized or human PSCA antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al, 1986, *Nature* 321: 522-525; Riechmann et al., 1988, *Nature* 332: 323-327; Verhoeyen et al., 1988, *Science* 239: 1534-1536). See also, Carter et al., 1993, *Proc. Natl. Acad. Sci. USA* 89: 4285 and Sims et al., 1993, *J. Immunol.* 151: 2296.

Methods for producing fully human monoclonal antibodies include phage display and transgenic methods (for review, see Vaughan et al., 1998, *Nature Biotechnology* 16: 535-539). Fully human PSCA monoclonal antibodies can be generated using cloning technologies employing large human Ig gene combinatorial libraries (i.e., phage display) (Griffiths and Hoogenboom, Building an in vitro immune system: human antibodies from phage display libraries. In: *Protein Engineering of Antibody Molecules for Prophylactic and Therapeutic Applications in Man*, Clark, M. (Ed.), Nottingham Academic, pp 45-64 (1993); Burton and Barbas, *Human Antibodies from combinatorial libraries*. Id., pp 65-82). Fully human PSCA monoclonal antibodies can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, *Exp. Opin. Invest. Drugs* 7(4): 607-614; U.S. Pat. Nos. 6,162,963 issued 19 Dec. 2000; 6,150,584 issued 12 Nov. 2000; and, 6,114,598 issued 5 Sep. 2000). This method avoids the in vitro manipulation required with phage display technology and efficiently produces high affinity authentic human antibodies.

Reactivity of PSCA antibodies with a PSCA-related protein can be established by a number of well known means, including Western blot, immunoprecipitation, ELISA, and FACS analyses using, as appropriate, PSCA-related proteins, PSCA-expressing cells or extracts thereof. A PSCA antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more PSCA epitopes are generated using methods generally known in the art. Homodimeric antibodies can also be generated by cross-linking techniques known in the art (e.g., Wolff et al., *Cancer Res.* 53: 2560-2565).

In one embodiment, the invention provides for monoclonal antibodies identified as H1-1.10 that were sent (via Federal Express) to the American Type Culture Collection (ATCC), P.O. Box 1549, Manassas, Va. 20108 on 4 May 2005 and assigned Accession number PTA-6697.

V.) PSCA Cellular Immune Responses

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S. et al., *Cell* 47:1071, 1986; Babbitt, B. P. et al., *Nature* 317: 359, 1985; Townsend, A. and Bodmer, H., *Annu. Rev. Immunol.* 7:601, 1989; Germain, R. N., *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., *J. Immunol.* 160: 3363, 1998; Rammensee, et al., *Immunogenetics* 41:178, 1995; Rammensee et al., SYFPEITHI, access via World Wide Web at URL (134.2.96.221/scripts.hlaserver.dll/home.htm);

Sette, A. and Sidney, *J. Curr. Opin. Immunol.* 10:478, 1998; Engelhard, V. H., *Curr. Opin. Immunol.* 6:13, 1994; Sette, A. and Grey, H. M., *Curr. Opin. Immunol.* 4:79, 1992; Sinigaglia, F. and Hammer, *J. Curr. Biol.* 6:52, 1994; Ruppert et al., *Cell* 74:929-937, 1993; Kondo et al., *J. Immunol.* 155: 4307-4312, 1995; Sidney et al., *J. Immunol.* 157:3480-3490, 1996; Sidney et al., *Human Immunol.* 45:79-93, 1996; Sette, A. and Sidney, *J. Immunogenetics* 1999 November; 50(3-4): 201-12, Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present. (See, e.g., Madden, D. R. *Annu. Rev. Immunol.* 13:587, 1995; Smith, et al., *Immunity* 4:203, 1996; Fremont et al., *Immunity* 8:305, 1998; Stern et al., *Structure* 2:245, 1994; Jones, E. Y. *Curr. Opin. Immunol.* 9:75, 1997; Brown, J. H. et al., *Nature* 364:33, 1993; Guo, H. C. et al., *Proc. Natl. Acad. Sci. USA* 90:8053, 1993; Guo, H. C. et al., *Nature* 360:364, 1992; Silver, M. L. et al., *Nature* 360:367, 1992; Matsumura, M. et al., *Science* 257:927, 1992; Madden et al., *Cell* 70:1035, 1992; Fremont, D. H. et al., *Science* 257:919, 1992; Saper, M. A., Bjorkman, P. J. and Wiley, D. C., *J. Mol. Biol.* 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A. et al., *Mol. Immunol.* 32:603, 1995; Celis, E. et al., *Proc. Natl. Acad. Sci. USA* 91:2105, 1994; Tsai, V. et al., *J. Immunol.* 158:1796, 1997; Kawashima, I. et al., *Human Immunol.* 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or 51 Cr-release assay involving peptide sensitized target cells.

2) Immunization of HLA transgenic mice (see, e.g., Wentworth, P. A. et al., *J. Immunol.* 26:97, 1996; Wentworth, P. A. et al., *Int. Immunol.* 8:651, 1996; Alexander, J. et al., *J. Immunol.* 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a 51Cr-release assay involving peptide sensitized target cells and target cells expressing endogenously generated antigen.

3) Demonstration of recall T cell responses from immune individuals who have been either effectively vaccinated and/or from chronically ill patients (see, e.g., Rehermann, B. et al., *J. Exp. Med.* 181:1047, 1995; Doolan, D. L. et al., *Immunity* 7:97, 1997; Bertoni, R. et al., *J. Clin. Invest.* 100:503, 1997; Threlkeld, S. C. et al., *J. Immunol.* 159:1648, 1997; Diepolder, H. M. et al., *J. Virol.* 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including 51 Cr release involving peptide-sensitized targets, T cell proliferation, or lymphokine release.

VI.) PSCA Transgenic Animals

Nucleic acids that encode a PSCA-related protein can also be used to generate either transgenic animals or "knock out" animals that, in turn, are useful in the development and screening of therapeutically useful reagents. In accordance with established techniques, cDNA encoding PSCA can be used to clone genomic DNA that encodes PSCA. The cloned genomic sequences can then be used to generate transgenic animals containing cells that express DNA that encode PSCA. Methods for generating transgenic animals, particularly animals such as mice or rats, have become conventional in the art and are described, for example, in U.S. Pat. Nos. 4,736,866 issued 12 Apr. 1988, and 4,870,009 issued 26 Sep. 1989. Typically, particular cells would be targeted for PSCA transgene incorporation with tissue-specific enhancers.

Transgenic animals that include a copy of a transgene encoding PSCA can be used to examine the effect of increased expression of DNA that encodes PSCA. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of PSCA can be used to construct a PSCA "knock out" animal that has a defective or altered gene encoding PSCA as a result of homologous recombination between the endogenous gene encoding PSCA and altered genomic DNA encoding PSCA introduced into an embryonic cell of the animal. For example, cDNA that encodes PSCA can be used to clone genomic DNA encoding PSCA in accordance with established techniques. A portion of the genomic DNA encoding PSCA can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, *Cell,* 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell,* 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of a PSCA polypeptide.

VII.) Methods for the Detection of PSCA

Another aspect of the present invention relates to methods for detecting PSCA polynucleotides and PSCA-related proteins, as well as methods for identifying a cell that expresses PSCA. The expression profile of PSCA makes it a diagnostic marker for metastasized disease. Accordingly, the status of PSCA gene products provides information useful for predicting a variety of factors including susceptibility to advanced stage disease, rate of progression, and/or tumor aggressiveness. As discussed in detail herein, the status of PSCA gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of PSCA polynucleotides in a biological sample, such as serum, bone, prostate, and other tissues, urine, semen, cell preparations, and the like. Detectable PSCA polynucleotides include, for example, a PSCA gene or fragment thereof, PSCA mRNA, alternative splice variant PSCA mRNAs, and recombinant DNA or RNA molecules that contain a PSCA polynucleotide. A number of methods for amplifying and/or detecting the presence of PSCA polynucleotides are well known in the art and can be employed in the practice of this aspect of the invention.

In one embodiment, a method for detecting a PSCA mRNA in a biological sample comprises producing cDNA from the sample by reverse transcription using at least one primer; amplifying the cDNA so produced using a PSCA polynucleotides as sense and antisense primers to amplify PSCA cDNAs therein; and detecting the presence of the amplified PSCA cDNA. Optionally, the sequence of the amplified PSCA cDNA can be determined.

In another embodiment, a method of detecting a PSCA gene in a biological sample comprises first isolating genomic DNA from the sample; amplifying the isolated genomic DNA using PSCA polynucleotides as sense and antisense primers; and detecting the presence of the amplified PSCA gene. Any number of appropriate sense and antisense probe combinations can be designed from a PSCA nucleotide sequence (see, e.g., FIG. 1) and used for this purpose.

The invention also provides assays for detecting the presence of a PSCA protein in a tissue or other biological sample such as serum, semen, bone, prostate, urine, cell preparations, and the like. Methods for detecting a PSCA-related protein are also well known and include, for example, immunoprecipitation, immunohistochemical analysis, Western blot analysis, molecular binding assays, ELISA, ELIFA and the like. For example, a method of detecting the presence of a PSCA-related protein in a biological sample comprises first contacting the sample with a PSCA antibody, a PSCA-reactive fragment thereof, or a recombinant protein containing an antigen-binding region of a PSCA antibody; and then detecting the binding of PSCA-related protein in the sample.

Methods for identifying a cell that expresses PSCA are also within the scope of the invention. In one embodiment, an assay for identifying a cell that expresses a PSCA gene comprises detecting the presence of PSCA mRNA in the cell. Methods for the detection of particular mRNAs in cells are well known and include, for example, hybridization assays using complementary DNA probes (such as in situ hybridization using labeled PSCA riboprobes, Northern blot and related techniques) and various nucleic acid amplification assays (such as RT-PCR using complementary primers specific for PSCA, and other amplification type detection methods, such as, for example, branched DNA, SISBA, TMA and the like). Alternatively, an assay for identifying a cell that expresses a PSCA gene comprises detecting the presence of PSCA-related protein in the cell or secreted by the cell. Various methods for the detection of proteins are well known in the art and are employed for the detection of PSCA-related proteins and cells that express PSCA-related proteins.

PSCA expression analysis is also useful as a tool for identifying and evaluating agents that modulate PSCA gene expression. For example, PSCA expression is significantly upregulated in prostate cancer, and is expressed in cancers of the tissues listed in Table I. Identification of a molecule or biological agent that inhibits PSCA expression or over-expression in cancer cells is of therapeutic value. For example, such an agent can be identified by using a screen that quantifies PSCA expression by RT-PCR, nucleic acid hybridization or antibody binding.

VIII.) Methods for Monitoring the Status of PSCA-related Genes and their Products Oncogenesis is known to be a multistep process where cellular growth becomes progressively dysregulated and cells progress from a normal physiological state to precancerous and then cancerous states (see, e.g., Alers et al., *Lab Invest.* 77(5): 437-438 (1997) and Isaacs et al., *Cancer Surv.* 23: 19-32 (1995)). In this context, examining a biological sample for evidence of dysregulated cell growth (such as aberrant PSCA expression in cancers) allows for early detection of such aberrant physiology, before a pathologic state such as cancer has progressed to a stage that therapeutic options are more limited and or the prognosis is worse. In such examinations, the status of PSCA in a biological sample of interest can be compared, for example, to the status of PSCA in a corresponding normal sample (e.g. a sample from that individual or alternatively another individual that is not affected by a pathology). An alteration in the status of PSCA in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., *J. Comp. Neurol.* 1996 Dec. 9; 376(2): 306-14 and U.S. Pat. No. 5,837,501) to compare PSCA status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of PSCA expressing cells) as well as the level, and biological activity of expressed gene products (such as PSCA mRNA, polynucleotides and polypeptides). Typically, an alteration in the status of PSCA comprises a change in the location of PSCA and/or PSCA expressing cells and/or an increase in PSCA mRNA and/or protein expression.

PSCA status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of a PSCA gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of PSCA in a biological sample is evaluated by various methods utilized by skilled artisans including, but not limited to genomic Southern analysis (to examine, for example perturbations in a PSCA gene), Northern analysis and/or PCR analysis of PSCA mRNA (to examine, for example alterations in the polynucleotide sequences or expression levels of PSCA mRNAs), and, Western and/or immunohistochemical analysis (to examine, for example alterations in polypeptide sequences, alterations in polypeptide localization within a sample, alterations in expression levels of PSCA proteins and/or associations of PSCA proteins with polypeptide binding partners). Detectable PSCA polynucleotides include, for example, a PSCA gene or fragment thereof, PSCA mRNA, alternative splice variants, PSCA mRNAs, and recombinant DNA or RNA molecules containing a PSCA polynucleotide.

The expression profile of PSCA makes it a diagnostic marker for local and/or metastasized disease, and provides information on the growth or oncogenic potential of a biological sample. In particular, the status of PSCA provides information useful for predicting susceptibility to particular disease stages, progression, and/or tumor aggressiveness. The invention provides methods and assays for determining PSCA status and diagnosing cancers that express PSCA, such as cancers of the tissues listed in Table I. For example, because PSCA mRNA is so highly expressed in prostate and other cancers relative to normal prostate tissue, assays that evaluate the levels of PSCA mRNA transcripts or proteins in a biological sample can be used to diagnose a disease associated with PSCA dysregulation, and can provide prognostic information useful in defining appropriate therapeutic options.

The expression status of PSCA provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of PSCA in biological samples such as those from individuals suffering from, or suspected of suffering from a pathology characterized by dysregulated cellular growth, such as cancer.

As described above, the status of PSCA in a biological sample can be examined by a number of well-known procedures in the art. For example, the status of PSCA in a biological sample taken from a specific location in the body can be examined by evaluating the sample for the presence or absence of PSCA expressing cells (e.g. those that express PSCA mRNAs or proteins). This examination can provide evidence of dysregulated cellular growth, for example, when PSCA-expressing cells are found in a biological sample that does not normally contain such cells (such as a lymph node), because such alterations in the status of PSCA in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., *Prostate* 42(4): 315-317 (2000); Su et al., *Semin. Surg. Oncol.* 18(1): 17-28 (2000) and Freeman et al., *J Urol* 1995 August 154(2 Pt 1):474-8).

In one aspect, the invention provides methods for monitoring PSCA gene products by determining the status of PSCA gene products expressed by cells from an individual suspected of having a disease associated with dysregulated cell growth (such as hyperplasia or cancer) and then comparing the status so determined to the status of PSCA gene products in a corresponding normal sample. The presence of aberrant PSCA gene products in the test sample relative to the normal sample provides an indication of the presence of dysregulated cell growth within the cells of the individual.

In another aspect, the invention provides assays useful in determining the presence of cancer in an individual, comprising detecting a significant increase in PSCA mRNA or protein expression in a test cell or tissue sample relative to expression levels in the corresponding normal cell or tissue. The presence of PSCA mRNA can, for example, be evaluated in tissues including but not limited to those listed in Table I. The presence of significant PSCA expression in any of these tissues is useful to indicate the emergence, presence and/or severity of a cancer, since the corresponding normal tissues do not express PSCA mRNA or express it at lower levels.

In a related embodiment, PSCA status is determined at the protein level rather than at the nucleic acid level. For example, such a method comprises determining the level of PSCA protein expressed by cells in a test tissue sample and comparing the level so determined to the level of PSCA expressed in a corresponding normal sample. In one embodiment, the presence of PSCA protein is evaluated, for example, using immunohistochemical methods. PSCA antibodies or binding partners capable of detecting PSCA protein expression are used in a variety of assay formats well known in the art for this purpose.

In a further embodiment, one can evaluate the status of PSCA nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, *J. Cutan. Pathol.* 26(8):369-378). For example, a mutation in the sequence of PSCA may be indicative of the presence or promotion of a tumor. Such assays therefore have diagnostic and predictive value where a mutation in PSCA indicates a potential loss of function or increase in tumor growth.

A wide variety of assays for observing perturbations in nucleotide and amino acid sequences are well known in the art. For example, the size and structure of nucleic acid or amino acid sequences of PSCA gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 issued 7 Sep. 1999, and 5,952,170 issued 17 Jan. 1995).

Additionally, one can examine the methylation status of a PSCA gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., *Am. J. Pathol.* 155(6): 1985-1992 (1999)). In addition, this alteration is present in at least 70% of cases of high-grade prostatic intraepithelial neoplasia (PIN) (Brooks et al., *Cancer Epidemiol. Biomarkers Prev.,* 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., *Int. J. Cancer* 76(6): 903-908 (1998)). A variety of assays for examining methylation status of a gene are well known in the art. For example, one can utilize, in Southern hybridization approaches, methylation-sensitive restriction enzymes that cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in *Current Protocols In Molecular Biology*, Unit 12, Frederick M. Ausubel et al. eds., 1995.

Gene amplification is an additional method for assessing the status of PSCA. Gene amplification is measured in a sample directly, for example, by conventional Southern blotting or Northern blotting to quantitate the transcription of mRNA (Thomas, 1980, *Proc. Natl. Acad. Sci. USA*, 77:5201 5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA RNA hybrid duplexes or DNA protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect PSCA expression. The presence of RT-PCR amplifiable PSCA mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, *Urol. Res.* 25:373-384; Ghossein et al., 1995, *J. Clin. Oncol.* 13:1195-2000; Heston et al., 1995, *Clin. Chem.* 41:1687-1688).

A further aspect of the invention is an assessment of the susceptibility that an individual has for developing cancer. In one embodiment, a method for predicting susceptibility to cancer comprises detecting PSCA mRNA or PSCA protein in a tissue sample, its presence indicating susceptibility to cancer, wherein the degree of PSCA mRNA expression correlates to the degree of susceptibility. In a specific embodiment, the presence of PSCA in prostate or other tissue is examined, with the presence of PSCA in the sample providing an indication of prostate cancer susceptibility (or the emergence or existence of a prostate tumor). Similarly, one can evaluate the integrity PSCA nucleotide and amino acid sequences in a biological sample, in order to identify perturbations in the structure of these molecules such as insertions, deletions, substitutions and the like. The presence of one or more perturbations in PSCA gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of PSCA mRNA or PSCA protein expressed by tumor cells, comparing the level so determined to the level of PSCA mRNA or PSCA protein expressed in a corresponding normal tissue taken from the same individual or a normal tissue reference sample, wherein the degree of PSCA mRNA or PSCA protein expression in the tumor sample relative to the normal sample indicates the degree of aggressiveness. In a specific embodiment, aggressiveness of a tumor is evaluated by determining the extent to which PSCA is expressed in the tumor cells, with higher expression levels indicating more aggressive tumors. Another embodiment is the evaluation of the integrity of PSCA nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of PSCA mRNA or PSCA protein expressed by cells in a sample of the tumor, comparing the level so determined to the level of PSCA mRNA or PSCA protein expressed in an equivalent tissue sample taken from the same individual at a different time, wherein the degree of PSCA mRNA or PSCA protein expression in the tumor sample over time provides information on the progression of the cancer. In a specific embodiment, the progression of a cancer is evaluated by determining PSCA expression in the tumor cells over time, where increased expression over time indicates a progression of the cancer. Also, one can evaluate the integrity PSCA nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of PSCA gene and PSCA gene products (or perturbations in PSCA gene and PSCA gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et al., 1984, *Anal Quant. Cytol.* 6(2):74-88; Epstein, 1995, *Hum. Pathol.* 26(2):223-9; Thorson et al., 1998, *Mod. Pathol.* 11(6):543-51; Baisden et al., 1999, *Am J. Surg. Pathol.* 23(8):918-24). Methods for observing a coincidence between the expression of PSCA gene and PSCA gene products (or perturbations in PSCA gene and PSCA gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of PSCA gene and PSCA gene products (or perturbations in PSCA gene and PSCA gene products) and another factor associated with malignancy entails detecting the overexpression of PSCA mRNA or protein in a tissue sample, detecting the overexpression of PSA mRNA or protein in a tissue sample (or PSCA or PSM expression), and observing a coincidence of PSCA mRNA or protein and PSA mRNA or protein overexpression (or PSCA or PSM expression). In a specific embodiment, the expression of PSCA and PSA mRNA in prostate tissue is examined, where the coincidence of PSCA and PSA mRNA overexpression in the sample indicates the existence of prostate cancer, prostate cancer susceptibility or the emergence or status of a prostate tumor.

Methods for detecting and quantifying the expression of PSCA mRNA or protein are described herein, and standard nucleic acid and protein detection and quantification technologies are well known in the art. Standard methods for the detection and quantification of PSCA mRNA include in situ hybridization using labeled PSCA riboprobes, Northern blot and related techniques using PSCA polynucleotide probes, RT-PCR analysis using primers specific for PSCA, and other amplification type detection methods, such as, for example, branched DNA, SISBA, TMA and the like. In a specific embodiment, semi-quantitative RT-PCR is used to detect and quantify PSCA mRNA expression. Any number of primers capable of amplifying PSCA can be used for this purpose, including but not limited to the various primer sets specifically described herein. In a specific embodiment, polyclonal or monoclonal antibodies specifically reactive with the wild-type PSCA protein can be used in an immunohistochemical assay of biopsied tissue.

IX.) Identification of Molecules that Interact with PSCA

The PSCA protein and nucleic acid sequences disclosed herein allow a skilled artisan to identify proteins, small molecules and other agents that interact with PSCA, as well as pathways activated by PSCA via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. Nos. 5,955,280 issued 21 Sep. 1999, U.S. Pat. No. 5,925,523 issued 20 Jul. 1999, U.S. Pat. No. 5,846,722 issued 8 Dec. 1998 and U.S. Pat. No. 6,004,746 issued 21 Dec. 1999. Algorithms are also available in the art for genome-based predictions of protein function (see, e.g., Marcotte, et al., *Nature* 402: 4 Nov. 1999, 83-86).

Alternatively one can screen peptide libraries to identify molecules that interact with PSCA protein sequences. In such methods, peptides that bind to PSCA are identified by screening libraries that encode a random or controlled collection of amino acids. Peptides encoded by the libraries are expressed as fusion proteins of bacteriophage coat proteins, the bacteriophage particles are then screened against the PSCA protein(s).

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with PSCA protein sequences are disclosed for example in U.S. Pat. Nos. 5,723,286 issued 3 Mar. 1998 and U.S. Pat. No. 5,733,731 issued 31 Mar. 1998.

Alternatively, cell lines that express PSCA are used to identify protein-protein interactions mediated by PSCA. Such interactions can be examined using immunoprecipitation techniques (see, e.g., Hamilton B. J., et al. *Biochem. Biophys. Res. Commun.* 1999, 261:646-51). PSCA protein can be immunoprecipitated from PSCA-expressing cell lines using anti-PSCA antibodies. Alternatively, antibodies against His-tag can be used in a cell line engineered to express fusions of PSCA and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with PSCA can be identified through related embodiments of such screening assays. For example, small molecules can be identified that interfere with protein function, including molecules that interfere with PSCA's ability to mediate phosphorylation and de-phosphorylation, interaction with DNA or RNA molecules as an indication of regulation of cell cycles, second messenger signaling or tumorigenesis. Similarly, small molecules that modulate PSCA-related ion channel, protein pump, or cell communication functions are identified and used to treat patients that have a cancer that expresses PSCA (see, e.g., Hille, B., *Ionic Channels of Excitable Membranes* 2nd Ed., Sinauer Assoc., Sunderland, Mass., 1992). Moreover, ligands that regulate PSCA function can be identified based on their ability to bind PSCA and activate a reporter construct. Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of PSCA and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators, which activate or inhibit PSCA.

An embodiment of this invention comprises a method of screening for a molecule that interacts with a PSCA amino acid sequence shown in FIG. 1, comprising the steps of contacting a population of molecules with a PSCA amino acid sequence, allowing the population of molecules and the PSCA amino acid sequence to interact under conditions that facilitate an interaction, determining the presence of a molecule that interacts with the PSCA amino acid sequence, and then separating molecules that do not interact with the PSCA amino acid sequence from molecules that do. In a specific embodiment, the method further comprises purifying, characterizing and identifying a molecule that interacts with the PSCA amino acid sequence. The identified molecule can be used to modulate a function performed by PSCA. In a preferred embodiment, the PSCA amino acid sequence is contacted with a library of peptides.

X.) Therapeutic Methods and Compositions

The identification of PSCA as a protein that is normally expressed in a restricted set of tissues, but which is also expressed in cancers such as those listed in Table I, opens a number of therapeutic approaches to the treatment of such cancers.

Of note, targeted antitumor therapies have been useful even when the targeted protein is expressed on normal tissues, even vital normal organ tissues. A vital organ is one that is necessary to sustain life, such as the heart or colon. A non-vital organ is one that can be removed whereupon the individual is still able to survive. Examples of non-vital organs are ovary, breast, and prostate.

For example, Herceptin® is an FDA approved pharmaceutical that consists of an antibody which is immunoreactive with the protein variously known as HER2, HER2/neu, and erb-b-2. It is marketed by Genentech and has been a commercially successful antitumor agent. Herceptin® sales reached almost $400 million in 2002. Herceptin® is a treatment for HER2 positive metastatic breast cancer. However, the expression of HER2 is not limited to such tumors. The same protein is expressed in a number of normal tissues. In particular, it is known that HER2/neu is present in normal kidney and heart, thus these tissues are present in all human recipients of Herceptin. The presence of HER2/neu in normal kidney is also confirmed by Latif, Z., et al., *B.J.U. International* (2002) 89:5-9. As shown in this article (which evaluated whether renal cell carcinoma should be a preferred indication for anti-HER2 antibodies such as Herceptin) both protein and mRNA are produced in benign renal tissues. Notably, HER2/neu protein was strongly overexpressed in benign renal tissue.

Despite the fact that HER2/neu is expressed in such vital tissues as heart and kidney, Herceptin® is a very useful, FDA approved, and commercially successful drug. The effect of Herceptin® on cardiac tissue, i.e., "cardiotoxicity," has merely been a side effect to treatment. When patients were treated with Herceptin® alone, significant cardiotoxicity occurred in a very low percentage of patients. To minimize cardiotoxicity there is a more stringent entry requirement for the treatment with HER2/neu. Factors such as predisposition to heart condition are evaluated before treatment can occur.

Of particular note, although kidney tissue is indicated to exhibit normal expression, possibly even higher expression than cardiac tissue, kidney has no appreciable Herceptin® side effect whatsoever. Moreover, of the diverse array of normal tissues in which HER2 is expressed, there is very little occurrence of any side effect. Only cardiac tissue has manifested any appreciable side effect at all. A tissue such as kidney, where HER2/neu expression is especially notable, has not been the basis for any side effect.

Furthermore, favorable therapeutic effects have been found for antitumor therapies that target epidermal growth factor receptor (EGFR); Erbitux (ImClone). EGFR is also expressed in numerous normal tissues. There have been very limited side effects in normal tissues following use of anti-EGFR therapeutics. A general side effect that occurs with the EGFR treatment is a severe skin rash observed in 100% of the patients undergoing treatment.

Thus, expression of a target protein in normal tissue, even vital normal tissue, does not defeat the utility of a targeting agent for the protein as a therapeutic for certain tumors in which the protein is also overexpressed. For example, expression in vital organs is not in and of itself detrimental. In addition, organs regarded as dispensable, such as the prostate and ovary, can be removed without affecting mortality. Finally, some vital organs are not affected by normal organ expression because of an immunoprivilege. Immunoprivileged organs are organs that are protected from blood by a blood-organ barrier and thus are not accessible to immunotherapy. Examples of immunoprivileged organs are the brain and testis.

Accordingly, therapeutic approaches that inhibit the activity of a PSCA protein are useful for patients suffering from a cancer that expresses PSCA. These therapeutic approaches generally fall into three classes. The first class modulates PSCA function as it relates to tumor cell growth leading to inhibition or retardation of tumor cell growth or inducing its killing. The second class comprises various methods for inhibiting the binding or association of a PSCA protein with its binding partner or with other proteins. The third class comprises a variety of methods for inhibiting the transcription of a PSCA gene or translation of PSCA mRNA.

X.A.) Anti-Cancer Vaccines

The invention provides cancer vaccines comprising a PSCA-related protein or PSCA-related nucleic acid. In view of the expression of PSCA, cancer vaccines prevent and/or treat PSCA-expressing cancers with minimal or no effects on non-target tissues. The use of a tumor antigen in a vaccine that generates cell-mediated humoral immune responses as anti-cancer therapy is well known in the art and has been employed in prostate cancer using human PSMA and rodent PAP immunogens (Hodge et al., 1995, *Int. J. Cancer* 63:231-237; Fong et al., 1997, *J. Immunol.* 159:3113-3117).

Such methods can be readily practiced by employing a PSCA-related protein, or a PSCA-encoding nucleic acid molecule and recombinant vectors capable of expressing and presenting the PSCA immunogen (which typically comprises a number of T-cell epitopes or antibody). Skilled artisans understand that a wide variety of vaccine systems for delivery of immunoreactive epitopes are known in the art (see, e.g., Heryln et al., *Ann Med* 1999 February 31(1):66-78; Maruyama et al., *Cancer Immunol Immunother* 2000 June 49(3):123-32) Briefly, such methods of generating an immune response (e.g. cell-mediated and/or humoral) in a mammal, comprise the steps of: exposing the mammal's immune system to an immunoreactive epitope (e.g. an epitope present in a PSCA protein shown in FIG. 1 or analog or homolog thereof) so that the mammal generates an immune response that is specific for that epitope (e.g. generates antibodies that specifically recognize that epitope).

The entire PSCA protein, immunogenic regions or epitopes thereof can be combined and delivered by various means. Such vaccine compositions can include, for example, lipopeptides (e.g., Vitiello, A. et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287-294, 1991: Alonso et al., *Vaccine* 12:299-306, 1994; Jones et al., *Vaccine* 13:675-681, 1995), peptide compositions contained in immune stimulating complexes (ISCOMS) (see, e.g., Takahashi et al., Nature 344:873-875, 1990; Hu et al., *Clin Exp Immunol.* 113:235-243, 1998), multiple antigen peptide systems (MAPs) (see e.g., Tam, J. P., *Proc. Natl. Acad. Sci. U.S.A.* 85:5409-5413, 1988; Tam, J. P., *J. Immunol. Methods* 196:17-32, 1996), peptides formulated as multivalent peptides; peptides for use in ballistic delivery systems, typically crystallized peptides, viral delivery vectors (Perkus, M. E. et al, In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (e.g., Kofler, N. et al., *J. Immunol. Methods.* 192:25, 1996; Eldridge, J. H. et al., *Sem. Hematol.*

30:16, 1993; Falo, L. D., Jr. et al., *Nature Med.* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148: 1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

In patients with PSCA-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within PSCA protein that bind corresponding HLA alleles (see e.g., Table IV; Epimer™ and Epimatrix™, Brown University (URL brown.edu/Research/TB-HIV_Lab/epimatrix/epimatrix.html); and, BIMAS, (URL bimas.dcrt.nih.gov/; SYFPEITHI at URL syfpeithi.bmi-heidelberg.com/). In a preferred embodiment, a PSCA immunogen contains one or more amino acid sequences identified using techniques well known in the art, such as the sequences shown in Tables V-XVIII and XXII-LI or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. a PSCA protein) so that an immune response is generated. A typical embodiment consists of a method for generating an immune response to PSCA in a host, by contacting the host with a sufficient amount of at least one PSCA B cell or cytotoxic T-cell epitope or analog thereof, and at least one periodic interval thereafter re-contacting the host with the PSCA B cell or cytotoxic T-cell epitope or analog thereof. A specific embodiment consists of a method of generating an immune response against a PSCA-related protein or a man-made multiepitopic peptide comprising: administering PSCA immunogen (e.g. a PSCA protein or a peptide fragment thereof, a PSCA fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., *J. Immunol.* 2000 164(3); 164(3): 1625-1633; Alexander et al., *Immunity* 1994 1(9): 751-761 and Alexander et al., *Immunol. Res.* 1998 18(2): 79-92). An alternative method comprises generating an immune response in an individual against a PSCA immunogen by: administering in vivo to muscle or skin of the individual's body a DNA molecule that comprises a DNA sequence that encodes a PSCA immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered. In addition, an antiidiotypic antibody can be administered that mimics PSCA, in order to generate a response to the target antigen.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing PSCA. Constructs comprising DNA encoding a PSCA-related protein/immunogen and appropriate regulatory sequences can be injected directly into muscle or skin of an individual, such that the cells of the muscle or skin take-up the construct and express the encoded PSCA protein/immunogen. Alternatively, a vaccine comprises a PSCA-related protein. Expression of the PSCA-related protein immunogen results in the generation of prophylactic or therapeutic humoral and cellular immunity against cells that bear a PSCA protein. Various prophylactic and therapeutic genetic immunization techniques known in the art can be used (for review, see information and references published at Internet address genweb.com). Nucleic acid-based delivery is described, for instance, in Wolff et. al., *Science* 247:1465 (1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and Sindbis virus (see, e.g., Restifo, 1996, *Curr. Opin. Immunol.* 8:658-663; Tsang et al. *J. Natl. Cancer Inst.* 87:982-990 (1995)). Non-viral delivery systems can also be employed by introducing naked DNA encoding a PSCA-related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., *Nature* 351:456-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Thus, gene delivery systems are used to deliver a PSCA-related nucleic acid molecule. In one embodiment, the full-length human PSCA cDNA is employed. In another embodiment, PSCA nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present PSCA antigen to a patient's immune system. Dendritic cells express MHC class I and II molecules, B7 costimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, *Prostate* 28:65-69; Murphy et al., 1996, *Prostate* 29:371-380). Thus, dendritic cells can be used to present PSCA peptides to T cells in the context of MHC class I or II molecules. In one embodiment, autologous dendritic cells are pulsed with PSCA peptides capable of binding to MHC class I and/or class II molecules. In another embodiment, dendritic cells are pulsed with the complete PSCA protein. Yet another embodiment involves engineering the overexpression of a PSCA gene in dendritic cells using various implementing vectors known in the art, such as adenovirus (Arthur et al., 1997, *Cancer Gene Ther.* 4:17-25), retrovirus (Henderson et al., 1996, *Cancer Res.* 56:3763-3770), lentivirus, adeno-associated virus, DNA transfection (Ribas et al., 1997, *Cancer Res.* 57:2865-2869), or tumor-derived RNA transfection (Ashley et al., 1997, *J. Exp. Med.* 186:1177-1182). Cells that express PSCA can also be engineered to express immune modulators, such as GM-CSF, and used as immunizing agents.

X.B.) PSCA as a Target for Antibody-based Therapy

PSCA is an attractive target for antibody-based therapeutic strategies. A number of antibody strategies are known in the art for targeting both extracellular and intracellular molecules (see, e.g., complement and ADCC mediated killing as well as the use of intrabodies). Because PSCA is expressed by cancer cells of various lineages relative to corresponding normal cells, systemic administration of PSCA-immunoreactive compositions are prepared that exhibit excellent sensitivity without toxic, non-specific and/or non-target effects caused by binding of the immunoreactive composition to non-target organs and tissues. Antibodies specifically reactive with domains of PSCA are useful to treat PSCA-expressing cancers systemically, either as conjugates with a toxin or therapeutic agent, or as naked antibodies capable of inhibiting cell proliferation or function.

PSCA antibodies can be introduced into a patient such that the antibody binds to PSCA and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of PSCA, inhibition of ligand binding or signal transduction pathways, modulation of tumor cell differentiation, alteration of tumor angiogenesis factor profiles, and/or apoptosis. Examples include Rituxan® for Non-Hodgkins Lymphoma, Herceptin® for metastatic breast cancer, and Erbitux® for colorectal cancer.

Those skilled in the art understand that antibodies can be used to specifically target and bind immunogenic molecules such as an immunogenic region of a PSCA sequence shown in FIG. 1. In addition, skilled artisans understand that it is routine to conjugate antibodies to cytotoxic agents (see, e.g., Slevers et al. *Blood* 93:11 3678-3684 (Jun. 1, 1999)). When cytotoxic and/or therapeutic agents are delivered directly to cells, such as by conjugating them to antibodies specific for a molecule expressed by that cell (e.g. PSCA), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-PSCA antibody) that binds to a marker (e.g. PSCA) expressed, accessible to binding or localized on the cell surfaces. A typical embodiment is a method of delivering a cytotoxic and/or therapeutic agent to a cell expressing PSCA, comprising conjugating the cytotoxic agent to an antibody that immunospecifically binds to a PSCA epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-PSCA antibodies can be done in accordance with various approaches that have been successfully employed in the treatment of other types of cancer, including but not limited to colon cancer (Arlen et al., 1998, *Crit. Rev. Immunol.* 18:133-138), multiple myeloma (Ozaki et al., 1997, *Blood* 90:3179-3186, Tsunenari et al., 1997, *Blood* 90:2437-2444), gastric cancer (Kasprzyk et al., 1992, *Cancer Res.* 52:2771-2776), B-cell lymphoma (Funakoshi et al., 1996, *J. Immunother. Emphasis Tumor Immunol.* 19:93-101), leukemia (Zhong et al., 1996, *Leuk. Res.* 20:581-589), colorectal cancer (Moun et al., 1994, *Cancer Res.* 54:6160-6166; Velders et al., 1995, *Cancer Res.* 55:4398-4403), and breast cancer (Shepard et al., 1991, *J. Clin. Immunol.* 11:117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals) respectively, while others involve co-administration of antibodies and other therapeutic agents, such as Herceptin® (trastuzuMAb) with paclitaxel (Genentech, Inc.). The antibodies can be conjugated to a therapeutic agent. To treat prostate cancer, for example, PSCA antibodies can be administered in conjunction with radiation, chemotherapy or hormone ablation. Also, antibodies can be conjugated to a toxin such as calicheamicin (e.g., Mylotarg™, Wyeth-Ayerst, Madison, N.J., a recombinant humanized $IgG_4$ kappa antibody conjugated to antitumor antibiotic calicheamicin) or a maytansinoid (e.g., taxane-based Tumor-Activated Prodrug, TAP, platform, ImmunoGen, Cambridge, Mass., also see e.g., U.S. Pat. No. 5,416,064) or Auristatin E (*Nat. Biotechnol.* 2003 July; 21(7):778-84. (Seattle Genetics)).

Although PSCA antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (*Cancer Res.* 53:4637-4642, 1993), Prewett et al. (*International J. of Onco.* 9:217-224, 1996), and Hancock et al. (*Cancer Res.* 51:4575-4580, 1991) describe the use of various antibodies together with chemotherapeutic agents.

Although PSCA antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of PSCA expression, preferably using immunohistochemical assessments of tumor tissue, quantitative PSCA imaging, or other techniques that reliably indicate the presence and degree of PSCA expression. Immunohistochemical analysis of tumor biopsies or surgical specimens is preferred for this purpose. Methods for immunohistochemical analysis of tumor tissues are well known in the art.

Anti-PSCA monoclonal antibodies that treat prostate and other cancers include those that initiate a potent immune response against the tumor or those that are directly cytotoxic. In this regard, anti-PSCA monoclonal antibodies (MAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-PSCA MAbs that exert a direct biological effect on tumor growth are useful to treat cancers that express PSCA. Mechanisms by which directly cytotoxic MAbs act include: inhibition of cell growth, modulation of cellular differentiation, modulation of tumor angiogenesis factor profiles, and the induction of apoptosis. The mechanism(s) by which a particular anti-PSCA MAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric MAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target PSCA antigen with high affinity but exhibit low or no antigenicity in the patient.

Therapeutic methods of the invention contemplate the administration of single anti-PSCA MAbs as well as combinations, or cocktails, of different MAbs. Such MAb cocktails can have certain advantages inasmuch as they contain MAbs that target different epitopes, exploit different effector mechanisms or combine directly cytotoxic MAbs with MAbs that rely on immune effector functionality. Such MAbs in combination can exhibit synergistic therapeutic effects. In addition, anti-PSCA MAbs can be administered concomitantly with other therapeutic modalities, including but not limited to various chemotherapeutic agents, androgen-blockers, immune modulators (e.g., IL-2, GM-CSF), surgery or radiation. The anti-PSCA MAbs are administered in their "naked" or unconjugated form, or can have a therapeutic agent(s) conjugated to them.

Anti-PSCA antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-PSCA antibody preparation, via an acceptable route of administration such as intravenous injection (IV), typically at a dose in the range of about 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg MAb per week are effective and well tolerated.

Based on clinical experience with the Herceptin™ MAb in the treatment of metastatic breast cancer, an initial loading dose of approximately 4 mg/kg patient body weight IV, followed by weekly doses of about 2 mg/kg IV of the anti-PSCA MAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or MAbs used, the degree of PSCA expression in the patient, the extent of circulating shed PSCA antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of PSCA in a given sample (e.g. the levels of circulating PSCA antigen and/or PSCA expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-PSCA antibodies can also be used in anti-cancer therapy as a vaccine for inducing an immune response to cells expressing a PSCA-related protein. In particular, the generation of anti-idiotypic antibodies is well known in the art; this methodology can readily be adapted to generate anti-idiotypic anti-PSCA antibodies that mimic an epitope on a PSCA-related protein (see, for example, Wagner et al., 1997, *Hybridoma* 16: 33-40; Foon et al., 1995, *J. Clin. Invest.* 96:334-342; Herlyn et al., 1996, *Cancer Immunol. Immunother.* 43:65-76). Such an anti-idiotypic antibody can be used in cancer vaccine strategies.

An object of the present invention is to provide PSCA antibodies, which inhibit or retard the growth of tumor cells expressing PSCA. A further object of this invention is to provide methods to inhibit angiogenesis and other biological functions and thereby reduce tumor growth in mammals, preferably humans, using such PSCA antibodies, and in particular using such PSCA antibodies combined with radiation and chemotherapy or both.

In one embodiment, there is synergy when tumors, including human tumors, are treated with PSCA antibodies in conjunction with chemotherapeutic agents or radiation or combinations thereof. In other words, the inhibition of tumor growth by a PSCA antibody is enhanced more than expected when combined with chemotherapeutic agents or radiation or combinations thereof. Synergy may be shown, for example, by greater inhibition of tumor growth with combined treatment than would be expected from a treatment of only PSCA antibodies or the additive effect of treatment with a PSCA antibody and a chemotherapeutic agent or radiation. Preferably, synergy is demonstrated by remission of the cancer where remission is not expected from treatment either from a naked PSCA antibody or with treatment using an additive combination of a PSCA antibody and a chemotherapeutic agent or radiation.

The method for inhibiting growth of tumor cells using a PSCA antibody and a combination of chemotherapy or radiation or both comprises administering the PSCA antibody before, during, or after commencing chemotherapy or radiation therapy, as well as any combination thereof (i.e. before and during, before and after, during and after, or before, during, and after commencing the chemotherapy and/or radiation therapy). For example, the PSCA antibody is typically administered between 1 and 60 days, preferably between 3 and 40 days, more preferably between 5 and 12 days before commencing radiation therapy and/or chemotherapy. However, depending on the treatment protocol and the specific patient needs, the method is performed in a manner that will provide the most efficacious treatment and ultimately prolong the life of the patient.

The administration of chemotherapeutic agents can be accomplished in a variety of ways including systemically by the parenteral and enteral routes. In one embodiment, the PSCA antibody and the chemotherapeutic agent are administered as separate molecules. In another embodiment, the PSCA antibody is attached, for example, by conjugation, to a chemotherapeutic agent. (See the Example entitled "Human Clinical Trials for the Treatment and Diagnosis of Human Carcinomas through use of Human Anti-PSCA Antibodies in vivo") and (See section entitled "PSCA as a Target for Antibody-based Therapy"). Particular examples of chemotherapeutic agents or chemotherapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol and combinations thereof.

The source of radiation, used in combination with a PSCA antibody, can be either external or internal to the patient being treated. When the source is external to the patient, the therapy is known as external beam radiation therapy (EBRT). When the source of radiation is internal to the patient, the treatment is called brachytherapy (BT).

The radiation is administered in accordance with well known standard techniques using standard equipment manufactured for this purpose, such as AECL Theratron and Varian Clinac. The dose of radiation depends on numerous factors as is well known in the art. Such factors include the organ being treated, the healthy organs in the path of the radiation that might inadvertently be adversely affected, the tolerance of the patient for radiation therapy, and the area of the body in need of treatment. The dose will typically be between 1 and 100 Gy, and more particularly between 2 and 80 Gy. Some doses that have been reported include 35 Gy to the spinal cord, 15 Gy to the kidneys, 20 Gy to the liver, and 65-80 Gy to the prostate. It should be emphasized, however, that the invention is not limited to any particular dose. The dose will be determined by the treating physician in accordance with the particular factors in a given situation, including the factors mentioned above.

The distance between the source of the external radiation and the point of entry into the patient may be any distance that represents an acceptable balance between killing target cells and minimizing side effects. Typically, the source of the external radiation is between 70 and 100 cm from the point of entry into the patient.

Brachytherapy is generally carried out by placing the source of radiation in the patient. Typically, the source of radiation is placed approximately 0-3 cm from the tissue being treated. Known techniques include interstitial, intercavitary, and surface brachytherapy. The radioactive seeds can be implanted permanently or temporarily. Some typical radioactive atoms that have been used in permanent implants include iodine-125 and radon. Some typical radioactive atoms that have been used in temporary implants include radium, cesium-137, and iridium-192. Some additional radioactive atoms that have been used in brachytherapy include americium-241 and gold-198. The dose of radiation for brachytherapy can be the same as that mentioned above for external beam radiation therapy. In addition to the factors mentioned above for determining the dose of external beam radiation therapy, the nature of the radioactive atom used is also taken into account in determining the dose of brachytherapy.

X.C.) PSCA as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$). Moreover, an adjuvant such as a synthetic cytosine-phosphorothiolated-guanine-containing (CpG) oligonucleotides has been found to increase CTL responses 10- to 100-fold (see, e.g. Davila and Celis, J. Immunol. 165:539-547 (2000)).

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later development of cells that express or overexpress PSCA antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3-4 epitopes that come from at least one tumor associated antigen (TAA). For HLA Class II a similar rationale is employed; again 3-4 epitopes are selected from at least one TAA (see, e.g., Rosenberg et al., Science 278:1447-1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., J. Immunol. 162:3915-3925, 1999; An, L.

and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived PSCA, the PADRE™ universal helper T cell epitope or multiple HTL epitopes from PSCA (see e.g., Tables V-XVIII and XXII to LI), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g., ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, *BioTechniques* 6(7): 682 (1988); U.S. Pat. No. 5,279,833; WO 91/06309; and Felgner, et al., *Proc. Nat'l Acad. Sci. USA* 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the ε- and α-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to ε- and α-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime virus specific CTL when covalently attached to an appropriate peptide (see, e.g., Deres, et al., *Nature* 342:561, 1989). Peptides of the invention can be coupled to P3CSS, for example, and the lipopeptide administered to an individual to prime specifically an immune response to the target antigen. Moreover, because the induction of neutralizing antibodies can also be primed with P3CSS-conjugated epitopes, two such compositions can be combined to more effectively elicit both humoral and cell-mediated responses.

X.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to PSCA. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses PSCA.

X.D.) Adoptive Immunotherapy

Antigenic PSCA-related peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E.) Administration of Vaccines for Therapeutic or Prophylactic Purposes

Pharmaceutical and vaccine compositions of the invention are typically used to treat and/or prevent a cancer that expresses or overexpresses PSCA. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses PSCA. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of PSCA-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses PSCA, a vaccine comprising PSCA-specific CTL may be more efficacious in killing tumor cells in patient with advanced disease than alternative embodiments.

It is generally important to provide an amount of the peptide epitope delivered by a mode of administration sufficient to stimulate effectively a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 µg and the higher value is about 10,000; 20,000; 30,000; or 50,000 µg. Dosage values for a human typically range from about 500 µg to about 50,000 µg per 70 kilogram patient. Boosting dosages of between about 1.0 µg to about 50,000 µg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 µg and the higher value is about 10,000; 20,000; 30,000; or 50,000 µg. Dosage values for a human typically range from about 500 µg to about 50,000 µg per 70 kilogram patient. This is followed by boosting dosages of between about 1.0 µg to about 50,000 µg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., *Remington's Pharmaceutical Sciences*, 17th Edition, A. Gennaro, Editor, Mack Publishing Co., Easton, Pa., 1985). For example a peptide dose for initial immunization can be from about 1 to about 50,000 µg, generally 100-5,000 µg, for a 70 kg patient. For example, for nucleic acids an initial immunization may be performed using an expression vector in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of $5\text{-}10^7$ to $5\times10^9$ pfu.

For antibodies, a treatment generally involves repeated administration of the anti-PSCA antibody preparation, via an acceptable route of administration such as intravenous injection (IV), typically at a dose in the range of about 0.1 to about 10 mg/kg body weight. In general, doses in the range of 10-500 mg MAb per week are effective and well tolerated. Moreover, an initial loading dose of approximately 4 mg/kg patient body weight IV, followed by weekly doses of about 2 mg/kg IV of the anti-PSCA MAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of PSCA expression in the patient, the extent of circulating shed PSCA antigen, the desired steady-state concentration level, frequency of treatment, and the influence of chemotherapeutic or other agents used in combination with the treatment method of the invention, as well as the health status of a particular patient. Non-limiting preferred human unit doses are, for example, 500 μg-1 mg, 1 mg -50 mg, 50 mg-100 mg, 100 mg-200 mg, 200 mg-300 mg, 400 mg-500 mg, 500 mg-600 mg, 600 mg-700 mg, 700 mg-800 mg, 800 mg-900 mg, 900 mg-1g, or 1 mg-700 mg. In certain embodiments, the dose is in a range of 2-5 mg/kg body weight, e.g., with follow on weekly doses of 1-3 mg/kg; 0.5 mg, 1, 2, 3, 4, 5, 6, 7, 8, 9, 10 mg/kg body weight followed, e.g., in two, three or four weeks by weekly doses; 0.5-10 mg/kg body weight, e.g., followed in two, three or four weeks by weekly doses; 225, 250, 275, 300, 325, 350, 375, 400 mg m$^2$ of body area weekly; 1-600 mg m$^2$ of body area weekly; 225-400 mg m$^2$ of body area weekly; these does can be followed by weekly doses for 2, 3, 4, 5, 6, 7, 8, 9, 19, 11, 12 or more weeks.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $5 \times 10^{10}$ cells. A dose may also about $10^6$ cells/m$^2$ to about $10^{10}$ cells/m$^2$, or about $10^6$ cells/m$^2$ to about $10^8$ cells/m$^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, immunogenic peptides are preferably supplied in finely divided form along with a surfactant and propellant. Typical percentages of peptides are about 0.01%-20% by weight, preferably about 1%-10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%-20% by weight of the composition, preferably about 0.25-5%. The balance of the composition is ordinarily propellant. A carrier can also be included, as desired, as with, e.g., lecithin for intranasal delivery.

XI.) Diagnostic and Prognostic Embodiments of PSCA

As disclosed herein, PSCA polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in the Example entitled "Expression analysis of PSCA in normal tissues, and patient specimens").

PSCA can be analogized to a prostate associated antigen PSA, the archetypal marker that has been used by medical practitioners for years to identify and monitor the presence of prostate cancer (see, e.g., Merrill et al., *J. Urol.* 163(2): 503-5120 (2000); Polascik et al., *J. Urol. Aug;* 162(2):293-306 (1999) and Fortier et al., *J. Nat. Cancer Inst.* 91(19): 1635-1640 (1999)). A variety of other diagnostic markers are also used in similar contexts including p53 and K-ras (see, e.g., Tulchinsky et al., *Int J Mol Med* 1999 July 4(1):99-102 and Minimoto et al., *Cancer Detect Prev* 2000; 24(1):1-12). Therefore, this disclosure of PSCA polynucleotides and polypeptides (as well as PSCA polynucleotide probes and anti-PSCA antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the PSCA polynucleotides, polypeptides, reactive T cells and antibodies are analogous to those methods from well-established diagnostic assays, which employ, e.g., PSA polynucleotides, polypeptides, reactive T cells and antibodies. For example, just as PSA polynucleotides are used as probes (for example in Northern analysis, see, e.g., Sharief et al., *Biochem. Mol. Biol. Int.* 33(3):567-74 (1994)) and primers (for example in PCR analysis, see, e.g., Okegawa et al., *J. Urol.* 163(4): 1189-1190 (2000)) to observe the presence and/or the level of PSA mRNAs in methods of monitoring PSA overexpression or the metastasis of prostate cancers, the PSCA polynucleotides described herein can be utilized in the same way to detect PSCA overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., *Urology* 55(4):560-3 (2000)) or the metastasis of prostate cells (see, e.g., Alanen et al., *Pathol. Res. Pract.* 192(3):233-7 (1996)), the PSCA polypeptides described herein can be utilized to generate antibodies for use in detecting PSCA overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing PSCA polynucleotides and/or polypeptides can be used to provide evidence of metastasis. For example, when a biological sample from tissue that does not normally contain PSCA-expressing cells (lymph node) is found to contain PSCA-expressing cells such as the PSCA expression seen in LAPC4 and LAPC9, xenografts isolated from lymph node and bone metastasis, respectively, this finding is indicative of metastasis.

Alternatively PSCA polynucleotides and/or polypeptides can be used to provide evidence of cancer, for example, when cells in a biological sample that do not normally express PSCA or express PSCA at a different level are found to express PSCA or have an increased expression of PSCA (see, e.g., the PSCA expression in the cancers listed in Table I and in patient samples etc. shown in the accompanying Figures). In such assays, artisans may further wish to generate supplementary evidence of metastasis by testing the biological sample for the presence of a second tissue restricted marker (in addition to PSCA) such as PSA, PSCA etc. (see, e.g., Alanen et al., *Pathol. Res. Pract.* 192(3): 233-237 (1996)).

The use of immunohistochemistry to identify the presence of a PSCA polypeptide within a tissue section can indicate an altered state of certain cells within that tissue. It is well understood in the art that the ability of an antibody to localize to a polypeptide that is expressed in cancer cells is a way of diagnosing presence of disease, disease stage, progression and/or tumor aggressiveness. Such an antibody can also detect an altered distribution of the polypeptide within the cancer cells, as compared to corresponding non-malignant tissue.

The PSCA polypeptide and immunogenic compositions are also useful in view of the phenomena of altered subcellular protein localization in disease states. Alteration of cells from normal to diseased state causes changes in cellular morphology and is often associated with changes in subcellular protein localization/distribution. For example, cell membrane proteins that are expressed in a polarized manner in normal cells can be altered in disease, resulting in distribution of the protein in a non-polar manner over the whole cell surface.

The phenomenon of altered subcellular protein localization in a disease state has been demonstrated with MUC1 and Her2 protein expression by use of immunohistochemical means. Normal epithelial cells have a typical apical distribution of MUC1, in addition to some supranuclear localization of the glycoprotein, whereas malignant lesions often demonstrate an apolar staining pattern (Diaz et al, *The Breast Journal*, 7; 40-45 (2001); Zhang et al, *Clinical Cancer Research*, 4; 2669-2676 (1998): Cao, et al, *The Journal of Histochemistry and Cytochemistry*, 45: 1547-1557 (1997)). In addition, normal breast epithelium is either negative for Her2 protein or exhibits only a basolateral distribution whereas malignant cells can express the protein over the whole cell surface (De Potter, et al, *International Journal of Cancer*, 44; 969-974 (1989): McCormick, et al, 117; 935-943 (2002)). Alternatively, distribution of the protein may be altered from a surface only localization to include diffuse cytoplasmic expression in the diseased state. Such an example can be seen with MUC1 (Diaz, et al, *The Breast Journal*, 7: 40-45 (2001)).

Alteration in the localization/distribution of a protein in the cell, as detected by immunohistochemical methods, can also provide valuable information concerning the favorability of certain treatment modalities. This last point is illustrated by a situation where a protein may be intracellular in normal tissue, but cell surface in malignant cells; the cell surface location makes the cells favorably amenable to antibody-based diagnostic and treatment regimens. When such an alteration of protein localization occurs for PSCA, the PSCA protein and immune responses related thereto are very useful. Accordingly, the ability to determine whether alteration of subcellular protein localization occurred for 24P4C12 make the PSCA protein and immune responses related thereto very useful. Use of the PSCA compositions allows those skilled in the art to make important diagnostic and therapeutic decisions.

Immunohistochemical reagents specific to PSCA are also useful to detect metastases of tumors expressing PSCA when the polypeptide appears in tissues where PSCA is not normally produced.

Thus, PSCA polypeptides and antibodies resulting from immune responses thereto are useful in a variety of important contexts such as diagnostic, prognostic, preventative and/or therapeutic purposes known to those skilled in the art.

Just as PSA polynucleotide fragments and polynucleotide variants are employed by skilled artisans for use in methods of monitoring PSA, PSCA polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472-476, 478-480 (1998); Robertson et al., Methods Mol. Biol. 98:121-154 (1998)). An additional illustration of the use of such fragments is provided in the Example entitled "Expression analysis of PSCA in normal tissues, and patient specimens," where a PSCA polynucleotide fragment is used as a probe to show the expression of PSCA RNAs in cancer cells. In addition, variant polynucleotide sequences are typically used as primers and probes for the corresponding mRNAs in PCR and Northern analyses (see, e.g., Sawai et al., Fetal Diagn. Ther. 1996 November-December 11(6):407-13 and Current Protocols In Molecular Biology, Volume 2, Unit 2, Frederick M. Ausubel et al. eds., 1995)). Polynucleotide fragments and variants are useful in this context where they are capable of binding to a target polynucleotide sequence (e.g., a PSCA polynucleotide shown in FIG. 1 or variant thereof) under conditions of high stringency.

Furthermore, PSA polypeptides which contain an epitope that can be recognized by an antibody or T cell that specifically binds to that epitope are used in methods of monitoring PSA. PSCA polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubel et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. Nos. 5,840,501 and 5,939,533). For example it may be preferable to utilize a polypeptide comprising one of the PSCA biological motifs discussed herein or a motif-bearing subsequence which is readily identified by one of skill in the art based on motifs available in the art. Polypeptide fragments, variants or analogs are typically useful in this context as long as they comprise an epitope capable of generating an antibody or T cell specific for a target polypeptide sequence (e.g. a PSCA polypeptide shown in FIG. 1).

As shown herein, the PSCA polynucleotides and polypeptides (as well as the PSCA polynucleotide probes and anti-PSCA antibodies or T cells used to identify the presence of these molecules) exhibit specific properties that make them useful in diagnosing cancers such as those listed in Table I. Diagnostic assays that measure the presence of PSCA gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., Pathol. Res. Pract. 192(3): 233-237 (1996)), and consequently, materials such as PSCA polynucleotides and polypeptides (as well as the PSCA polynucleotide probes and anti-PSCA antibodies used to identify the presence of these molecules) need to be employed to confirm a metastases of prostatic origin.

Finally, in addition to their use in diagnostic assays, the PSCA polynucleotides disclosed herein have a number of other utilities such as their use in the identification of oncogenetic associated chromosomal abnormalities in the chromosomal region to which the PSCA gene maps (see the Example entitled "Chromosomal Mapping of PSCA" below). Moreover, in addition to their use in diagnostic assays, the PSCA-related proteins and polynucleotides disclosed herein have other utilities such as their use in the forensic analysis of tissues of unknown origin (see, e.g., Takahama K Forensic Sci Int 1996 Jun. 28; 80(1-2): 63-9).

Additionally, PSCA-related proteins or polynucleotides of the invention can be used to treat a pathologic condition characterized by the over-expression of PSCA. For example, the amino acid or nucleic acid sequence of FIG. 1, or fragments of either, can be used to generate an immune response to a PSCA antigen. Antibodies or other molecules that react with PSCA can be used to modulate the function of this molecule, and thereby provide a therapeutic benefit.

XII.) Inhibition of PSCA Protein Function

The invention includes various methods and compositions for inhibiting the binding of PSCA to its binding partner or its association with other protein(s) as well as methods for inhibiting PSCA function.

XII.A.) Inhibition of PSCA with Intracellular Antibodies

In one approach, a recombinant vector that encodes single chain antibodies that specifically bind to PSCA are introduced into PSCA expressing cells via gene transfer technologies. Accordingly, the encoded single chain anti-PSCA antibody is expressed intracellularly, binds to PSCA protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to target precisely the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture PSCA in the nucleus, thereby preventing its activity within the nucleus. Nuclear targeting signals are engineered into such PSCA intrabodies in order to achieve the desired targeting. Such PSCA intrabodies are designed to bind specifically to a particular PSCA domain. In another embodiment, cytosolic intrabodies that specifically bind to a PSCA protein are used to prevent PSCA from gaining access to the nucleus, thereby preventing it from exerting any biological activity within the nucleus (e.g., preventing PSCA from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

XII.B.) Inhibition of PSCA with Recombinant Proteins

In another approach, recombinant molecules bind to PSCA and thereby inhibit PSCA function. For example, these recombinant molecules prevent or inhibit PSCA from accessing/binding to its binding partner(s) or associating with other protein(s). Such recombinant molecules can, for example, contain the reactive part(s) of a PSCA specific antibody molecule. In a particular embodiment, the PSCA binding domain of a PSCA binding partner is engineered into a dimeric fusion protein, whereby the fusion protein comprises two PSCA ligand binding domains linked to the Fc portion of a human IgG, such as human $IgG_1$. Such IgG portion can contain, for example, the $CH_2$ and $CH_3$ domains and the hinge region, but not the $CH_1$ domain. Such dimeric fusion proteins are administered in soluble form to patients suffering from a cancer associated with the expression of PSCA, whereby the dimeric fusion protein specifically binds to PSCA and blocks PSCA interaction with a binding partner. Such dimeric fusion proteins are further combined into multimeric proteins using known antibody linking technologies.

XII.C.) Inhibition of PSCA Transcription or Translation

The present invention also comprises various methods and compositions for inhibiting the transcription of the PSCA gene. Similarly, the invention also provides methods and compositions for inhibiting the translation of PSCA mRNA into protein.

In one approach, a method of inhibiting the transcription of the PSCA gene comprises contacting the PSCA gene with a PSCA antisense polynucleotide. In another approach, a method of inhibiting PSCA mRNA translation comprises contacting a PSCA mRNA with an antisense polynucleotide. In another approach, a PSCA specific ribozyme is used to cleave a PSCA message, thereby inhibiting translation. Such antisense and ribozyme based methods can also be directed to the regulatory regions of the PSCA gene, such as PSCA promoter and/or enhancer elements. Similarly, proteins capable of inhibiting a PSCA gene transcription factor are used to inhibit PSCA mRNA transcription. The various polynucleotides and compositions useful in the aforementioned methods have been described above. The use of antisense and ribozyme molecules to inhibit transcription and translation is well known in the art.

Other factors that inhibit the transcription of PSCA by interfering with PSCA transcriptional activation are also useful to treat cancers expressing PSCA. Similarly, factors that interfere with PSCA processing are useful to treat cancers that express PSCA. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing PSCA (i.e., antisense, ribozyme, polynucleotides encoding intrabodies and other PSCA inhibitory molecules). A number of gene therapy approaches are known in the art. Recombinant vectors encoding PSCA antisense polynucleotides, ribozymes, factors capable of interfering with PSCA transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of PSCA to a binding partner, etc.

In vivo, the effect of a PSCA therapeutic composition can be evaluated in a suitable animal model. For example, xenogenic prostate cancer models can be used, wherein human prostate cancer explants or passaged xenograft tissues are introduced into immune compromised animals, such as nude or SCID mice (Klein et al., 1997, *Nature Medicine* 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, *Remington's Pharmaceutical Sciences* 16th Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XIII.) Identification, Characterization and Use of Modulators of PSCA

Methods to Identify and Use Modulators

In one embodiment, screening is performed to identify modulators that induce or suppress a particular expression profile, suppress or induce specific pathways, preferably generating the associated phenotype thereby. In another embodiment, having identified differentially expressed genes important in a particular state; screens are performed to identify modulators that alter expression of individual genes, either increase or decrease. In another embodiment, screening is performed to identify modulators that alter a biological function of the expression product of a differentially expressed gene. Again, having identified the importance of a gene in a particular state, screens are performed to identify agents that bind and/or modulate the biological activity of the gene product.

In addition, screens are done for genes that are induced in response to a candidate agent. After identifying a modulator (one that suppresses a cancer expression pattern leading to a normal expression pattern, or a modulator of a cancer gene that leads to expression of the gene as in normal tissue) a screen is performed to identify genes that are specifically modulated in response to the agent. Comparing expression profiles between normal tissue and agent-treated cancer tissue reveals genes that are not expressed in normal tissue or cancer tissue, but are expressed in agent treated tissue, and vice versa. These agent-specific sequences are identified and used by methods described herein for cancer genes or proteins. In particular these sequences and the proteins they encode are used in marking or identifying agent-treated cells. In addition, antibodies are raised against the agent-induced proteins and used to target novel therapeutics to the treated cancer tissue sample.

Modulator-related Identification and Screening Assays:
Gene Expression-related Assays Proteins, nucleic acids, and antibodies of the invention are used in screening assays. The cancer-associated proteins, antibodies, nucleic acids, modified proteins and cells containing these sequences are used in screening assays, such as evaluating the effect of drug candidates on a "gene expression profile," expression profile of polypeptides or alteration of biological function. In one embodiment, the expression profiles are used, preferably in conjunction with high throughput screening techniques to allow monitoring for expression profile genes after treatment with a candidate agent (e.g., Davis, G F, et al, *J Biol Screen* 7:69 (2002); Zlokarnik, et al., *Science* 279:84-8 (1998); Heid, *Genome Res* 6:986-94, 1996).

The cancer proteins, antibodies, nucleic acids, modified proteins and cells containing the native or modified cancer proteins or genes are used in screening assays. That is, the present invention comprises methods for screening for compositions which modulate the cancer phenotype or a physiological function of a cancer protein of the invention. This is done on a gene itself or by evaluating the effect of drug candidates on a "gene expression profile" or biological function. In one embodiment, expression profiles are used, preferably in conjunction with high throughput screening techniques to allow monitoring after treatment with a candidate agent, see Zlokarnik, supra.

A variety of assays are executed directed to the genes and proteins of the invention. Assays are run on an individual nucleic acid or protein level. That is, having identified a particular gene as up regulated in cancer, test compounds are screened for the ability to modulate gene expression or for binding to the cancer protein of the invention. "Modulation" in this context includes an increase or a decrease in gene expression. The preferred amount of modulation will depend on the original change of the gene expression in normal versus tissue undergoing cancer, with changes of at least 10%, preferably 50%, more preferably 100-300%, and in some embodiments 300-1000% or greater. Thus, if a gene exhibits a 4-fold increase in cancer tissue compared to normal tissue, a decrease of about four-fold is often desired; similarly, a 10-fold decrease in cancer tissue compared to normal tissue a target value of a 10 -fold increase in expression by the test compound is often desired. Modulators that exacerbate the type of gene expression seen in cancer are also useful, e.g., as an upregulated target in further analyses.

The amount of gene expression is monitored using nucleic acid probes and the quantification of gene expression levels, or, alternatively, a gene product itself is monitored, e.g., through the use of antibodies to the cancer protein and standard immunoassays. Proteomics and separation techniques also allow for quantification of expression.

Expression Monitoring to Identify Compounds that Modify Gene Expression

In one embodiment, gene expression monitoring, i.e., an expression profile, is monitored simultaneously for a number of entities. Such profiles will typically involve one or more of the genes of FIG. 1. In this embodiment, e.g., cancer nucleic acid probes are attached to biochips to detect and quantify cancer sequences in a particular cell. Alternatively, PCR can be used. Thus, a series, e.g., wells of a microtiter plate, can be used with dispensed primers in desired wells. A PCR reaction can then be performed and analyzed for each well.

Expression monitoring is performed to identify compounds that modify the expression of one or more cancer-associated sequences, e.g., a polynucleotide sequence set out in FIG. 1. Generally, a test modulator is added to the cells prior to analysis. Moreover, screens are also provided to identify agents that modulate cancer, modulate cancer proteins of the invention, bind to a cancer protein of the invention, or interfere with the binding of a cancer protein of the invention and an antibody or other binding partner.

In one embodiment, high throughput screening methods involve providing a library containing a large number of potential therapeutic compounds (candidate compounds).

Such "combinatorial chemical libraries" are then screened in one or more assays to identify those library members (particular chemical species or subclasses) that display a desired characteristic activity. The compounds thus identified can serve as conventional "lead compounds," as compounds for screening, or as therapeutics.

In certain embodiments, combinatorial libraries of potential modulators are screened for an ability to bind to a cancer polypeptide or to modulate activity. Conventionally, new chemical entities with useful properties are generated by identifying a chemical compound (called a "lead compound") with some desirable property or activity, e.g., inhibiting activity, creating variants of the lead compound, and evaluating the property and activity of those variant compounds. Often, high throughput screening (HTS) methods are employed for such an analysis.

As noted above, gene expression monitoring is conveniently used to test candidate modulators (e.g., protein, nucleic acid or small molecule). After the candidate agent has been added and the cells allowed to incubate for a period, the sample containing a target sequence to be analyzed is, e.g., added to a biochip.

If required, the target sequence is prepared using known techniques. For example, a sample is treated to lyse the cells, using known lysis buffers, electroporation, etc., with purification and/or amplification such as PCR performed as appropriate. For example, an in vitro transcription with labels covalently attached to the nucleotides is performed. Generally, the nucleic acids are labeled with biotin-FITC or PE, or with cy3 or cy5.

The target sequence can be labeled with, e.g., a fluorescent, a chemiluminescent, a chemical, or a radioactive signal, to provide a means of detecting the target sequence's specific binding to a probe. The label also can be an enzyme, such as alkaline phosphatase or horseradish peroxidase, which when provided with an appropriate substrate produces a product that is detected. Alternatively, the label is a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. Unbound labeled streptavidin is typically removed prior to analysis.

As will be appreciated by those in the art, these assays can be direct hybridization assays or can comprise "sandwich assays", which include the use of multiple probes, as is generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124, 246; and 5,681,697. In this embodiment, in general, the target nucleic acid is prepared as outlined above, and then added to the biochip comprising a plurality of nucleic acid probes, under conditions that allow the formation of a hybridization complex.

A variety of hybridization conditions are used in the present invention, including high, moderate and low stringency conditions as outlined above. The assays are generally run under stringency conditions which allow formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc. These parameters may also be used to control non-specific binding, as is generally outlined in U.S. Pat. No. 5,681,697. Thus, it can be desirable to perform certain steps at higher stringency conditions to reduce nonspecific binding.

The reactions outlined herein can be accomplished in a variety of ways. Components of the reaction can be added simultaneously, or sequentially, in different orders, with preferred embodiments outlined below. In addition, the reaction may include a variety of other reagents. These include salts, buffers, neutral proteins, e.g. albumin, detergents, etc. which can be used to facilitate optimal hybridization and detection, and/or reduce nonspecific or background interactions. Reagents that otherwise improve the efficiency of the assay, such as protease inhibitors, nuclease inhibitors, anti-microbial agents, etc., may also be used as appropriate, depending on the sample preparation methods and purity of the target. The assay data are analyzed to determine the expression levels of individual genes, and changes in expression levels as between states, forming a gene expression profile.

Biological Activity-related Assays

The invention provides methods identify or screen for a compound that modulates the activity of a cancer-related gene or protein of the invention. The methods comprise adding a test compound, as defined above, to a cell comprising a cancer protein of the invention. The cells contain a recombinant nucleic acid that encodes a cancer protein of the invention. In another embodiment, a library of candidate agents is tested on a plurality of cells.

In one aspect, the assays are evaluated in the presence or absence or previous or subsequent exposure of physiological signals, e.g. hormones, antibodies, peptides, antigens, cytokines, growth factors, action potentials, pharmacological agents including chemotherapeutics, radiation, carcinogenics, or other cells (i.e., cell-cell contacts). In another example, the determinations are made at different stages of the cell cycle process. In this way, compounds that modulate genes or proteins of the invention are identified. Compounds with pharmacological activity are able to enhance or interfere with the activity of the cancer protein of the invention. Once identified, similar structures are evaluated to identify critical structural features of the compound.

In one embodiment, a method of modulating (e.g., inhibiting) cancer cell division is provided; the method comprises administration of a cancer modulator. In another embodiment, a method of modulating (e.g., inhibiting) cancer is provided; the method comprises administration of a cancer modulator. In a further embodiment, methods of treating cells or individuals with cancer are provided; the method comprises administration of a cancer modulator.

In one embodiment, a method for modulating the status of a cell that expresses a gene of the invention is provided. As used herein status comprises such art-accepted parameters such as growth, proliferation, survival, function, apoptosis, senescence, location, enzymatic activity, signal transduction, etc. of a cell. In one embodiment, a cancer inhibitor is an antibody as discussed above. In another embodiment, the cancer inhibitor is an antisense molecule. A variety of cell growth, proliferation, and metastasis assays are known to those of skill in the art, as described herein.

High Throughput Screening to Identify Modulators

The assays to identify suitable modulators are amenable to high throughput screening. Preferred assays thus detect enhancement or inhibition of cancer gene transcription, inhibition or enhancement of polypeptide expression, and inhibition or enhancement of polypeptide activity.

In one embodiment, modulators evaluated in high throughput screening methods are proteins, often naturally occurring proteins or fragments of naturally occurring proteins. Thus, e.g., cellular extracts containing proteins, or random or directed digests of proteinaceous cellular extracts, are used. In this way, libraries of proteins are made for screening in the methods of the invention. Particularly preferred in this embodiment are libraries of bacterial, fungal, viral, and mammalian proteins, with the latter being preferred, and human proteins being especially preferred. Particularly useful test compound will be directed to the class of proteins to which the target belongs, e.g., substrates for enzymes, or ligands and receptors.

Use of Soft Agar Growth and Colony Formation to Identify and Characterize Modulators Normal cells require a solid substrate to attach and grow. When cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, can regenerate normal phenotype and once again require a solid substrate to attach to and grow. Soft agar growth or colony formation in assays are used to identify modulators of cancer sequences, which when expressed in host cells, inhibit abnormal cellular proliferation and transformation. A modulator reduces or eliminates the host cells' ability to grow suspended in solid or semisolid media, such as agar.

Techniques for soft agar growth or colony formation in suspension assays are described in Freshney, *Culture of Animal Cells a Manual of Basic Technique* (3rd ed., 1994). See also, the methods section of Garkavtsev et al. (1996), supra.

Evaluation of Contact Inhibition and Growth Density Limitation to Identify and Characterize Modulators Normal cells typically grow in a flat and organized pattern in cell culture until they touch other cells. When the cells touch one another, they are contact inhibited and stop growing. Transformed cells, however, are not contact inhibited and continue to grow to high densities in disorganized foci. Thus, transformed cells grow to a higher saturation density than corresponding normal cells. This is detected morphologically by the formation of a disoriented monolayer of cells or cells in foci. Alternatively, labeling index with (3H)-thymidine at saturation density is used to measure density limitation of growth, similarly an MTT or Alamar blue assay will reveal proliferation capacity of cells and the ability of modulators to affect same. See Freshney (1994), supra. Transformed cells, when transfected with tumor suppressor genes, can regenerate a normal phenotype and become contact inhibited and would grow to a lower density.

In this assay, labeling index with 3H)-thymidine at saturation density is a preferred method of measuring density limitation of growth. Transformed host cells are transfected with a cancer-associated sequence and are grown for 24 hours at saturation density in non-limiting medium conditions. The percentage of cells labeling with (3H)-thymidine is determined by incorporated cpm.

Contact independent growth is used to identify modulators of cancer sequences, which had led to abnormal cellular proliferation and transformation. A modulator reduces or eliminates contact independent growth, and returns the cells to a normal phenotype.

Evaluation of Growth Factor or Serum Dependence to Identify and Characterize Modulators Transformed cells have lower serum dependence than their normal counterparts (see, e.g., Temin, *J. Natl. CancerInst.* 37:167-175 (1966); Eagle et al., *J. Exp. Med* 131:836-879 (1970)); Freshney, supra. This is in part due to release of various growth factors by the transformed cells. The degree of growth factor or serum dependence of transformed host cells can be compared with that of control. For example, growth factor or serum dependence of a cell is monitored in methods to identify and characterize compounds that modulate cancer-associated sequences of the invention.

Use of Tumor-specific Marker Levels to Identify and Characterize Modulators

Tumor cells release an increased amount of certain factors (hereinafter "tumor specific markers") than their normal counterparts. For example, plasminogen activator (PA) is released from human glioma at a higher level than from normal brain cells (see, e.g., Gullino, *Angiogenesis, Tumor Vascularization, and Potential Interference with Tumor Growth, in Biological Responses in Cancer*, pp. 178-184 (Mihich (ed.) 1985)). Similarly, Tumor Angiogenesis Factor (TAF) is released at a higher level in tumor cells than their normal counterparts. See, e.g., Folkman, *Angiogenesis and Cancer, Sem. Cancer Biol.* (1992)), while bFGF is released from endothelial tumors (Ensoli, B et al.).

Various techniques which measure the release of these factors are described in Freshney (1994), supra. Also, see, Unkless et al., *J. Biol. Chem.* 249:4295-4305 (1974); Strickland & Beers, *J. Biol. Chem.* 251:5694-5702 (1976); Whur et al., *Br. J. Cancer* 42:305 312 (1980); Gullino, *Angiogenesis, Tumor Vascularization, and Potential Interference with Tumor Growth, in Biological Responses in Cancer*, pp. 178-184 (Mihich (ed.) 1985); Freshney, *Anticancer Res.* 5:111-130 (1985). For example, tumor specific marker levels are monitored in methods to identify and characterize compounds that modulate cancer-associated sequences of the invention.

Invasiveness into Matrigel to Identify and Characterize Modulators

The degree of invasiveness into Matrigel or an extracellular matrix constituent can be used as an assay to identify and characterize compounds that modulate cancer associated sequences. Tumor cells exhibit a positive correlation between malignancy and invasiveness of cells into Matrigel or some other extracellular matrix constituent. In this assay, tumorigenic cells are typically used as host cells. Expression of a tumor suppressor gene in these host cells would decrease invasiveness of the host cells. Techniques described in *Cancer Res.* 1999; 59:6010; Freshney (1994), supra, can be used. Briefly, the level of invasion of host cells is measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

Evaluation of Tumor Growth In Vivo to Identify and Characterize Modulators

Effects of cancer-associated sequences on cell growth are tested in transgenic or immune-suppressed organisms. Transgenic organisms are prepared in a variety of art-accepted ways. For example, knock-out transgenic organisms, e.g., mammals such as mice, are made, in which a cancer gene is disrupted or in which a cancer gene is inserted. Knock-out transgenic mice are made by insertion of a marker gene or other heterologous gene into the endogenous cancer gene site in the mouse genome via homologous recombination. Such mice can also be made by substituting the endogenous cancer gene with a mutated version of the cancer gene, or by mutating the endogenous cancer gene, e.g., by exposure to carcinogens.

To prepare transgenic chimeric animals, e.g., mice, a DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells some of which are derived from the mutant cell line. Therefore, by breeding the chimeric mice it is possible to obtain a new line of mice containing the introduced genetic lesion (see, e.g., Capecchi et al., *Science* 244:1288 (1989)). Chimeric mice can be derived according to U.S. Pat. No. 6,365,797, issued 2 Apr. 2002; U.S. Pat. No. 6,107,540 issued 22 Aug. 2000; Hogan et al., *Manipulating the Mouse Embryo: A laboratory Manual*, Cold Spring Harbor Laboratory (1988) and *Teratocarcinomas and Embryonic Stem Cells: A Practical Approach*, Robertson, ed., IRL Press, Washington, D.C., (1987).

Alternatively, various immune-suppressed or immune-deficient host animals can be used. For example, a genetically athymic "nude" mouse (see, e.g., Giovanella et al., *J. Natl. Cancer Inst.* 52:921 (1974)), a SCID mouse, a thymectornized mouse, or an irradiated mouse (see, e.g., Bradley et al., *Br. J. Cancer* 38:263 (1978); Selby et al., *Br. J. Cancer* 41:52 (1980)) can be used as a host. Transplantable tumor cells (typically about $10^6$ cells) injected into isogenic hosts produce invasive tumors in a high proportion of cases, while normal cells of similar origin will not. In hosts which developed invasive tumors, cells expressing cancer-associated sequences are injected subcutaneously or orthotopically. Mice are then separated into groups, including control groups and treated experimental groups) e.g. treated with a modulator). After a suitable length of time, preferably 4-8 weeks, tumor growth is measured (e.g., by volume or by its two largest dimensions, or weight) and compared to the control. Tumors that have statistically significant reduction (using, e.g., Student's T test) are said to have inhibited growth.

In Vitro Assays to Identify and Characterize Modulators

Assays to identify compounds with modulating activity can be performed in vitro. For example, a cancer polypeptide is first contacted with a potential modulator and incubated for a suitable amount of time, e.g., from 0.5 to 48 hours. In one embodiment, the cancer polypeptide levels are determined in vitro by measuring the level of protein or mRNA. The level of protein is measured using immunoassays such as Western blotting, ELISA and the like with an antibody that selectively binds to the cancer polypeptide or a fragment thereof. For measurement of mRNA, amplification, e.g., using PCR, LCR, or hybridization assays, e.g., Northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using a cancer protein promoter operably linked to a reporter gene such as luciferase, green fluorescent protein, CAT, or P-gal. The reporter construct is typically transfected into a cell. After treatment with a potential modulator, the amount of reporter gene transcription, translation, or activity is measured according to standard techniques known to those of skill in the art (Davis G F, supra; Gonzalez, J. & Negulescu, P. *Curr. Opin. Biotechnol.* 1998: 9:624).

As outlined above, in vitro screens are done on individual genes and gene products. That is, having identified a particular differentially expressed gene as important in a particular state, screening of modulators of the expression of the gene or the gene product itself is performed.

In one embodiment, screening for modulators of expression of specific gene(s) is performed. Typically, the expression of only one or a few genes is evaluated. In another embodiment, screens are designed to first find compounds that bind to differentially expressed proteins. These compounds are then evaluated for the ability to modulate differentially expressed activity. Moreover, once initial candidate compounds are identified, variants can be further screened to better evaluate structure activity relationships.

Binding Assays to Identify and Characterize Modulators

In binding assays in accordance with the invention, a purified or isolated gene product of the invention is generally used. For example, antibodies are generated to a protein of the invention, and immunoassays are run to determine the amount and/or location of protein. Alternatively, cells comprising the cancer proteins are used in the assays.

Thus, the methods comprise combining a cancer protein of the invention and a candidate compound such as a ligand, and determining the binding of the compound to the cancer protein of the invention. Preferred embodiments utilize the human cancer protein; animal models of human disease of can also be developed and used. Also, other analogous mammalian proteins also can be used as appreciated by those of skill in the art. Moreover, in some embodiments variant or derivative cancer proteins are used.

Generally, the cancer protein of the invention, or the ligand, is non-diffusibly bound to an insoluble support. The support can, e.g., be one having isolated sample receiving areas (a microtiter plate, an array, etc.). The insoluble supports can be made of any composition to which the compositions can be bound, is readily separated from soluble material, and is otherwise compatible with the overall method of screening. The surface of such supports can be solid or porous and of any convenient shape.

Examples of suitable insoluble supports include microtiter plates, arrays, membranes and beads. These are typically made of glass, plastic (e.g., polystyrene), polysaccharide, nylon, nitrocellulose, or Teflon™, etc. Microtiter plates and arrays are especially convenient because a large number of assays can be carried out simultaneously, using small amounts of reagents and samples. The particular manner of binding of the composition to the support is not crucial so long as it is compatible with the reagents and overall methods of the invention, maintains the activity of the composition and is nondiffusable. Preferred methods of binding include the use of antibodies which do not sterically block either the ligand binding site or activation sequence when attaching the protein to the support, direct binding to "sticky" or ionic supports, chemical crosslinking, the synthesis of the protein or agent on the surface, etc. Following binding of the protein or ligand/binding agent to the support, excess unbound material is removed by washing. The sample receiving areas may then be blocked through incubation with bovine serum albumin (BSA), casein or other innocuous protein or other moiety.

Once a cancer protein of the invention is bound to the support, and a test compound is added to the assay. Alternatively, the candidate binding agent is bound to the support and the cancer protein of the invention is then added. Binding agents include specific antibodies, non-natural binding agents identified in screens of chemical libraries, peptide analogs, etc.

Of particular interest are assays to identify agents that have a low toxicity for human cells. A wide variety of assays can be used for this purpose, including proliferation assays, cAMP assays, labeled in vitro protein-protein binding assays, electrophoretic mobility shift assays, immunoassays for protein binding, functional assays (phosphorylation assays, etc.) and the like.

A determination of binding of the test compound (ligand, binding agent, modulator, etc.) to a cancer protein of the invention can be done in a number of ways. The test compound can be labeled, and binding determined directly, e.g., by attaching all or a portion of the cancer protein of the invention to a solid support, adding a labeled candidate compound (e.g., a fluorescent label), washing off excess reagent, and determining whether the label is present on the solid support. Various blocking and washing steps can be utilized as appropriate.

In certain embodiments, only one of the components is labeled, e.g., a protein of the invention or ligands labeled. Alternatively, more than one component is labeled with different labels, e.g., $I^{125}$, for the proteins and a fluorophore for the compound. Proximity reagents, e.g., quenching or energy transfer reagents are also useful.

Competitive Binding to Identify and Characterize Modulators

In one embodiment, the binding of the "test compound" is determined by competitive binding assay with a "competitor." The competitor is a binding moiety that binds to the target molecule (e.g., a cancer protein of the invention). Competitors include compounds such as antibodies, peptides, binding partners, ligands, etc. Under certain circumstances, the competitive binding between the test compound and the competitor displaces the test compound. In one embodiment, the test compound is labeled. Either the test compound, the competitor, or both, is added to the protein for a time sufficient to allow binding. Incubations are performed at a temperature that facilitates optimal activity, typically between four and 40° C. Incubation periods are typically optimized, e.g., to facilitate rapid high throughput screening; typically between zero and one hour will be sufficient. Excess reagent is generally removed or washed away. The second component is then added, and the presence or absence of the labeled component is followed, to indicate binding.

In one embodiment, the competitor is added first, followed by the test compound. Displacement of the competitor is an indication that the test compound is binding to the cancer protein and thus is capable of binding to, and potentially modulating, the activity of the cancer protein. In this embodiment, either component can be labeled. Thus, e.g., if the competitor is labeled, the presence of label in the post-test compound wash solution indicates displacement by the test compound. Alternatively, if the test compound is labeled, the presence of the label on the support indicates displacement.

In an alternative embodiment, the test compound is added first, with incubation and washing, followed by the competitor. The absence of binding by the competitor indicates that the test compound binds to the cancer protein with higher affinity than the competitor. Thus, if the test compound is labeled, the presence of the label on the support, coupled with a lack of competitor binding, indicates that the test compound binds to and thus potentially modulates the cancer protein of the invention.

Accordingly, the competitive binding methods comprise differential screening to identity agents that are capable of modulating the activity of the cancer proteins of the invention. In this embodiment, the methods comprise combining a cancer protein and a competitor in a first sample. A second sample comprises a test compound, the cancer protein, and a competitor. The binding of the competitor is determined for both samples, and a change, or difference in binding between the two samples indicates the presence of an agent capable of binding to the cancer protein and potentially modulating its activity. That is, if the binding of the competitor is different in the second sample relative to the first sample, the agent is capable of binding to the cancer protein.

Alternatively, differential screening is used to identify drug candidates that bind to the native cancer protein, but cannot bind to modified cancer proteins. For example the structure of the cancer protein is modeled and used in rational drug design to synthesize agents that interact with that site, agents which generally do not bind to site-modified proteins. Moreover, such drug candidates that affect the activity of a native cancer protein are also identified by screening drugs for the ability to either enhance or reduce the activity of such proteins.

Positive controls and negative controls can be used in the assays. Preferably control and test samples are performed in at least triplicate to obtain statistically significant results. Incubation of all samples occurs for a time sufficient to allow for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g. albumin, detergents, etc. which are used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components is added in an order that provides for the requisite binding.

Use of Polynucleotides to Down-regulate or Inhibit a Protein of the Invention.

Polynucleotide modulators of cancer can be introduced into a cell containing the target nucleotide sequence by formation of a conjugate with a ligand-binding molecule, as described in WO 91/04753. Suitable ligand-binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a polynucleotide modulator of cancer can be introduced into a cell containing the target nucleic acid sequence, e.g., by formation of a polynucleotide-lipid complex, as described in WO 90/10448. It is understood that the use of antisense molecules or knock out and knock in models may also be used in screening assays as discussed above, in addition to methods of treatment.

Inhibitory and Antisense Nucleotides

In certain embodiments, the activity of a cancer-associated protein is down-regulated, or entirely inhibited, by the use of antisense polynucleotide or inhibitory small nuclear RNA (snRNA), i.e., a nucleic acid complementary to, and which can preferably hybridize specifically to, a coding mRNA nucleic acid sequence, e.g., a cancer protein of the invention, mRNA, or a subsequence thereof. Binding of the antisense polynucleotide to the mRNA reduces the translation and/or stability of the mRNA.

In the context of this invention, antisense polynucleotides can comprise naturally occurring nucleotides, or synthetic species formed from naturally occurring subunits or their close homologs. Antisense polynucleotides may also have altered sugar moieties or inter-sugar linkages. Exemplary among these are the phosphorothioate and other sulfur containing species which are known for use in the art. Analogs are comprised by this invention so long as they function effectively to hybridize with nucleotides of the invention. See, e.g., Isis Pharmaceuticals, Carlsbad, Calif.; Sequitor, Inc., Natick, Mass.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

Antisense molecules as used herein include antisense or sense oligonucleotides. Sense oligonucleotides can, e.g., be employed to block transcription by binding to the anti-sense strand. The antisense and sense oligonucleotide comprise a single stranded nucleic acid sequence (either RNA or DNA) capable of binding to target mRNA (sense) or DNA (antisense) sequences for cancer molecules. Antisense or sense oligonucleotides, according to the present invention, comprise a fragment generally at least about 12 nucleotides, preferably from about 12 to 30 nucleotides. The ability to derive an antisense or a sense oligonucleotide, based upon a cDNA sequence encoding a given protein is described in, e.g., Stein & Cohen (Cancer Res. 48:2659 (1988 and van der Krol et al. (BioTechniques 6:958 (1988)).

Ribozymes

In addition to antisense polynucleotides, ribozymes can be used to target and inhibit transcription of cancer-associated nucleotide sequences. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g., Castanotto et al., *Adv. in Pharmacology* 25: 289-317 (1994) for a general review of the properties of different ribozymes).

The general features of hairpin ribozymes are described, e.g., in Hampel et al., *Nucl Acids Res.* 18:299-304 (1990); European Patent Publication No. 0360257; U.S. Pat. No. 5,254,678. Methods of preparing are well known to those of skill in the art (see, e.g., WO 94/26877; Ojwang et al., *Proc. Natl. Acad. Sci. USA* 90:6340-6344 (1993); Yamada et al., *Human Gene Therapy* 1:39-45 (1994); Leavitt et al., *Proc. Natl. Acad. Sci. USA* 92:699-703 (1995); Leavitt et al., *Human Gene Therapy* 5: 1151-120 (1994); and Yamada et al., *Virology* 205: 121-126 (1994)).

Use of Modulators in Phenotypic Screening

In one embodiment, a test compound is administered to a population of cancer cells, which have an associated cancer expression profile. By "administration" or "contacting" herein is meant that the modulator is added to the cells in such a manner as to allow the modulator to act upon the cell, whether by uptake and intracellular action, or by action at the cell surface. In some embodiments, a nucleic acid encoding a proteinaceous agent (i.e., a peptide) is put into a viral construct such as an adenoviral or retroviral construct, and added to the cell, such that expression of the peptide agent is accomplished, e.g., PCT US97/01019. Regulatable gene therapy systems can also be used. Once the modulator has been administered to the cells, the cells are washed if desired and are allowed to incubate under preferably physiological conditions for some period. The cells are then harvested and a new gene expression profile is generated. Thus, e.g., cancer tissue is screened for agents that modulate, e.g., induce or suppress, the cancer phenotype. A change in at least one gene, preferably many, of the expression profile indicates that the agent has an effect on cancer activity. Similarly, altering a biological function or a signaling pathway is indicative of modulator activity. By defining such a signature for the cancer phenotype, screens for new drugs that alter the phenotype are devised. With this approach, the drug target need not be known and need not be represented in the original gene/protein expression screening platform, nor does the level of transcript for the target protein need to change. The modulator inhibiting function will serve as a surrogate marker As outlined above, screens are done to assess genes or gene products. That is, having identified a particular differentially expressed gene as important in a particular state, screening of modulators of either the expression of the gene or the gene product itself is performed.

Use of Modulators to Affect Peptides of the Invention

Measurements of cancer polypeptide activity, or of the cancer phenotype are performed using a variety of assays. For example, the effects of modulators upon the function of a cancer polypeptide(s) are measured by examining parameters described above. A physiological change that affects activity is used to assess the influence of a test compound on the polypeptides of this invention. When the functional outcomes are determined using intact cells or animals, a variety of effects can be assesses such as, in the case of a cancer associated with solid tumors, tumor growth, tumor metastasis, neovascularization, hormone release, transcriptional changes to both known and uncharacterized genetic markers (e.g., by Northern blots), changes in cell metabolism such as cell growth or pH changes, and changes in intracellular second messengers such as cGNIP.

Methods of Identifying Characterizing Cancer-associated Sequences

Expression of various gene sequences is correlated with cancer. Accordingly, disorders based on mutant or variant cancer genes are determined. In one embodiment, the invention provides methods for identifying cells containing variant cancer genes, e.g., determining the presence of, all or part, the sequence of at least one endogenous cancer gene in a cell. This is accomplished using any number of sequencing techniques. The invention comprises methods of identifying the cancer genotype of an individual, e.g., determining all or part of the sequence of at least one gene of the invention in the individual. This is generally done in at least one tissue of the individual, e.g., a tissue set forth in Table I, and may include the evaluation of a number of tissues or different samples of the same tissue. The method may include comparing the sequence of the sequenced gene to a known cancer gene, i.e., a wild-type gene to determine the presence of family members, homologies, mutations or variants. The sequence of all or part of the gene can then be compared to the sequence of a known cancer gene to determine if any differences exist. This is done using any number of known homology programs, such as BLAST, Bestfit, etc. The presence of a difference in the sequence between the cancer gene of the patient and the known cancer gene correlates with a disease state or a propensity for a disease state, as outlined herein.

In a preferred embodiment, the cancer genes are used as probes to determine the number of copies of the cancer gene in the genome. The cancer genes are used as probes to determine the chromosomal localization of the cancer genes. Information such as chromosomal localization finds use in providing a diagnosis or prognosis in particular when chromosomal abnormalities such as translocations, and the like are identified in the cancer gene locus.

XIV.) RNAi and Therapeutic Use of Small Interfering RNA (siRNAs)

The present invention is also directed towards siRNA oligonucleotides, particularly double stranded RNAs encompassing at least a fragment of the PSCA coding region or 5" UTR regions, or complement, or any antisense oligonucleotide specific to the PSCA sequence. In one embodiment such oligonucleotides are used to elucidate a function of PSCA, or are used to screen for or evaluate modulators of PSCA function or expression. In another embodiment, gene expression of PSCA is reduced by using siRNA transfection and results in significantly diminished proliferative capacity of transformed cancer cells that endogenously express the antigen; cells treated with specific PSCA siRNAs show reduced survival as measured, e.g., by a metabolic readout of cell viability, correlating to the reduced proliferative capacity. Thus, PSCA siRNA compositions comprise siRNA (double stranded RNA) that correspond to the nucleic acid ORF sequence of the PSCA protein or subsequences thereof, these subsequences are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more than 35 contiguous RNA nucleotides in length and contain sequences that are complementary and non-complementary to at least a portion of the mRNA coding sequence In a preferred embodiment, the subsequences are 19-25 nucleotides in length, most preferably 21-23 nucleotides in length.

RNA interference is a novel approach to silencing genes in vitro and in vivo, thus small double stranded RNAs (siRNAs) are valuable therapeutic agents. The power of siRNAs to silence specific gene activities has now been brought to animal models of disease and is used in humans as well. For example, hydrodynamic infusion of a solution of siRNA into a mouse with a siRNA against a particular target has been proven to be therapeutically effective.

The pioneering work by Song et al. indicates that one type of entirely natural nucleic acid, small interfering RNAs (siRNAs), served as therapeutic agents even without further chemical modification (Song, E., et al. "RNA interference targeting Fas protects mice from fulminant hepatitis" *Nat. Med.* 9(3): 347-51 (2003)). This work provided the first in vivo evidence that infusion of siRNAs into an animal could alleviate disease. In that case, the authors gave mice injections of siRNA designed to silence the FAS protein (a cell death receptor that when over-activated during inflammatory response induces hepatocytes and other cells to die). The next day, the animals were given an antibody specific to Fas. Control mice died of acute liver failure within a few days, while over 80% of the siRNA-treated mice remained free from serious disease and survived. About 80% to 90% of their liver cells incorporated the naked siRNA oligonucleotides. Furthermore, the RNA molecules functioned for 10 days before losing effect after 3 weeks.

For use in human therapy, siRNA is delivered by efficient systems that induce long-lasting RNAi activity. A major caveat for clinical use is delivering siRNAs to the appropriate cells. Hepatocytes seem to be particularly receptive to exogenous RNA. Today, targets located in the liver are attractive because liver is an organ that can be readily targeted by nucleic acid molecules and viral vectors. However, other tissue and organs targets are preferred as well.

Formulations of siRNAs with compounds that promote transit across cell membranes are used to improve administration of siRNAs in therapy. Chemically modified synthetic siRNA, that are resistant to nucleases and have serum stability have concomitant enhanced duration of RNAi effects, are an additional embodiment.

Thus, siRNA technology is a therapeutic for human malignancy by delivery of siRNA molecules directed to PSCA to individuals with the cancers, such as those listed in Table 1. Such administration of siRNAs leads to reduced growth of cancer cells expressing PSCA, and provides an anti-tumor therapy, lessening the morbidity and/or mortality associated with malignancy.

The effectiveness of this modality of gene product knockdown is significant when measured in vitro or in vivo. Effectiveness in vitro is readily demonstrable through application of siRNAs to cells in culture (as described above) or to aliquots of cancer patient biopsies when in vitro methods are used to detect the reduced expression of PSCA protein.

XV.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a probe that is or can be detectably labeled. Such probe can be an antibody or polynucleotide specific for a protein or a gene or message of the invention, respectively. Where the method utilizes nucleic acid hybridization to detect the target nucleic acid, the kit can also have containers containing nucleotide(s) for amplification of the target nucleic acid sequence. Kits can comprise a container comprising a reporter, such as a biotin-binding protein, such as avidin or streptavidin, bound to a reporter molecule, such as an enzymatic, fluorescent, or radioisotope label; such a reporter can be used with, e.g., a nucleic acid or antibody. The kit can include all or part of the amino acid sequences in FIG. 1, FIG. 2, or FIG. 3 or analogs thereof, or a nucleic acid molecule that encodes such amino acid sequences.

The kit of the invention will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label a can be on a container when letters, numbers or other characters forming the label are molded or etched into the container itself, a label can be associated with a container when it is present within a receptacle or carrier that also holds the container, e.g., as a package insert. The label can indicate that the composition is used for diagnosing, treating, prophylaxing or prognosing a condition, such as a neoplasia of a tissue set forth in Table I.

The terms "kit" and "article of manufacture" can be used as synonyms.

In another embodiment of the invention, an article(s) of manufacture containing compositions, such as amino acid sequence(s), small molecule(s), nucleic acid sequence(s), and/or antibody(s), e.g., materials useful for the diagnosis, prognosis, prophylaxis and/or treatment of neoplasias of tissues such as those set forth in Table I is provided. The article of manufacture typically comprises at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/ or antibody(s). In one embodiment, the container holds a polynucleotide for use in examining the mRNA expression profile of a cell, together with reagents used for this purpose. In another embodiment a container comprises an antibody, binding fragment thereof or specific binding protein for use in evaluating protein expression of PSCA in cells and tissues, or for relevant laboratory, prognostic, diagnostic, prophylactic and therapeutic purposes; indications and/or directions for such uses can be included on or with such container, as can reagents and other compositions or tools used for these purposes. In another embodiment, a container comprises materials for eliciting a cellular or humoral immune response, together with associated indications and/or directions. In another embodiment, a container comprises materials for adoptive immunotherapy, such as cytotoxic T cells (CTL) or helper T cells (HTL), together with associated indications and/or directions; reagents and other compositions or tools used for such purpose can also be included.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding PSCA and modulating the function of PSCA.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which is intended to limit the scope of the invention.

Example 1

Expression Analysis of PSCA Variants in Normal Tissues and Patient Specimens

Previously, PSCA, herein referred to as PSCA v.1, was identified as an antigen expressed in prostate cancer. Its expression was detected in greater than 80% of primary prostate cancers and in the majority of prostate metastasis. It has also been shown to be expressed in bladder cancer, ovary cancer, and pancreatic cancer; these cancers are listed in Table I. By immunohistochemical analysis, PSCA has been shown to be overexpressed on the cell surface of most urothelial transitional carcinoma, and in 60% of primary pancreatic adenocarcinomas. The PSCA expression data has been reported in patent publications (PCT/US98/04664, PCT/US/ 28883, PCT/US00/19967) and in peer-reviewed articles (Saffran et al., *Proc Natl Acad Sci USA*. 2001 Feb. 27; 98(5): 2658-2663; Amara et al., *Cancer Res*. 2001 Jun. 15; 61(12): 4660-65; Reiter et al., *Proc Natl Acad Sci USA*. 1998 Feb. 17; 95(4): 1735-40; Argani et al., *Cancer Res*. 2001 Jun. 1; 61(11): 4320-24).

Specific expression of different PSCA variants is studied in normal and cancer patient specimens. Primers were designed to differentiate between PSCA v.1/v.2/v.4, PSCA v.3 and PSCA v.5. PSCA v.1/v.2/v.4 lead to a PCR product of 425 bp, PSCA v.3 leads to a PCR product of 300 bp, whereas PSCA v.5 leads to a PCR product of 910 bp in size (FIG. 1I(a)).

First strand cDNA was prepared from normal bladder, brain, heart, kidney, liver, lung, prostate, spleen, skeletal muscle, testis, pancreas, colon, stomach, pools of prostate cancer, bladder cancer, kidney cancer, colon cancer, lung cancer, ovary cancer, breast cancer, cancer metastasis, and pancreas cancer (FIG. 1I(b)). Normalization was performed by PCR using primers to actin. Semi-quantitative PCR, using the variant specific primers was performed at 30 cycles of amplification.

Results show expression of PSCA v.5 mainly in breast cancer, cancer metastasis, and pancreas cancer, and at lower level in colon cancer and lung cancer. PSCA v.1/v.2/v.4 PCR product was detected in prostate cancer, bladder cancer, kidney cancer, colon cancer, lung cancer, ovary cancer, breast cancer, cancer metastasis, and pancreas cancer. Amongst normal tissues, PSCA v.1/v.2/v.4 PCR product was detected only in prostate, stomach and at lower level in kidney and lung, whereas PSCA v.5 was not detected in any normal tissue. PSCA v.3 PCR detected product was not detected in any of the samples tested.

Primers were designed to differentiate between PSCA v.4 and PSCA v.5 (FIG. 1J(a)). PSCA v.4 lead to a PCR product of 460 bp, whereas PSCA v.5 lead to a PCR product of 945 bp in size.

First strand cDNA was prepared from normal bladder, brain, heart, kidney, liver, lung, prostate, spleen, skeletal muscle, testis, pancreas, colon, stomach, pools of prostate cancer, bladder cancer, and multi-xenograft pool (prostate cancer, kidney cancer and bladder cancer xenografts) (FIG. 1J(b)). Normalization was performed by PCR using primers to actin. Semi-quantitative PCR, using the variant specific primers was performed at 30 cycles of amplification.

Results show expression of PSCA v.4 in prostate cancer, bladder cancer, and multi-xenograft pool, normal kidney and prostate. PSCA v.5 was detected only in normal prostate and bladder cancer.

The restricted expression of PSCA variants in normal tissues and the expression detected in cancer patient specimens indicate that PSCA variants are therapeutic, prognostic, laboratory, prophylactic, and diagnostic targets for human cancers.

Example 2

Splice Variants of PSCA

As used herein, the term variant includes transcript variants and single nucleotide polymorphisms (SNPs). Transcript variants are variants of mature mRNA from the same gene which arise by alternative transcription or alternative splicing. Alternative transcripts are transcripts from the same gene but start transcription at different points. Splice variants are mRNA variants spliced differently from the same transcript. In eukaryotes, when a multi-exon gene is transcribed from genomic DNA, the initial RNA is spliced to produce functional mRNA, which has only exons and is used for translation into an amino acid sequence. Accordingly, a given gene can have zero to many alternative transcripts and each transcript can have zero to many splice variants. Each transcript variant has a unique exon makeup, and can have different coding and/or non-coding (5' or 3' end) portions, from the original transcript. Transcript variants can code for the same, similar or different proteins, such proteins having the same or a similar function or a different function. The variant proteins can be expressed in the same tissue at the same time, in a different tissue at the same time, or in the same tissue at different times, or in a different tissue at a different time. Proteins encoded by a transcript variant can have similar or different subcellular or extracellular localizations (e.g., secreted versus intracellular).

Transcript variants are identified by a variety of art-accepted methods. For example, alternative transcripts and splice variants are identified by full-length cloning, or by use of full-length transcript and EST sequences. First, all human ESTs were grouped into clusters which show direct or indirect identity with each other. Second, ESTs in the same cluster were further grouped into sub-clusters and assembled into a consensus sequence. The original gene sequence is compared to the consensus sequence(s) or other full-length sequences. Each consensus sequence is a potential splice variant for that gene. Several confirmation modalities are known in the art, such as identification of the variant by Northern analysis, full length cloning or by use of probe libraries, etc. Even when a variant is identified that is not yet a full-length clone, that portion of the variant is very useful as a research tool, e.g., for antigen generation or for further cloning of the full-length splice variant, using techniques known in the art.

Moreover, computer programs are available in the art that identify transcript variants based on genomic sequences. Genomic-based transcript variant identification programs include FgenesH (A. Salamov and V. Solovyev, "Ab initio gene finding in *Drosophila* genomic DNA," *Genome Research*. 2000 April; 10(4):516-22); Grail (URL compbio.ornl.gov/Grail-bin/EmptyGrailForm) and GenScan (URL genes.mit.edu/GENSCAN.html). For a general discussion of splice variant identification protocols see, e.g., Southan, C., A genomic perspective on human proteases, *FEBS Lett*. 2001 Jun. 8; 498(2-3):214-8; de Souza, S. J., et al., Identification of human chromosome 22 transcribed sequences with ORF expressed sequence tags, *Proc. Natl. Acad Sci USA*. 2000 Nov. 7; 97(23):12690-3.

To further confirm the parameters of a transcript variant, a variety of techniques are available in the art, such as full-length cloning, proteomic validation, PCR-based validation, and 5' RACE validation, etc. (see e.g., Proteomic Validation: Brennan, S. O., et al, Albumin banks peninsula: a new termination variant characterized by electrospray mass spectrometry, *Biochem Biophys Acta*. 1999 Aug. 17; 1433(1-2):321-6; Ferranti P, et al., Differential splicing of pre-messenger RNA produces multiple forms of mature caprine alpha(s1)-casein, *Eur J Biochem*. 1997 Oct. 1; 249(1):1-7. For PCR-based Validation: Wellmann S, et al., Specific reverse transcription-PCR quantification of vascular endothelial growth factor (VEGF) splice variants by LightCycler technology, *Clin Chem*. 2001 April; 47(4):654-60; Jia, H. P., et al., Discovery of new human beta-defensins using a genomics-based approach, *Gene*. 2001 Jan. 24; 263(1-2):211-8. For PCR-based and 5' RACE Validation: Brigle, K. E., et al., Organization of the murine reduced folate carrier gene and identification of variant splice forms, *Biochem Biophys Acta*. 1997 Aug. 7; 1353(2): 191-8).

It is known in the art that genomic regions are modulated in cancers. When the genomic region to which a gene maps is modulated in a particular cancer, the alternative transcripts or splice variants of the gene are modulated as well. Disclosed herein is that PSCA has a particular expression profile related to cancer (see, e.g., Table I). Alternative transcripts and splice variants of PSCA are also involved in cancers, for example in one or more of these tissues and in certain additional tissues as well. The variants thus serve as tumor-associated markers/antigens.

Using the full-length PSCA gene together with EST sequences, four additional transcript variants were identified, designated as PSCA v.2, v.3, v.4, and v.5. The boundaries of exons in the original transcript, PSCA v.1 were shown in Table VI. The sequences for PSCA and the PSCA variants are set forth in FIG. 1.

Example 3

Single Nucleotide Polymorphisms of PSCA

A Single Nucleotide Polymorphism (SNP) is a single base pair variation in a nucleotide sequence at a specific location. At any given point of the genome, there are four possible nucleotide base pairs: A/T, C/G, G/C, and T/A. As used herein, an allele is one of a series of alternative forms of a given gene, differing in DNA sequence, and affecting a product (RNA and/or protein).

A SNP that occurs on a cDNA is called a cSNP. This cSNP may change amino acids of the protein encoded by the gene and thus change the function of the protein. Some SNPs cause inherited diseases; others contribute to quantitative variations in phenotype and reactions to environmental factors including diet and drugs among individuals. Therefore, the existence of a SNP and/or combinations of alleles (called haplotypes) have many useful applications, such as diagnosis of inherited diseases, determination of drug reactions and dosage, identification of genes responsible for diseases, and analysis of the genetic relationship between individuals (P. Nowotny, J. M. Kwon and A. M. Goate, "SNP analysis to dissect human traits," *Curr. Opin. Neurobiol*. 2001 October; 11(5):637-641; M. Pirmohamed and B. K. Park, "Genetic susceptibility to adverse drug reactions," *Trends Pharmacol. Sci*. 2001 June; 22(6):298-305; J. H. Riley, C. J. Allan, E. Lai and A. Roses, "The use of single nucleotide polymorphisms in the isolation of common disease genes," *Pharmacogenomics*. 2000 February; 1(1):39 -47; R. Judson, J. C. Stephens and A. Windemuth, "The predictive power of haplotypes in clinical response," *Pharmacogenomics*. 2000 February; 1(1):15-26).

SNPs are identified by a variety of art-accepted methods (P. Bean, "The promising voyage of SNP target discovery," *Am. Clin. Lab*. 2001 October-November; 20(9):18-20; K. M. Weiss, "In search of human variation," *Genome Res*. 1998 July; 8(7):691-697; M. M. She, "Enabling large-scale pharmacogenetic studies by high-throughput mutation detection and genotyping technologies," *Clin. Chem*. 2001 February; 47(2):164-172). For example, SNPs are identified by sequencing DNA fragments that show polymorphism by gel-based methods such as restriction fragment length polymorphism (RFLP) and denaturing gradient gel electrophoresis (DGGE). They are also discovered by direct sequencing of DNA samples pooled from different individuals or by comparing sequences from different DNA samples. With the rapid accumulation of sequence data in public and private databases, one also discovers SNPs by comparing sequences using computer programs (Z. Gu, L. Hillier and P. Y. Kwok, "Single nucleotide polymorphism hunting in cyberspace," *Hum. Mutat*. 1998; 12(4):221-225). SNPs can be verified and the genotype or haplotype of an individual can be determined by a variety of methods including direct sequencing and high throughput microarrays (P. Y. Kwok, "Methods for genotyping single nucleotide polymorphisms," *Annu. Rev. Genomics Hum. Genet*. 2001; 2:235-258; M. Kokoris, K. Dix, K. Moynihan, J. Mathis, B. Erwin, P. Grass, B. Hines and A.

Duesterhoeft, "High-throughput SNP genotyping with the Masscode system," *Mol. Diagn.* 2000 December; 5(4):329-340).

Using the methods described above, thirteen SNP were identified in the transcript for PSCA v.2. Variant 2 was used, rather than for example variant 1, as it had fewer ambiguous bases than variant 1. Accordingly, SNPs were identified in PSCA v.2, at positions 57 (t/c), 367 (c/t), 424 (a/c), 495 (c/g), 499 (c/t), 563 (c/t), 567 (g/a), 627 (g/a), 634 (t/g), 835 (g/a), 847 (g/a), 878 (g/a), and 978 (c/g). The transcripts or proteins with alternative alleles were designated as variant PSCA v.6 through v.18, as shown in FIG. 1B and FIG. 1G.

The nucleotide change in v.6 changed the start codon of v.1 and thus, the translation would not start until the next ATG (AUG in mRNA), resulting in a protein 9 AA shorter than v.1 protein. The nucleotide changes for v.7 and v.8 were silent at the protein level.

Twelve of these 13 SNPs were also present in variant 4. The 12 SNP variants relative to PSCA v.4 are designated PSCA v.19 through v.30. Variants 19 through 27 encode alternative amino acids as shown in FIG. 1H.

Example 4

Production of Recombinant PSCA in Prokaryotic Systems

To express recombinant PSCA and PSCA variants in prokaryotic cells, the full or partial length PSCA and PSCA variant cDNA sequences are cloned into any one of a variety of expression vectors known in the art. One or more of the following regions of PSCA variants are expressed: the full length sequence presented in FIG. 1, or any 8, 9, 10, 11, 12, 13, 14, 15, 16, 17, 18, 19, 20, 21, 22, 23, 24, 25, 26, 27, 28, 29, 30 or more contiguous amino acids from PSCA, variants, or analogs thereof.

A. In vitro Transcription and Translation Constructs:

pCRII: To generate PSCA sense and anti-sense RNA probes for RNA in situ investigations, pCRII constructs (Invitrogen, Carlsbad Calif.) are generated encoding either all or fragments of the PSCA cDNA. The pCRII vector has Sp6 and T7 promoters flanking the insert to drive the transcription of PSCA RNA for use as probes in RNA in situ hybridization experiments. These probes are used to analyze the cell and tissue expression of PSCA at the RNA level. Transcribed PSCA RNA representing the cDNA amino acid coding region of the PSCA gene is used in in vitro translation systems such as the TnT™ Coupled Reticulolysate System (Promega, Corp., Madison, Wis.) to synthesize PSCA protein.

B. Bacterial Constructs:

pGEX Constructs: To generate recombinant PSCA proteins in bacteria that are fused to the Glutathione S-transferase (GST) protein, all or parts of the PSCA cDNA protein coding sequence are cloned into the pGEX family of GST-fusion vectors (Amersham Pharmacia Biotech, Piscataway, N.J.). These constructs allow controlled expression of recombinant PSCA protein sequences with GST fused at the amino-terminus and a six histidine epitope (6xHis) at the carboxyl-terminus. The GST and 6xHis tags permit purification of the recombinant fusion protein from induced bacteria with the appropriate affinity matrix and allow recognition of the fusion protein with anti-GST and anti-His antibodies. The 6xHis tag is generated by adding 6 histidine codons to the cloning primer at the 3' end, e.g., of the open reading frame (ORF). A proteolytic cleavage site, such as the PreScission™ recognition site in pGEX-6P-1, may be employed such that it permits cleavage of the GST tag from PSCA-related protein. The ampicillin resistance gene and pBR322 origin permits selection and maintenance of the pGEX plasmids in *E. coli*.

pMAL Constructs: To generate, in bacteria, recombinant PSCA proteins that are fused to maltose-binding protein (MBP), all or parts of the PSCA cDNA protein coding sequence are fused to the MBP gene by cloning into the pMAL-c2X and pMAL-p2X vectors (New England Biolabs, Beverly, Mass.). These constructs allow controlled expression of recombinant PSCA protein sequences with MBP fused at the amino-terminus and a 6xHis epitope tag at the carboxyl-terminus. The MBP and 6xHis tags permit purification of the recombinant protein from induced bacteria with the appropriate affinity matrix and allow recognition of the fusion protein with anti-MBP and anti-His antibodies. The 6xHis epitope tag is generated by adding 6 histidine codons to the 3' cloning primer. A Factor Xa recognition site permits cleavage of the pMAL tag from PSCA. The pMAL-c2X and pMAL-p2X vectors are optimized to express the recombinant protein in the cytoplasm or periplasm respectively. Periplasm expression enhances folding of proteins with disulfide bonds.

pET Constructs: To express PSCA in bacterial cells, all or parts of the PSCA cDNA protein coding sequence are cloned into the pET family of vectors (Novagen, Madison, Wis.). These vectors allow tightly controlled expression of recombinant PSCA protein in bacteria with and without fusion to proteins that enhance solubility, such as NusA and thioredoxin (Trx), and epitope tags, such as 6xHis and S-Tag™ that aid purification and detection of the recombinant protein. For example, constructs are made utilizing pET NusA fusion system 43.1 such that regions of the PSCA protein are expressed as amino-terminal fusions to NusA.

C. Yeast Constructs:

pESC Constructs: To express PSCA in the yeast species *Saccharomyces cerevisiae* for generation of recombinant protein and functional studies, all or parts of the PSCA cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm protein-protein interactions of PSCA. In addition, expression in yeast yields similar post-translational modifications, such as glycosylations and phosphorylations, that are found when expressed in eukaryotic cells.

pESP Constructs: To express PSCA in the yeast species *Saccharomyces pombe*, all or parts of the PSCA cDNA protein coding sequence are cloned into the pESP family of vectors. These vectors allow controlled high level of expression of a PSCA protein sequence that is fused at either the amino terminus or at the carboxyl terminus to GST which aids purification of the recombinant protein. A Flag™ epitope tag allows detection of the recombinant protein with anti-Flag™ antibody.

Example 5

Production of Recombinant PSCA in Higher Eukaryotic Systems

A. Mammalian Constructs:

To express recombinant PSCA in eukaryotic cells, the full or partial length PSCA cDNA sequences, or variants thereof, can be cloned into any one of a variety of expression vectors known in the art. One or more of the following regions of PSCA are expressed in these constructs, amino acids 1 to 123, or any 8, 9, 10, 11, 12, 13, 14, 15, 16, 17, 18, 19, 20, 21, 22, 23, 24, 25, 26, 27, 28, 29, 30 or more contiguous amino acids from PSCA v.1, PSCA variants, or analogs thereof.

The constructs can be transfected into any one of a wide variety of mammalian cells such as 293T cells. Transfected 293T cell lysates can be probed with the anti-PSCA polyclonal serum, described herein.

pcDNA4/HisMax Constructs: To express PSCA in mammalian cells, a PSCA ORF, or portions thereof, of PSCA are cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6×His) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in E. coli.

pcDNA3.1/MycHis Constructs: To express PSCA in mammalian cells, a PSCA ORF, or portions thereof, of PSCA with a consensus Kozak translation initiation site was cloned into pcDNA3.1/MycHis Version A (Invitrogen, Carlsbad, Calif.). Protein expression is driven from the cytomegalovirus (CMV) promoter. The recombinant proteins have the myc epitope and 6×His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in E. coli.

pcDNA3.1/CT-GFP-TOPO Construct: To express PSCA in mammalian cells and to allow detection of the recombinant proteins using fluorescence, a PSCA ORF, or portions thereof, with a consensus Kozak translation initiation site are cloned into pcDNA3.1/CT-GFP-TOPO (Invitrogen, CA). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1/CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in E. coli. Additional constructs with an amino-terminal GFP fusion are made in pcDNA3.1/NT-GFP-TOPO spanning the entire length of a PSCA protein.

PAPtag: A PSCA ORF, or portions thereof, is cloned into pAPtag-5 (GenHunter Corp. Nashville, Tenn.). This construct generates an alkaline phosphatase fusion at the carboxyl-terminus of a PSCA protein while fusing the IgGK signal sequence to the amino-terminus. Constructs are also generated in which alkaline phosphatase with an amino-terminal IgGK signal sequence is fused to the amino-terminus of a PSCA protein. The resulting recombinant PSCA proteins are optimized for secretion into the media of transfected mammalian cells and can be used to identify proteins such as ligands or receptors that interact with PSCA proteins. Protein expression is driven from the CMV promoter and the recombinant proteins also contain myc and 6×His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in E. coli.

ptag5: A PSCA ORF, or portions thereof, was cloned into pTag-5. This vector is similar to pAPtag but without the alkaline phosphatase fusion. This construct generates PSCA protein with an amino-terminal IgGK signal sequence and myc and 6×His epitope tags at the carboxyl-terminus that facilitate detection and affinity purification. The resulting recombinant PSCA protein is optimized for secretion into the media of transfected mammalian cells, and is used as immunogen or ligand to identify proteins such as ligands or receptors that interact with the PSCA proteins. Protein expression is driven from the CMV promoter. The Zeocin resistance gene present in the vector allows for selection of mammalian cells expressing the protein, and the ampicillin resistance gene permits selection of the plasmid in E. coli.

PsecFc: A PSCA ORF, or portions thereof, was cloned into psecFc. The psecFc vector was assembled by cloning the human immunoglobulin G1 (IgG) Fc (hinge, CH2, CH3 regions) into pSecTag2 (Invitrogen, California). This construct generates an IgG1 Fc fusion at the carboxyl-terminus of the PSCA proteins, while fusing the IgGK signal sequence to N-terminus. PSCA fusions utilizing the murine IgG1 Fc region are also used. The resulting recombinant PSCA proteins are optimized for secretion into the media of transfected mammalian cells, and can be used as immunogens or to identify proteins such as ligands or receptors that interact with PSCA protein. Protein expression is driven from the CMV promoter. The hygromycin resistance gene present in the vector allows for selection of mammalian cells that express the recombinant protein, and the ampicillin resistance gene permits selection of the plasmid in E. coli.

FIG. 8 shows expression and purification of PSCA.psecFc protein from 293T cells.

pSRα Constructs: To generate mammalian cell lines that express PSCA constitutively, PSCA ORF, or portions thereof, of PSCA were cloned into pSRα constructs. Amphotropic and ecotropic retroviruses were generated by transfection of pSRα constructs into the 293T-10A1 packaging line or co-transfection of pSRα and a helper plasmid (containing deleted packaging sequences) into the 293 cells, respectively. The retrovirus is used to infect a variety of mammalian cell lines, resulting in the integration of the cloned gene, PSCA, into the host cell-lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in E. coli. The retroviral vectors can thereafter be used for infection and generation of various cell lines using, for example, PC3, NIH 3T3, TsuPr1, 293 or rat-1 cells.

FIG. 6 shows expression of PSCA in recombinant murine, rat and human cell lines using the PSCA.pSRα construct. The indicated murine, rat, and human cell lines were infected with retrovirus carrying the human PSCA cDNA and a neomycin resistance gene or with only the neomycin resistance gene. Stable recombinant cell lines were created by G418 drug selection. PSCA expression was determined by FACS staining with the 1G8 anti-PSCA MAb (5 ug/ml). Shown is the FACS profile of each cell line showing a fluorescent shift only in the PSCA infected line indicating cell surface PSCA expression. These lines are useful in MAb development as immunogens, MAb screening reagents, and in functional assays.

Additional pSRα constructs are made that fuse an epitope tag such as the FLAG™ tag to the carboxyl-terminus of PSCA sequences to allow detection using anti-Flag antibodies. For example, the FLAG™ sequence 5' gat tac aag gat gac gac gat aag 3' (SEQ ID NO: 19) is added to cloning primer at the 3' end of the ORF. Additional pSRα constructs are made to produce both amino-terminal and carboxyl-terminal GFP and myc/6xHis fusion proteins of the full-length PSCA proteins.

Additional Viral Vectors: Additional constructs are made for viral-mediated delivery and expression of PSCA. High virus titer leading to high level expression of PSCA is achieved in viral delivery systems such as adenoviral vectors and herpes amplicon vectors. A PSCA coding sequences or fragments thereof are amplified by PCR and subcloned into the AdEasy shuttle vector (Stratagene). Recombination and virus packaging are performed according to the manufacturer's instructions to generate adenoviral vectors. Alternatively, PSCA coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems: To control expression of PSCA in mammalian cells, coding sequences of PSCA, or portions thereof, are cloned into regulated mammalian expression systems such as the T-Rex System (Invitrogen), the GeneSwitch System (Invitrogen) and the tightly-regulated Ecdysone System (Stratagene). These systems allow the study of the temporal and concentration dependent effects of recombinant PSCA. These vectors are thereafter used to control expression of PSCA in various cell lines such as PC3, NIH 3T3, 293 or rat-1 cells.

B. Baculovirus Expression Systems

To generate recombinant PSCA proteins in a baculovirus expression system, PSCA ORF, or portions thereof, are cloned into the baculovirus transfer vector pBlueBac 4.5 (Invitrogen), which provides a His-tag at the N-terminus. Specifically, pBlueBac-PSCA is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant PSCA protein is then generated by infection of HighFive insect cells (Invitrogen) with purified baculovirus. Recombinant PSCA protein can be detected using anti-PSCA or anti-His-tag antibody. PSCA protein can be purified and used in various cell-based assays or as immunogen to generate polyclonal and monoclonal antibodies specific for PSCA.

C. Expression Vectors for PSCA Orthologs

Mouse and monkey orthologs of PSCA were cloned into pcDNA3.1/MycHis Version A (Invitrogen, Carlsbad, Calif.). Protein expression is driven from the cytomegalovirus (CMV) promoter. The recombinant proteins have the myc epitope and 6xHis epitope fused to the carboxyl-terminus. These vectors allow expression of PSCA orthologs to assay cross-reactivity of monoclonal anti-human PSCA antibodies.

Mouse and monkey orthologs of PSCA were also cloned into pSRα constructs. The pSRα constructs allow for the generation of mammalian cell lines that express PSCA orthologs constitutively. Protein expression is driven from the cytomegalovirus (CMV) promoter. The recombinant proteins have the myc epitope and 6x His epitope fused to the carboxyl-terminus. These vectors allow expression of PSCA orthologs to assay cross-reactivity of monoclonal anti-human PSCA antibodies and to study functional activity of PSCA orthologs. Amphotropic and ecotropic retroviruses were generated by transfection of pSRα constructs into the 293T-10A1 packaging line or co-transfection of pSRα and a helper plasmid (containing deleted packaging sequences) into the 293 cells, respectively. The retrovirus is used to infect a variety of mammalian cell lines, resulting in the integration of the cloned gene, PSCA ortholog, into the host cell-lines.

FIG. 7 shows expression of mouse and simian PSCA.pcDNA3.1/MycHis following transfection into 293T cells. 293T cells were transfected with either mouse PSCA.pcDNA3.1/MycHis or simian PSCA.pcDNA3.1/MycHis or pcDNA3.1/MycHis vector control. Forty hours later, cells were collected and analyzed by flow cytometry using anti-PSCA monoclonal antibodies.

Example 6

Antigenicity Profiles and Secondary Structure

Amino acid profiles of PSCA variants 1, 3, and 4, were found accessing the ProtScale website on the World Wide Web at (.expasy.ch/cgi-bin/protscale.pl) on the ExPasy molecular biology server.

These profiles: Hydrophilicity, (Hopp T. P., Woods K. R., 1981. *Proc. Natl. Acad. Sci. U.S.A.* 78:3824-3828); Hydropathicity, (Kyte J., Doolittle R. F., 1982. *J. Mol. Biol.* 157: 105-132); Percentage Accessible Residues (Janin J., 1979 *Nature* 277:491-492); Average Flexibility, (Bhaskaran R., and Ponnuswamy P. K., 1988. *Int. J. Pept. Protein Res.* 32:242-255); Beta-turn (Deleage, G., Roux B. 1987 *Protein Engineering* 1:289-294); and optionally others available in the art, such as on the ProtScale website, were used to identify antigenic regions of each of the PSCA variant proteins. Each of the above amino acid profiles of PSCA variants were generated using the following ProtScale parameters for analysis: 1) A window size of 9; 2) 100% weight of the window edges compared to the window center; and, 3) amino acid profile values normalized to lie between 0 and 1.

Hydrophilicity, Hydropathicity, and Percentage Accessible Residues profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus available for immune recognition, such as by antibodies.

Average Flexibility and Beta-turn profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the PSCA variant proteins indicated, e.g., by the profiles described above are used to prepare immunogens, either peptides or nucleic acids that encode them, to generate therapeutic and diagnostic anti-PSCA antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from the PSCA protein variants listed in FIG. 1 of which the amino acid profiles can be inferred because the variant contains sequence that is the same as a variant depicted. In particular, peptide immunogens of the invention can comprise, a peptide region of at least 5 amino acids of FIG. 1 in any whole number increment that includes an amino acid position having a value greater than 0.5 in the Hydrophilicity profile; a peptide region of at least 5 amino acids of FIG. 1 in any whole number increment that includes an amino acid position having a value less than 0.5 in the Hydropathicity profile; a peptide region of at least 5 amino acids of FIG. 1 in any whole number increment that includes an amino acid position having a value greater than 0.5 in the Percent Accessible Residues profiles; a peptide region of at least 5 amino acids of FIG. 1 in any whole number increment that includes an amino acid position having a value greater than 0.5 in the Average Flexibility profiles; and, a peptide region of at least 5 amino acids of FIG. 1 in any whole number increment that includes an amino acid position having a value greater than 0.5 in the Beta-turn profile. Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

The secondary structure of PSCA protein variants 1, 3, 4, and 6, namely the predicted presence and location of alpha helices, extended strands, and random coils, is predicted from the primary amino acid sequence using the HNN—Hierarchical Neural Network method (NPS@: *Network Protein Sequence Analysis TIBS* 2000 March Vol. 25, No 3 [291]:147-150 Combet C., Blanchet C., Geourjon C. and Deléage G., http://pbil.ibcp.fr/cgi-bin/npsa_automat.pl?page=npsa_nn.html), accessed from the ExPasy molecular biology server located on the World Wide Web at (.expasy.ch/tools/). The analysis indicates that PSCA variant 1 is composed of 30.89% alpha helix, 21.95% extended strand, and 47.15% random coil. PSCA protein variant 3 is composed of 14.89% alpha helix, 8.51% extended strand, and 76.60% random coil. PSCA protein variant 4 is composed of 9.52% alpha helix, 8.99% extended strand, and 81.48% random coil. PSCA protein variant 6 is composed of 24.56% alpha helix, 21.93% extended strand, and 53.51% random coil.

Analysis for the potential presence of transmembrane domains in the PSCA variant proteins was carried out using a variety of transmembrane prediction algorithms accessed from the ExPasy molecular biology server located on the World Wide Web at (.expasy.ch/tools/).

Example 7

Generation of PSCA Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with a full length PSCA protein variant, computer algorithms are employed in design of immunogens that, based on amino acid sequence analysis contain characteristics of being antigenic and available for recognition by the immune system of the immunized host (see the Example entitled "Antigenicity Profiles and Secondary Structure"). Such regions would be predicted to be hydrophilic, flexible, in beta-turn conformations, and be exposed on the surface of the protein.

For example, recombinant bacterial fusion proteins or peptides containing hydrophilic, flexible, beta-turn regions of PSCA protein variants are used as antigens to generate polyclonal antibodies in New Zealand White rabbits or monoclonal antibodies as described in the Example entitled "Generation of PSCA Monoclonal Antibodies (MAbs)". For example, in PSCA variant 1, such regions include, but are not limited to, amino acids 28-56 and amino acids 66-94. For variant 3, such regions include, but are not limited to, amino acids 7-39 and amino acids 70-94. For variant 4 such regions include, but are not limited to, amino acids 6-18, amino acids 27-39, amino acids 103-133, and 177-189. For variant 6, such regions include, but are not limited to, amino acids 19-35 and amino acids 57-85. It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids 103-133 of PSCA variant 4 is conjugated to KLH and used to immunize a rabbit. Alternatively the immunizing agent may include all or portions of the PSCA variant proteins, analogs or fusion proteins thereof. For example, the PSCA variants amino acid sequences can be fused using recombinant DNA techniques to any one of a variety of fusion protein partners that are well known in the art, such as glutathione-S-transferase (GST) and HIS tagged fusion proteins. In one embodiment, the PSCA variant 1 sequence, amino acids 18-98 was fused to GST using recombinant techniques in the pGEX expression vector, expressed, purified and used to immunize both rabbits and mice to generate polyclonal and monoclonal antibodies respectively. Such fusion proteins are purified from induced bacteria using the appropriate affinity matrix.

Other recombinant bacterial fusion proteins that may be employed include maltose binding protein, LacZ, thioredoxin, NusA, or an immunoglobulin constant region (see the section entitled "Production of PSCA in Prokaryotic Systems" and *Current Protocols In Molecular Biology*, Volume 2, Unit 16, Frederick M. Ausubul et al. eds., 1995; Linsley, P. S., Brady, W., Urnes, M., Grosmaire, L., Damle, N., and Ledbetter, L. (1991) *J. Exp. Med.* 174, 561-566).

In addition to bacterial derived fusion proteins, mammalian expressed protein antigens are also used. These antigens are expressed from mammalian expression vectors such as the Tag5 and Fc-fusion vectors (see the section entitled "Production of Recombinant PSCA in Eukaryotic Systems"), and retain post-translational modifications such as glycosylations found in native protein. In one embodiment, the cDNA of PSCA variant 1, minus the N-terminal leader peptide and C-terminal GPI anchor was cloned into the Tag5 mammalian secretion vector, and expressed in 293T cells. The recombinant protein was purified by metal chelate chromatography from tissue culture supernatants of 293T cells stably expressing the recombinant vector. The purified Tag5 PSCA protein was then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 µg, typically 100-200 µg, of fusion protein or peptide conjugated to KLH mixed in complete Freund's adjuvant (CFA). Rabbits are then injected subcutaneously every two weeks with up to 200 µg, typically 100-200

μg, of the immunogen in incomplete Freund's adjuvant (IFA). Test bleeds are taken approximately 7-10 days following each immunization and used to monitor the titer of the antiserum by ELISA.

To test reactivity and specificity of immune serum, such as rabbit serum derived from immunization with a GST-fusion of PSCA variant 3 or 4 protein, the respective full-length PSCA variant cDNA is cloned into pcDNA 3.1 myc-his expression vector (Invitrogen, see the Example entitled "Production of Recombinant PSCA in Eukaryotic Systems"). After transfection of the constructs into 293T cells, cell lysates are probed with the anti-variant serum and with anti-His antibody (Santa Cruz Biotechnologies, Santa Cruz, Calif.) to determine specific reactivity to denatured variant protein using the Western blot technique. In addition, the immune serum is tested by fluorescence microscopy, flow cytometry and immunoprecipitation against 293T and other recombinant PSCA variant-expressing cells to determine specific recognition of native protein. Western blot, immunoprecipitation, fluorescent microscopy, and flow cytometric techniques using cells that endogenously express PSCA are also carried out to test reactivity and specificity.

Anti-serum from rabbits immunized with PSCA variant fusion proteins, such as GST and MBP fusion proteins, are purified by depletion of antibodies reactive to the fusion partner sequence by passage over an affinity column containing the fusion partner either alone or in the context of an irrelevant fusion protein. For example, antiserum derived from a GST-PSCA variant 1 fusion protein is first purified by passage over a column of GST protein covalently coupled to AffiGel matrix (BioRad, Hercules, Calif.). The antiserum is then affinity purified by passage over a column composed of a MBP-PSCA fusion protein covalently coupled to Affigel matrix. The serum is then further purified by protein G affinity chromatography to isolate the IgG fraction. Sera from other His-tagged antigens and peptide immunized rabbits as well as fusion partner depleted sera are affinity purified by passage over a column matrix composed of the original protein immunogen or free peptide.

Example 8

Generation of PSCA Monoclonal Antibodies (MAbs)

In one embodiment, therapeutic Monoclonal Antibodies ("MAbs") to PSCA and PSCA variants comprise those that react with epitopes specific for each protein or specific to sequences in common between the variants that would bind, internalize, disrupt or modulate the biological function of PSCA or PSCA variants, for example, those that would disrupt the interaction with ligands and binding partners. Immunogens for generation of such MAbs include those designed to encode or contain the extracellular domain or the entire PSCA protein sequence, regions predicted to contain functional motifs, and regions of the PSCA protein variants predicted to be antigenic from computer analysis of the amino acid sequence. Immunogens include peptides, recombinant bacterial proteins such as GST-PSCA fusion proteins (FIG. 8) and His tagged PSCA pET vector protein (FIG. 6) and mammalian expressed purified His tagged proteins (FIG. 7) and human and murine IgG FC fusion proteins. In addition, Cells engineered through retroviral transduction to express high levels of PSCA variant 1, such as RAT1-PSCA, 293T-PSCA, 3T3-PSCA or 300.19-PSCA are used to immunize mice (FIG. 5).

To generate Monoclonal Antibodies to PSCA, mice were first immunized in the foot pad (FP) with, typically, 5-50 μg of protein immunogen or between $10^6$ and $10^7$ PSCA-expressing cells mixed in a suitable adjuvant. Examples of suitable adjuvants for FP immunizations are TiterMax (Sigma) for the initial FP injection followed by alum gel with Immuneasy (Qiagen). Following the initial injection mice were subsequently immunized twice a week until the time they are sacrificed and B cells obtained from the lymph node used for fusion.

During the immunization protocol, test bleeds were taken to monitor the titer and specificity of the immune response. In most cases, once appropriate reactivity and specificity was obtained as determined by ELISA, Western blotting, immunoprecipitation, fluorescence microscopy or flow cytometric analyses, fusion and hybridoma generation was then carried out using electrocell fusion (BTX, ECM2000).

In one embodiment, the invention provides for monoclonal antibodies designated, H1-1.10. The antibodies were identified and are shown to react and bind with cell surface or immobilized PSCA.

MAbs to PSCA were generated using XenoMouse Technology™ wherein the murine heavy and kappa light chain loci have been inactivated and a majority of the human heavy and kappa light chain immunoglobulin loci have been inserted. H1-1.10 was generated after immunizing human gamma 1 producing Xenomice with a cell based immunization using B300.19/PSCA cells. The anti-PSCA MAbs, H1-1.10 bind endogenous cell surface PSCA expressed in prostate cancer xenograft cells.

The antibodies designated H1-1.10 were sent (via Federal Express) to the American Type Culture Collection (ATCC), P.O. Box 1549, Manassas, Va. 20108 on 4 May 2005 and assigned Accession numbers PTA-6697.

DNA coding sequences for anti PSCA MAb H1-1.10, were determined after isolating mRNA from the respective hybridoma cells with Trizol reagent (Life Technologies, Gibco BRL). Total RNA was purified and quantified. First strand cDNAs was generated from total RNA with oligo (dT)12 18 priming using the Gibco BRL Superscript Preamplification system. First strand cDNA was amplified using human immunoglobulin variable heavy chain primers, and human immunoglobulin variable light chain primers. PCR products were cloned into the pCRScript vector (Stratagene, La Jolla). Several clones were sequenced and the variable heavy and light chain regions determined. The nucleic acid and amino acid sequences of the variable heavy and light chain regions are listed in FIGS. 2A and 2B and FIGS. 3A and 3B. Alignment of PSCA H1-1.10 antibodies to germline V-D-J Sequences is shown in FIGS. 4A and 4B.

Example 9

Screening and Identification of PSCA Antibodies

Antibodies generated using the procedures set forth in the example entitled "Generation of PSCA Monoclonal Antibodies (MAbs)" were initially screened using F-MAT and then subsequently screened and identified using a combination of assays including ELISA, FACS, epitope grouping, and affinity for PSCA expressed on the cell surface.

A. PSCA Human MAb Screening by FACS.

Primary hybridoma screening for MAbs to PSCA was performed by FACS. The protocol was as follows: 50 ul/well of hybridoma supernatant (neat) or purified antibodies (in serial dilutions) were added to 96-well FACS plates and mixed with PSCA-expressing cells (endogenous or recombinant, 50,000 cells/well). The mixture was incubated at 4° C. for two hours. At the end of incubation, the cells were washed with FACS Buffer and incubated with 100 ul of detection antibody (anti-hIgG-PE) for 45 minutes at 4° C. At the end of incubation, the cells were washed with FACS Buffer, fixed with Formaldehyde and analyzed using FACScan. Data were analyzed using CellQuest Pro software. Filled histograms indicate data with a negative control IgG1, and open histograms represent data from PSCA-positive cells (FIG. 9).

Positive hybridomas identified from primary screens were transferred to 24-well plates and supernatants collected for confirmatory screens. Confirmatory screens included FACs analysis on B300.19-PSCA/300.19-neo, Rat1-PSCA/Rat1-neo, PC3 -PSCA/neo, SW780 (bladder cancer cell line), LAPC9AI (prostate cancer cell line), HPAC (pancreatic cancer cell line), and ELISA assay using Tag5-PSCA, GST-PSCA, GST-PSCA N-term, Med. C-Term, and pET-PSCA.

B. PSCA H1-1.0 Human MAb Relative Affinity Analysis

The hybridoma supernatants were tested to determine their relative binding affinity to cell surface PSCA. Hybridoma supernatants were serially diluted in FACS Buffer (FB), from µg/ml to sub-ng/ml; and evaluated in a FACS binding assay using LAPC9AI cells. High affinity antibodies gave high MFI values. MFI values of each point were obtained using CellQuest Pro software and used for affinity calculation using Graphpad Prism software (Table VII and Table VIII): Sigmoidal Dose-Response (variable slope) equation. The results of the relative affinity analysis is set forth in Table IX.

C. Epitope Grouping

PSCA antibodies were grouped according to epitope by evaluating their binding pattern on LAPC9AI cells. In brief, a small amount of each of the antibodies was biotinylated; then each of the biotinylated antibodies were incubated with LAPC9AI in the presence of excess (100×) amount of non-biotinylated antibodies at 4° C. for 1 hour during the incubation. Generally, an excess amount of antibodies will compete with biotinylated antibodies if they bind to the same epitope. At the end of incubation, cells were washed and incubated with Streptavidin-PE for 45 min at 4° C. After washing off the unbound streptavidin-PE, the cells were analyzed using FACS. MFI determinations were used for data analysis (Table VII). As shown in Table XI, cells highlighted in yellow indicate self-competition (100% competition), the MFI in these cells are background control for each biotinylated antibody. Cells with no color indicate that the two antibodies compete each other (low MFI), high MFI (highlighted in blue) indicate that the two antibodies bind to two distinct epitopes. The antibodies that have same binding pattern bind to same epitope among the antibodies. There are 6 epitope groups within the antibodies tested. Table XI shows that PSCA H1-1.10 binds to its unique epitope.

Example 10

Characterization and Expression of PSCA Antibodies

A. Cross Reactivity with Monkey PSCA and Mouse PSCA

MAbs were screened and characterized for their ability to react with PSCA from mouse and simian origin. This property is useful to understand the consequences of MAb engagement of PSCA on cells and tissues when using mouse and simian animal models. The Cynomolgus monkey and mouse PSCA genes were cloned, expressed in a retrovirus and transiently infected into 293-T cells. Testing antibodies were incubated with either monkey or mouse PSCA expressing 293-T cells. 293T-neo was used as negative controls. Bound antibodies were detected with anti-hIgG-PE detection antibody. The results presented in Table X shows that PSCA MAb H1-1.10 does not cross-react with monkey-PSCA or Mouse-PSCA.

Example 11

PSCA Antibody Internalization

Internalization of H1-1.10 was studied using PC3-PSCA cells. In brief, H1-1.10 was incubated with cells at 4° C. for 90 min to allow binding of the antibodies to the cell surface. The cells were then split into two groups and incubation continued at either 37° C. to allow antibody internalization or at 4° C. as controls (no internalization). An acid-wash after 37° C./4° C. incubation was employed to remove PSCA 4.121 bound on cell surface. Subsequent permeabilization allowed detection of antibodies bound to internalized PSCA. After incubation with secondary detection antibodies, cells were analyzed using FACS or observed under fluorescence microscope. Approximately 30% of H1-1.10 internalized after incubation at 37° C. for two hours (FIG. 10).

Example 12

Antibody Mediated Killing

PSCA H1-1.0 MAb mediates killing in PC-3/PSCA cells when co-incubated with a conjugated secondary antibody. PC-3 cells engineered to express either the neomycin resistance gene (neo) or PSCA were plated in triplicate into 96 well tissue culture dishes. After allowing the cells to attach overnight, medium was removed and replaced with fresh medium containing the indicated concentrations of anti-PSCA MAb H1-1.10 or H1-1.10 together with a 3 fold excess of the indicated saporin conjugated secondary antibody (Advanced Targeting systems, San Diego, Calif.). The cells were allowed to incubate for 4 days and the percent viability determined using an MTT assay (Promega Corp). The PSCA antibody H1-1.10 was specific as it did not mediate killing of cells that did not express PSCA (FIG. 11-Panel A). H1-1.10 mediated cell killing when incubated together with a secondary antibody that recognized the human Fc region but not with a secondary antibody that recognized the Fc region of a goat antibody (FIG. 11-Panel B). These results indicate that drugs or cytotoxic proteins can selectively be delivered to PSCA expressing cells using an appropriate anti-PSCA MAb.

Additionally, PSCA H1-1.10 MAb mediates killing in LNCaP/PSCA cells co-incubated with a conjugated secondary antibody. LNCap cells engineered to express either the neomycin resistance gene (neo) or PSCA were plated in triplicate into 96 well tissue culture dishes. After allowing the cells to attach overnight, medium was removed and replaced with fresh medium containing the indicated concentrations of anti-PSCA MAb H1-1.10 or H1-1.10 together with a 3 fold excess of anti-human or anti-human saporin conjugated secondary antibody (Advanced Targeting systems, San Diego, Calif.). The cells were allowed to incubate for 4 days and the percent viability determined using an MTT assay (Promega Corp). The PSCA antibody H1-1.10 was specific as it did not mediate killing of LNCap cells that did not express PSCA. (FIG. 12).

Example 13

Antibody Mediated Immune Cytotoxicity

PSCA antibodies were evaluated to determine their ability to mediate immune dependent cytotoxicity. H1-1.10 (0-50

μg/ml) was diluted with RHB buffer (RPMI 1640, Gibco Life Technologies, 20 mM HEPES). B300.19-PSCA expressing cells were washed in RHB buffer and resuspended at a density of $10^6$ cells/ml. In a typical assay, 50 μl of PSCA antibody, 50 μl of diluted rabbit complement serum (Cedarlane, Ontario, Can), and 50 μl of a cell suspension were added together into a flat-bottom tissue culture 96-well plate. The mixture was incubated for 2 hr. at 37° C. in a 5% CO2 incubator to facilitate complement-mediated cell lysis. 50 μl of Alamar Blue (Biosource Intl. Camarillo, Calif.) was added to each well and incubation continued for an additional 4-5 hr at 37° C. The fluorescence in each well was read using a 96-well fluorometer with excitation at 530 nm and emission at 590 nm. The results show that H1-1.10, a human Ig1, was able to mediate complement dependent lysis of target cells. (FIG. 13).

ADCC (Antibody-Dependent Cellular Cytotoxicity) is an immune mediate lytic attack on cells bound with an antibody targeted to a specific cell surface antigen. Immune cells recognize the Fc portion of the antibody through binding to Fcγ receptors on the surface of leukocyte, monocyte and NK cells triggering a lytic attack that results in cell death. Generally, Panc0203 cells are incubated in vitro with $^{51}$chromium for 1 hr. After washing with fresh medium the labeled cells are incubated with 2.5 μg/ml human PSCA MAbs and freshly isolated peripheral blood monocytes at different effector target cell ratios (E:T Ratio). After 4 hours at 37 C, the cells are gently centrifuged and the supernatant containing $^{51}$Cr released from the cells is counted in a Beta counter. The results demonstrate that mediate antibody dependent cell killing that increases when the effector to target cell ratio is increased. The specificity of the assay is determined by showing that an IgG1 Control MAb and incubation of target cells and effector cells in the absence of antibody did not cause cell killing.

Example 14

Generation of F(Ab')2 Fragments

Generation of F(Ab')2 fragments of MAbs is useful to study the effects of MAb molecules that retain their bivalent antigen binding site but lack the immune effector Fc domain in in vitro and in vivo therapeutic models. The protocol is as follows, 20 mgs of MAb H1-1.10 in 20 mM sodium acetate buffer pH 4.5 is incubated with and without immobilized pepsin (Pierce. Rockford Ill.) for the indicated times. Intact MAb and digested Fc fragments are removed by protein A chromatography. A SDS-PAGE Coomassie stained gel of intact undigested unreduced MAb, unreduced aliquots of digested material taken at the indicated times, and a reduced sample of the final digested F(ab')2 product are observed. This reagent can be used to treat animals bearing PSCA expressing tumors. The anti-tumor activity observed with this antibody fragment can distinguish intrinsic biologic activity from activity mediated by immune dependent mechanisms.

Example 15

Expression of Human Antibodies Using Recombinant DNA Methods

To express anti-PSCA MAbs recombinantly in transfected cells, anti-PSCA variable heavy and light chain sequences were cloned upstream of the human heavy chain IgG1 and light chain Igκ constant regions respectively. The complete anti-PSCA human heavy chain and light chain cassettes were cloned downstream of the CMV promoter/enhancer in a cloning vector. A polyadenylation site was included downstream of the MAb coding sequence. The recombinant anti-PSCA MAb expressing constructs were transfected into 293T, Cos, and CHO cells. The H1-1.10 antibody secreted from recombinant 293-T cells is evaluated for binding to cell surface of PSCA and then can be compared with the same antibody produced from the original hybridoma.

Example 16

HLA Class I and Class II Binding Assays

HLA class I and class II binding assays using purified HLA molecules are performed in accordance with disclosed protocols (e.g., PCT publications WO 94/20127 and WO 94/03205; Sidney et al., Current Protocols in Immunology 18.3.1 (1998); Sidney, et al., J. Immunol. 154:247 (1995); Sette, et al., Mol. Immunol. 31:813 (1994)). Briefly, purified MHC molecules (5 to 500 nM) are incubated with various unlabeled peptide inhibitors and 1-10 nM $^{125}$I-radiolabeled probe peptides as described. Following incubation, MHC-peptide complexes are separated from free peptide by gel filtration and the fraction of peptide bound is determined. Typically, in preliminary experiments, each MHC preparation is titered in the presence of fixed amounts of radiolabeled peptides to determine the concentration of HLA molecules necessary to bind 10-20% of the total radioactivity. All subsequent inhibition and direct binding assays are performed using these HLA concentrations.

Since under these conditions [label]<[HLA] and $IC_{50} \geq$ [HLA], the measured $IC_{50}$ values are reasonable approximations of the true KD values. Peptide inhibitors are typically tested at concentrations ranging from 120 μg/ml to 1.2 ng/ml, and are tested in two to four completely independent experiments. To allow comparison of the data obtained in different experiments, a relative binding figure is calculated for each peptide by dividing the $IC_{50}$ of a positive control for inhibition by the $IC_{50}$ for each tested peptide (typically unlabeled versions of the radiolabeled probe peptide). For database purposes, and inter-experiment comparisons, relative binding values are compiled. These values can subsequently be converted back into IC50 nM values by dividing the IC50 nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermotif and/or HLA motif-bearing peptides (see Table IV).

Example 17

Construction of "Minigene" Multi-Epitope DNA Plasmids

This example discusses the construction of a minigene expression plasmid. Minigene plasmids may, of course, contain various configurations of B cell, CTL and/or HTL epitopes or epitope analogs as described herein.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived PSCA, are selected such that multiple supermotifs/motifs are represented to ensure broad population coverage. Similarly, HLA class II epitopes are selected from PSCA to provide broad population coverage, i.e. both HLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in the art, wherein the CLIP sequence of the Ii protein is removed and replaced with an HLA class II epitope sequence so that HLA class II epitope is directed to the endoplasmic reticulum, where the epitope binds to an HLA class II molecule.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene is prepared as follows. For a first PCR reaction, 5 µg of each of two oligonucleotides are annealed and extended: In an example using eight oligonucleotides, i.e., four pairs of primers, oligonucleotides 1+2, 3+4, 5+6, and 7+8 are combined in 100 µl reactions containing Pfu polymerase buffer (1×=10 mM KCL, 10 mM (NH$_4$)$_2$SO$_4$, 20 mM Tris-chloride, pH 8.75, 2 mM MgSO4, 0.1% Triton X-100, 100 µg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 18

The Plasmid Construct and the Degree to which it Induces Immunogenicity

The degree to which a plasmid construct, for example a plasmid constructed in accordance with the previous Example, is able to induce immunogenicity is confirmed in vitro by determining epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683-692, 1996; Demotz et al., *Nature* 342:682-684, 1989); or the number of peptide-HLA class I complexes can be estimated by measuring the amount of lysis or lymphokine release induced by diseased or transfected target cells, and then determining the concentration of peptide necessary to obtain equivalent levels of lysis or lymphokine release (see, e.g., Kageyama et al., *J. Immunol.* 154:567-576, 1995).

Alternatively, immunogenicity is confirmed through in vivo injections into mice and subsequent in vitro assessment of CTL and HTL activity, which are analyzed using cytotoxicity and proliferation assays, respectively, as detailed e.g., in Alexander et al., *Immunity* 1:751-761, 1994.

For example, to confirm the capacity of a DNA minigene construct containing at least one HLA-A2 supermotif peptide to induce CTLs in vivo, HLA-A2.1/K$^b$ transgenic mice, for example, are immunized intramuscularly with 100 µg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}$Cr release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, I-A$^b$-restricted mice, for example, are immunized intramuscularly with 100 µg of plasmid DNA. As a means of comparing the level of HTLs induced by DNA immunization, a group of control animals is also immunized with an actual peptide composition emulsified in complete Freund's adjuvant. CD4+ T cells, i.e. HTLs, are purified from splenocytes of immunized animals and stimulated with each of the respective compositions (peptides encoded in the minigene). The HTL response is measured using a $^3$H-thymidine incorporation proliferation assay, (see, e.g., Alexander et al. *Immunity* 1:751-761, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., Barnett et al., *Aids Res. and Human Retroviruses* 14, Supplement 3:S299-S309, 1998) or recombinant vaccinia, for example, expressing a minigene or DNA encoding the complete protein of interest (see, e.g., Hanke et al., *Vaccine* 16:439-445, 1998; Sedegah et al., *Proc. Natl. Acad. Sci. USA* 95:7648-53, 1998; Hanke and McMichael, *Immunol. Letters* 66:177-181, 1999; and Robinson et al., *Nature Med.* 5:526-34, 1999).

For example, the efficacy of the DNA minigene used in a prime boost protocol is initially evaluated in transgenic mice. In this example, A2.1/K$^b$ transgenic mice are immunized IM with 100 μg of a DNA minigene encoding the immunogenic peptides including at least one HLA-A2 supermotif-bearing peptide. After an incubation period (ranging from 3-9 weeks), the mice are boosted IP with $10^7$ pfu/mouse of a recombinant vaccinia virus expressing the same sequence encoded by the DNA minigene. Control mice are immunized with 100 μg of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes. The use of prime boost protocols in humans is described below in the Example entitled "Induction of CTL Responses Using a Prime Boost Protocol."

Example 19

Polyepitopic Vaccine Compositions from Multiple Antigens

The PSCA peptide epitopes of the present invention are used in conjunction with epitopes from other target tumor-associated antigens, to create a vaccine composition that is useful for the prevention or treatment of cancer that expresses PSCA and such other antigens. For example, a vaccine composition can be provided as a single polypeptide that incorporates multiple epitopes from PSCA as well as tumor-associated antigens that are often expressed with a target cancer associated with PSCA expression, or can be administered as a composition comprising a cocktail of one or more discrete epitopes. Alternatively, the vaccine can be administered as a minigene construct or as dendritic cells which have been loaded with the peptide epitopes in vitro.

Example 20

Use of Peptides to Evaluate an Immune Response

Peptides of the invention may be used to analyze an immune response for the presence of specific antibodies, CTL or HTL directed to PSCA. Such an analysis can be performed in a manner described by Ogg et al., *Science* 279:2103-2106, 1998. In this Example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, PSCA HLA-A*0201-specific CTL frequencies from HLA A*0201-positive individuals at different stages of disease or following immunization comprising a PSCA peptide containing an A*0201 motif. Tetrameric complexes are synthesized as described (Musey et al., *N. Engl. J. Med.* 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 μl of cold phosphate-buffered saline. Tricolor analysis is performed with the tetramer-phycoerythrin, along with anti-CD8 -Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A*0201-positive non-diseased donors. The percentage of cells stained with the tetramer is then determined by flow cytometry. The results indicate the number of cells in the PBMC sample that contain epitope-restricted CTLs, thereby readily indicating the extent of immune response to the PSCA epitope, and thus the status of exposure to PSCA, or exposure to a vaccine that elicits a protective or therapeutic response.

Example 21

Induction of Immune Responses Using a Prime Boost Protocol

A prime boost protocol similar in its underlying principle to that used to confirm the efficacy of a DNA vaccine in transgenic mice, such as described above in the Example entitled "The Plasmid Construct and the Degree to Which It Induces Immunogenicity," can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of "Minigene" Multi-Epitope DNA Plasmids" in the form of naked nucleic acid administered IM (or SC or ID) in the amounts of 0.5-5 mg at multiple sites. The nucleic acid (0.1 to 1000 μg) can also be administered using a gene gun. Following an incubation period of 3-4 weeks, a booster dose is then administered. The booster can be recombinant fowlpox virus administered at a dose of $5\text{-}10^7$ to $5\times10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples are obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve a therapeutic or protective immunity against PSCA is generated.

Example 22

Complementary Polynucleotides

Sequences complementary to the PSCA-encoding sequences (FIG. 1 or FIG. 3), or any parts thereof, are used to detect, decrease, or inhibit expression of naturally occurring PSCA. Although use of oligonucleotides comprising from about 15 to 30 base pairs is described, essentially the same procedure is used with smaller (9-mer or 10-mer) or with larger (40-90) sequence fragments. Appropriate oligonucleotides are designed using, e.g., OLIGO 4.06 software (National Biosciences) and the coding sequence of PSCA. To inhibit transcription, a complementary oligonucleotide is designed from the most unique 5' sequence and used to prevent promoter binding to the coding sequence. To inhibit translation, a complementary oligonucleotide is designed to prevent ribosomal binding to a PSCA-encoding transcript.

Example 23

Purification of Naturally-occurring or Recombinant PSCA Using PSCA-Specific Antibodies Naturally occurring or recombinant PSCA is substantially purified by immunoaffinity chromatography using antibodies specific for PSCA. An immunoaffinity column is constructed by covalently coupling anti-PSCA antibody to an activated chromatographic resin, such as CNBr-activated SEPHAROSE (Amersham Pharmacia Biotech). After the coupling, the resin is blocked and washed according to the manufacturer's instructions.

Media containing PSCA are passed over the immunoaffinity column, and the column is washed under conditions that allow the preferential absorbance of PSCA (e.g., high ionic strength buffers in the presence of detergent). The column is eluted under conditions that disrupt antibody/PSCA binding (e.g., a buffer of pH 2 to pH 3, or a high concentration of a chaotrope, such as urea or thiocyanate ion), and GCR.P is collected.

Example 24

Identification of Molecules which Interact with PSCA

PSCA, or biologically active fragments thereof, are labeled with 121 1 Bolton-Hunter reagent. (See, e.g., Bolton et al. (1973) *Biochem. J.* 133:529.) Candidate molecules previously arrayed in the wells of a multi-well plate are incubated with the labeled PSCA, washed, and any wells with labeled PSCA complex are assayed. Data obtained using different concentrations of PSCA are used to calculate values for the number, affinity, and association of PSCA with the candidate molecules.

Example 25

In Vivo Assay for PSCA Tumor Growth Promotion

The effect of the PSCA protein on tumor cell growth is evaluated in vivo by evaluating tumor development and growth of cells expressing or lacking PSCA. For example, SCID mice are injected subcutaneously on each flank with $1 \times 10^6$ of either 3T3, or prostate cancer cell lines (e.g. PC3 cells) containing tkNeo empty vector or PSCA. At least two strategies may be used: (1) Constitutive PSCA expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) Regulated expression under control of an inducible vector system, such as ecdysone, tetracycline, etc., provided such promoters are compatible with the host cell systems. Tumor volume is then monitored by caliper measurement at the appearance of palpable tumors and followed over time to determine if PSCA-expressing cells grow at a faster rate and whether tumors produced by PSCA-expressing cells demonstrate characteristics of altered aggressiveness (e.g. enhanced metastasis, vascularization, reduced responsiveness to chemotherapeutic drugs).

Additionally, mice can be implanted with $1 \times 10^5$ of the same cells orthotopically to determine if PSCA has an effect on local growth in the prostate, and whether PSCA affects the ability of the cells to metastasize, specifically to lymph nodes, and bone (Miki T et al, *Oncol Res.* 2001; 12:209; Fu X et al, *Int J. Cancer.* 1991, 49:938). The effect of PSCA on bone tumor formation and growth may be assessed by injecting prostate tumor cells intratribially.

The assay is also useful to determine the PSCA inhibitory effect of candidate therapeutic compositions, such as for example, PSCA intrabodies, PSCA antisense molecules and ribozymes.

Example 26

PSCA Monoclonal Antibody-mediated Inhibition of Tumors In Vivo

The significant expression of PSCA on the cell surface of tumor tissues, together with its restrictive expression in normal tissues makes PSCA a good target for antibody therapy. Similarly, PSCA is a target for T cell-based immunotherapy. Thus, the therapeutic efficacy of anti-PSCA MAbs in human prostate cancer xenograft mouse models and human pancreatic cancer xenograft mouse models is evaluated by using recombinant cell lines such as PC3 -PSCA, and 3T3-PSCA (see, e.g., Kaighn, M. E., et al., *Invest Urol,* 1979. 17(1): 16-23), as well as human prostate xenograft models such as LAPC 9AD (Saffran et al *PNAS* 1999, 10:1073-1078).

Antibody efficacy on tumor growth and metastasis formation is studied, e.g., in a mouse orthotopic prostate or pancreatic cancer xenograft models. The antibodies can be unconjugated, as discussed in this Example, or can be conjugated to a therapeutic modality, as appreciated in the art. Anti-PSCA MAbs inhibit formation of pancreatic, prostate and bladder tumor xenografts. Anti-PSCA MAbs also retard the growth of established orthotopic tumors and prolonged survival of tumor-bearing mice. These results indicate the utility of anti-PSCA MAbs in the treatment of local and advanced stages prostate cancer, pancreatic cancer and those cancers set forth in Table I. (See, e.g., Saffran, D., et al., *PNAS* 10: 1073-1078 or world wide web URL pnas.org/cgi/doi/10.1073/pnas.051624698).

Administration of the anti-PSCA MAbs led to retardation of established orthotopic tumor growth and inhibition of metastasis to distant sites, resulting in a significant prolongation in the survival of tumor-bearing mice. These studies indicate that PSCA is an attractive target for immunotherapy and demonstrate the therapeutic potential of anti-PSCA MAbs for the treatment of local and metastatic prostate and pancreatic cancer. This example demonstrates that unconjugated PSCA monoclonal antibodies are effective to inhibit the growth of human prostate tumor xenografts grown in SCID mice; accordingly a combination of such efficacious monoclonal antibodies is also effective.

Tumor Inhibition Using Multiple PSCA MAbs
  Materials and Methods
  PSCA Monoclonal Antibodies:
  Monoclonal antibodies were raised against PSCA as described in the Example entitled "Generation of PSCA Monoclonal Antibodies (MAbs)." The antibodies are characterized by ELISA, Western blot, FACS, and immunoprecipitation for their capacity to bind PSCA. Epitope mapping data for the anti-PSCA MAbs, as determined by ELISA and Western analysis, recognize epitopes on the PSCA protein. Immunohistochemical analysis of prostate cancer tissues and cells with these antibodies is performed.

The monoclonal antibodies are purified from ascites or hybridoma tissue culture supernatants by Protein-G or Protein-A Sepharose chromatography, dialyzed against PBS, filter sterilized, and stored at −20° C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of LAPC9 AD and HPAC tumor xenografts.

Cell Lines and Xenografts
  The prostate cancer cell lines, PC3 and LNCaP cell line as well as the fibroblast line NIH 3T3 (American Type Culture Collection) are maintained in RPMI and DMEM respectively, supplemented with L-glutamine and 10% FBS.

PC3-PSCA and 3T3-PSCA cell populations are generated by retroviral gene transfer as described in Hubert, R. S., et al., *Proc Natl Acad Sci USA*, 1999. 96(25): 14523.

The LAPC-9 xenograft, which expresses a wild-type androgen receptor and produces prostate-specific antigen (PSA), is passaged in 6- to 8-week-old male ICR-severe combined immunodeficient (SCID) mice (Taconic Farms) by s.c. trocar implant (Craft, N., et al., *Nat Med*. 1999, 5:280). Single-cell suspensions of LAPC-9 tumor cells are prepared as described in Craft, et al.

Xenograft Mouse Models.
  Subcutaneous (s.c.) tumors are generated by injection of $1 \times 10^6$ cancer cells mixed at a 1:1 dilution with Matrigel (Collaborative Research) in the right flank of male SCID mice. To test antibody efficacy on tumor formation, i.e. antibody injections are started on the same day as tumor-cell injections. As a control, mice are injected with either purified human IgG or PBS; or a purified monoclonal antibody that recognizes an irrelevant antigen not expressed in human cells. Tumor sizes are determined by caliper measurements, and the tumor volume is calculated as length×width2/2. Mice with Subcutaneous tumors greater than 1.5 cm in diameter are sacrificed.

Orthotopic injections are performed under anesthesia by using ketamine/xylazine. For prostate orthotopic studies, an incision is made through the abdomen to expose the prostate and LAPC or PC3 tumor cells ($2 \times 10^6$) mixed with Matrigel are injected into the prostate capsule in a 10-µl volume. To monitor tumor growth, mice are palpated and blood is collected on a weekly basis to measure PSA levels. The mice are segregated into groups for the appropriate treatments, with anti-PSCA or control MAbs being injected i.p.

Anti-PSCA MAbs Inhibit Growth of PSCA-Expressing Xenograft-Cancer Tumors

The effect of anti-PSCA MAbs on tumor formation is tested by using HPAC and LAPC9 orthotopic models. As compared with the s.c. tumor model, the orthotopic model, which requires injection of tumor cells directly in the mouse pancreas or prostate, respectively, results in a local tumor growth, development of metastasis in distal sites, deterioration of mouse health, and subsequent death (Saffran, D., et al., *PNAS* supra). These features make the orthotopic model more representative of human disease progression and allowed us to follow the therapeutic effect of MAbs on clinically relevant end points.

Accordingly, tumor cells are injected into the mouse prostate, and 2 days later, the mice are segregated into two groups and treated with either: a) 250-1000 µg, of anti-PSCA Ab, or b) control antibody three times per week for two to five weeks.

A major advantage of the orthotopic cancer models is the ability to study the development of metastases. Formation of metastasis in mice bearing established orthotopic tumors is studied by IHC analysis on lung sections using an antibody against a tumor-specific cell-surface protein such as anti-CK19 for prostate cancer (Lin et al., *Cancer Detect Prev*. (2001) 25:202).

Another advantage of xenograft cancer models is the ability to study neovascularization and angiogenesis. Tumor growth is partly dependent on new blood vessel development. Although the capillary system and developing blood network is of host origin, the initiation and architecture of the neovasculature is regulated by the xenograft tumor (Davidoff et al., *Clin Cancer Res*. (2001) 7:2870; Solesvik et al., *Eur J Cancer Clin Oncol*. (1984) 20: 1295). The effect of antibody and small molecule on neovascularization is studied in accordance with procedures known in the art, such as by IHC analysis of tumor tissues and their surrounding microenvironment.

Mice bearing established orthotopic tumors are administered injections of either anti-PSCA MAb or Control antibody over a 4-week period. Mice in both groups are allowed to establish a high tumor burden, to ensure a high frequency of metastasis formation in mouse lungs. Mice then are killed and their bladders, livers, bone and lungs are analyzed for the presence of tumor cells by IHC analysis. These studies demonstrate a broad anti-tumor efficacy of anti-PSCA antibodies on initiation and progression of prostate cancer in xenograft mouse models. Anti-PSCA antibodies inhibit tumor formation of tumors as well as retarding the growth of already established tumors and prolong the survival of treated mice. Moreover, anti-PSCA MAbs demonstrate a dramatic inhibitory effect on the spread of local prostate tumor to distal sites, even in the presence of a large tumor burden. Thus, anti-PSCA MAbs are efficacious on major clinically relevant end points (tumor growth), prolongation of survival, and health.

Effect of PSCA MAbs on the Growth of Human Prostate Cancer in Mice

Using the above methodology, UGB-1, human androgen-independent prostate tumor cells ($2.0 \times 10^6$ cells/mouse) were injected subcutaneously into male SCID mice. The mice were randomized into groups (n=10 mice in each group) and treatment initiated intraperitoneally (i.p.) on Day 0 with H1-1.10, PBS or control human IgG1 MAb as indicated. Animals were treated twice weekly for a total of 5 doses until study day 16.

Tumor growth was monitored using caliper measurements every 3 to 4 days as indicated. Tumor volume was calculated as Width2×Length/2, where width is the smallest dimension and length is the largest. The results show human anti-PSCA monoclonal antibody H1-1.10 significantly inhibited the growth of human prostate cancer xenografts implanted subcutaneously in SCID mice (p<0.01, by Kruskal-Wallis test). (FIG. 14).

In another experiment, PSCA MAb H1-1.10 inhibits the subcutaneous growth of established human androgen-independent prostate cancer xenografts in SCID mice. UGB-1, human androgen independent human prostate tumor cells (1.5×106 cells/mouse) were injected subcutaneously into male SCID mice. When tumors reached about 70 mm3, mice were randomized into groups (n=10 mice in each group) and treatment initiated intraperitoneally (i.p.) on Day 0 with H1-1.10 or with vehicle control as indicated. Animals were treated twice weekly for a total of 7 doses until study day 21. Tumor growth was monitored using caliper measurements every 3 to 4 days as indicated. Tumor volume was calculated as Width2×Length/2, where width is the smallest dimension and length is the largest. The results show human anti-PSCA monoclonal antibody H1-1.10 significantly inhibited the growth of established human prostate cancer xenografts implanted subcutaneously in SCID mice (p<0.05, by the Student's t-test). (FIG. 15).

In another experiment, PSCA MAb H1-1.10 inhibits the subcutaneous growth of human androgen dependent prostate cancer xenografts implanted in SCID mice. LAPC9-AD, human androgen-dependent tumor cells (2.0×106 cells/mouse) were injected subcutaneously into male SCID mice. The mice were randomized into groups (n=10 mice in each group) and treatment initiated intraperitoneally (i.p.) on Day 0 with H1-1.10 or controls as indicated. Animals were treated twice weekly for a total of 6 doses until study day 18. Tumor growth was monitored using caliper measurements every 3 to 4 days as indicated. Tumor volume was calculated as Width2×Length/2, where width is the smallest dimension and length is the largest. The results show human anti-PSCA monoclonal antibody H1-1.0 significantly inhibited the growth of human prostate cancer xenografts implanted subcutaneously in SCID mice (p<0.01, by Kruskal-Wallis test). (FIG. 16).

Effect of PSCA MAbs on the Growth of Human Pancreatic Cancer in Mice

In another experiment, HPAC, human pancreatic tumor cells (3.0×106 cells/mouse) were injected subcutaneously into male SCID mice. The mice were randomized into groups (n=10 mice in each group) and treatment initiated intraperitoneally (i.p.) on Day 0 with H1-1.10 or control human IgG1 as indicated. Animals were treated twice weekly for a total of 5 doses until study day 18. Tumor growth was monitored using caliper measurements every 3 to 4 days as indicated. Tumor volume was calculated as Width2×Length/2, where width is the smallest dimension and length is the largest. The results show human anti-PSCA monoclonal antibody H1-1.10 significantly inhibited the growth of human pancreatic cancer xenografts implanted subcutaneously in SCID mice (p<0.05, by the Student's t-test). (FIG. 17).

Effect of PSCA MAbs on the Growth of Human Bladder Cancer in Mice

In another experiment, Human bladder cancer SW780 cells (2.0×106 cells/mouse) were injected subcutaneously into male SCID mice. The mice were randomized into groups (n=10 mice in each group) and treatment initiated intraperitoneally (i.p.) on Day 0 with H1-1.10, PBS or control human IgG1 MAb as indicated. Animals were treated twice weekly for a total of 6 doses until study day 18. Tumor growth was monitored using caliper measurements every 3 to 4 days as indicated. Tumor volume was calculated as Width2×Length/2, where width is the smallest dimension and length is the largest. The results show human anti-PSCA monoclonal antibody H1-1.10 significantly inhibited the growth of SW780 human bladder cancer xenografts implanted subcutaneously in SCID mice (p<0.05, by Dunnett test). (FIG. 18).

The results of these experiments show that PSCA MAbs can be used for therapeutic and diagnostic purposes to treat and manage cancers set forth in Table I.

Example 27

Therapeutic and Diagnostic Use of Anti-PSCA Antibodies in Humans

Anti-PSCA monoclonal antibodies are safely and effectively used for diagnostic, prophylactic, prognostic and/or therapeutic purposes in humans. Western blot and immunohistochemical analysis of cancer tissues and cancer xenografts with anti-PSCA MAb show strong extensive staining in carcinoma but significantly lower or undetectable levels in normal tissues. Detection of PSCA in carcinoma and in metastatic disease demonstrates the usefulness of the MAb as a diagnostic and/or prognostic indicator. Anti-PSCA antibodies are therefore used in diagnostic applications such as immunohistochemistry of kidney biopsy specimens to detect cancer from suspect patients.

As determined by flow cytometry, anti-PSCA MAb specifically binds to carcinoma cells. Thus, anti-PSCA antibodies are used in diagnostic whole body imaging applications, such as radioimmunoscintigraphy and radioimmunotherapy, (see, e.g., Potamianos S., et. al. *Anticancer Res* 20(2A):925-948 (2000)) for the detection of localized and metastatic cancers that exhibit expression of PSCA. Shedding or release of an extracellular domain of PSCA into the extracellular milieu, such as that seen for alkaline phosphodiesterase B10 (Meerson, N. R., *Hepatology* 27:563-568 (1998)), allows diagnostic detection of PSCA by anti-PSCA antibodies in serum and/or urine samples from suspect patients.

Anti-PSCA antibodies that specifically bind PSCA are used in therapeutic applications for the treatment of cancers that express PSCA. Anti-PSCA antibodies are used as an unconjugated modality and as conjugated form in which the antibodies are attached to one of various therapeutic or imaging modalities well known in the art, such as a prodrugs, enzymes or radioisotopes. In preclinical studies, unconjugated and conjugated anti-PSCA antibodies are tested for efficacy of tumor prevention and growth inhibition in the SCID mouse cancer xenograft models, e.g., kidney cancer models AGS-K3 and AGS-K6, (see, e.g., the Example entitled "PSCA Monoclonal Antibody-mediated Inhibition of Tumors In Vivo"). Either conjugated and unconjugated anti-PSCA antibodies are used as a therapeutic modality in human clinical trials either alone or in combination with other treatments as described in following Examples.

Example 28

Human Clinical Trials for the Treatment and Diagnosis of Human Carcinomas Through Use of Human Anti-PSCA Antibodies In vivo Antibodies are used in accordance with the present invention which recognize an epitope on PSCA, and are used in the treatment of certain tumors such as those listed in Table I. Based upon a number of factors, including PSCA expression levels, tumors such as those listed in Table I are presently preferred indications. In connection with each of these indications, three clinical approaches are successfully pursued.

I.) Adjunctive therapy: In adjunctive therapy, patients are treated with anti-PSCA antibodies in combination with a chemotherapeutic or antineoplastic agent and/or radiation therapy. Primary cancer targets, such as those listed in Table I, are treated under standard protocols by the addition anti-PSCA antibodies to standard first and second line therapy. Protocol designs address effectiveness as assessed by reduction in tumor mass as well as the ability to reduce usual doses of standard chemotherapy. These dosage reductions allow additional and/or prolonged therapy by reducing dose-related toxicity of the chemotherapeutic agent. Anti-PSCA antibodies are utilized in several adjunctive clinical trials in combination with the chemotherapeutic or antineoplastic agents adriamycin (advanced prostrate carcinoma), cisplatin (advanced head and neck and lung carcinomas), taxol (breast cancer), and doxorubicin (preclinical).

II.) Monotherapy: In connection with the use of the anti-PSCA antibodies in monotherapy of tumors, the antibodies are administered to patients without a chemotherapeutic or antineoplastic agent. In one embodiment, monotherapy is conducted clinically in end stage cancer patients with extensive metastatic disease. Patients show some disease stabilization. Trials demonstrate an effect in refractory patients with cancerous tumors.

III.) Imaging Agent: Through binding a radionuclide (e.g., iodine or yttrium ($I^{131}$, $Y^{90}$) to anti-PSCA antibodies, the radiolabeled antibodies are utilized as a diagnostic and/or imaging agent. In such a role, the labeled antibodies localize to both solid tumors, as well as, metastatic lesions of cells expressing PSCA. In connection with the use of the anti-PSCA antibodies as imaging agents, the antibodies are used as an adjunct to surgical treatment of solid tumors, as both a pre-surgical screen as well as a post-operative follow-up to determine what tumor remains and/or returns. In one embodiment, a ($_{111}$In)-PSCA antibody is used as an imaging agent in a Phase I human clinical trial in patients having a carcinoma that expresses PSCA (by analogy see, e.g., Divgi et al. *J. Natl. Cancer Inst.* 83:97-104 (1991)). Patients are followed with standard anterior and posterior gamma camera. The results indicate that primary lesions and metastatic lesions are identified.

Dose and Route of Administration

As appreciated by those of ordinary skill in the art, dosing considerations can be determined through comparison with the analogous products that are in the clinic. Thus, anti-PSCA antibodies can be administered with doses in the range of 5 to 400 mg/m$^2$, with the lower doses used, e.g., in connection with safety studies. The affinity of anti-PSCA antibodies relative to the affinity of a known antibody for its target is one parameter used by those of skill in the art for determining analogous dose regimens. Further, anti-PSCA antibodies that are fully human antibodies, as compared to the chimeric antibody, have slower clearance; accordingly, dosing in patients with such fully human anti-PSCA antibodies can be lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults.

Three distinct delivery approaches are useful for delivery of anti-PSCA antibodies. Conventional intravenous delivery is one standard delivery technique for many tumors. However, in connection with tumors in the peritoneal cavity, such as tumors of the ovaries, biliary duct, other ducts, and the like, intraperitoneal administration may prove favorable for obtaining high dose of antibody at the tumor and to also minimize antibody clearance. In a similar manner, certain solid tumors possess vasculature that is appropriate for regional perfusion. Regional perfusion allows for a high dose of antibody at the site of a tumor and minimizes short term clearance of the antibody.

Clinical Development Plan (CDP)

Overview: The CDP follows and develops treatments of anti-PSCA antibodies in connection with adjunctive therapy, monotherapy, and as an imaging agent. Trials initially demonstrate safety and thereafter confirm efficacy in repeat doses. Trails are open label comparing standard chemotherapy with standard therapy plus anti-PSCA antibodies. As will be appreciated, one criteria that can be utilized in connection with enrollment of patients is PSCA expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express PSCA. Standard tests and follow-up are utilized to monitor each of these safety concerns. Anti-PSCA antibodies are found to be safe upon human administration.

Example 29

Human Clinical Trial

Monotherapy with Human Anti-PSCA Antibody

Anti-PSCA antibodies are safe in connection with the above-discussed adjunctive trial, a Phase II human clinical trial confirms the efficacy and optimum dosing for monotherapy. Such trial is accomplished, and entails the same safety and outcome analyses, to the above-described adjunctive trial with the exception being that patients do not receive chemotherapy concurrently with the receipt of doses of anti-PSCA antibodies.

Example 30

Human Clinical Trial: Diagnostic Imaging with Anti-PSCA Antibody

Once again, as the adjunctive therapy discussed above is safe within the safety criteria discussed above, a human clinical trial is conducted concerning the use of anti-PSCA antibodies as a diagnostic imaging agent. The protocol is designed in a substantially similar manner to those described in the art, such as in Divgi et al. *J. Natl. Cancer Inst.* 83:97-104 (1991). The antibodies are found to be both safe and efficacious when used as a diagnostic modality.

Example 31

Human Clinical Trial Adjunctive Therapy with Human Anti-PSCA Antibody and Chemotherapeutic, Radiation, and/or Hormone Ablation Therapy A phase I human clinical trial is initiated to assess the safety of six intravenous doses of a human anti-PSCA antibody in connection with the treatment of a solid tumor, e.g., a cancer of a tissue listed in Table I. In the study, the safety of single doses of anti-PSCA antibodies when utilized as an adjunctive therapy to an antineoplastic or chemotherapeutic or hormone ablation agent as defined herein, such as, without limitation: cisplatin, topotecan, doxorubicin, adriamycin, taxol, Lupron, Zoladex, Eulexin, Casodex, Anandron or the like, is assessed. The trial design includes delivery of approximately six single doses of an anti-PSCA antibody with dosage of antibody escalating from approximately about 25 mg/m² to about 275 mg/m² over the course of the treatment in accordance with the following or similar schedule:

|  | Day 0 | Day 7 | Day 14 | Day 21 | Day 28 | Day 35 |
| --- | --- | --- | --- | --- | --- | --- |
| MAb Dose | 25 mg/m² | 75 mg/m² | 125 mg/m² | 175 mg/m² | 225 mg/m² | 275 mg/m² |
| Chemotherapy (standard dose) | + | + | + | + | + | + |

Patients are closely followed for one-week following each administration of antibody and chemotherapy. In particular, patients are assessed for the safety concerns mentioned above: (i) cytokine release syndrome, i.e., hypotension, fever, shaking, chills; (ii) the development of an immunogenic response to the material (i.e., development of human antibodies by the patient to the human antibody therapeutic, or HAHA response); and, (iii) toxicity to normal cells that express PSCA. Standard tests and follow-up are utilized to monitor each of these safety concerns. Patients are also assessed for clinical outcome, and particularly reduction in tumor mass as evidenced by MRI or other imaging.

The anti-PSCA antibodies are demonstrated to be safe and efficacious. Phase II trials confirm the efficacy and refine optimum dosing.

Example 32

RNA Interference (RNAi)

RNA interference (RNAi) technology is implemented to a variety of cell assays relevant to oncology. RNAi is a post-transcriptional gene silencing mechanism activated by double-stranded RNA (dsRNA). RNAi induces specific mRNA degradation leading to changes in protein expression and subsequently in gene function. In mammalian cells, these dsRNAs called short interfering RNA (siRNA) have the correct composition to activate the RNAi pathway targeting for degradation, specifically some mRNAs. See, Elbashir S. M., et al., "Duplexes of 21-nucleotide RNAs Mediate RNA interference in Cultured Mammalian Cells," Nature 411(6836): 494-8 (2001). Thus, RNAi technology is used successfully in mammalian cells to silence targeted genes.

Loss of cell proliferation control is a hallmark of cancerous cells; thus, assessing the role of PSCA in cell survival/proliferation assays is relevant. Accordingly, RNAi was used to investigate the function of the PSCA antigen. To generate siRNA for PSCA, algorithms were used that predict oligonucleotides that exhibit the critical molecular parameters (G:C content, melting temperature, etc.) and have the ability to significantly reduce the expression levels of the PSCA protein when introduced into cells. In accordance with this Example, PSCA siRNA compositions are used that comprise siRNA (double stranded, short interfering RNA) that correspond to the nucleic acid ORF sequence of the PSCA protein or subsequences thereof. Thus, siRNA subsequences are used in this manner are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more than 35 contiguous RNA nucleotides in length. These siRNA sequences are complementary and non-complementary to at least a portion of the mRNA coding sequence. In a preferred embodiment, the subsequences are 19-25 nucleotides in length, most preferably 21-23 nucleotides in length. In preferred embodiments, these siRNA achieve knockdown of PSCA antigen in cells expressing the protein and have functional effects as described below.

The selected siRNA (PSCA.b oligo) was tested in numerous cell lines in the survival/proliferation MTS assay (measures cellular metabolic activity). Tetrazolium-based calorimetric assays (i.e., MTS) detect viable cells exclusively, since living cells are metabolically active and therefore can reduce tetrazolium salts to colored formazan compounds; dead cells, however do not. Moreover, this PSCA.b oligo achieved knockdown of PSCA antigen in cells expressing the protein and had functional effects as described below using the following protocols.

Mammalian siRNA transfections: The day before siRNA transfection, the different cell lines were plated in media (RPMI 1640 with 10% FBS w/o antibiotics) at 2×10³ cells/well in 80 µl (96 well plate format) for the survival/MTS assay. In parallel with the PSCA specific siRNA oligo, the following sequences were included in every experiment as controls: a) Mock transfected cells with Lipofectamine 2000 (Invitrogen, Carlsbad, Calif.) and annealing buffer (no siRNA); b) Luciferase-4 specific siRNA (targeted sequence: 5'-AAGGGACGAAGACGAACA CUUCTT-3') (SEQ ID NO: 20); and c) Eg5 specific siRNA (targeted sequence: 5'-AACTGAA GACCTGAAGACAATAA-3') (SEQ ID NO: 21). SiRNAs were used at 10 nM and 1 µg/ml Lipofectamine 2000 final concentration.

The procedure was as follows: The siRNAs were first diluted in OPTIMEM (serum-free transfection media, Invitrogen) at 0.1 uM µM (10-fold concentrated) and incubated 5-10 min RT. Lipofectamine 2000 was diluted at 10 µg/ml (10-fold concentrated) for the total number transfections and incubated 5-10 minutes at room temperature (RT). Appropriate amounts of diluted 10-fold concentrated Lipofectamine 2000 were mixed 1:1 with diluted 10-fold concentrated siRNA and incubated at RT for 20-30" (5-fold concentrated transfection solution). 20 µls of the 5-fold concentrated transfection solutions were added to the respective samples and incubated at 37° C. for 96 hours before analysis.

MTS assay: The MTS assay is a colorimetric method for determining the number of viable cells in proliferation, cytotoxicity or chemosensitivity assays based on a tetrazolium compound [3-(4,5-dimethylthiazol-2-yl)-5-(3-carboxymethoxyphenyl)-2-(4-sulfophenyl)-2H-tetrazolium, inner salt; MTS(b)] and an electron coupling reagent (phenazine ethosulfate; PES). Assays were performed by adding a small amount of the Solution Reagent directly to culture wells, incubating for 1-4 hours and then recording absorbance at 490 nm with a 96-well plate reader. The quantity of colored formazan product as measured by the amount of 490 nm absorbance is directly proportional to the mitochondrial activity and/or the number of living cells in culture.

In order to address the function of PSCA in cells, PSCA is silenced by transfecting the endogenously expressing PSCA cell lines.

Another embodiment of the invention is a method to analyze PSCA related cell proliferation is the measurement of DNA synthesis as a marker for proliferation. Labeled DNA precursors (i.e. 3H-Thymidine) are used and their incorporation to DNA is quantified. Incorporation of the labeled precursor into DNA is directly proportional to the amount of cell division occurring in the culture. Another method used to measure cell proliferation is performing clonogenic assays. In these assays, a defined number of cells are plated onto the appropriate matrix and the number of colonies formed after a period of growth following siRNA treatment is counted.

In PSCA cancer target validation, complementing the cell survival/proliferation analysis with apoptosis and cell cycle profiling studies are considered. The biochemical hallmark of the apoptotic process is genomic DNA fragmentation, an irreversible event that commits the cell to die. A method to observe fragmented DNA in cells is the immunological detection of histone-complexed DNA fragments by an immunoassay (i.e. cell death detection ELISA) which measures the enrichment of histone-complexed DNA fragments (mono- and oligo-nucleosomes) in the cytoplasm of apoptotic cells. This assay does not require pre-labeling of the cells and can detect DNA degradation in cells that do not proliferate in vitro (i.e. freshly isolated tumor cells).

The most important effector molecules for triggering apoptotic cell death are caspases. Caspases are proteases that when activated cleave numerous substrates at the carboxy-terminal site of an aspartate residue mediating very early stages of apoptosis upon activation. All caspases are synthesized as pro-enzymes and activation involves cleavage at aspartate residues. In particular, caspase 3 seems to play a central role in the initiation of cellular events of apoptosis. Assays for determination of caspase 3 activation detect early events of apoptosis. Following RNAi treatments, Western blot detection of active caspase 3 presence or proteolytic cleavage of products (i.e. PARP) found in apoptotic cells further support an active induction of apoptosis. Because the cellular mechanisms that result in apoptosis are complex, each has its advantages and limitations. Consideration of other criteria/endpoints such as cellular morphology, chromatin condensation, membrane blebbing, apoptotic bodies help to further support cell death as apoptotic. Since not all the gene targets that regulate cell growth are anti-apoptotic, the DNA content of permeabilized cells is measured to obtain the profile of DNA content or cell cycle profile. Nuclei of apoptotic cells contain less DNA due to the leaking out to the cytoplasm (sub-G1 population). In addition, the use of DNA stains (i.e., propidium iodide) also differentiate between the different phases of the cell cycle in the cell population due to the presence of different quantities of DNA in G0/G1, S and G2/M. In these studies the subpopulations can be quantified.

For the PSCA gene, RNAi studies facilitate the understanding of the contribution of the gene product in cancer pathways. Such active RNAi molecules have use in identifying assays to screen for MAbs that are active anti-tumor therapeutics. Further, siRNA are administered as therapeutics to cancer patients for reducing the malignant growth of several cancer types, including those listed in Table 1. When PSCA plays a role in cell survival, cell proliferation, tumorigenesis, or apoptosis, it is used as a target for diagnostic, prognostic, preventative and/or therapeutic purposes.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLES

TABLE I

Tissues that express PSCA when malignant.

Prostate
Pancreas
Bladder
Kidney
Colon
Lung
Ovary
Breast

TABLE II

Amino Acid Abbreviations

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Amino Acid Substitution Matrix

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | −2 | −1 | −2 | 0 | −2 | −1 | −1 | −1 | −1 | −2 | −1 | −1 | −1 | 1 | 0 | 0 | −3 | −2 | A |
|  | 9 | −3 | −4 | −2 | −3 | −3 | −1 | −3 | −1 | −1 | −3 | −3 | −3 | −3 | −1 | −1 | −1 | −2 | −2 | C |
|  |  | 6 | 2 | −3 | −1 | −1 | −3 | −1 | −4 | −3 | 1 | −1 | 0 | −2 | 0 | −1 | −3 | −4 | −3 | D |
|  |  |  | 5 | −3 | −2 | 0 | −3 | 1 | −3 | −2 | 0 | −1 | 2 | 0 | 0 | −1 | −2 | −3 | −2 | E |

TABLE III-continued

Amino Acid Substitution Matrix

| A | C | D | E | F | G | H | I | K | L | M | N | P | Q | R | S | T | V | W | Y | |
|---|---|---|---|---|---|---|---|---|---|---|---|---|---|---|---|---|---|---|---|---|
| | | | | 6 | -3 | -1 | 0 | -3 | 0 | 0 | -3 | -4 | -3 | -3 | -2 | -2 | -1 | 1 | 3 | F |
| | | | | | 6 | -2 | -4 | -2 | -4 | -3 | 0 | -2 | -2 | -2 | 0 | -2 | -3 | -2 | -3 | G |
| | | | | | | 8 | -3 | -1 | -3 | -2 | 1 | -2 | 0 | 0 | -1 | -2 | -3 | -2 | 2 | H |
| | | | | | | | 4 | -3 | 2 | 1 | -3 | -3 | -3 | -3 | -2 | -1 | 3 | -3 | -1 | I |
| | | | | | | | | 5 | -2 | -1 | 0 | -1 | 1 | 2 | 0 | -1 | -2 | -3 | -2 | K |
| | | | | | | | | | 4 | 2 | -3 | -3 | -2 | -2 | -2 | -1 | 1 | -2 | -1 | L |
| | | | | | | | | | | 5 | -2 | -2 | 0 | -1 | -1 | -1 | 1 | -1 | -1 | M |
| | | | | | | | | | | | 6 | -2 | 0 | 0 | 1 | 0 | -3 | -4 | -2 | N |
| | | | | | | | | | | | | 7 | -1 | -2 | -1 | -1 | -2 | -4 | -3 | P |
| | | | | | | | | | | | | | 5 | 1 | 0 | -1 | -2 | -2 | -1 | Q |
| | | | | | | | | | | | | | | 5 | -1 | -1 | -3 | -3 | -2 | R |
| | | | | | | | | | | | | | | | 4 | 1 | -2 | -3 | -2 | S |
| | | | | | | | | | | | | | | | | 5 | 0 | -2 | -2 | T |
| | | | | | | | | | | | | | | | | | 4 | -3 | -1 | V |
| | | | | | | | | | | | | | | | | | | 11 | 2 | W |
| | | | | | | | | | | | | | | | | | | | 7 | Y |

Adapted from the GCG Software 9.0 BLOSUM62 amino acid substitution matrix (block substitution matrix). The higher the value, the more likely a substitution is found in related, natural proteins. (See world wide web URL ikp.unibe.ch/manual/blosum62.html)

Table IV: HLA Class I/II Motifs/Supermotifs

TABLE IV (A)

HLA Class I Supermotifs/Motifs

| SUPER-MOTIF | POSITION 2 (Primary Anchor) | POSITION 3 (Primary Anchor) | POSITION C C Terminus (Primary Anchor) |
|---|---|---|---|
| A1 | TILVMS (SEQ ID NO: 22) | | FWY |
| A2 | LIVMATQ (SEQ ID NO: 23) | | IVMATL (SEQ ID NO: 35) |
| A3 | VSMATLI (SEQ ID NO: 24) | | RK |
| A24 | YFWIVLMT (SEQ ID NO: 25) | | FIYWLM (SEQ ID NO: 36) |
| B7 | | P | VILFMWYA (SEQ ID NO: 37) |
| B27 | RHK | | FYLWMIVA (SEQ ID NO: 38) |
| B44 | ED | | FWYLIMVA (SEQ ID NO: 39) |
| B58 | ATS | | FWYLIVMA (SEQ ID NO: 40) |
| B62 | QLIVMP (SEQ ID NO: 26) | | FWYMIVLA (SEQ ID NO: 41) |

MOTIFS

| | | | |
|---|---|---|---|
| A1 | TSM | | Y |
| A1 | | DEAS (SEQ ID NO: 34) | Y |
| A2.1 | LMVQIAT (SEQ ID NO: 27) | | VLIMAT (SEQ ID NO: 42) |
| A3 | LMVISATFCGD (SEQ ID NO: 28) | | KYRHFA (SEQ ID NO: 43) |
| A11 | VTLMISAGNCDF (SEQ ID NO: 29) | | KRYH (SEQ ID NO: 44) |

TABLE IV (A)-continued

HLA Class I Supermotifs/Motifs

| SUPER-MOTIF | POSITION 2 (Primary Anchor) | POSITION 3 (Primary Anchor) | POSITION C C Terminus (Primary Anchor) |
|---|---|---|---|
| A24 | YFWM (SEQ ID NO: 30) | | FLIW (SEQ ID NO: 45) |
| A*3101 | MVTALIS (SEQ ID NO: 31) | | RK |
| A*3301 | MVALFIST (SEQ ID NO: 32) | | RK |
| A*6801 | AVTMSLI (SEQ ID NO: 33) | | RK |
| B*0702 | | P | LMFWYAIV (SEQ ID NO: 46) |
| B*3501 | | P | LMFWYIVA (SEQ ID NO: 47) |
| B51 | | P | LIVFWYAM (SEQ ID NO: 48) |
| B*5301 | | P | IMFWYALV (SEQ ID NO: 49) |
| B*5401 | | P | ATIVLMFWY (SEQ ID NO: 50) |

Bolded residues are preferred, italicized residues are less preferred: A peptide is considered motif-bearing if it has primary anchors at each primary anchor position for a motif or supermotif as specified in the above table.

TABLE IV (B)

HLA Class II Supermotif

| 1 | 6 | 9 |
|---|---|---|
| W, F, Y, V, I, L | A, V, I, L, P, C, S, T | A, V, I, L, C, S, T, M, Y |

TABLE IV (C)

HLA Class II Motifs

| MOTIFS | | 1° anchor 1 | 2 | 3 | 4 | 5 | 1° anchor 6 | 7 | 8 | 9 |
|---|---|---|---|---|---|---|---|---|---|---|
| DR4 | preferred | FMY*LIVW* (SEQ ID NO: 51) | M | T | | I | VST*CPALIM* (SEQ ID NO: 52) | | MH | MH |
| | deleterious | | | | W | | | | R | WDE |
| DR1 | preferred | MF*LIVWY* (SEQ ID NO: 53) | | | PAMQ (SEQ ID NO:54) | | VMAT*SPLIC* (SEQ ID NO: 55) | | M | AVM |
| | deleterious | | C | CH | FD | | CWD | | GDE | D |
| DR7 | preferred | MF*LIVWY* (SEQ ID NO: 56) | M | W | A | | IVMSA*CTPL* (SEQ ID NO: 57) | | M | IV |
| | deleterious | | C | | G | | | | GRD N | G |

| DR3 | MOTIFS | 1° anchor 1 | 2 | 3 | 1° anchor 4 | 5 | 1° anchor 6 |
|---|---|---|---|---|---|---|---|
| Motif a preferred | | LIVMFY (SEQ ID NO: 58) | | D | | | |
| Motif b preferred | | LIVMFAY (SEQ ID NO: 59) | | DNQEST (SEQ ID NO: 60) | | KRH | |
| DR Super-motif | | MF*LIVWY* (SEQ ID NO: 61) | | | VMSTA*CPLI* (SEQ ID NO: 62) | | |

Italicized residues indicate less preferred or "tolerated" residues

TABLE IV (D)

HLA Class I Supermotifs

| SUPER-MOTIFS | POSITION | 1 | 2 | 3 | 4 | 5 | 6 | 7 | 8 | C-terminus |
|---|---|---|---|---|---|---|---|---|---|---|
| A1 | | | 1° Anchor TI*LVMS* (SEQ ID NO: 63) | | | | | | | 1° Anchor FWY |
| A2 | | | 1° Anchor LIVMAT*Q* (SEQ ID NO: 64) | | | | | | | 1° Anchor LIVMAT (SEQ ID NO: 65) |
| A3 | Preferred | | 1° Anchor VSMA*TLI* (SEQ ID NO: 66) | YFW (4/5) | | | YFW (3/5) | YFW (4/5) | P (4/5) | 1° Anchor RK |
| | deleterious | | DE (3/5); P (5/5) | DE (4/5) | | | | | | |
| A24 | | | 1° Anchor YF*WIVLMT* (SEQ ID NO: 67) | | | | | | | 1° Anchor FIY*WLM* (SEQ ID NO: 68) |
| B7 | Preferred | FWY (5/5) LIVM (3/5) (SEQ ID NO: 123) | 1° Anchor P | FWY (4/5) | | | | | FWY (3/5) | 1° Anchor VILF*MWYA* (SEQ ID NO: 69) |
| | deleterious | DE (3/5); P (5/5); G (4/5); | | | | DE (3/5) | G (4/5) | QN (4/5) | DE (4/5) | |

TABLE IV (D)-continued

HLA Class I Supermotifs

| SUPER-MOTIFS | POSITION | 1 | 2 | 3 | 4 | 5 | 6 | 7 | 8 | C-terminus |
|---|---|---|---|---|---|---|---|---|---|---|
| | | | A (3/5;) QN (3/5) | | | | | | | |
| B27 | | | 1° Anchor RHK | | | | | | | 1° Anchor FYL*WMIVA* (SEQ ID NO: 70) |
| B44 | | | 1° Anchor ED | | | | | | | 1° Anchor FWYLIMVA (SEQ ID NO: 71) |
| B58 | | | 1° Anchor ATS | | | | | | | 1° Anchor FWY*LIVMA* (SEQ ID NO: 72) |
| B62 | | | 1° Anchor Q*LIVMP* (SEQ ID NO: 73) | | | | | | | 1° Anchor FWY*MIVLA* (SEQ ID NO: 74) |

Italicized residues indicate less preferred or "tolerated" residues

TABLE IV (E)

HLA Class I Motifs

| | Position | 1 | 2 | 3 | 4 | 5 | 6 | 7 | 8 | 9 or C-terminus | C-terminus |
|---|---|---|---|---|---|---|---|---|---|---|---|
| A1 9-mer | preferred | GFYW (SEQ ID NO: 75) | 1° Anchor STM | DEA | YFW | | P | DEQN (SEQ ID NO: 126) | YFW | 1° Anchor Y | |
| | deleterious | DE | | RHKLIVMP (SEQ ID NO: 76) | A | G | A | | | | |
| A1 9-mer | preferred | GRHK (SEQ ID NO: 77) | ASTCLIVM (SEQ ID NO: 78) | 1° Anchor DEAS (SEQ ID NO: 89) | GSTC (SEQ ID NO: 79) | | ASTC (SEQ ID NO: 80) | LIVM (SEQ ID NO: 81) | DE | 1° Anchor Y | |
| | deleterious | A | RHKDEPYFW (SEQ ID NO: 82) | | DE | PQN | RHK | PG | GP | | |
| A1 10-mer | preferred | YFW | 1° Anchor STM | DEAQN (SEQ ID NO: 83) | A | YFWQN (SEQ ID NO: 84) | | PASTC (SEQ ID NO: 85) | GDE | P | 1° Anchor Y |
| | deleterious | GP | | RHKGLIVM (SEQ ID NO: 86) | DE | RHK | QNA | RHKYFW (SEQ ID NO: 87) | RHK | A | |
| A1 10-mer | preferred | YFW | STCLIVM (SEQ ID NO: 88) | 1° Anchor DEAS (SEQ ID NO: 89) | A | YFW | | PG | G | YFW | 1° Anchor Y |
| | deleterious | RHK | RHKDEPYFW (SEQ ID NO: 90) | | | P | G | PRHK (SEQ ID NO: 91) | QN | | |
| A2.1 9-mer | preferred | YFW | 1° Anchor LMIVQAT (SEQ ID NO: 92) | YFW | STC | YFW | | A | P | 1° Anchor V*LIMAT* (SEQ ID NO: 93) | |

TABLE IV (E)-continued

HLA Class I Motifs

| | | Position 1 | 2 | 3 | 4 | 5 | 6 | 7 | 8 | 9 or C-terminus | C-terminus |
|---|---|---|---|---|---|---|---|---|---|---|---|
| | deleterious | | DEP | | DERKH (SEQ ID NO: 94) | | | RKH | DERKH (SEQ ID NO: 94) | | |
| A2.1 10-mer | preferred | | AYFW (SEQ ID NO: 95) | 1° Anchor LMIVQAT (SEQ ID NO: 96) | LVIM (SEQ ID NO: 97) | G | | G | | FYWLVIM (SEQ ID NO: 98) | 1° Anchor VLIMAT (SEQ ID NO: 93) |
| | deleterious | | DEP | | DE | RKHA (SEQ ID NO: 99) | P | | RKH | DERKHRKH (SEQ ID NO: 100) | |
| A3 | preferred | | RHK | 1° Anchor LMVISATFCGC (SEQ ID NO: 102) | YFW | PRHKYFW (SEQ ID NO: 103) | A | YFW | | P | 1° Anchor KYRHFA (SEQ ID NO: 104) |
| | deleterious | | DEP | | DE | | | | | | |
| A11 | preferred | | A | 1° Anchor VTLMISAGNCDF (SEQ ID NO: 105) | YFW | YFW | A | YFW | YFW | P | 1° Anchor KRYH (SEQ ID NO: 106) |
| | deleterious | | DEP | | | | | | A | G | |
| A24 9-mer | preferred | | YFWRHK (SEQ ID NO: 107) | 1° Anchor YFWM (SEQ ID NO: 108) | | STC | | | YFW | YFW | 1° Anchor FLIW (SEQ ID NO: 109) |
| | deleterious | | DEG | | DE | G | QNP | DERHKG (SEQ ID NO: 110) | | AQN | |
| A24 10-mer | Preferred | | | 1° Anchor YFWM (SEQ ID NO: 111) | | P | YFWP (SEQ ID NO: 112) | | P | | 1° Anchor FLIW (SEQ ID NO: 113) |
| | Deleterious | | | | GDE | QN | RHK | DE | A | QN | DEA |
| A3101 | Preferred | | RHK | 1° Anchor MVTALIS (SEQ ID NO: 114) | YFW | P | | YFW | YFW | AP | 1° Anchor RK |
| | Deleterious | | DEP | | DE | | ADE | DE | DE | DE | |
| A3301 | Preferred | | | 1° Anchor MVALFIST (SEQ ID NO: 115) | YFW | | | | AYFW (SEQ ID NO: 116) | | 1° Anchor RK |
| | Deleterious | | GP | | DE | | | | | | |
| A6801 | Preferred | | YFWSTC (SEQ ID NO: 117) | 1° Anchor AVTMSLI (SEQ ID NO: 118) | | | YFWLIVM (SEQ ID NO: 119) | YFW | P | | 1° Anchor RK |
| | deleterious | | GP | | DEG | | RHK | | | A | |

TABLE IV (E)-continued

| | | Position 1 | 2 | 3 | 4 | 5 | 6 | 7 | 8 | 9 or C-terminus | C-terminus |
|---|---|---|---|---|---|---|---|---|---|---|---|
| B0702 | Preferred | RHKFWY (SEQ ID NO: 120) | 1° Anchor P | RHK | | RHK | RHK | RHK | PA | 1° Anchor LMFWYAIV (SEQ ID NO: 121) | |
| A1 9-mer | preferred | GFYW (SEQ ID NO: 75) | 1° Anchor STM | DEA | YFW | | P | DEQN (SEQ ID NO: 126) | YFW | 1° Anchor Y | |
| | deleterious | DE | | RHKLIVMP (SEQ ID NO: 125) | | G | A | | | | |
| A1 9-mer | preferred | GRHK (SEQ ID NO: 77) | ASTCLIVM (SEQ ID NO: 127) | 1° Anchor DEAS (SEQ ID NO: 128) | GSTC | | ASTC (SEQ ID NO: 129) | LIVM (SEQ ID NO: 139) | DE | 1° Anchor Y | |
| | deleterious | A | RHKDEPYFW (SEQ ID NO: 130) | | DE | PQN | RHK | PG | GP | | |
| B0702 | deleterious | DEQNP (SEQ ID NO: 122) | | DEP | DE | DE | GDE | QN | DE | | |
| B3501 | Preferred | FWYLIVM (SEQ ID NO: 123) | 1° Anchor P | FWY | | | | FWY | | 1° Anchor LMFWYIVA (SEQ ID NO: 124) | |
| | deleterious | AGP | | | | G | G | | | | |
| B51 | Preferred | LIVMFWY (SEQ ID NO: 132) | 1° Anchor P | FWY | STC | FWY | | G | FWY | 1° Anchor LIVFWYAM (SEQ ID NO: 131) | |
| | deleterious | AGPDERHKSTC (SEQ ID NO: 133) | | | | DE | G | DEQN (SEQ ID NO: 126) | GDE | | |
| B5301 | preferred | LIVMFWY (SEQ ID NO: 132) | 1° Anchor P | FWY | STC | FWY | | LIVMFWY (SEQ ID NO: 134) | FWY | 1° Anchor IMFWYALV (SEQ ID NO: 135) | |
| | deleterious | AGPQN (SEQ ID NO: 136) | | | | | G | RHKQN (SEQ ID NO: 137) | DE | | |
| B5401 | preferred | FWY | 1° Anchor P | FWYLIVM (SEQ ID NO: 138) | | LIVM (SEQ ID NO: 139) | | ALIVM (SEQ ID NO: 140) | FWYAP (SEQ ID NO: 141) | 1° Anchor ATIVLMFWY (SEQ ID NO: 142) | |
| | deleterious | GPQNDE (SEQ ID NO: 143) | | GDESTC (SEQ ID NO: 144) | | RHKDE (SEQ ID NO: 145) | DE | QNDGE (SEQ ID NO: 146) | DE | | |

TABLE IV (F)

Summary of HLA-supertypes
Overall phenotypic frequencies of HLA-supertypes in different ethnic populations

| | Specificity | | Phenotypic frequency | | | | | |
|---|---|---|---|---|---|---|---|---|
| Supertype | Position 2 | C-Terminus | Caucasian | N.A. Black | Japanese | Chinese | Hispanic | Average |
| B7 | P | AILMVFWY (SEQ ID NO: 147) | 43.2 | 55.1 | 57.1 | 43.0 | 49.3 | 49.5 |
| A3 | AILMVST (SEQ ID NO: 148) | RK | 37.5 | 42.1 | 45.8 | 52.7 | 43.1 | 44.2 |
| A2 | AILMVT (SEQ ID NO: 149) | AILMVT (SEQ ID NO: 150) | 45.8 | 39.0 | 42.4 | 45.9 | 43.0 | 42.2 |
| A24 | YF (WIVLMT) (SEQ ID NO: 151) | FI (YWLM) (SEQ ID NO: 152) | 23.9 | 38.9 | 58.6 | 40.1 | 38.3 | 40.0 |
| B44 | E (D) | FWYLIMVA (SEQ ID NO: 153) | 43.0 | 21.2 | 42.9 | 39.1 | 39.0 | 37.0 |
| A1 | TI (LVMS) (SEQ ID NO: 154) | FWY | 47.1 | 16.1 | 21.8 | 14.7 | 26.3 | 25.2 |
| B27 | RHK | FYL (WMI) (SEQ ID NO: 155) | 28.4 | 26.1 | 13.3 | 13.9 | 35.3 | 23.4 |
| B62 | QL (IVMP) (SEQ ID NO: 156) | FWY (MIV) (SEQ ID NO: 157) | 12.6 | 4.8 | 36.5 | 25.4 | 11.1 | 18.1 |
| B58 | ATS | FWY (LIV) (SEQ ID NO: 158) | 10.0 | 25.1 | 1.6 | 9.0 | 5.9 | 10.3 |

TABLE IV (G)

Calculated population coverage afforded by different HLA-supertype combinations

| | Phenotypic frequency | | | | | |
|---|---|---|---|---|---|---|
| HLA-supertypes | Caucasian | N.A Blacks | Japanese | Chinese | Hispanic | Average |
| A2, A3 and B7 | 83.0 | 86.1 | 87.5 | 88.4 | 86.3 | 86.2 |
| A2, A3, B7, A24, B44 and A1 | 99.5 | 98.1 | 100.0 | 99.5 | 99.4 | 99.3 |
| A2, A3, B7, A24, B44, A1, B27, B62, and B 58 | 99.9 | 99.6 | 100.0 | 99.8 | 99.9 | 99.8 |

Motifs indicate the residues defining supertype specificites. The motifs incorporate residues determined on the basis of published data to be recognized by multiple alleles within the supertype. Residues within brackets are additional residues also predicted to be tolerated by multiple alleles within the supertype.

TABLE V

Frequently Occurring Motifs

| Name | avrg. % identity | Description | Potential Function |
|---|---|---|---|
| zf-C2H2 | 34% | Zinc finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |

TABLE V-continued

Frequently Occurring Motifs

| Name | avrg. % identity | Description | Potential Function |
|---|---|---|---|
| Ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| Pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| Rvt | 49% | Reverse transcriptase (RNA-dependent DNA polymerase) | |
| Ank | 25% | Ank repeat | Cytoplasmic protein, associates integral membrane proteins to the cytoskeleton |
| Oxidored_q1 | 32% | NADH-Ubiquinone/plastoquinone (complex I), various chains | membrane associated. Involved in proton translocation across the membrane |
| Efhand | 24% | EF hand | calcium-binding domain, consists of a 12 residue loop flanked on both sides by a 12 residue alpha-helical domain |
| Rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| Fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE VI

Exon boundaries of transcript PSCA v.1

| Exon Number | Start | End | Length |
|---|---|---|---|
| 1 | 10 | 69 | 60 |
| 2 | 70 | 177 | 108 |
| 3 | 178 | 985 | 808 |

TABLE VII

MFI values of each data points used for affinity calculation.

| nM | REF#288 | REF#288 | H1/1.10.1.1 - #1 | H1/1.10.1.1 - #2 |
|---|---|---|---|---|
| 40 | 622.86 | 1406.94 | 1113.5 | 1060.56 |
| 20 | 1513.15 | 1464.75 | 1178.13 | 1077.91 |
| 10 | 1493.2 | 1428.77 | 827.98 | 913.76 |
| 5 | 1470.18 | 1456.57 | 929.88 | 897.58 |
| 2.5 | 1402.73 | 1422.59 | 805.46 | 751.15 |
| 1.25 | 1391.11 | 1393.62 | 638.27 | 651.75 |
| 0.625 | 1238.71 | 1302.08 | 495.79 | 467.92 |
| 0.3125 | 1039.89 | 1129.29 | 279.87 | 337.3 |
| 0.15625 | 739.63 | 745.06 | 232.76 | 195.28 |
| 0.07813 | 462.79 | 418.21 | 109.33 | 116.94 |
| 0.03906 | 249.08 | 254.03 | 59.85 | 64.21 |
| 0.01953 | 134.61 | 148.12 | 40.8 | 31.91 |
| 0.00977 | 73.3 | 72.26 | 19 | 16.81 |
| 0.00488 | 35.27 | 37.97 | 11.2 | 11.54 |
| 0.00244 | 24.62 | 21.73 | 7.59 | 7.71 |
| 0.00122 | 15.38 | 14.57 | 6.12 | 6.39 |
| 0.00061 | 11.9 | 16.33 | 5.78 | 5.97 |
| 0.00031 | 8.09 | 7.67 | 5.87 | 6.07 |
| 0.00015 | 6.36 | 5.99 | 6.08 | 5.39 |
| 0.00008 | 5.93 | 5.48 | 4.82 | 4.85 |
| 0.00004 | 5.35 | 5.46 | 5.3 | 5.14 |

TABLE VIII

Affinity calculated from binding saturation curve using Graphpad Prism software: One-site binding (hyperbola).

| | REF#288 | REF#288 | H1/1.10.1.1 - #1 | H1/1.10.1.1 - #2 |
|---|---|---|---|---|
| Best-fit values | | | | |
| BMAX | 1534 | 1527 | 958.9 | 977.8 |
| KD | 0.1674 | 0.1554 | 0.5932 | 0.6359 |
| Std. Error | | | | |
| BMAX | 13.45 | 27.49 | 26.19 | 10.79 |
| KD | 0.00669 | 0.01288 | 0.05968 | 0.02548 |

TABLE IX

FACS based affinity on fully human PSCA MAbs
FACS-Based Affinity

| Sample ID | Kd (nM) |
|---|---|
| H1-1.10 | 0.60 |

TABLE X

Antibodies that cross-react with Monkey PSCA and/or Mouse PSCA.

| Hybridoma ID | Cross-react with Monkey-PSCA | Cross-react with Mouse-PSCA |
|---|---|---|
| H1-1.10 | − | − |
| Ha1-1.16 | + | − |
| Ha1-1.78 | + | − |
| Ha1-1.41 | + | − |
| Ha1-4.5 | + | − |
| Ha1-4.37 | + | − |
| Ha1-4.117 | + | + |
| Ha1-4.120 | + | − |
| Ha1-4.121 | + | − |
| Ha1-5.99 | + | − |

TABLE XI

PSCA: Epitope Grouping by FACS analysis.

| Groups | 1 | | 2 | 3 | 4 | 5 | | | 6 |
|---|---|---|---|---|---|---|---|---|---|
| mAb ID/MFI | 4.37 | 4.120 | 4.5 | 5.99 | 4.121 | 1.10 | 1.41 | 1.16 | 1G8 | 3.18 |
| 4.37 | 5.73 | 6.45 | 7.35 | 7.28 | 11.63 | 13.65 | 28.88 | 26.86 | 23.92 | 45.76 |
| 4.120 | 5.31 | 6.24 | 6.73 | 7.32 | 7.3 | 6.1 | 23.81 | 20.91 | 15.41 | 44.48 |
| 4.5 | 5.36 | 5.75 | 5.86 | 6.82 | 7.47 | 7.92 | 16.46 | 22.91 | 13.45 | 28.63 |
| 5.99 | 23.77 | 22.33 | 30.82 | 7.38 | 45.45 | 46.37 | 60.06 | 63.63 | 29.5 | 87.32 |
| 4.121 | 5.4 | 5.63 | 10.51 | 15.15 | 6.16 | 13.5 | 34.63 | 37.64 | 26.38 | 46.42 |
| 1.10 | 6.76 | 5.91 | 5.57 | 6.43 | 7.38 | 6.28 | 28.14 | 22.21 | 17.74 | 67.68 |
| 1.41 | 10.21 | 6.37 | 6.03 | 9.45 | 9.54 | 7.68 | 6.75 | 9.8 | 5.77 | 23.93 |
| 1.16 | 7.51 | 8 | 8.01 | 6.7 | 22.88 | 17.11 | 14.34 | 10.7 | 6.89 | 48.45 |
| 1G8 | 11.65 | 12.45 | 13.77 | 8.21 | 28.69 | 16.57 | 16.43 | 14.26 | 6.48 | 65.56 |
| 3.18 | 7.73 | 8.23 | 10.66 | 7.74 | 8.73 | 8.55 | 9.89 | 12.56 | 8.68 | 6.93 |

Legend:
- self-competition (100%), bkgd control for each biotinylated antibody
- no color: 100% competition
- strong competition
- none to weak competition

The invention claimed is:

1. A method for detecting the presence of a PSCA protein comprising the amino acid sequence of SEQ ID NO: 2 in a test sample comprising:
    (a) obtaining a test sample from a subject suspected of having cancer;
    (b) contacting the sample with a monoclonal antibody or an antigen-binding fragment thereof comprising the amino acid sequence of the variable heavy chain region and the variable light chain region of the antibody secreted by the hybridoma assigned A.T.C.C. Accession No. PTA-6697, wherein the monoclonal antibody or the antigen-binding fragment thereof specifically bind to the PSCA protein; and
    (c) detecting binding of the PSCA protein in the sample.

2. The method of claim 1, further comprising the steps:
    (d) determining the level of expression of the PSCA protein in the test sample; and
    (e) comparing the level so determined to the expression level of the PSCA protein in a normal tissue sample of the same type as the test sample.

3. The method of claim 1, wherein the cancer is selected from the group consisting of cancer of prostate, pancreas, bladder, kidney, colon, lung, ovary, and breast.

4. The method of claim 1, wherein the antibody is a fully human antibody.

5. The method of claim 1, wherein the antigen-binding fragment is an Fab, F(ab')$_2$, Fv or Sfv fragment.

6. A method for detecting a PSCA protein in a biological sample, comprising steps of:
    providing the biological sample and control sample;
    contacting the biological sample and the control sample with a monoclonal antibody or an antigen-binding fragment thereof comprising the amino acid sequence of the variable heavy chain region and the variable light chain region of the antibody secreted by the hybridoma assigned A.T.C.C. Accession No. PTA-6697, wherein the monoclonal antibody or the antigen-binding fragment thereof specifically bind to the PSCA protein, which comprises the amino acid sequence of SEQ ID NO: 2; and
    determining an amount of complex of the substance with the PSCA protein and the antibody present in the biological sample and the control sample.

7. The method of claim 6, further comprising:
    taking the biological sample and the control sample from a patient who has or who is suspected of having a cancer selected from the group of cancer of prostate, pancreas, bladder, kidney, colon, lung, ovary, and breast.

* * * * *